US010172886B2

(12) United States Patent
Pulé et al.

(10) Patent No.: US 10,172,886 B2
(45) Date of Patent: Jan. 8, 2019

(54) CELL

(71) Applicant: UCL BUSINESS PLC, London (GB)

(72) Inventors: Martin Pulé, London (GB); Khai Kong, London (GB); Shaun Cordoba, London (GB)

(73) Assignee: UCL BUSINESS PLC, London (GB)

( * ) Notice: Subject to any disclaimer, the term of this patent is extended or adjusted under 35 U.S.C. 154(b) by 267 days.

(21) Appl. No.: 15/037,414

(22) PCT Filed: Nov. 21, 2014

(86) PCT No.: PCT/GB2014/053452
§ 371 (c)(1),
(2) Date: May 18, 2016

(87) PCT Pub. No.: WO2015/075469
PCT Pub. Date: May 28, 2015

(65) Prior Publication Data
US 2016/0289294 A1    Oct. 6, 2016

(30) Foreign Application Priority Data

Nov. 21, 2013 (GB) .................................. 1320573.7
Jun. 19, 2014 (GB) .................................. 1410934.2

(51) Int. Cl.
| | |
|---|---|
| *A61K 35/17* | (2015.01) |
| *A61K 39/00* | (2006.01) |
| *C07K 14/725* | (2006.01) |
| *C07K 14/705* | (2006.01) |
| *C07K 16/28* | (2006.01) |
| *C12N 5/0783* | (2010.01) |
| *C12N 15/86* | (2006.01) |
| *C12N 9/16* | (2006.01) |
| *A61K 38/00* | (2006.01) |

(52) U.S. Cl.
CPC .......... *A61K 35/17* (2013.01); *A61K 39/0011* (2013.01); *C07K 14/7051* (2013.01); *C07K 14/70503* (2013.01); *C07K 14/70517* (2013.01); *C07K 14/70521* (2013.01); *C07K 14/70589* (2013.01); *C07K 16/2803* (2013.01); *C12N 5/0636* (2013.01); *C12N 5/0637* (2013.01); *C12N 5/0638* (2013.01); *C12N 5/0646* (2013.01); *C12N 9/16* (2013.01); *C12N 15/86* (2013.01); *C12Y 301/03048* (2013.01); *A61K 38/00* (2013.01); *A61K 2039/5158* (2013.01); *C07K 2317/52* (2013.01); *C07K 2317/622* (2013.01); *C07K 2319/01* (2013.01); *C07K 2319/02* (2013.01); *C07K 2319/03* (2013.01); *C07K 2319/74* (2013.01); *C12N 2510/00* (2013.01); *C12N 2740/10043* (2013.01); *C12N 2740/15043* (2013.01)

(58) Field of Classification Search
None
See application file for complete search history.

(56) References Cited

U.S. PATENT DOCUMENTS

| 7,052,906 B1 | 5/2006 | Lawson et al. |
| 2016/0289293 A1 | 10/2016 | Pule et al. |
| 2016/0296562 A1 | 10/2016 | Pule et al. |
| 2018/0104321 A1 | 4/2018 | Pule et al. |

FOREIGN PATENT DOCUMENTS

| WO | WO-2000/063372 A1 | 10/2000 |
| WO | WO-2017/068361 A1 | 4/2017 |

OTHER PUBLICATIONS

Whilding, L. et al., Mol. Oncology, 2015, vol. 9: pp. 1994-2018.*
Chicaybam et al., A conditional system for the activation of lymphocytes expressing activating and inhibitory CARs. *Hum. Gene Ther.* 21(10): 1418 (2010).
Cordoba et al., Chimeric antigen receptor logical and gate based on CD45/CD148 phosphatase. *Molec. Ther.* 22: S59 (2014).
Duong et al., Enhancing the specificity of T-cell cultures for adoptive immunotherapy of cancer. *Immunother.* 3(1): 33-48 (2011).
Fedorov et al., Inhibitory chimeric antigen receptors (iCARs) limit undesirable side effects of T-cell therapies. *Exp. Hematol.* 41(8): S75 (2013). ABSTRACT.
Furukawa et al., Specific interaction of the CD45 protein-tyrosine phosphatase with tyrosine-phosphorylated CD3 zeta chain. *Proc. Natl. Acad. Sci. USA*, 91(23): 10928-32 (1994).
Hedge et al., Combinational targeting offsets antigen escape and enhances effector functions of adoptively transferred T cells in glioblastoma. *Molec. Ther.* 21(11): 2087-101 (2013).
Hombach et al., Adoptive immunotherapy with genetically engineered T cells: modification of the IgG1 Fc 'spacer' domain in the extracellular moiety of chimeric antigen receptors avoids 'off-target' activation and unintended initiation of an innate immune response. *Gene Ther.* 17(10): 1206-13 (2010).
Kloss et al., Conbinatorial antigen recognition with balanced signaling promotes selective tumor eradication by engineered T cells. *Nat. Biotechnol.* 31(1): 71-5 (2013).
Lamers et al., Treatment of metastatic renal cell carcinoma with CAIX CAR-engineered T cells: Clinical evaluation and management of on-target toxicity. *Mol. Ther.* 21(4): 904-12 (2013).

(Continued)

*Primary Examiner* — Michael D Burkhart
(74) *Attorney, Agent, or Firm* — Marshall, Gerstein & Borun LLP

(57) ABSTRACT

The present invention provides a cell which co-expresses a first chimeric antigen receptor (CAR) and second CAR at the cell surface, each CAR comprising: (i) an antigen-binding domain; (ii) a spacer (iii) a trans-membrane domain; and (iv) an endodomain wherein the antigen binding domains of the first and second CARs bind to different antigens, wherein the spacer of the first CAR is different to the spacer of the second CAR and wherein one of the first or second CARs is an activating CAR comprising an activating endodomain and the other CAR is an inhibitory CAR comprising a ligation-off inhibitory endodomain.

16 Claims, 32 Drawing Sheets
Specification includes a Sequence Listing.

(56) References Cited

OTHER PUBLICATIONS

Lanitis et al., Chimeric antigen receptor T cells with dissociated signaling domains exhibit focused antitumor activity with reduced potential for toxicity in vivo. *Cancer Immunol. Res.* 1(1): 43-53 (2013).
Pule et al., A chimeric T cell antigen receptor that augments cytokine release and supports clonal expansion of primary human T cells. *Mole. Ther.* 12(5): 933-41 (2005).
Rossig et al., Epstein-Barr virus-specific human T lymphocytes expressing antitumor chimeric T-cell receptors: Potential for improved immunotherapy. *Blood*, 99(6): 2009-16 (2002).
Staub et al., Systematic identification of immunoreceptor tyrosine-based inhibitory motifs in the human proteome. *Cell Signal*, 16(14): 435-56 (2004).
Wilkie et al., Dual targeting of ErbB2 and MUC1 in breast cancer using chimeric antigen receptors engineered to provide complementary signaling. *J. Clin. Immunol.* 32(5): 1059-70 (2012).
U.S. Appl. No. 15/037,391, filed May 18, 2016.
U.S. Appl. No. 15/037,405, filed May 18, 2016.
U.S. Appl. No. 15/568,874, filed Oct. 24, 2017.

* cited by examiner

>MP13974.SFG.aCD19fmc63_clean-CD8STK-CD28tmZ-2A-aCD33glx-HCH2CH3pvaa-CD28tmZw

MSLPVTALLLPLALLLHAARPDIQMTQTTSSLSASLGDRVTISCRASQDISKYLNWYQQKPDGTVKLLIYHTSRLHSGVPSRF
SGSGSGTDYSLTISNLEQEDIATYFCQQGNTLPYTFGGGTKLEITKAGGGGSGGGGSGGGGSGGGGSEVKLQESGPGLVAPSQ
SLSVTCTVSGVSLPDYGVSWIRQPPRKGLEWLGVIWGSETTYYNSALKSRLTIIKDNSKSQVFLKMNSLQTDDTAIYYCAKHY
YYGGSYAMDYWGQGTSVTVS*SDP*TTTPAPRPPTPAPTIASQPLSLRPEACRPAAGGAVHTRGLDFACDIFWVLVVVGGVLACY
SLLVTVAFIIFWVRRVKFSRSADAPAYQQGQNQLYNELNLGRREEYDVLDKRRGRDPEMGGKPRRKNPQEGLYNELQKDKMAE
AYSEIGMKGERRRGKGHDGLYQGLSTATKDTYDALHMQALPPRRAEGRGSLLTCGDVEENPGPMAVPTQVLGLLLLWLTDARC
DIQMTQSPSSLSASVGDRVTITCRASEDIYENLVWYQQKPGKAPKLLIYDTNRLADGVPSRFSGSGSGTQYTLTISSLQPEDF
ATYYCQHYKNYPLTFGQGTKLEIKRSGGGGSGGGGSGGGGSGGGGSRSEVQLVESGGGLVQPGGSLRLSCAASGFTLSNYGMH
WLRQAPGKGLEWVSSISLNGGSTYYRDSVKGRFTISRDNAKSTLYLQMNSLRAEDTAVYYCAAQDAYTGGYFDYWGQGTLVTV
SS*MDP*AEPKSPDKTHTCPPCPAPPVAGPSVFLFPPKPKDTLMIARTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCSVMHEALHNHYTQKSLSLSPGKKDPKFWVLVVVG
GVLACYSLLVTVAFIIFWVRSRVKFSRSADAPAYQQGQNQLYNELNLGRREEYDVLDKRRGRDPEMGGKPRRKNPQEGLYNEL
QKDKMAEAYSEIGMKGERRRGKGHDGLYQGLSTATKDTYDALHMQALPPR

| Region | Description |
|---|---|
| Signal1 | Signal peptide 1 |
| scFv1 | scFv 1 – anti-CD19 |
| SDP | Linker and chain break |
| STK | CD8alpha stalk |
| CD28tmZ | CD28 transmembrane domain and CD3 Zeta endodomain |
| FMD-2A | Foot-and-mouth disease 2A peptide |
| Signal2 | Signal peptide 2 |
| scFv2 | scFv 2 – anti-CD33 |
| MDP | Linker and chain break |
| HCH2CH3 | Hinge, CH2 and CH3 of human IgG1 |
| CD28tmZ' | CD28 transmembrane domain and CD3 Zeta endodomain |

FIG. 15

>MP14801.SFG.aCD19fmc63_clean-CD8STK-CD28tmZ-2A-aCD33glx-HCH2CH3pvaa-dCD148

MSLPVTALLLPLALLLHAARPDIQMTQTTSSLSASLGDRVTISCRASQDISKYLNWYQQKPDGTVKLLIYHTSRLHSGVPSRF
SGSGSGTDYSLTISNLEQEDIATYFCQQGNTLPYTFGGGTKLEITKAGGGGSGGGGSGGGGSGGGGSEVKLQESGPGLVAPSQ
SLSVTCTVSGVSLPDYGVSWIRQPPRKGLEWLGVIWGSETTYYNSALKSRLTIIKDNSKSQVFLKMNSLQTDDTAIYYCAKHY
YYGGSYAMDYWGQGTSVTVSSDPTTTPAPRPPTPAPTIASQPLSLRPEACRPAAGGAVHTRGLDFACDIFWVLVVVGGVLACY
SLLVTVAFIIFWVRRVKFSRSADAPAYQQGQNQLYNELNLGRREEYDVLDKRRGRDPEMGGKPRRKNPQEGLYNELQKDKMAE
AYSEIGMKGERRRGKGHDGLYQGLSTATKDTYDALHMQALPPRAEGRGSLLTCGDVEENPGPMAVPTQVLGLLLLWLTDARC
DIQMTQSPSSLSASVGDRVTITCRASEDIYFNLVWYQQKPGKAPKLLIYDTNRLADGVPSRESGSGSGTQYTLTISSLQPEDF
ATYYCQHYKNYPLTFGQGTKLEIKRSGGGGSGGGGSGGGGSGGGGSRSEVQLVESGGGLVQPGGSLRLSCAASGFTLSNYGMH
WIRQAPGKGLEWVSSISLNGGSTYYRDSVKGRFTISRDNAKSTLYLQMNSLRAEDTAVYYCAAQDAYTGGYFDYWGQGTLVTV
SSMDPAEPKSPDKTHTCPPCPAPPVAGPSVFLFPPKPKDTLMIARTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCSVMHEALHNHYTQKSLSLSPGKKDPKAVFGCIFG
ALVIVTVGGFIFWRKKRKDAKNNEVSFSQIKPKKSKLIRVENFEAYFKKQQADSNCGFAEEYEDLKLVGISQPKYAAELAENR
GKNRYNNVLPYDISRVKLSVQTHSTDDYINANYMPGYHSKKDFIATQGPLPNTLKDFWRMVWEKNVYAIIMLTKCVEQGRTKC
EEYWPSKQAQDYGDITVAMTSEIVLPEWTIRDFTVKNIQTSESHPLRQFHFTSWPDHGVPDTTDLLINFRYLVRDYMKQSPPE
SPILVHCSAGVGRTGTFIAIDRLIYQIENENTVDVYGIVYDLRMHRPLMVQTEDQYVFLNQCVLDIVRSQKDSKVDLIYQNTT
AMTIYENLAPVTTFGKTNGYIA

MP14802. SFG.aCD19fmc63_clean-CD8STK-CD28tmZ-2A-aCD33glx-HCH2CH3pvaa-dCD45

MSLPVTALLLPLALLLHAARPDIQMTQTTSSLSASLGDRVTISCRASQDISKYLNWYQQKPDGTVKLLIYHTSRLHSGVPSRF
SGSGSGTDYSLTISNLEQEDIATYFCQQGNTLPYTFGGGTKLEITKAGGGGSGGGGSGGGGSGGGGSEVKLQESGPGLVAPSQ
SLSVTCTVSGVSLPDYGVSWIRQPPRKGLEWLGVIWGSETTYYNSALKSRLTIIKDNSKSQVFLKMNSLQTDDTAIYYCAKHY
YYGGSYAMDYWGQGTSVTVSSDPTTTPAPRPPTPAPTIASQPLSLRPEACRPAAGGAVHTRGLDFACDIFWVLVVVGGVLACY
SLLVTVAFIIFWVRRVKFSRSADAPAYQQGQNQLYNELNLGRREEYDVLDKRRGRDPEMGGKPRRKNPQEGLYNELQKDKMAE
AYSEIGMKGERRRGKGHDGLYQGLSTATKDTYDALHMQALPPRAEGRGSLLTCGDVEENPGPMAVPTQVLGLLLLWLTDARC
DIQMTQSPSSLSASVGDRVTITCRASEDIYFNLVWYQQKPGKAPKLLIYDTNRLADGVPSRFSGSGSGTQYTLTISSLQPEDF
ATYYCQHYKNYPLTFGQGTKLEIKRSGGGGSGGGGSGGGGSGGGGSRSEVQLVESGGGLVQPGGSLRLSCAASGFTLSNYGMH
WIRQAPGKGLEWVSSISLNGGSTYYRDSVKGRFTISRDNAKSTLYLQMNSLRAEDTAVYYCAAQDAYTGGYFDYWGQGTLVTV
SSMDPAEPKSPDKTHTCPPCPAPPVAGPSVFLFPPKPKDTLMIARTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCSVMHEALHNHYTQKSLSLSPGKKDPKALIAFLAF
LIIVTSIALLVVLYKIQLDHKKRSCNLDEQQELVERDDEKQLMNVEPIHADILLETYKRKIADEGRLFLAEFQSIPRVFSKFP
IKEARKPFNQNKNRYVDILPYDYNRVELSEINGDAGSNYINASYIDGFKEPRKYIAAQGPRDETVDDFWRMIWEQKATVIVMV
TRCEEGNRNKCAEYWPSMEEGTRAFGDVVVKINQHKRCPDYIIQKLNIVNKKEKATGREVTHIQFTSWPDHGVPEDPHLLLKL
RRRVNAFSNFFSGPIVVHCSAGVGRTGTYIGIDAMLEGLEAENKVDVYGYVVKLRRQRCLMVQVEAQYILIHQALVEYNQFGE
TEVNLSELHPYLHNMKKRDPPSEPSPLEAEFQRLPSYRSWRTQHIGNQEENKSKNRNSNVIPYDYNRVPLKHELEMSKESEHD
SDESSDDDSDSEEPSKYINASFIMSYWKPEVMIAAQGPLKETIGDFWQMIFQRKVKVIVMLTELKHGDQEICAQYWGEGKQTY
GDIEVDLKDTDKSSTYTLRVFELRHSKRKDSRTVYQYQYTNWSVEQLPAEPKELISMIQVVKQKLPQKNSSEGNKHHKSTPLL
IHCRDGSQQTGIFCALLNLLESAETEEVVDIFQVVKALRKARPGMVSTFEQYQFLYDVIASTYPAQNGQVKKNNHQEDKIEFD
NEVDKVKQDANCVNPLGAPEKLPEAKEQAEGSEPTSGTEGPEHSVNGPASPALNQGS

| Region | Description |
|---|---|
| Signal1 | Signal peptide 1 |
| scFv1 | scFv 1 – anti-CD19 |
| SDP | Linker and chain break |
| STK | CD8alpha stalk |
| CD28tmZ | CD28 transmembrane domain and CD3 Zeta endodomain |
| FMD-2A | Foot-and-mouth disease 2A peptide |
| Signal2 | Signal peptide 2 |
| scFv2 | scFv 2 – anti-CD33 |
| MDP | Linker and chain break |
| HCH2CH3 | Hinge, CH2 and CH3 of human IgG1 |
| dCD148 / dCD45 | Trans-membrane and endo-domains of CD148 and CD45 |

FIG. 16

>16076.SFG.aCD19fmc63-CD8STK-CD28tmZ-2A-aCD33glx-muCD8STK-tm-dPTPN6
MSLPVTALLLPLALLLHAARPDIQMTQTTSSLSASLGDRVTISCRASQDISKYLNWYQQKPDGTVKLLIYHTSRLHSGVPSRFSGSGS
GTDYSLTISNLEQEDIATYFCQQGNTLPYTFGGGTKLEITKAGGGGSGGGGSGGGGSGGGGSEVKLQESGPGLVAPSQSLSVTCTVSG
VSLPDYGVSWIRQPPRKGLEWLGVIWGSETTYYNSALKSRLTIIKDNSKSQVFLKMNSLQTDDTAIYYCAKHYYYGGSYAMDYWGQGT
SVTVSSDPTTTPAPRPPTPAPTIASQPLSLRPEACRPAAGGAVHTRGLDFACDIFWVLVVVGGVLACYSLLVTVAFIIFWVRRVKFSR
SADAPAYQQGQNQLYNELNLGRREEYDVLDKRRGRDPEMGGKPRRKNPQEGLYNELQKDKMAEAYSEIGMKGERRRGKGHDGLYQGLS
TATKDTYDALHMQALPPRRAEGRGSLLTCGDVEENPGPMAVPTQVLGLLLLWLTDARCDIQMTQSPSSLSASVGDRVTITCRASEDIY
FNLVWYQQKPGKAPKLLIYDTNRLADGVPSRFSGSGSGTQYTLTISSLQPEDFATYYCQHYKNYPLTFGQGTKLEIKRSGGGGSGGGG
SGGGGSGGGGSRSEVQLVESGGGLVQPGGSLRLSCAASGFTLSNYGMHWIRQAPGKGLEWVSSISLNGGSTYYRDSVKGRFTISRDNA
KSTLYLQMNSLRAEDTAVYYCAAQDAYTGGYFDYWGQGTLVTVSSMDPATNRKKVERTRSEVHPTGTSQPQRPEDGCRPRGSVKGTGTDD
EAGDIYWAPLAGICVALLLSLIITLICYHRSRKVCKSGGGSFWEEFESLQKQEVKNLHQRLEGQRPENKGKNRYKNILPFDHSRVIL
QGRDSNIPGSDYINANYIKNQLLGPDENAKTYIASQGCLEATVNDFWQMAWQENSRVIVMTTREVEKGRNKCVPYWPEVGMQRAYGPY
SVTNCGEHDTTEYKLRTLQVSPLDNGDLIREIWHYQYLSWPDHGVPSEPGGVLSFLDQINQRQESLPHAGPIIVHCSAGIGRTGTIIV
IDMLMENISTKGLDCDIDIQKTIQMVRAQRSGMVQTEAQYKFIYVAIAQFIETTKKKL >MP16091.SFG.aCD19fmc63-CD8STK-CD28tmZ-2A-aCD33glx-muCD8STK-LAIR1tm-endo
MSLPVTALLLPLALLLHAARPDIQMTQTTSSLSASLGDRVTISCRASQDISKYLNWYQQKPDGTVKLLIYHTSRLHSGVPSRFSGSGS
GTDYSLTISNLEQEDIATYFCQQGNTLPYTFGGGTKLEITKAGGGGSGGGGSGGGGSGGGGSEVKLQESGPGLVAPSQSLSVTCTVSG
VSLPDYGVSWIRQPPRKGLEWLGVIWGSETTYYNSALKSRLTIIKDNSKSQVFLKMNSLQTDDTAIYYCAKHYYYGGSYAMDYWGQGT
SVTVSSDPTTTPAPRPPTPAPTIASQPLSLRPEACRPAAGGAVHTRGLDFACDIFWVLVVVGGVLACYSLLVTVAFIIFWVRRVKFSR
SADAPAYQQGQNQLYNELNLGRREEYDVLDKRRGRDPEMGGKPRRKNPQEGLYNELQKDKMAEAYSEIGMKGERRRGKGHDGLYQGLS
TATKDTYDALHMQALPPRRAEGRGSLLTCGDVEENPGPMAVPTQVLGLLLLWLTDARCDIQMTQSPSSLSASVGDRVTITCRASEDIY
FNLVWYQQKPGKAPKLLIYDTNRLADGVPSRFSGSGSGTQYTLTISSLQPEDFATYYCQHYKNYPLTFGQGTKLEIKRSGGGGSGGGG
SGGGGSGGGGSRSEVQLVESGGGLVQPGGSLRLSCAASGFTLSNYGMHWIRQAPGKGLEWVSSISLNGGSTYYRDSVKGRFTISRDNA
KSTLYLQMNSLRAEDTAVYYCAAQDAYTGGYFDYWGQGTLVTVSSMDPATNRKKVERTRSEVHPTGTSQPQRPEDGCRPRGSVKGTGTDD
EAGDILIGVSVVFLFCLLLLVLFCLHRQNQIKQGPPRSKDEEQKPQQRPDLAVDVLERTADKATVNGLPEKDRETDTSALAAGSSQEV
TYAQLDHWALTQRTARAVSPQSTKPMAESITYAAVARH >MP16092.SFG.aCD19fmc63-CD8STK-CD28tmZ-2A-aCD33glx-muCD8STK-LAIR1tm-endo-2A-PTPN6_SH2-dCD148
MSLPVTALLLPLALLLHAARPDIQMTQTTSSLSASLGDRVTISCRASQDISKYLNWYQQKPDGTVKLLIYHTSRLHSGVPSRFSGSGS
GTDYSLTISNLEQEDIATYFCQQGNTLPYTFGGGTKLEITKAGGGGSGGGGSGGGGSGGGGSEVKLQESGPGLVAPSQSLSVTCTVSG
VSLPDYGVSWIRQPPRKGLEWLGVIWGSETTYYNSALKSRLTIIKDNSKSQVFLKMNSLQTDDTAIYYCAKHYYYGGSYAMDYWGQGT
SVTVSSDPTTTPAPRPPTPAPTIASQPLSLRPEACRPAAGGAVHTRGLDFACDIFWVLVVVGGVLACYSLLVTVAFIIFWVRRVKFSR
SADAPAYQQGQNQLYNELNLGRREEYDVLDKRRGRDPEMGGKPRRKNPQEGLYNELQKDKMAEAYSEIGMKGERRRGKGHDGLYQGLS
TATKDTYDALHMQALPPRRAEGRGSLLTCGDVEENPGPMAVPTQVLGLLLLWLTDARCDIQMTQSPSSLSASVGDRVTITCRASEDIY
FNLVWYQQKPGKAPKLLIYDTNRLADGVPSRFSGSGSGTQYTLTISSLQPEDFATYYCQHYKNYPLTFGQGTKLEIKRSGGGGSGGGG
SGGGGSGGGGSRSEVQLVESGGGLVQPGGSLRLSCAASGFTLSNYGMHWIRQAPGKGLEWVSSISLNGGSTYYRDSVKGRFTISRDNA
KSTLYLQMNSLRAEDTAVYYCAAQDAYTGGYFDYWGQGTLVTVSSMDPATNRKKVERTRSEVHPTGTSQPQRPEDGCRPRGSVKGTGTDD
EAGDILIGVSVVFLFCLLLLVLFCLHRQNQIKQGPPRSKDEEQKPQQRPDLAVDVLERTADKATVNGLPEKDRETDTSALAAGSSQEV
TYAQLDHWALTQRTARAVSPQSTKPMAESITYAAVARHRAEGRGSLLTCGDVEENPGPWYHGHMSGGQAETLLQAKGEPWTFLVRESLS
QPGDFVLSVLSDQPKAGPGSPLRVTHIKVMCEGGRYTVGGLETFDSLTDLVEHFKKTGIEEASGAFVYLRQPYYATROPYSGGGGSEEAYEKKQQ
ADSNGCPEEYEVKELDKINGCISQEPTYEALIAEHLRYANKLPYDISRVKLSVQTHSTDDYINANYIMPGYHSKKDFIATQGPLPNTLKD
FWRMVWEKNVYAITMLTKGVEQGRTKCERYWPESKQAQDYGDLTVAMFSEIALPEWILIRDDTMVKNIQTSESHPVRTFHLTSWPDICYPD
TIDLITNFRYLVRDYMKQSPPESPILVHCSAGVGRTGTFIATDRLIYQIENENTVDVYGIVYDLRMHRPLMVQTEDQMVFLNQCVLDI
VRSQKDSKVDLIYQNTTAMTIYENLAPVTTFGKTNGYIASGS

| Region | Description |
|---|---|
| Signal1 | Signal peptide 1 |
| scFv1 | scFv 1 – anti-CD19 |
| SDP | Linker and chain break |
| STK | Human CD8alpha stalk |
| CD28tmZ | CD28 transmembrane domain and CD3 Zeta endodomain |
| FMD-2A | Foot-and-mouth disease 2A peptide |
| Signal2 | Signal peptide 2 |
| scFV2 | scFv 2 – anti-CD33 |
| MDP | Linker and chain break |
| STK | Mouse CD8alpha stalk |
| dLAIR1 | Hinge, CH2 and CH3 of human IgG1 |
| dPTPN6 | Phosphatase domain of PTPN6 |
| FMD-2A | Foot-and-mouth disease 2A peptide codon wobbled |
| PTPN6_SH2 | SH2 domain of PTPN6 |
| SGGGGS | Serine glycine linker and chain break |
| dCD148 | Phosphatase domain of CD148 |

METDTLLLWVLLLWVPGSTGSVLHLVPINATSKDDSDVTEVMWQPALRRGRGLQAQGYGVRIQDAGVY
LLYSQVLFQDVTFTMGQVVSREGQGRQETLFRCIRSMPSHPDRAYNSCYSAGVFHLHQGDILSVIIPR
ARAKLNLSPHGTFLGFVKL*SGGGSDP*PTTTPAPRPPTPAPTIASQPLSLRPEACRPAAGGAVHTRGLDF
ACDIFWVLVVVGGVLACYSLLVTVAFIIFWVRSKRSRLLHSDYMNMTPRRPGPTRKHYQPYAPPRDFA
AYRSRDQRLPPDAHKPPGGGSFRTPIQEEQADAHSTLAKIRVKFSRSADAPAYQQGQNQLYNELNLGR
REEYDVLDKRRGRDPEMGGKPRRKNPQEGLYNELQKDKMAEAYSEIGMKGERRRGKGHDGLYQGLSTA
TKDTYDALHMQALPPR

B

METDTLLLWVLLLWVPGSTGSVLHLVPINATSKDDSDVTEVMWQPALRRGRGLQAQGYGVRIQDAGVY
LLYSQVLFQDVTFTMGQVVSREGQGRQETLFRCIRSMPSHPDRAYNSCYSAGVFHLHQGDILSVIIPR
ARAKLNLSPHGTFLGFVKL*SGGGSDP*AEPKSPDKTHTCPPCPKDPKFWVLVVVGGVLACYSLLVTVAF
IIFWVRSKRSRLLHSDYMNMTPRRPGPTRKHYQPYAPPRDFAAYRSRDQRLPPDAHKPPGGGSFRTPI
QEEQADAHSTLAKIRVKFSRSADAPAYQQGQNQLYNELNLGRREEYDVLDKRRGRDPEMGGKPRRKNP
QEGLYNELQKDKMAEAYSEIGMKGERRRGKGHDGLYQGLSTATKDTYDALHMQALPPR

C

METDTLLLWVLLLWVPGSTGSVLHLVPINATSKDDSDVTEVMWQPALRRGRGLQAQGYGVRIQDAGVY
LLYSQVLFQDVTFTMGQVVSREGQGRQETLFRCIRSMPSHPDRAYNSCYSAGVFHLHQGDILSVIIPR
ARAKLNLSPHGTFLGFVKL*SGGGSDP*AEPKSPDKTHTCPPCPAPPVAGPSVFLFPPKPKDTLMIARTP
EVTCVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGKKDPKFWVLVVVGGV
LACYSLLVTVAFIIFWVRSKRSRLLHSDYMNMTPRRPGPTRKHYQPYAPPRDFAAYRSRDQRLPPDAH
KPPGGGSFRTPIQEEQADAHSTLAKIRVKFSRSADAPAYQQGQNQLYNELNLGRREEYDVLDKRRGRD
PEMGGKPRRKNPQEGLYNELQKDKMAEAYSEIGMKGERRRGKGHDGLYQGLSTATKDTYDALHMQALP
PR

| | |
|---|---|
| Signal Peptide | Efficient signal peptide |
| dAPRIL | Truncated APRIL |
| Spacer | Either hinge-CH2CH3 of human IgG1, human CD8α stalk and human IgG1 hinge |
| TM and endodomain | Compound endodomain comprising of the CD28TM domain, CD28 endodomain and OX40 and CD3-Zeta endodomains |

FIG. 26

A
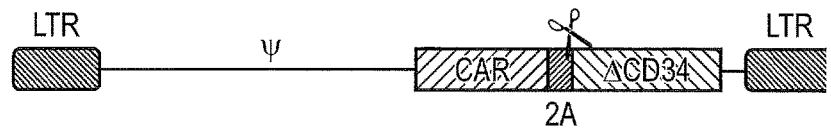
B
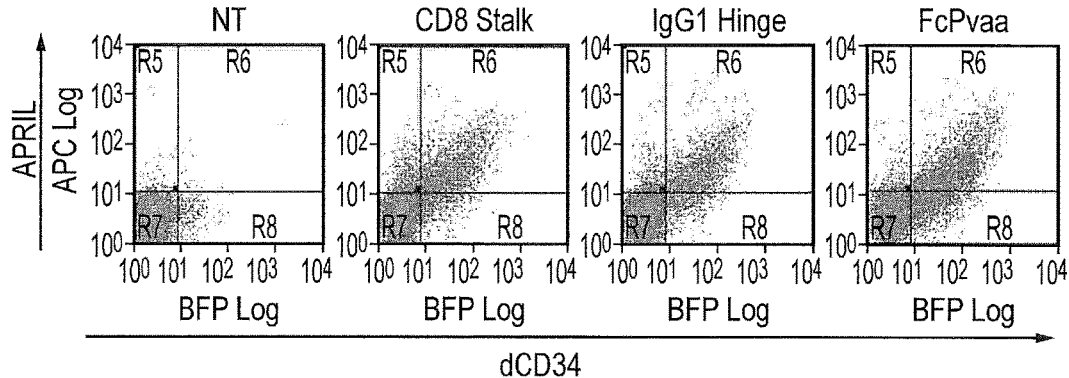
C
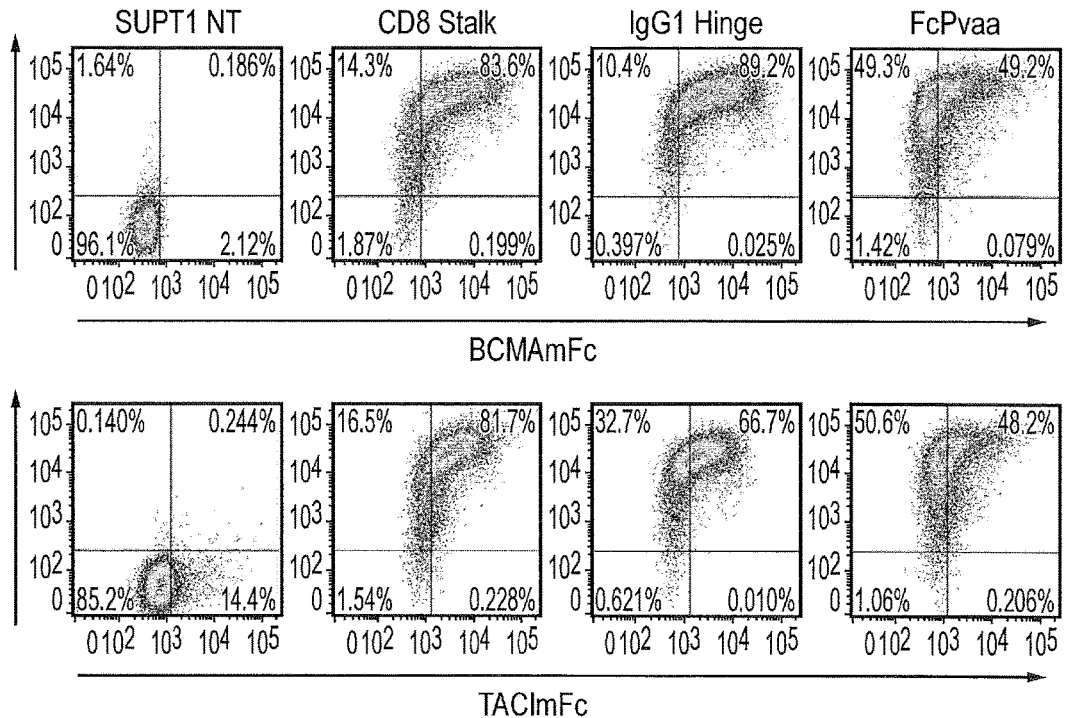
FIG. 27

CELL

FIELD OF THE INVENTION

The present invention relates to a cell which comprises more than one chimeric antigen receptor (CAR). The cell may be capable of specifically recognising a target cell, due to a differential pattern of expression (or non-expression) of two or more antigens by the target cell.

BACKGROUND TO THE INVENTION

A number of immunotherapeutic agents have been described for use in cancer treatment, including therapeutic monoclonal antibodies (mAbs), immunoconjugated mAbs, radioconjugated mAbs and bi-specific T-cell engagers.

Typically these immunotherapeutic agents target a single antigen: for instance, Rituximab targets CD20; Myelotarg targets CD33; and Alemtuzumab targets CD52.

However, it is relatively rare for the presence (or absence) of a single antigen effectively to describe a cancer, which can lead to a lack of specificity.

Most cancers cannot be differentiated from normal tissues on the basis of a single antigen. Hence, considerable "on-target off-tumour" toxicity occurs whereby normal tissues are damaged by the therapy. For instance, whilst targeting CD20 to treat B-cell lymphomas with Rituximab, the entire normal B-cell compartment is depleted, whilst targeting CD52 to treat chronic lymphocytic leukaemia, the entire lymphoid compartment is depleted, whilst targeting CD33 to treat acute myeloid leukaemia, the entire myeloid compartment is damaged etc. The predicted problem of "on-target off-tumour" toxicity has been borne out by clinical trials. For example, an approach targeting ERBB2 caused death to a patient with colon cancer metastatic to the lungs and liver. ERBB2 is over-expressed in colon cancer in some patients, but it is also expressed on several normal tissues, including heart and normal vasculature.

For some cancers, targeting the presence of two cancer antigens may be more selective and therefore effective than targeting one. For example, B-chronic lymphocytic leukaemia (B-CLL) is a common leukaemia which is currently treated by targeting CD19. This treats the lymphoma but also depletes the entire B-cell compartment such that the treatment has a considerable toxic effect. B-CLL has an unusual phenotype in that CD5 and CD19 are co-expressed. By targeting only cells which express CD5 and CD19, it would be possible to considerably reduce on-target off-tumour toxicity.

There is thus a need for immunotherapeutic agents which are capable of more targeting to reflect the complex pattern of marker expression that is associated with many cancers.

Chimeric Antigen Receptors (CARs)

Chimeric antigen receptors are proteins which graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals (see FIG. 1A).

The most common form of these molecules are fusions of single-chain variable fragments (scFv) derived from monoclonal antibodies which recognize a target antigen, fused via a spacer and a trans-membrane domain to a signaling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

However, the use of CAR-expressing T cells is also associated with on-target, off tumour toxicity. For example, a CAR-based approach targeting carboxy anyhydrase-IX (CAIX) to treat renal cell carcinoma resulted in liver toxicity which is thought to be caused by the specific attack on bile duct epithelial cells (Lamers et al (2013) Mol. Ther. 21:904-912).

Dual Targeting CAR Approaches

In order to address the problem of "on target, off tumour" toxicity, CAR T cells have been developed with dual antigen specificity. In the "dual targeting" approach, two complementary CARs are co-expressed in the same T-cell population, each directed to a distant tumour target and engineered to provide complementary signals.

Wlikie et al (2012 J Clin Immunol 32:1059-1070) describe a dual targeting approach in which ErbB2- and MUC1-specific CARs are co-expressed. The ErbB2-specific CAR provided the CD3ζ signal only and the MUC1-specific CAR provided the CD28 co-stimulatory signal only. It was found that complementary signalling occurred in the presence of both antigens, leading to IL-2 production. However, IL-2 production was modest when compared to control CAR-engineered T cells in which signaling is delivered by a fused CD28+CD3ζ endodomain.

A similar approach was described by Kloss et at (2013 Nature Biotechnol. 31:71-75) in which a CD-19 specific CAR was used which provides a CD3ζ-mediated activation signal in combination with a chimeric co-stimulatory receptor specific for PSMA. With this 'co-CAR' design, the CAR T-cell receives an activation signal when it encounters a target cell with one antigen, and a co-stimulatory signal when it encounters a target cell with the other antigen, and only receives both activatory and co-stimulatory signals upon encountering target cells bearing both antigens.

This represents an early attempt at restricting CAR activity to only a target cell bearing two antigens. This approach however is limited: although CAR T-cell activity will be greatest against targets expressing both antigens, CAR T-cells will still kill targets expressing only antigen recognized by the activatory CAR; further, co-stimulation results in prolonged effects on T-cells which last long after release of target cell. Hence, activity against single-antigen positive T-cells equal to that against double-positives might be possible for example in a situation where single-positive tissues are adjacent to, or in a migratory path from double positive tumour.

There is thus a need for improved CAR-based therapeutic approaches with reduced on-target off-tumour toxicity where T-cell activation is wholly restricted to target cells which express both antigens.

The invention relates to engineering T-cells to respond to logical rules of target cell antigen expression. This is best illustrated with an imaginary FACS scatter-plot. Target cell populations express both, either or neither of antigens "A" and "B". Different target populations (marked in red) are killed by T-cells transduced with a pair of CARs connected by different gates. With OR gated receptors, both single-positive and double-positive cells will be killed. With AND gated receptors, only double-positive target cells are killed. With AND NOT gating, double-positive targets are preserved while single-positive targets

Figure 3:
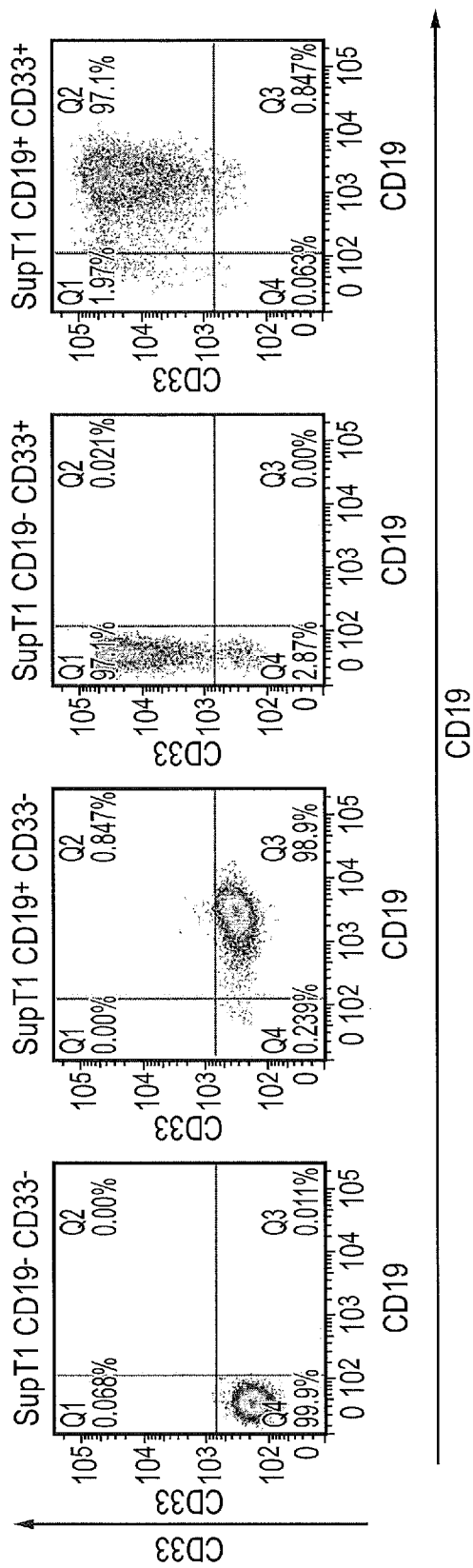

FIG. 3: Creation of target cell populations

SupT1 cells were used as target cells. These cells were transduced to express either CD19, CD33 or both CD19 and CD33. Target cells were stained with appropriate antibodies and analysed by flow cytometry.

Figure 4:
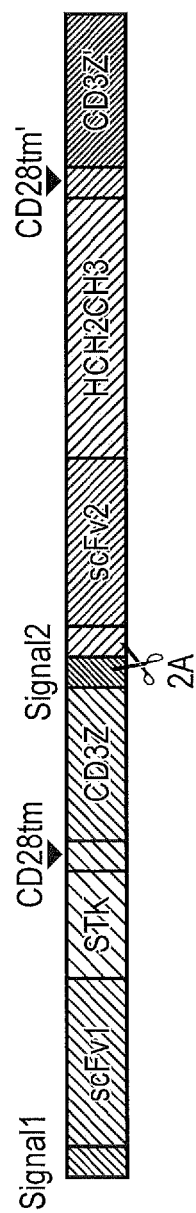

FIG. 4: Cassette design for an OR gate

A single open reading frame provides both CARs with an in-frame FMD-2A sequence resulting in two proteins. Signal1 is a signal peptide derived from IgG1 (but can be any effective signal peptide). scFv1 is the single-chain variable segment which recognizes CD19 (but can be a scFv or peptide loop or ligand or in fact any domain which recognizes any desired arbitrary target). STK is the CD8 stalk but may be any suitable extracellular domain. CD28tm is the CD28 trans-membrane domain but can by any stable type I protein transmembrane domain and CD3Z is the CD3 Zeta endodomain but can be any endodomain which contains ITAMs. Signal2 is a signal peptide derived from CD8 but can be any effective signal peptide which is different in DNA sequence from signal1. scFv recognizes CD33 but as for scFv1 is arbitrary. HC2CH3 is the hinge-CH2-CH3 of human IgG1 but can be any extracellular domain which does not cross-pair with the spacer used in the first CAR. CD28tm' and CD3Z' code for the same protein sequence as CD28tm and CD3Z but are codon-wobbled to prevent homologous recombination.

Figure 5:
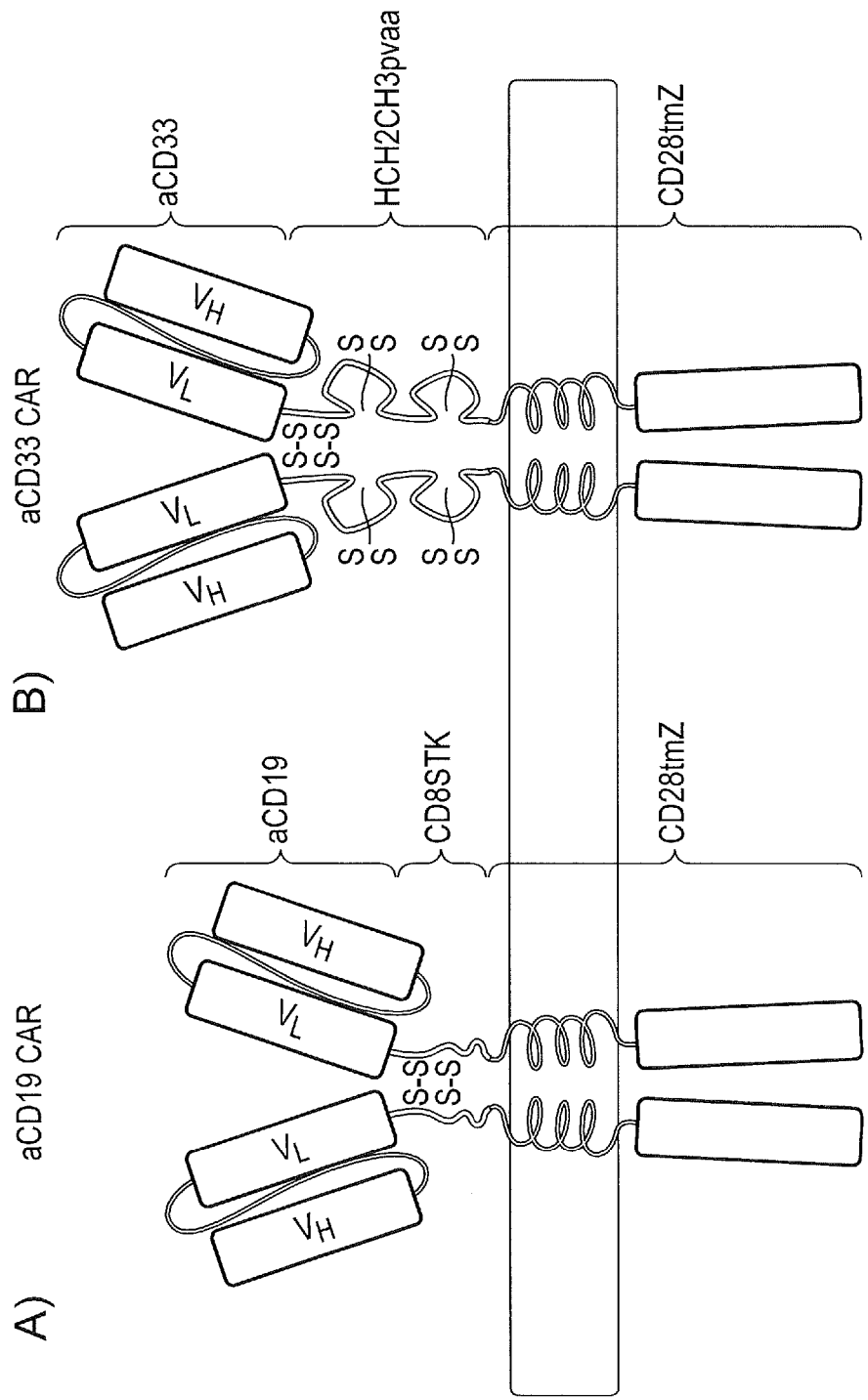

FIG. 5: Schematic representation of the chimeric antigen receptors (CARs) for an OR gate Stimulatory CARs were constructed consisting of either an N-terminal A) anti-CD19 scFv domain followed by the extracellular hinge region of human CD8 or B) anti-CD33 scFv domain followed by the extracellular hinge, CH2 and CH3 (containing a pvaa mutation to reduce FcR binding) region of human IgG1. Both receptors contain a human CD28 transmembrane domain and a human CD3 Zeta (CD247) intracellular domain. "S" depicts the presence of disulphide bonds.

Figure 6:
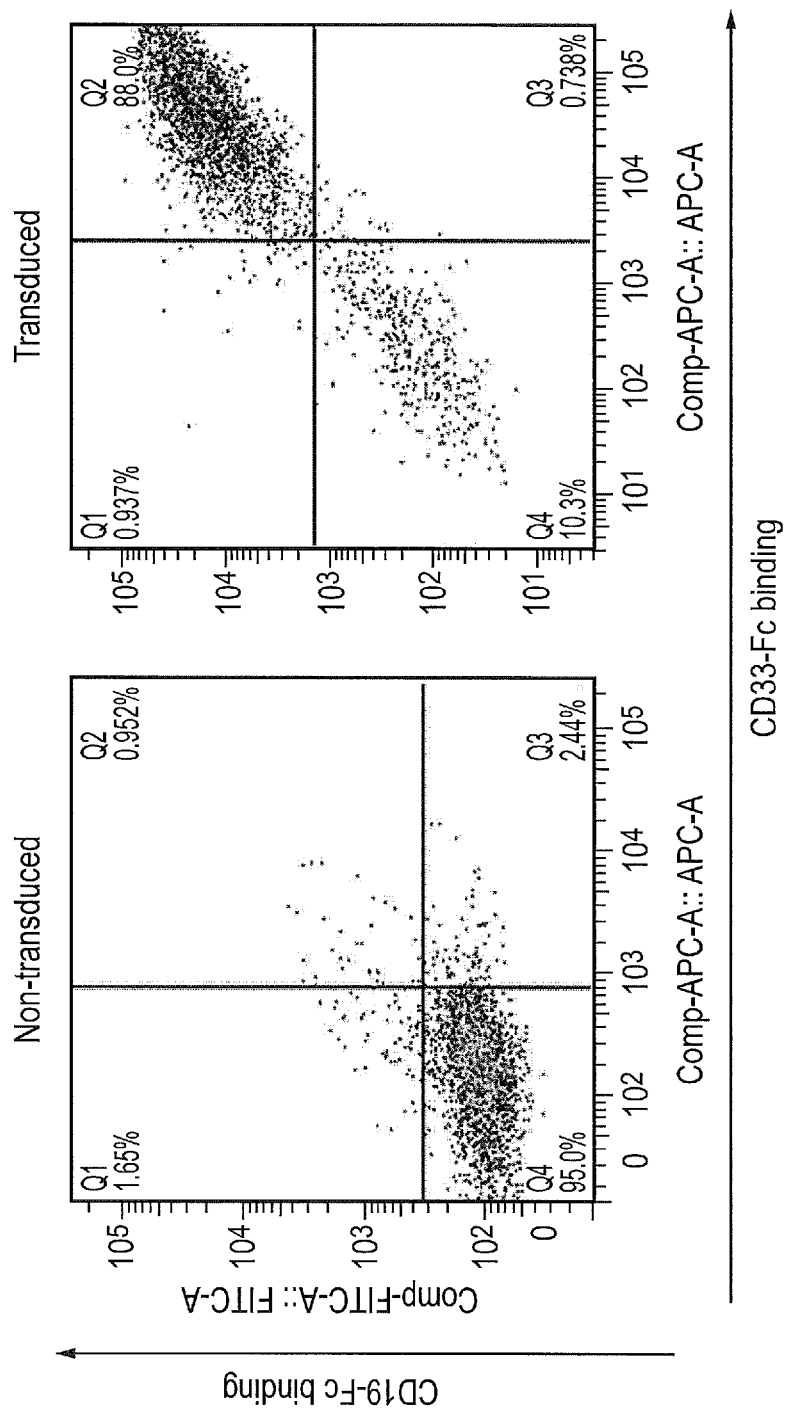

FIG. 6: Expression data showing co-expression of both CARs on the surface of one T-cell.

Figure 7:
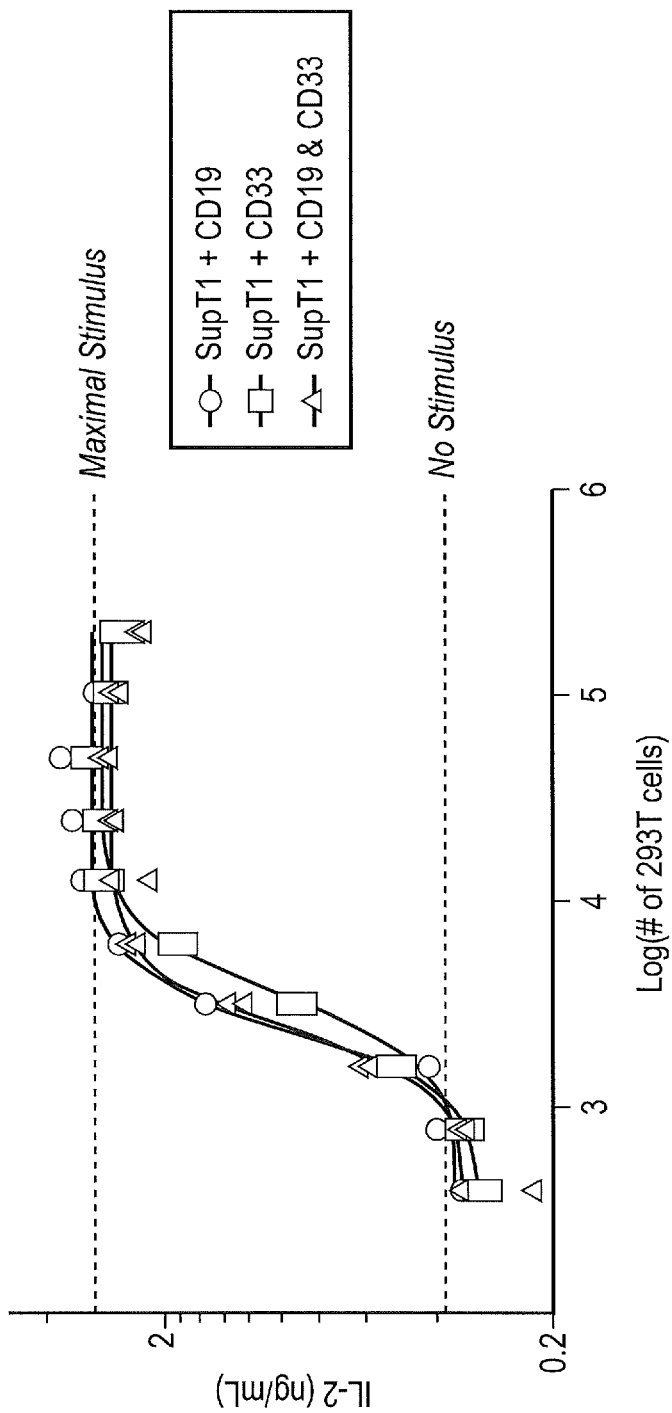

FIG. 7: Functional analysis of the OR gate

Effector cells (5×10^4 cells) expressing the OR gate construct were co-incubated with a varying number of target cells and IL-2 was analysed after 16 hours by ELISA. The graph displays the average maximum IL-2 secretion from a chemical stimulation (PMA and Ionomycin) of the effector cells alone and the average background IL-2 from effector cells without any stimulus from three replicates.

Figure 8:
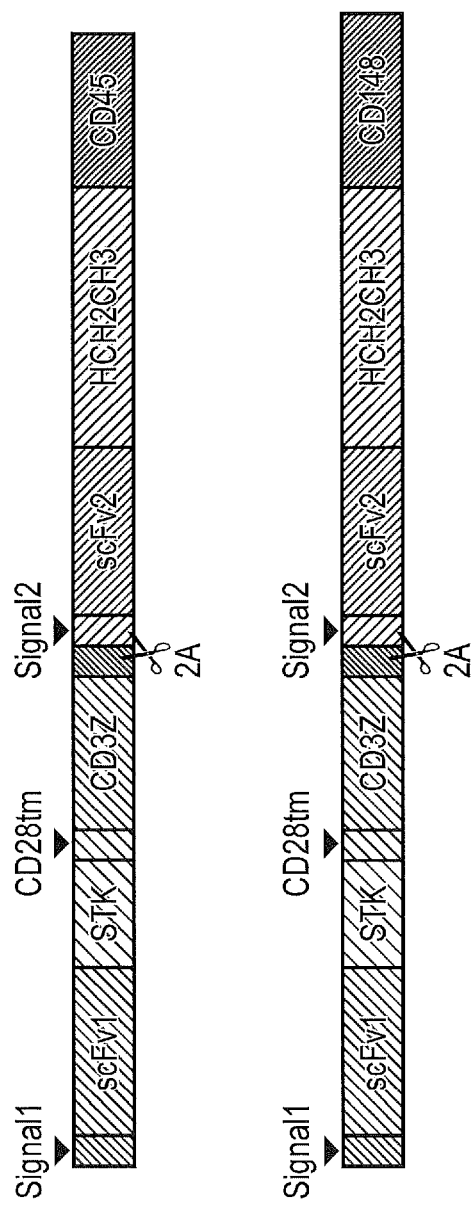

FIG. 8: Cartoon showing both versions of the cassette used to express both AND gates Activating and inhibiting CARs were co-expressed once again using a FMD-2A sequence. Signal1 is a signal peptide derived from IgG1 (but can be any effective signal peptide). scFv1 is the single-chain variable segment which recognizes CD19 (but can be a scFv or peptide loop or ligand or in fact any domain which recognizes any desired arbitrary target). STK is the CD8 stalk but may be any non-bulky extracellular domain. CD28tm is the CD28 trans-membrane domain but can by any stable type I protein transmembrane domain and CD3Z is the CD3 Zeta endodomain but can be any endodomain which contains ITAMs. Signal2 is a signal peptide derived from CD8 but can be any effective signal peptide which is different in DNA sequence from signal1. scFv recognizes CD33 but as for scFv1 is arbitrary. HC2CH3 is the hinge-CH2-CH3 of human IgG1 but can be any bulky extracellular domain. CD45 and CD148 are the transmembrane and endodomains of CD45 and CD148 respectively but can be derived from any of this class of protein.

Figure 9:
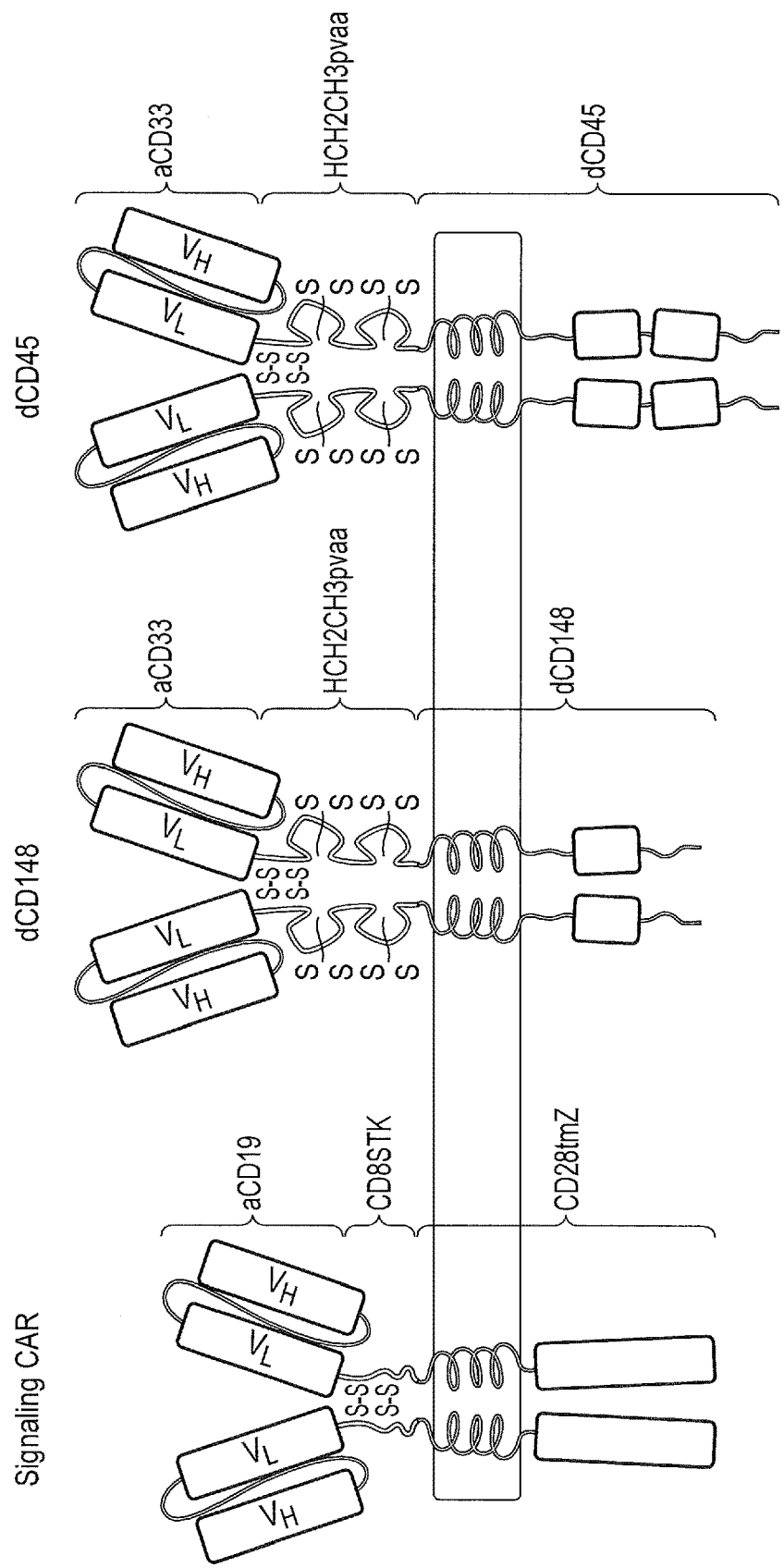

FIG. 9: Schematic representation of the protein structure of chimeric antigen receptors (CARs) for the AND gates The stimulatory CAR consisting of an N-terminal anti-CD19 scFv domain followed by the extracellular stalk region of human CD8, human CD28 transmembrane domain and human CD3 Zeta (CD247) intracellular domain. Two inhibitory CARs were tested. These consist of an N-terminal anti-CD33 scFv domain followed by the extracellular hinge, CH2 and CH3 (containing a pvaa mutation to reduce FcR binding) region of human IgG1 followed by the transmembrane and intracellular domain of either human CD148 or CD45. "S" depicts the presence of disulphide bonds.

Figure 10:
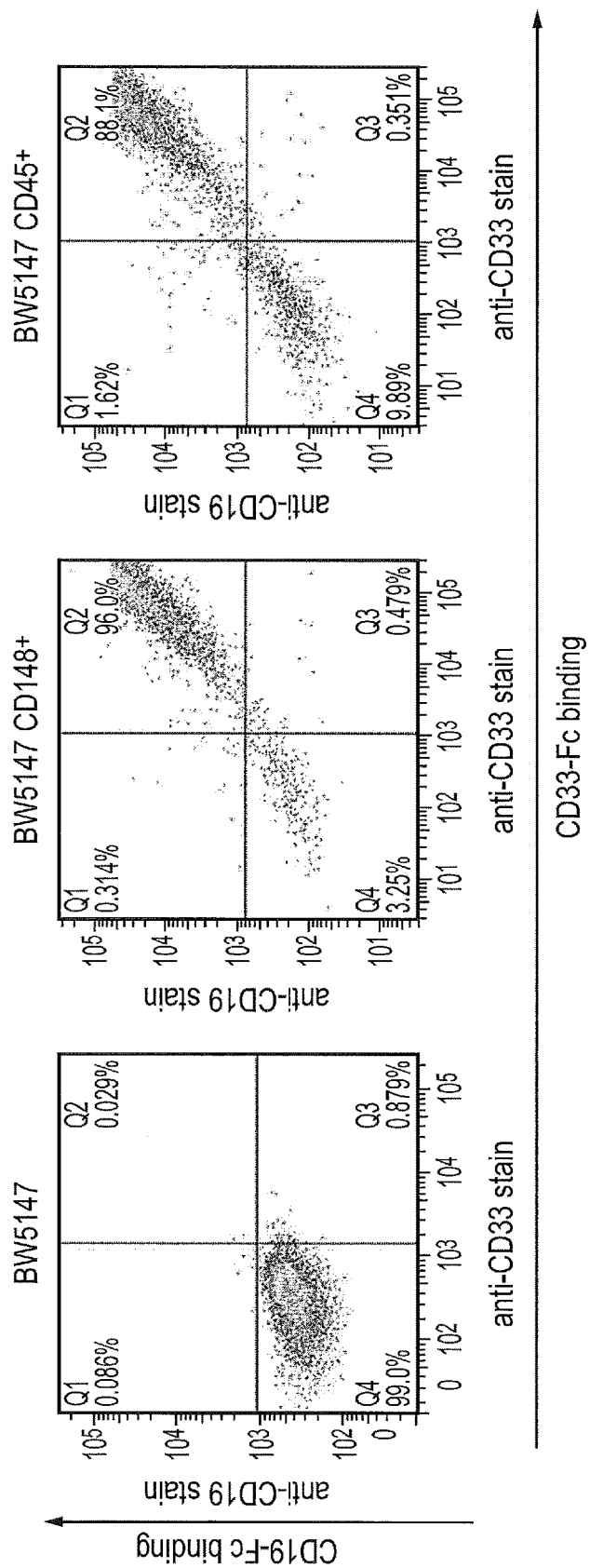

FIG. 10: Co-expression of activation and inhibitory CARs

BW5147 cells were used as effector cells and were transduced to express both the activation anti-CD19 CAR and one of the inhibitory anti-CD33 CARs. Effector cells were stained with CD19-mouse-Fc and CD33-rabbit-Fc and with appropriate secondary antibodies and analysed by flow cytometry.

Figure 11:
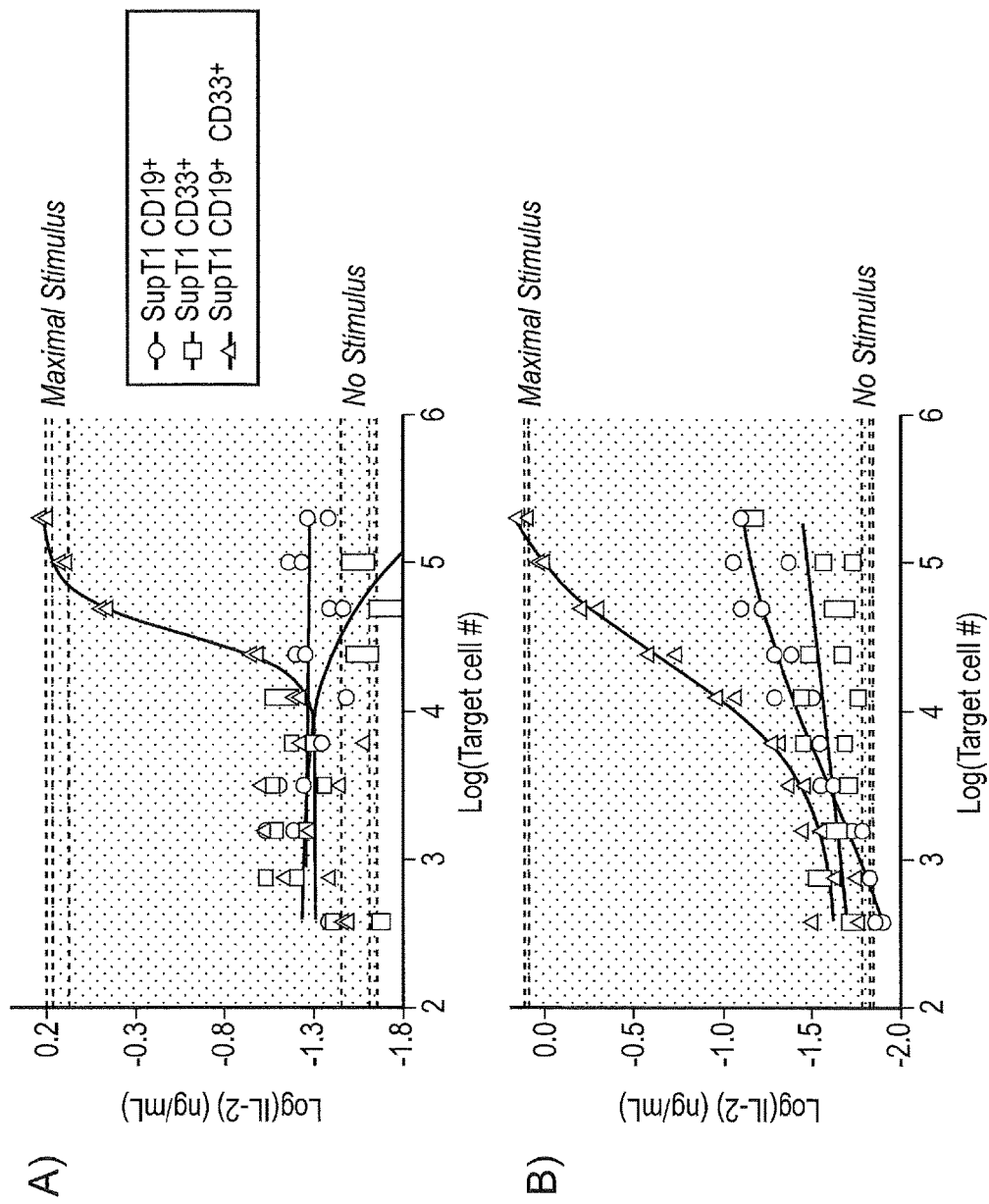

FIG. 11: Functional analysis of the AND gates

Effector cells (5×10^4 cells) expressing activation anti-CD19 CAR and the inhibitory anti-CD33 CAR with the A) CD148 or B) CXD45 intracellular domain were co-incubated with a varying number of target cells and IL-2 was analysed after 16 hours by ELISA. The graph displays the maximum IL-2 secretion from a chemical stimulation (PMA and Ionomycin) of the effector cells alone and the background IL-2 from effector cells without any stimulus from three replicates.

Figure 12:
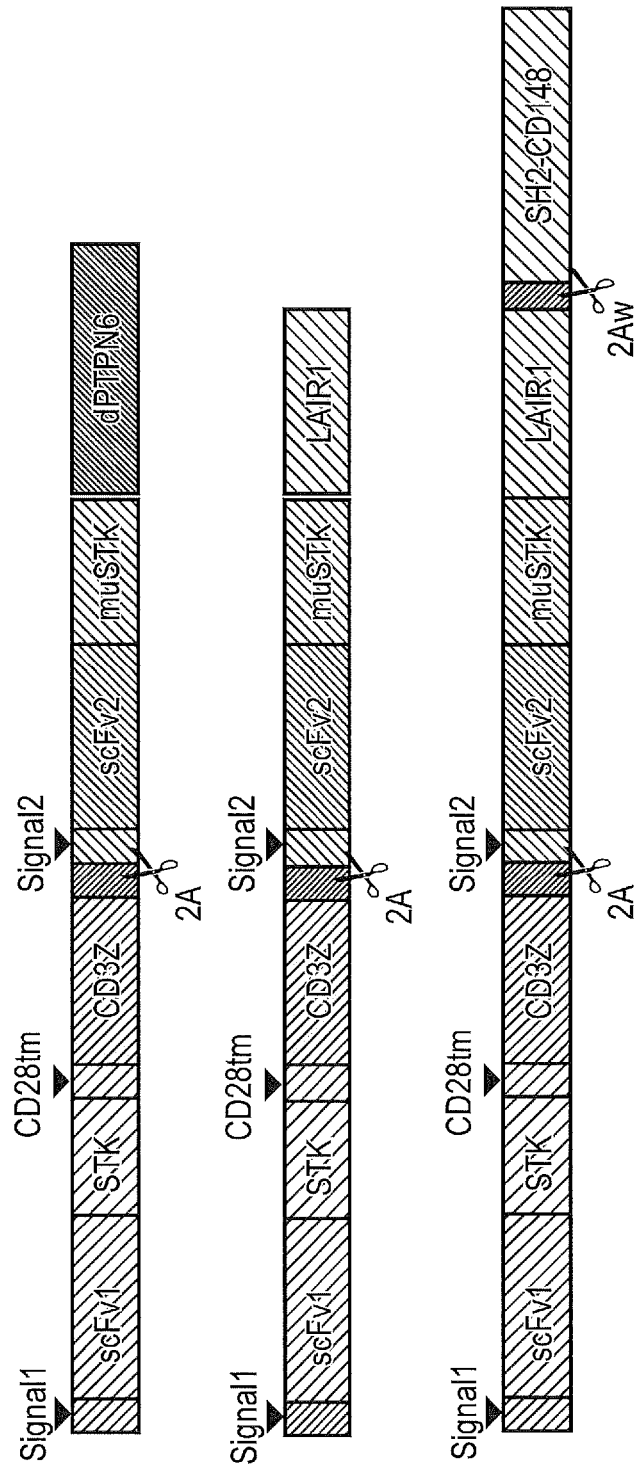

FIG. 12: Cartoon showing three versions of the cassette used to generate the AND NOT gate Activating and inhibiting CARs were co-expressed once again using a FMD-2A sequence. Signal1 is a signal peptide derived from IgG1 (but can be any effective signal peptide). scFv1 is the single-chain variable segment which recognizes CD19 (but can be a scFv or peptide loop or ligand or in fact any domain which recognizes any desired arbitrary target). STK is the human CD8 stalk but may be any non-bulky extracellular domain. CD28tm is the CD28 trans-membrane domain but can by any stable type I protein transmembrane domain and CD3Z is the CD3 Zeta endodomain but can be any endodomain which contains ITAMs. Signal2 is a signal peptide derived from CD8 but can be any effective signal peptide which is different in DNA sequence from signal1. scFv recognizes CD33 but as for scFv1 is arbitrary. muSTK is the mouse CD8 stalk but can be any spacer which co-localises but does not cross-pair with that of the activating CAR. dPTPN6 is the phosphatase domain of PTPN6. LAIR1 is the transmembrane and endodomain of LAIR1. 2Aw is a codon-wobbled version of the FMD-2A sequence. SH2-CD148 is the SH2 domain of PTPN6 fused with the phosphatase domain of CD148.

Figure 13:
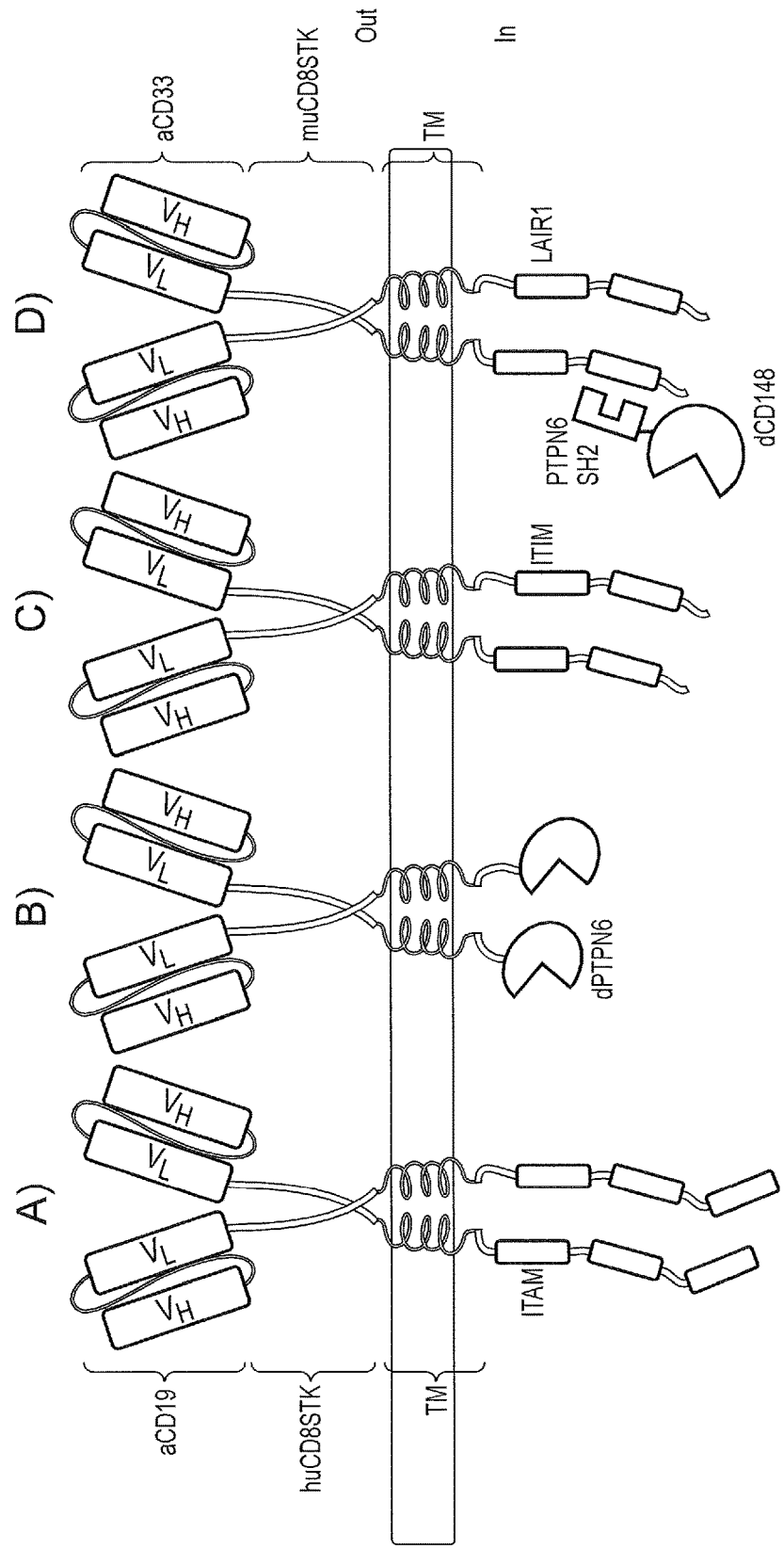

FIG. 13: Schematic representation of the chimeric antigen receptors (CARs) for the NOT AND gates A) A stimulatory CAR consisting of an N-terminal anti-CD19 scFv domain followed by the stalk region of human CD8, human CD28 transmembrane domain and human CD247 intracellular domain. B) An inhibitory CAR consisting of an N-terminal anti-CD33 scFv domain followed by the stalk region of mouse CD8, transmembrane region of mouse CD8 and the phosphatase domain of PTPN6. C) an inhibitory CAR consisting of an N-terminal anti-CD33 scFv domain followed by the stalk region of mouse CD8 and the transmembrane and intracellular segments of LAIR1. D) An inhibitory CAR identical to previous CAR except it is co-expressed with a fusion protein of the PTPN6 SH2 domain and the CD148 phosphatase domain.

Figure 14:
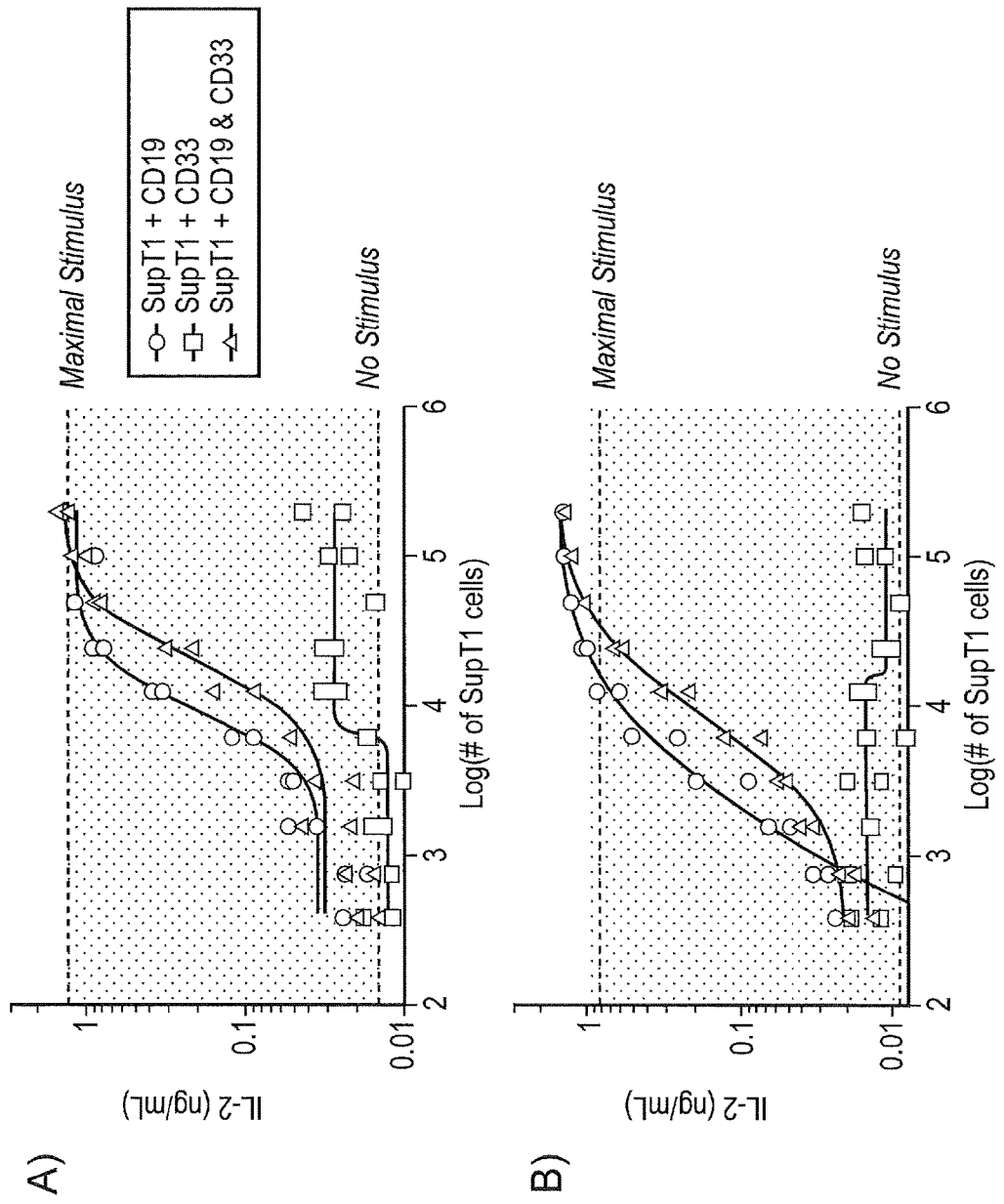

FIG. 14: Functional analysis of the NOT AND gate

Effector cells ($5\times10^4$ cells) expressing the A) full length SHP-1 or B) truncated form of SHP-1 were co-incubated with a varying number of target cells and IL-2 was analysed after 16 hours by ELISA. The graph displays the average maximum IL-2 secretion from a chemical stimulation (PMA and Ionomycin) of the effector cells alone and the average background IL-2 from effector cells without any stimulus from three replicates.

FIG. 15: Amino acid sequence of an OR gate

FIG. 16: Amino acid sequence of a CD148 and a CD145 based AND gate

FIG. 17: Amino acid sequence of two AND NOT gates

Figure 18:
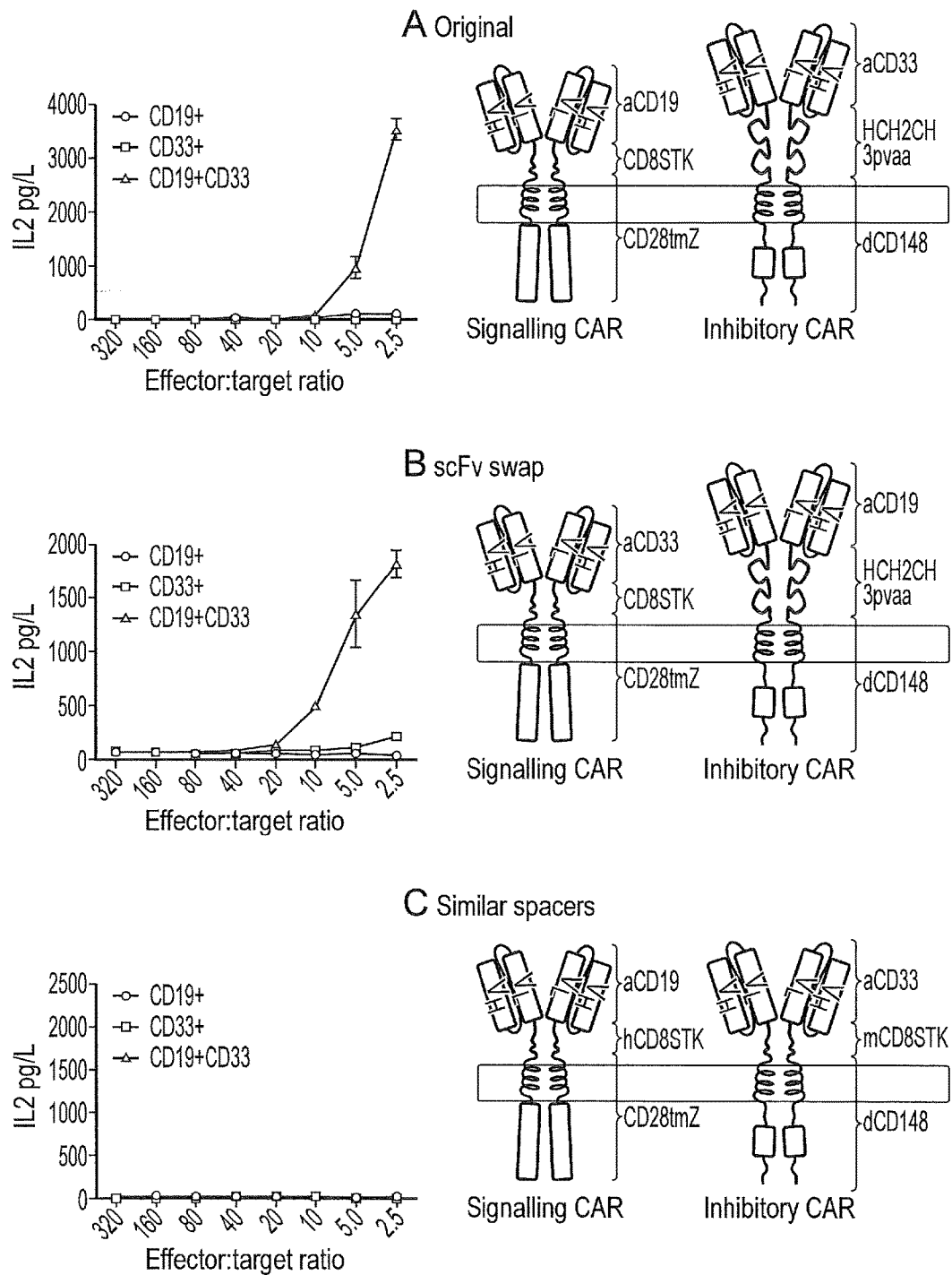

FIG. 18: Dissection of AND gate function

A. The prototype AND gate is illustrated on the right and its function in response to CD19, CD33 single and CD19, CD33 double positive targets is shown on the left. B. The scFvs are swapped so the activating endodomain is triggered by CD33 and the inhibitory endodomain is activated by CD19. This AND gate remains functional despite this scFv swap. C. The CD8 mouse stalk replaced Fc in the spacer of the inhibitory CAR. With this modification, the gate fails to respond to either CD19 single positive or CD19, CD33 double positive targets.

Figure 19:
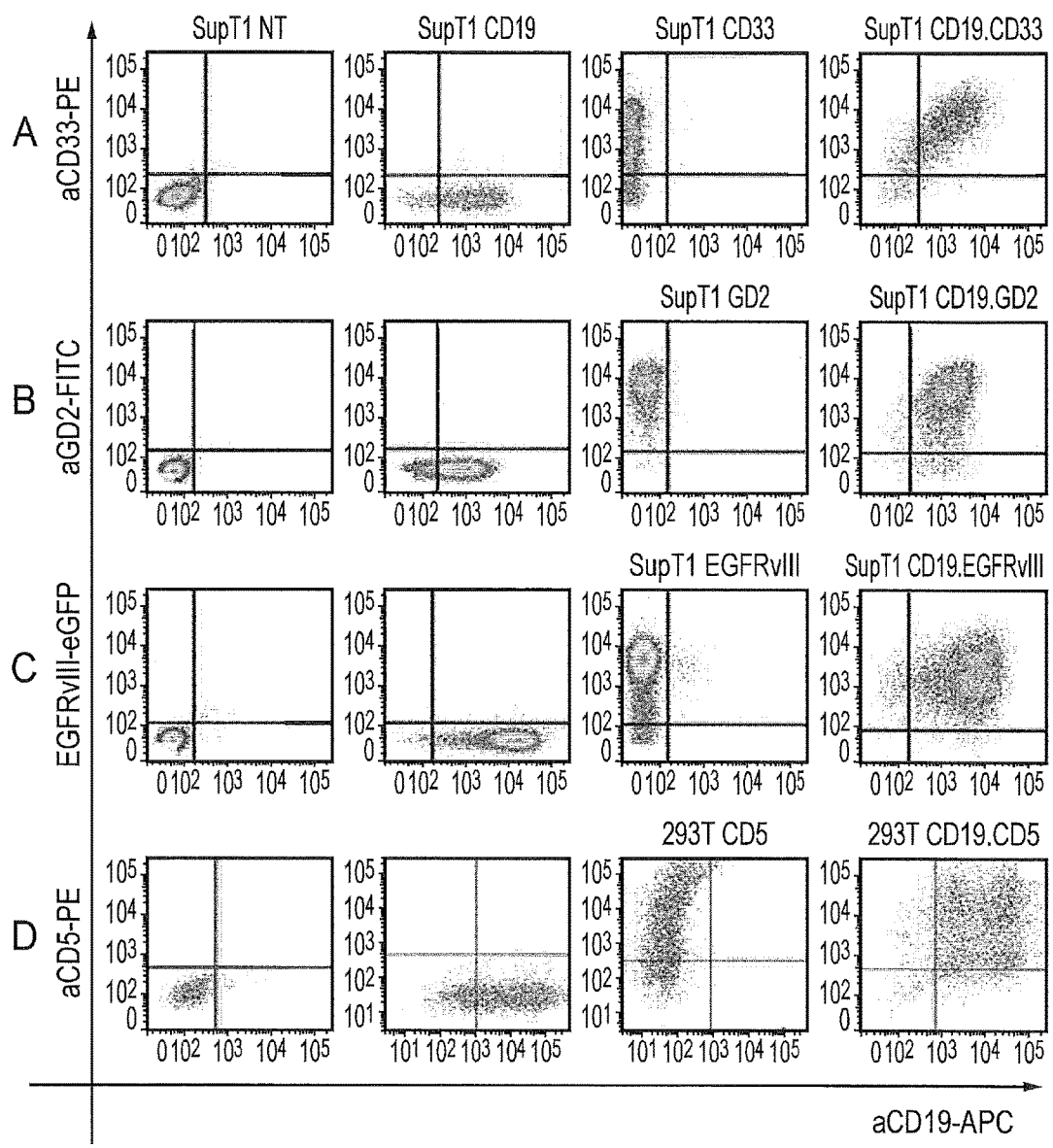

FIG. 19: Expression of target antigens on artificial target cells

A. Shows flow cytometry scatter plots CD19 vs CD33 of the original set of artificial target cells derived from SupT1 cells. From left to right: double negative SupT1 cells, SupT1 cells positive for CD19, positive for CD33 and positive for both CD19 and CD33. B. Shows flow cytometry scatter plots CD19 vs GD2 of the artificial target cells generated to test the CD19 AND GD2 gate: From left to right: negative SupT1 cells, SupT1 cells expressing CD19, SupT1 cells transduced with GD2 and GM3 synthase vectors which become GD2 positive and SupT1 cells transduced with CD19 as well as GD2 and GM3 synthase which are positive for both GD2 and CD19. C. Shows flow cytometry scatter plots of CD19 vs EGFRvIII of the artificial targets generated to test the CD19 AND EGFRvIII gate. From left to right: negative SupT1 cells, SupT1 cells expressing CD19, SupT1 cells transduced with EGFRvIII and SupT1 cells transduced with both CD19 and EGFRvIII. D. Shows flow cytometry scatter plots of CD19 vs CD5 of the artificial targets generated to test the CD19 AND CD5 gate. From left to right: negative 293T cells, 293T cells transduced with CD19, 293T cells transduced with CD5, 293T cells transduced with both CD5 and CD19 vectors.

Figure 20:
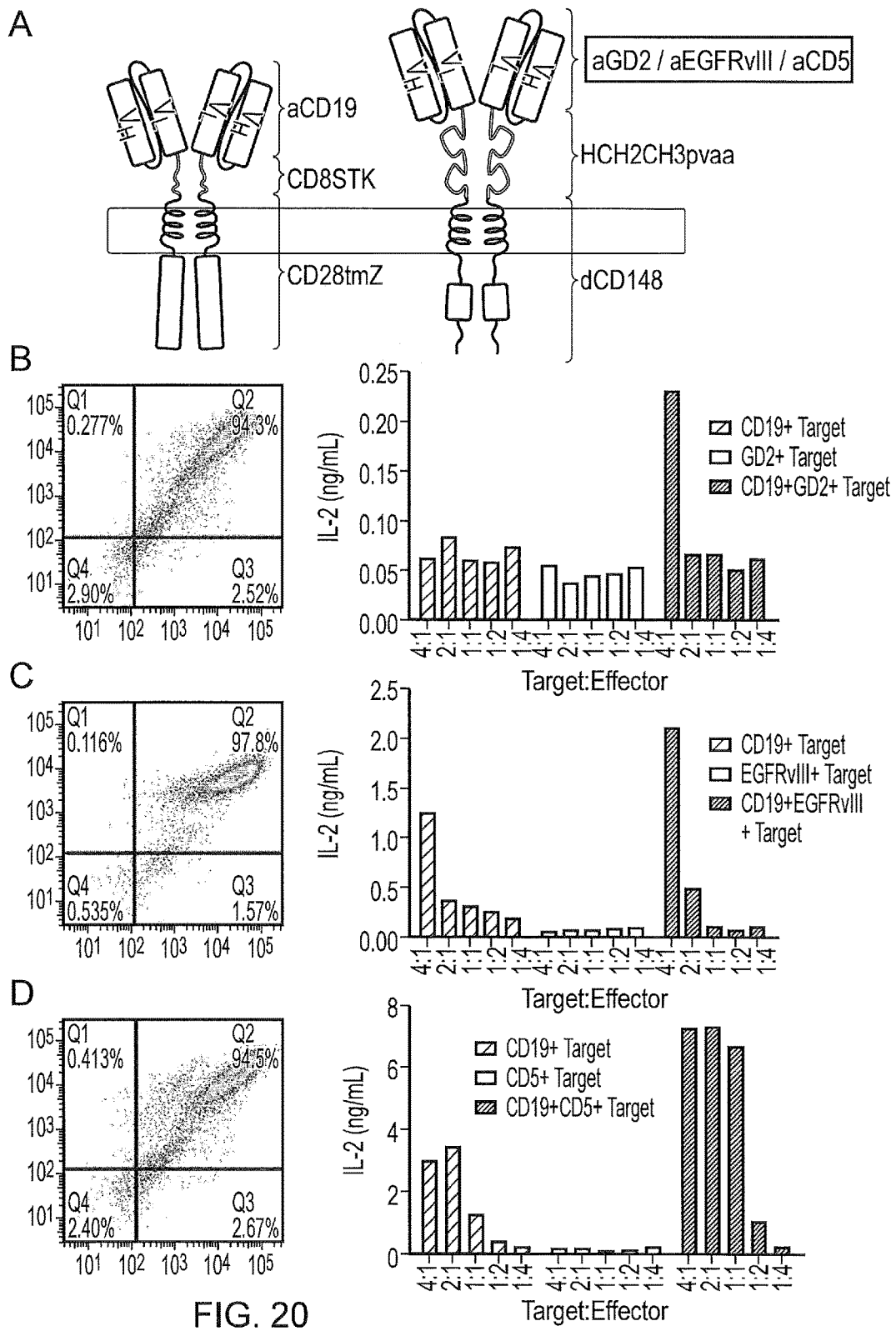

FIG. 20: Generalizability of the AND gate

A. Cartoon of AND gate modified so the second CAR's specificity is changed from the original specificity of CD33, to generate 3 new CARs: CD19 AND GD2, CD19 AND EGFRvIII, CD19 AND CD5. B. CD19 AND GD2 AND gate: Left: expression of AND gate is shown recombinant CD19-Fc staining (x-axis) for the CD19 CAR, versus anti-human-Fc staining (Y-axis) for the GD2 CAR. Right: function in response to single positive and double positive targets. C. CD19 AND EGFRvIII AND gate: Left: expression of AND gate is shown recombinant CD19-Fc staining (x-axis) for the CD19 CAR, versus anti-human-Fc staining (Y-axis) for the EGFRvIII CAR. Right: function in response to single positive and double positive targets. D. CD19 AND CD5 AND gate: Left: expression of AND gate is shown recombinant CD19-Fc staining (x-axis) for the CD19 CAR, versus anti-human-Fc staining (Y-axis) for the CD5 CAR. Right: function in response to single positive and double positive targets.

Figure 21:
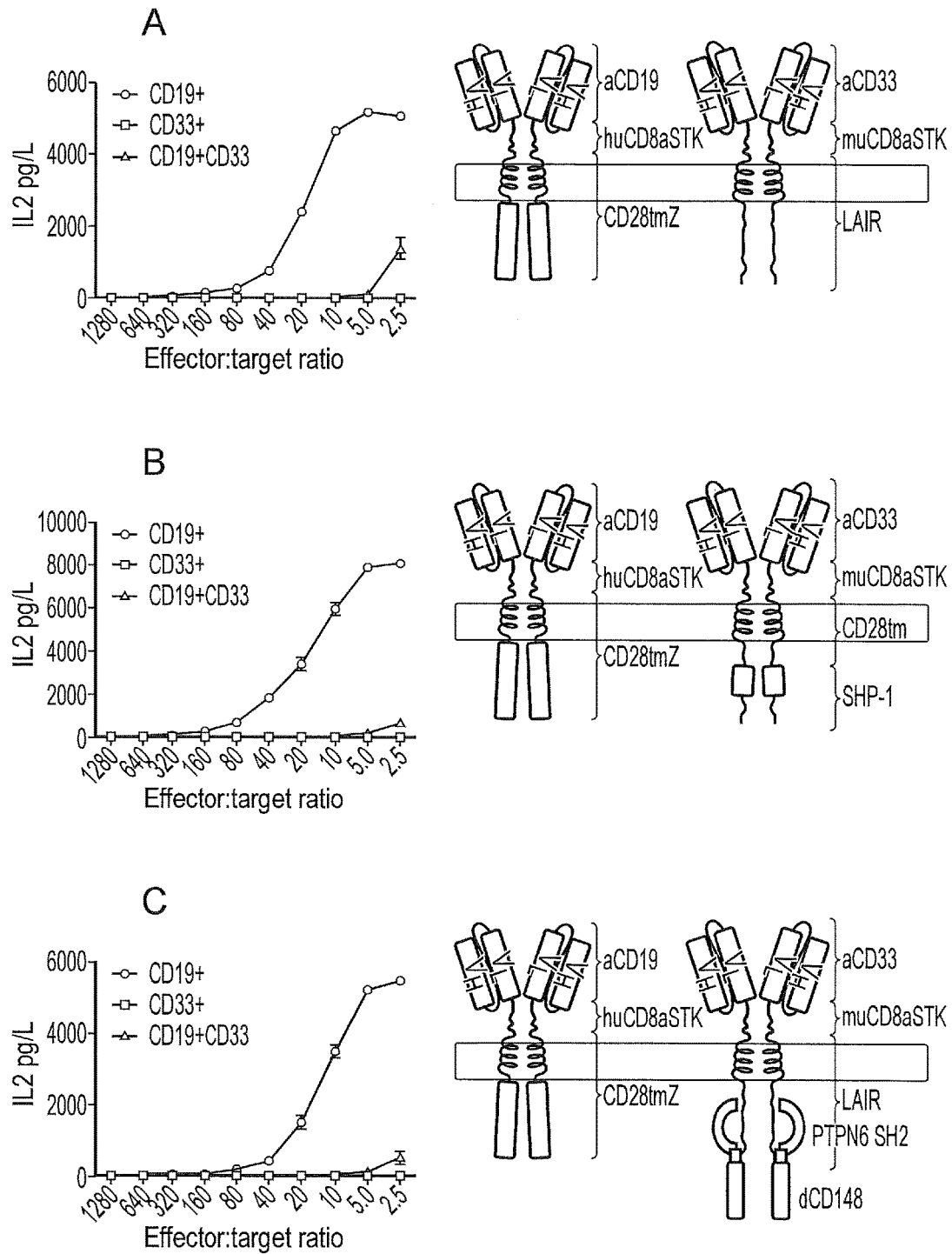

FIG. 21: Function of the AND NOT gates

Function of the three implementations of an AND NOT gate is shown. A cartoon of the gates tested is shown to the right, and function in response to single positive and double positive targets is shown to the left. A. PTPN6 based AND NOT gate whereby the first CAR recognizes CD19, has a human CD8 stalk spacer and an ITAM containing activating endodomain; is co-expressed with a second CAR that recognizes CD33, has a mouse CD8 stalk spacer and has an endodomain comprising of a PTPN6 phosphatase domain. B. ITIM based AND NOT gate is identical to the PTPN6 gate, except the endodomain is replaced by the endodomain from LAIR1. C. CD148 boosted AND NOT gate is identical to the ITIM based gate except an additional fusion between the PTPN6 SH2 and the endodomain of CD148 is expressed. All three gates work as expected with activation in response to CD19 but not in response to CD19 and CD33 together.

Figure 22:
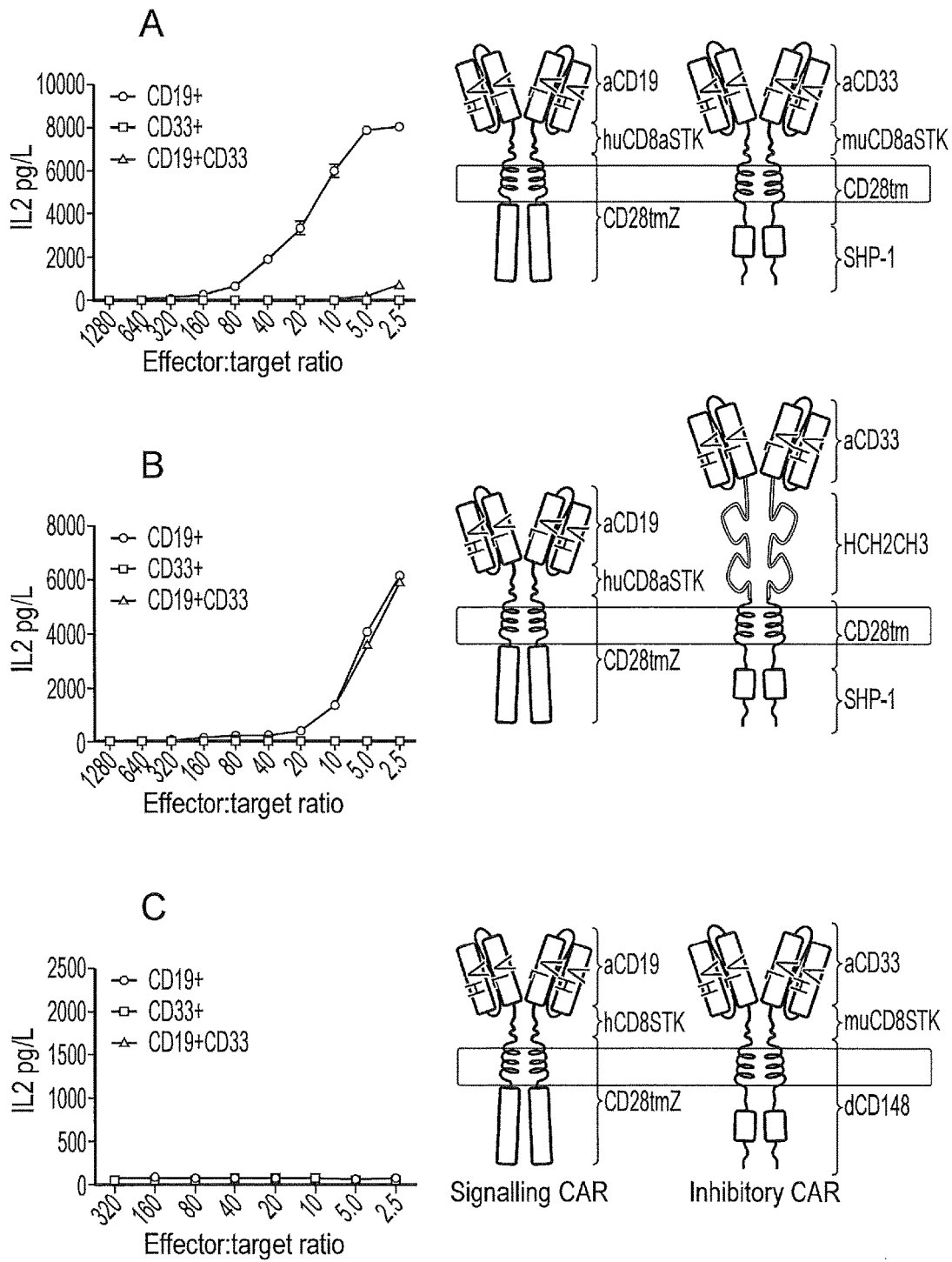

FIG. 22: Dissection of PTPN6 based AND NOT gate function

The original PTPN6 based AND NOT gate is compared with several controls to demonstrate the model. A cartoon of the gates tested is shown to the right, and function in response to single positive and double positive targets is shown to the left. A. Original AND NOT gate whereby the first CAR recognizes CD19, has a human CD8 stalk spacer and an ITAM containing activating endodomain; is co-expressed with a second CAR recognizes CD33, has a mouse CD8 stalk spacer and has an endodomain comprising of a PTPN6 phosphatase domain. B. AND NOT gate modified so the mouse CD8 stalk spacer is replaced with an Fc spacer. C AND NOT gate modified so that the PTPN6 phosphatase domain is replaced with the endodomain from CD148. Original AND NOT gate (A.) functions as expected triggering in response to CD19, but not in response to both CD19 and CD33. The gate in B. triggers both in response to CD19 along or CD19 and CD33 together. The gate in C. does not trigger in response to one or both targets.

Figure 23:
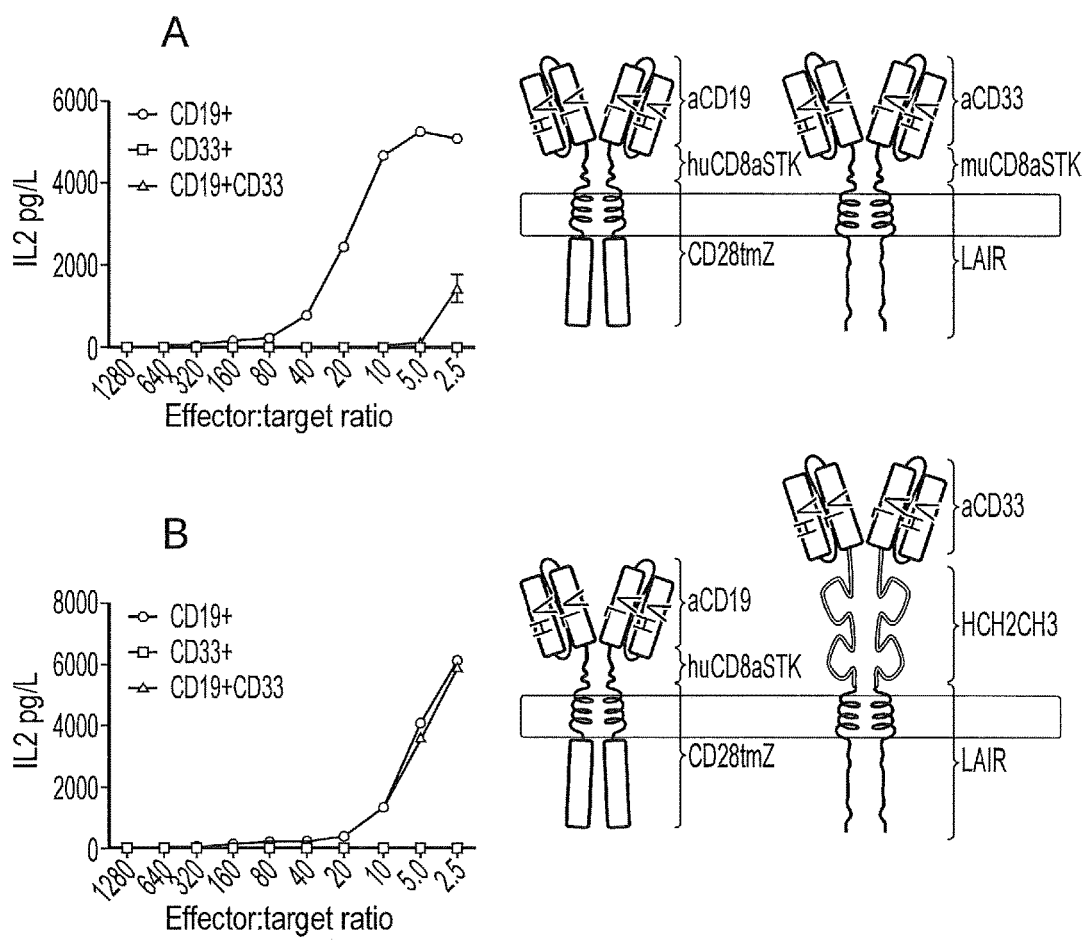

FIG. 23: Dissection of LAIR1 based AND NOT gate

Functional activity against CD19 positive, CD33 positive and CD19, CD33 double-positive targets is shown. A. Structure and activity of the original ITIM based AND NOT gate. This gate is composed of two CARs: the first recognizes CD19, has a human CD8 stalk spacer and an ITAM containing endodomain; the second CAR recognizes CD33, has a mouse CD8 stalk spacer and an ITIM containing endodomain. B Structure and activity of the control ITIM based gate where the mouse CD8 stalk spacer has been replaced by an Fc domain. This gate is composed of two CARs: the first recognizes CD19, has a human CD8 stalk spacer and an ITAM containing endodomain; the second CAR recognizes CD33, has an Fc spacer and an ITIM containing endodomain. Both gates respond to CD19 single positive targets, while only the original gate is inactive in response to CD19 and CD33 double positive targets.

Figure 24:
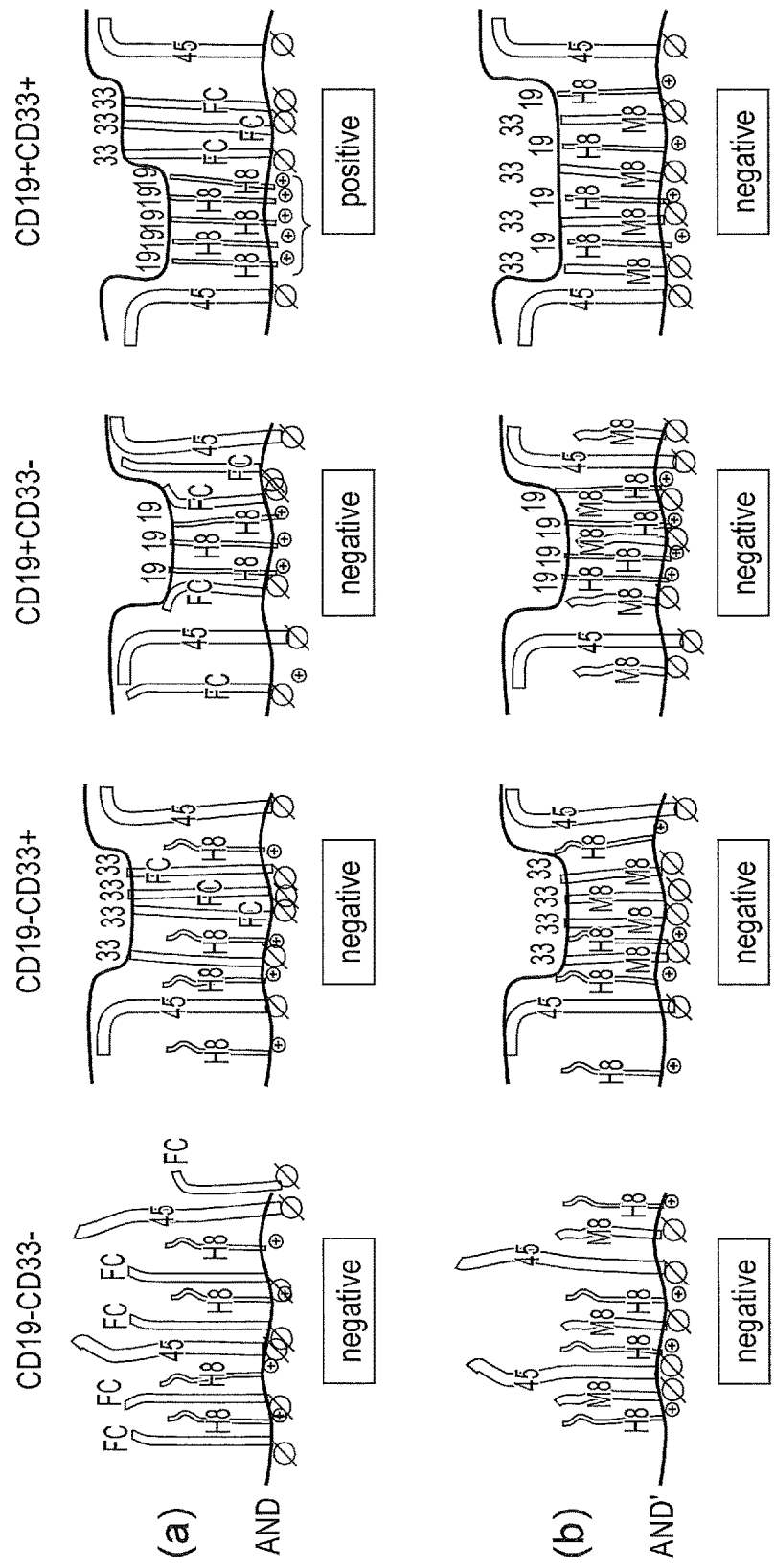
Figure 24:
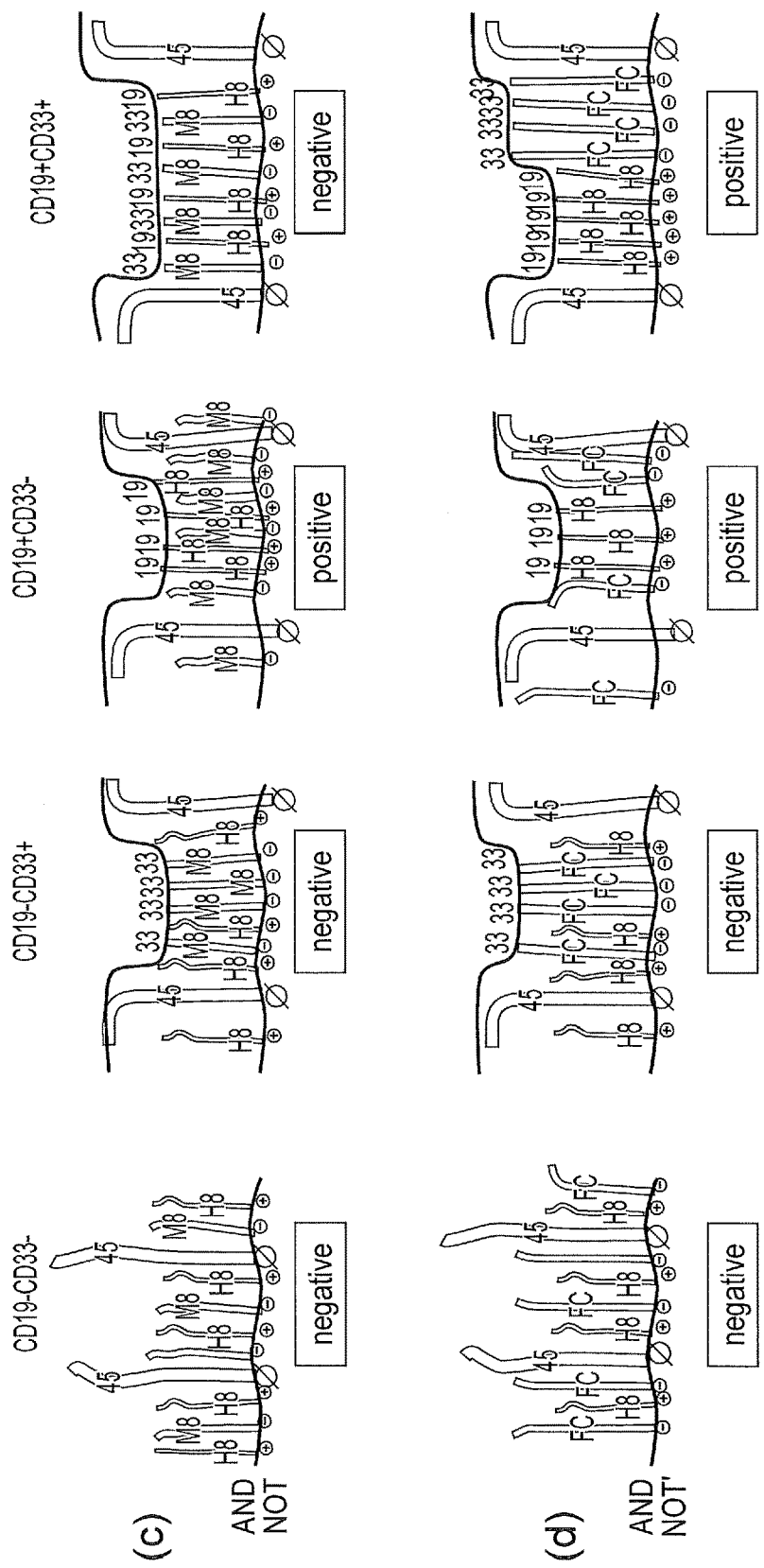

FIG. 24: Kinetic segregation model of CAR logic gates

Model of kinetic segregation and behaviour of AND gate, NOT AND gate and controls. CARs recognize either CD19 or CD33. The immunological synapse can be imagined between the blue line, which represents the target cell membrane and the red line, which represents the T-cell membrane. '45' is the native CD45 protein present on T-cells. 'H8' is a CAR ectodomain with human CD8 stalk as the spacer. 'Fc' is a CAR ectodomain with human HCH2CH3 as the spacer. 'M8' is a CAR ectodomain with murine CD8 stalk as the spacer. '19' represents CD19 on the target cell surface. '33' represents CD33 on the target cell surface. The symbol '⊕' represents an activating endodomain containing (TAMS. The symbol '⊖' represents a phosphatase with slow kinetics—a 'ligation on' endodomain such as one comprising of the catalytic domain of PTPN6 or an ITIM. The symbol 'Ø' represents a phosphatase with fast kinetics—a 'ligation off' endodomain such as the endodomain of CD45 or CD148. This symbol is enlarged in the figure to emphasize its potent activity.

(a) Shows the postulated behaviour of the functional AND gate which comprises of a pair of CARs whereby the first CAR recognizes CD19, has a human CD8 stalk spacer and an activating endodomain; and the second CAR recognizes CD33, has an Fc spacer and a CD148 endodomain;

(b) Shows the postulated behaviour of the control AND gate. Here, the first CAR recognizes CD19, has a human CD8 stalk spacer and an activating endodomain; and the second CAR recognizes CD33, but has a mouse CD8 stalk spacer and a CD148 endodomain;

(c) Shows the behaviour of a functional AND NOT gate which comprises of a pair of CARs whereby the first CAR recognizes CD19, has a human CD8 stalk spacer and an activating endodomain; and the second CAR recognizes CD33, has a mouse CD8 stalk spacer and a PTPN6 endodomain;

(d) Shows the postulated behaviour of the control AND NOT gate which comprises of a pair of CARs whereby the first CAR recognizes CD19, has a human CD8 stalk spacer and an activating endodomain; and the second CAR recognizes CD33, but has an Fc spacer and a PTPN6 endodomain;

In the first column, target cells are both CD19 and CD33 negative. In the second column, targets are CD19 negative and CD33 positive. In the third column, target cells are CD19 positive and CD33 negative. In the fourth column, target cells are positive for both CD19 and CD33.

Figure 25:
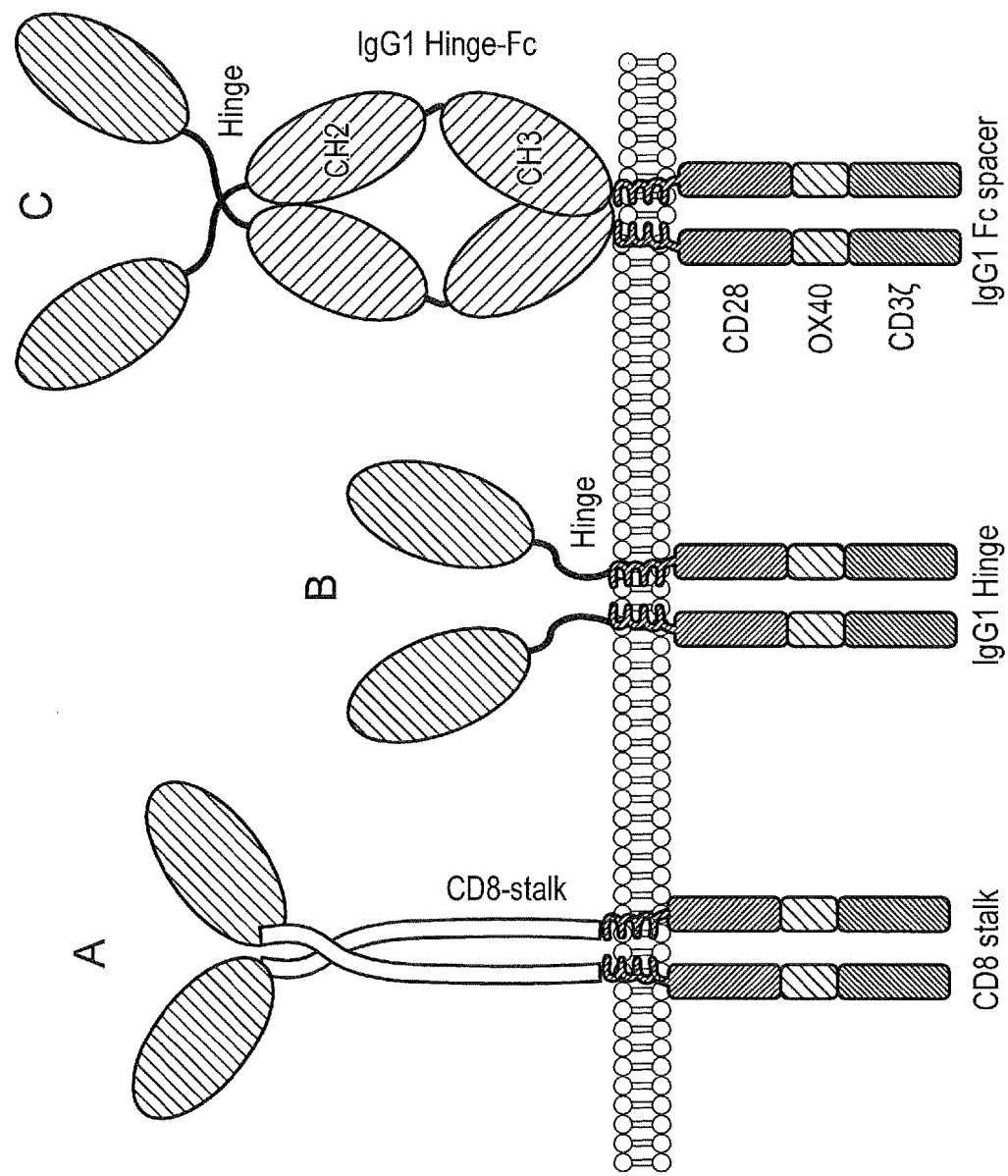

FIG. 25: Design of APRIL-based CARs.

The CAR design was modified so that the scFv was replaced with a modified form of A proliferation-inducing ligand (APRIL), which interacts with interacts with BCMA, TACI and proteoglycans, to act as an antigen binding domain: APRIL was truncated so that the proteoglycan binding amino-terminus is absent. A signal peptide was then attached to truncated APRIL amino-terminus to direct the protein to the cell surface. Three CARs were generated with this APRIL based binding domain: A. In the first CAR, the human CD8 stalk domain was used as a spacer domain. B. In the second CAR, the hinge from IgG1 was used as a spacer domain. C. In the third CAR, the hinge, CH2 and CH3 domains of human IgG1 modified with the pva/a mutations described by Hombach et al (2010 Gene Ther. 17:1206-1213) to reduce Fc Receptor binding was used as a spacer (henceforth referred as Fc-pvaa). In all CARs, these spacers were connected to the CD28 transmembrane domain and then to a tripartite endodomain containing a fusion of the CD28, OX40 and the CD3-Zeta endodomain (Pule et al, Molecular therapy, 2005: Volume 12; Issue 5; Pages 933-41).

FIG. 26: Annotated Amino acid sequence of the above three APRIL-CARS

A: Shows the annotated amino acid sequence of the CD8 stalk APRIL CAR; B: Shows the annotated amino acid sequence of the APRIL IgG1 hinge based CAR; C: Shows the annotated amino acid sequence of the APRIL Fc-pvaa based CAR.

FIG. 27: Expression and ligand binding of different APRIL based CARs

A. The receptors were co-expressed with a marker gene truncated CD34 in a retroviral gene vector. Expression of the marker gene on transduced cells allows confirmation of transduction. B. T-cells were transduced with APRIL based CARs with either the CD8 stalk spacer, IgG1 hinge or Fc spacer. To test whether these receptors could be stably expressed on the cell surface, T-cells were then stained with anti-APRIL-biotin/Streptavidin APC and anti-CD34. Flow-cytometric analysis was performed. APRIL was equally detected on the cell surface in the three CARs suggesting they are equally stably expressed. C. Next, the capacity of the CARs to recognize TACI and BCMA was determined. The transduced T-cells were stained with either recombinant BCMA or TACI fused to mouse IgG2a Fc fusion along with an anti-mouse secondary and anti-CD34. All three receptor formats showed binding to both BCMA and TACI. A surprising finding was that binding to BCMA seemed greater than to TACI. A further surprising finding was that although all three CARs were equally expressed, the CD8 stalk and IgG1 hinge CARs appeared better at recognizing BCMA and TACI than that with the Fc spacer.

Figure 28:
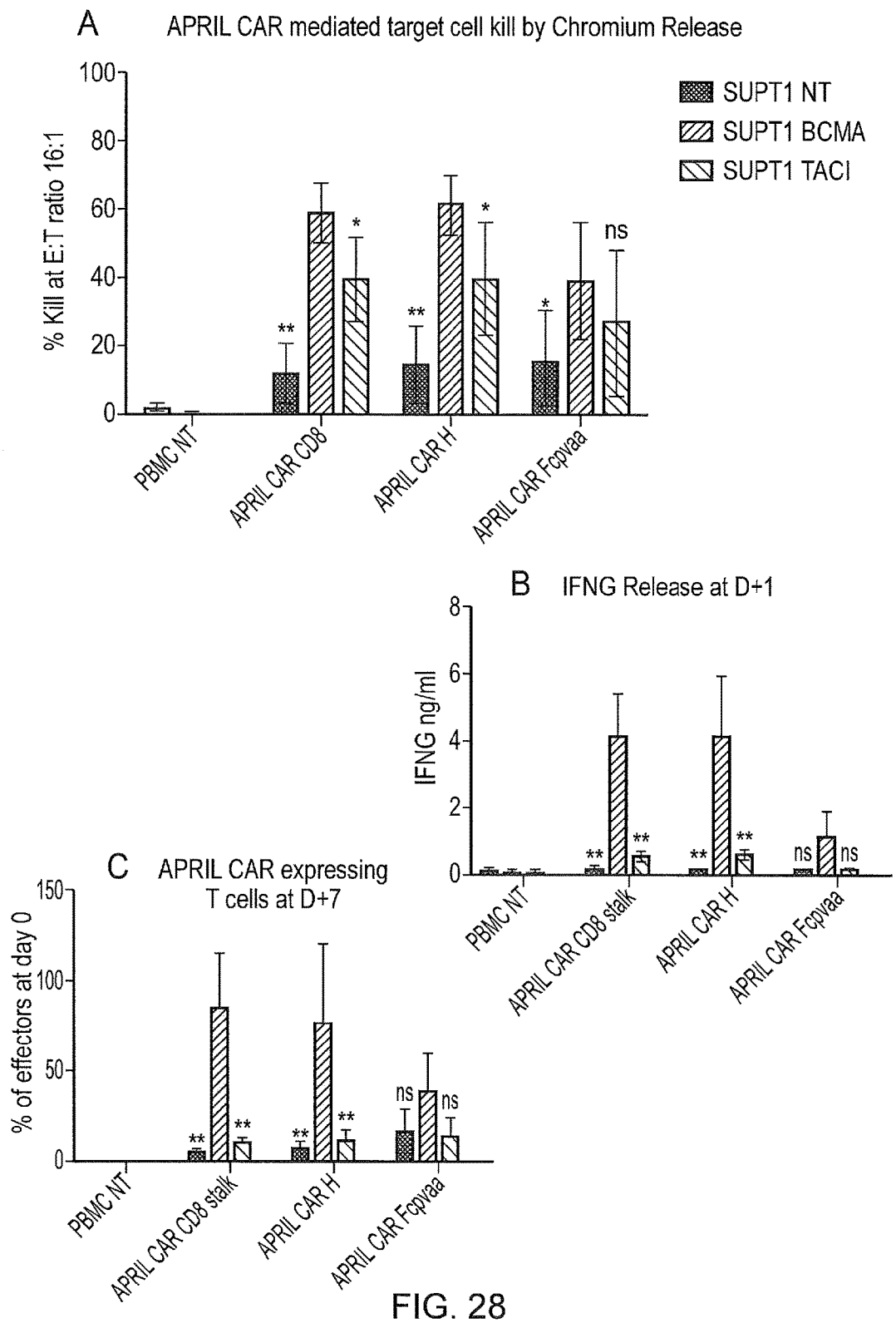

FIG. 28: Function of the different CAR constructs.

Functional assays were performed with the three different APRIL based CARs. Normal donor peripheral blood T-cells either non-transduced (NT), or transduced to express the different CARs. Transduction was performed using equal titer supernatant. These T-cells were then CD56 depleted to remove non-specific NK activity and used as effectors. SupT1 cells either non-transduced (NT), or transduced to express BCMA or TACI were used as targets. Data shown is mean and standard deviation from 5 independent experiments. A. Specific killing of BCMA and TACI expressing T-cells was determined using Chromium release. B. Interferon-µ release was also determined. Targets and effectors were co-cultured at a ratio of 1:1. After 24 hours, Interferon-µ in the supernatant was assayed by ELISA. C. Proliferation/survival of CAR T-cells were also determined by counting number of CAR T-cells in the same co-culture incubated for a further 6 days. All 3 CARs direct responses against BCMA and TACI expressing targets. The responses to BCMA were greater than for TACT.

Figure 29:
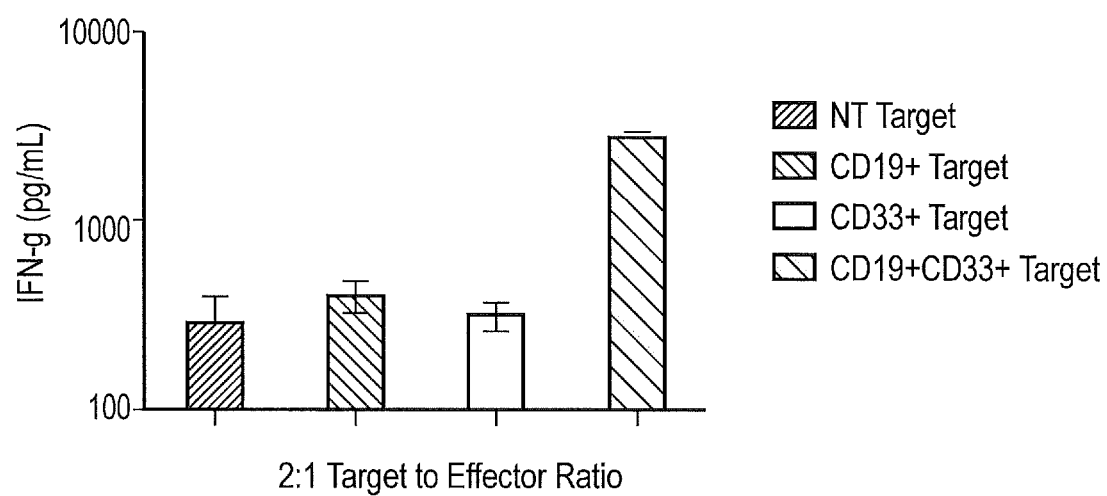

FIG. 29: AND gate functionality in primary cells

PBMCs were isolated from blood and stimulated using PHA and IL-2. Two days later the cells were transduced on retronectin coated plates with retro virus containing the CD19:CD33 AND gate construct. On day 5 the expression level of the two CARs translated by the AND gate construct was evaluated via flow cytometry and the cells were depleted of CD56+ cells (predominantly NK cells). On day 6 the PBMCs were placed in a co-culture with target cells at a 1:2 effector to target cell ratio. On day 8 the supernatant was collected and analysed for IFN-gamma secretion via ELISA.

Figure 30:
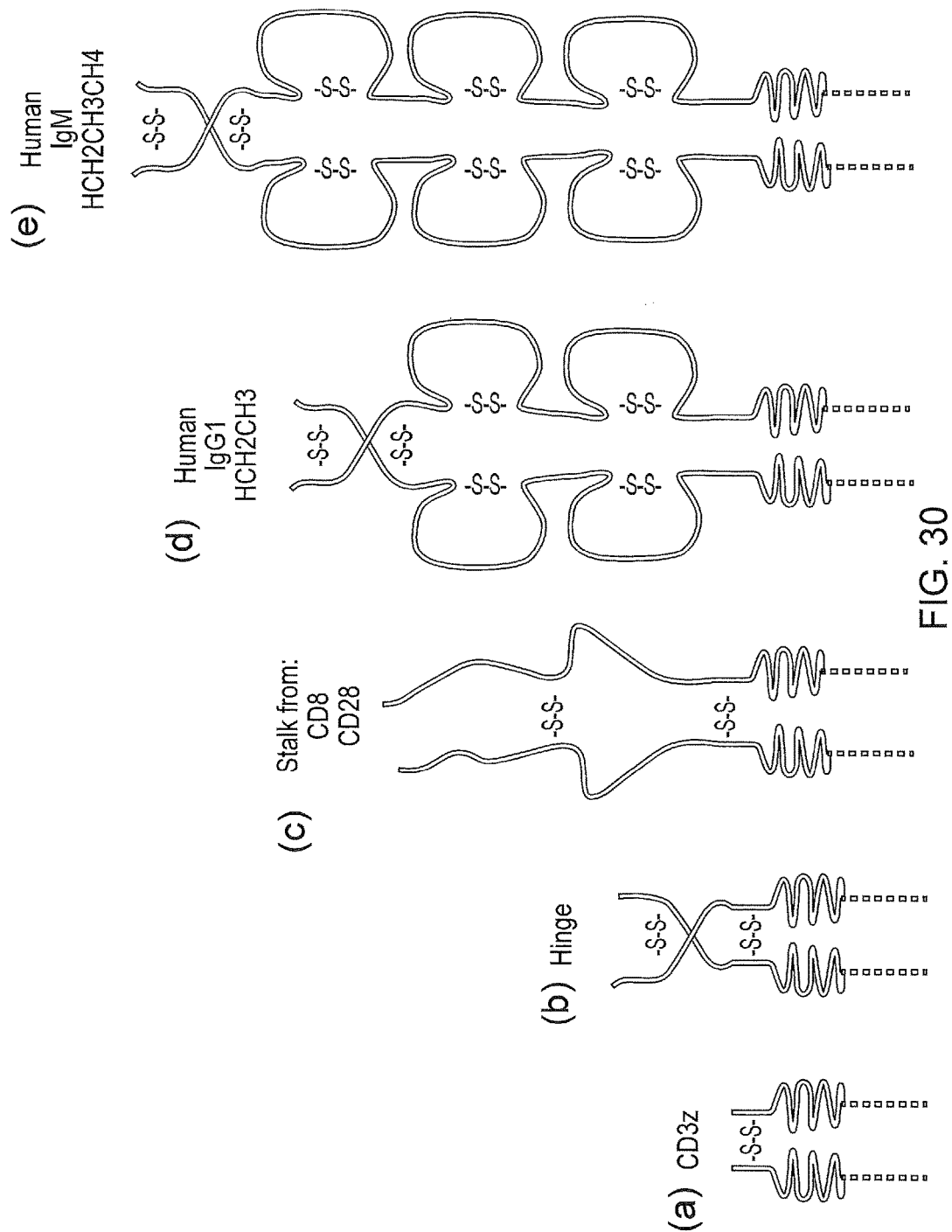

FIG. 30: A selection/hierarchy of possible spacer domains of increasing size is shown. The ectodomain of CD3-Zeta is suggested as the shortest possible spacer, followed by the (b) the IgG1 hinge. (c) murine or human CD8 stalk and the CD28 ectodomains are considered intermediate in size and co-segregate. (d) The hinge, CH2 and CH3 domain of IgG1 is bigger and bulkier, and (e) the hinge, CH2, CH3 and CH4 domain of IgM is bigger still. Given the properties of the target molecules, and the epitope of the binding domains on said target molecules, it is possible to use this hierarchy of spacers to create a CAR signaling system which either co-segregates or segregates apart upon synapse formation.

Figure 31:
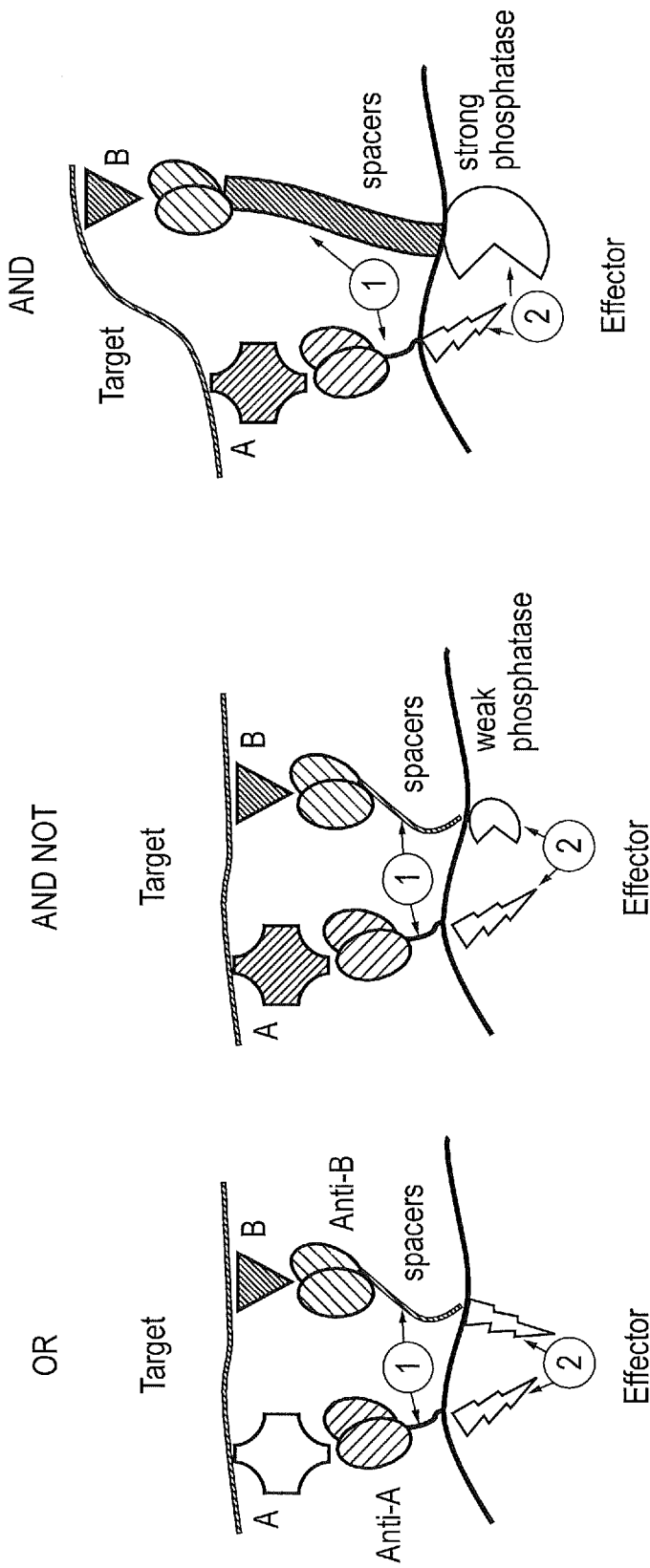

FIG. 31: Design rules for building logic gated CAR T-cells.

OR, AND NOT and AND gated CARs are shown in cartoon format with the target cell on top, and the T-cell at the bottom with the synapse in the middle. Target cells express arbitrary target antigens A, and B.

T-cells express two CARs which comprise of anti-A and anti-B recognition domains, spacers and endodomains. An OR gate requires (1) spacers simply which allow antigen recognition and CAR activation, and (2) both CARs to have activatory endodomains; An AND NOT gate requires (1) spacers which result in co-segregation of both CARs upon recognition of both antigens and (2) one CAR with an activatory endodomain, and the other whose endodomain comprises or recruits a weak phosphatase; An AND gate requires (1) spacers which result in segregation of both CARs into different parts of the immunological synapse upon recognition of both antigens and (2) one CAR with an activatory endodomain, and the other whose endodomain comprises of a potent phosphatase.

SUMMARY OF ASPECTS OF THE INVENTION

The present inventors have developed a panel of "logic-gated" chimeric antigen receptor pairs which, when expressed by a cell, such as a T cell, are capable of detecting a particular pattern of expression of at least two target antigens. If the at least two target antigens are arbitrarily denoted as antigen A and antigen B, the three possible options are as follows:

"OR GATE"-T cell triggers when either antigen A or antigen B is present on the target cell "AND GATE"-T cell triggers only when both antigens A and B are present on the target cell "AND NOT GATE"-T cell triggers if antigen A is present alone on the target cell, but not if both antigens A and B are present on the target cell Engineered T cells expressing these CAR combinations can be tailored to be exquisitely specific for cancer cells, based on their particular expression (or lack of expression) of two or more markers.

Thus in a first aspect, the present invention provides a cell which co-expresses a first chimeric antigen receptor (CAR) and second CAR at the cell surface, each CAR comprising:
 (i) an antigen-binding domain;
 (ii) a spacer
 (iii) a trans-membrane domain; and
 (iv) an intracellular T cell signaling domain (endodomain)
wherein the antigen binding domains of the first and second CARs bind to different antigens, and wherein the spacer of the first CAR is different to the spacer of the second CAR, such that the first and second CARs do not form heterodimers, and wherein
one of the first or second CARs is an activating CAR comprising an activating intracellular T cell signaling domain and the other CAR is an inhibitory CAR comprising a "ligation-off" (as defined herein) inhibitory intracellular T cell signaling domain.

The cell may be an immune effector cell, such as a T-cell or natural killer (NK) cell. Features mentioned herein in connection with a T cell apply equally to other immune effector cells, such as NK cells.

The spacer of the first CAR may have a different length and/or charge and/or shape and/or configuration and/or glycosylation to the spacer of the second CAR, such that when the first CAR and the second CAR bind their respective target antigens, the first CAR and second CAR become spatially separated on the T cell. Ligation of the first and second CARs to their respective antigens causes them to be compartmentalized together or separately in the immunological synapse resulting in control of activation. This may be understood when one considers the kinetic separation model of T-cell activation (see below).

The first spacer or the second spacer may comprise a CD8 stalk and the other spacer may comprise the hinge, CH2 and CH3 domain of an IgG1.

In the present invention, which relates to the "AND" gate, one of the first or second CARs is an activating CAR comprising an activating endodomain, and the other CAR is a "ligation-off" inhibitory CAR comprising an inhibitory endodomain. The ligation-off inhibitory CAR inhibits T-cell activation by the activating CAR in the absence of inhibitory CAR ligation, but does not significantly inhibit T-cell activation by the activating CAR when the inhibitory CAR is ligated. Since the spacer of the first CAR has a different length and/or charge and/or shape and/or configuration and/or glycosylation from the spacer of the second CAR, when both CARs are ligated they segregate. This causes the inhibitory CAR to be spatially separated from the activating CAR, so that T cell activation can occur. T cell activation therefore only occurs in response to a target cell bearing both cognate antigens.

The inhibitory endodomain may comprise all or part of the endodomain from a receptor-like tyrosine phosphatase, such as CD148 or CD45.

The antigen-binding domain of the first CAR may bind CD5 and the antigen-binding domain of the second CAR may bind CD19. This is of use in targeting chronic lymphocytic leukaemia (CLL). This disease can be treated by targeting CD19 alone, but at the cost of depleting the entire B-cell compartment. CLL cells are unusual in that they co-express CD5 and CD19. Targeting this pair of antigens with an AND gate will increase specificity and reduce toxicity.

In a second aspect, the present invention provides a nucleic acid sequence encoding both the first and second chimeric antigen receptors (CARs) as defined in the first aspect of the invention.

The nucleic acid sequence according may have the following structure: AgB1-spacer1-TM1-endo1-coexpr-AgB2-spacer2-TM2-endo2
in which
AgB1 is a nucleic acid sequence encoding the antigen-binding domain of the first CAR;
spacer 1 is a nucleic acid sequence encoding the spacer of the first CAR;
TM1 is a nucleic acid sequence encoding the transmembrane domain of the first CAR;
endo 1 is a nucleic acid sequence encoding the endodomain of the first CAR;
coexpr is a nucleic acid sequence allowing co-expression of two CARs (e.g. a cleavage site);
AgB2 is a nucleic acid sequence encoding the antigen-binding domain of the second CAR;
spacer 2 is a nucleic acid sequence encoding the spacer of the second CAR;

TM2 is a nucleic acid sequence encoding the transmembrane domain of the second CAR;
endo 2 is a nucleic acid sequence encoding the endodomain of the second CAR;
which nucleic acid sequence, when expressed in a T cell, encodes a polypeptide which is cleaved at the cleavage site such that the first and second CARs are co-expressed at the T cell surface.

The nucleic acid sequence allowing co-expression of two CARs may encode a self-cleaving peptide or a sequence which allows alternative means of co-expressing two CARs such as an internal ribosome entry sequence or a $2^{nd}$ promoter or other such means whereby one skilled in the art can express two proteins from the same vector.

Alternative codons may be used in regions of sequence encoding the same or similar amino acid sequences, in order to avoid homologous recombination.

In a third aspect, the present invention provides a kit which comprises
  (i) a first nucleic acid sequence encoding the first chimeric antigen receptor (CAR) as defined in the first aspect of the invention, which nucleic acid sequence has the following structure:
AgB1-spacer1-TM1-endo1
in which
AgB1 is a nucleic acid sequence encoding the antigen-binding domain of the first CAR;
spacer 1 is a nucleic acid sequence encoding the spacer of the first CAR;
TM1 is a nucleic acid sequence encoding the transmembrane domain of the first CAR;
endo 1 is a nucleic acid sequence encoding the endodomain of the first CAR; and
  (ii) a second nucleic acid sequence encoding the second chimeric antigen receptor (CAR) as defined in the first aspect of the invention, which nucleic acid sequence has the following structure:
AgB2-spacer2-TM2-endo2
AgB2 is a nucleic acid sequence encoding the antigen-binding domain of the second CAR;
spacer 2 is a nucleic acid sequence encoding the spacer of the second CAR;
TM2 is a nucleic acid sequence encoding the transmembrane domain of the second CAR;
endo 2 is a nucleic acid sequence encoding the endodomain of the second CAR.

In a fourth aspect, the present invention provides a kit comprising: a first vector which comprises the first nucleic acid sequence as defined above; and a second vector which comprises the first nucleic acid sequence as defined above.

The vectors may be plasmid vectors, retroviral vectors or transposon vectors. The vectors may be lentiviral vectors.

In a fifth aspect, the present invention provides a vector comprising a nucleic acid sequence according to the second aspect of the invention. The vector may be a lentiviral vector.

The vector may be a plasmid vector, a retroviral vector or a transposon vector.

In a sixth aspect, the present invention involves co-expressing more than two CARs in such a fashion that a complex pattern of more than two antigens can be recognized on the target cell.

In a seventh aspect, the present invention provides a method for making a T cell according to the first aspect of the invention, which comprises the step of introducing one or more nucleic acid sequence (s) encoding the first and second CARs; or one or more vector(s) as defined above into a T cell.

The T cell may be from a sample isolated from a patient, a related or unrelated haematopoietic transplant donor, a completely unconnected donor, from cord blood, differentiated from an embryonic cell line, differentiated from an inducible progenitor cell line, or derived from a transformed T cell line.

In an eighth aspect, the present invention provides a pharmaceutical composition comprising a plurality of T cells according to the first aspect of the invention.

In a ninth aspect, the present invention provides a method for treating and/or preventing a disease, which comprises the step of administering a pharmaceutical composition according to the eighth aspect of the invention to a subject.

The method may comprise the following steps:
  (i) isolation of a T cell as listed above.
  (ii) transduction or transfection of the T cells with one or more nucleic acid sequence(s) encoding the first and second CAR or one or more vector(s) comprising such nucleic acid sequence(s); and
  (iii) administering the T cells from (ii) to the subject.

The disease may be a cancer.

In a tenth aspect, the present invention provides a pharmaceutical composition according to the eighth aspect of the invention for use in treating and/or preventing a disease.

The disease may be a cancer.

In an eleventh aspect, the present invention provides use of a T cell according to the first aspect of the invention in the manufacture of a medicament for treating and/or preventing a disease.

The disease may be a cancer.

The present invention also provides a nucleic acid sequence which comprises:
a) a first nucleotide sequence encoding a first chimeric antigen receptor (CAR);
b) a second nucleotide sequence encoding a second CAR;
c) a sequence encoding a self-cleaving peptide positioned between the first and second nucleotide sequences, such that the two CARs are expressed as separate entities.

Alternative codons may be used in one or more portion(s) of the first and second nucleotide sequences in regions which encode the same or similar amino acid sequence(s).

The present invention also provides a vector and a cell comprising such a nucleic acid.

The kinetic-segregation based AND gate of the present invention offers a significant technical advantage to the previously described "co-CAR", i.e. the dual targeting approach in which two antigens are recognized by two CARs which supply either an activating or a co-stimulating signal to the T-cell.

With the co-CAR approach, although greatest activity might be expected against target cells bearing both antigens, considerable activity against tissues bearing only antigen recognized by the activating CAR can be expected. This activity can be expected to be at least that of a first-generation CAR. First generation CARs have resulted in considerable toxicity: for instance biliary toxicity was observed in clinical testing of a first generation CAR recognizing Carbonic anhydrase IX which was unexpectedly expressed on biliary epithelium (Rotterdam ref). Notably, terminally differentiated effectors do not require or respond to co-stimulatory signals, so any terminally differentiated CAR T-cells would act maximally despite the absence of a co-stimulatory CAR signal.

Further, co-stimulatory signals lead to long-lasting effects on the T-cell population. These effects long outlast the T-cell/target synapse interaction. Consequently, CAR T-cells which become fully activated within the tumour and migrate could have maximally potent activity against single-antigen bearing normal tissues. This "spill-over" effect may be most pronounced in tissues within, near or which drain from the tumour. In fact, strategies based on the concept of the activity of a first generation CAR being enhanced by co-stimulatory signals engaged not CAR activation but through a distinct receptor, have been proposed and tested (Rossig, Blood. 2002 Mar. 15; 99(6):2009-16.).

The co-CAR approach hence can be expected to result at best to a reduction but not abolition of toxicity towards single antigen expressing normal tissue. The present invention uses kinetic segregation at the immunological synapse formed between the T-cell/target cell to regulate T-cell triggering itself. Consequently tight absolute control of triggering in the absence of the second antigen is achieved. Hence the totality of T-cell activation is restricted to target cells expressing both antigens, the AND gate should function irrespective of the effector cell type or differentiation state, and no "spill-over" effect AND gate T-cell activation is possible.

Further Aspects of the Invention

The present invention also relates to the aspects listed in the following numbered paragraphs:

1. A T cell which co-expresses a first chimeric antigen receptor (CAR) and second CAR at the cell surface, each CAR comprising:
   (i) an antigen-binding domain;
   (ii) a spacer
   (iii) a trans-membrane domain; and
   (iv) an endodomain
wherein the antigen binding domains of the first and second CARs bind to different antigens, wherein the spacer of the first CAR is different to the spacer of the second CAR and wherein one of the first or second CARs is an activating CAR comprising an activating endodomain and the other CAR is either an activating CAR comprising an activating endodomain or an inhibitory CAR comprising a ligation-on or ligation-off inhibitory endodomain.

2. A T cell according to paragraph 1, wherein the spacer of the first CAR has a different length and/or charge and/or size and/or configuration and/or glycosylation of the spacer of the second CAR, such that when the first CAR and the second CAR bind their respective target antigens, the first CAR and second CAR become spatially separated on the T cell membrane.

3. A T cell according to paragraph 2, wherein either the first spacer or the second spacer comprises a CD8 stalk and the other spacer comprises the hinge, CH2 and CH3 domain of IgG1.

4. A T cell according to paragraph 1, wherein both the first and second CARs are activating CARs.

5. A T cell according to paragraph 4, wherein one CAR binds CD19 and the other CAR binds CD20.

6. A T cell according to paragraph 2 or 3, wherein one of the first or second CARs is an activating CAR comprising an activating endodomain, and the other CAR is an inhibitory CAR comprising a ligation-off inhibitory endodomain, which inhibitory CAR inhibits T-cell activation by the activating CAR in the absence of inhibitory CAR ligation, but does not significantly inhibit T-cell activation by the activating CAR when the inhibitory CAR is ligated.

7. A T cell according to paragraph 6, wherein the inhibitory endodomain comprises all or part of the endodomain from CD148 or CD45.

8. A T cell according to paragraph 6 or 7, wherein the antigen-binding domain of the first CAR binds CD5 and the antigen-binding domain of the second CAR binds CD19.

9. A T cell according to paragraph 1 wherein the first and second spacers are sufficiently different so as to prevent cross-pairing of the first and second CARs but are sufficiently similar to result in co-localisation of the first and second CARs following ligation.

10. A T cell according to paragraph 9, wherein one of the first or second CARs in an activating CAR comprising an activating endodomain, and the other CAR is an inhibitory CAR comprising a ligation-on inhibitory endodomain, which inhibitory CAR does not significantly inhibit T-cell activation by the activating CAR in the absence of inhibitory CAR ligation, but inhibits T-cell activation by the activating CAR when the inhibitory CAR is ligated.

11. A T cell according to paragraph 10, wherein the ligation-on inhibitory endodomain comprises at least part of a phosphatase.

12. A T cell according to paragraph 11, wherein the ligation-on inhibitory endodomain comprises all or part of PTPN6.

13. A T cell according to paragraph 10, wherein the ligation-on inhibitory endodomain comprises at least one ITIM domain.

14. A T cell according to paragraph 13, wherein activity of the ligation-on inhibitory endodomain is enhanced by co-expression of a PTPN6-CD45 or -CD148 fusion protein.

15. A T cell according to any of paragraphs 10 to 14, wherein the CAR comprising the activating endodomain comprises an antigen-binding domain which binds CD33 and the CAR which comprises the ligation-on inhibitory endodomain comprises an antigen-binding domain which binds CD34.

16. A T cell which comprises more than two CARs as defined in the preceding paragraphs such that it is specifically stimulated by a cell, such as a T cell, bearing a distinct pattern of more than two antigens.

17. A nucleic acid sequence encoding both the first and second chimeric antigen receptors (CARs) as defined in any of paragraphs 1 to 16.

18. A nucleic acid sequence according to paragraph 17, which has the following structure:
AgB1-spacer1-TM1-endo1-coexpr-AbB2-spacer2-TM2-endo2
in which
AgB1 is a nucleic acid sequence encoding the antigen-binding domain of the first CAR;
spacer 1 is a nucleic acid sequence encoding the spacer of the first CAR;
TM1 is a nucleic acid sequence encoding the transmembrane domain of the first CAR;
endo 1 is a nucleic acid sequence encoding the endodomain of the first CAR;
coexpr is a nucleic acid sequence enabling co-expression of both CARs
AgB2 is a nucleic acid sequence encoding the antigen-binding domain of the second CAR;
spacer 2 is a nucleic acid sequence encoding the spacer of the second CAR;
TM2 is a nucleic acid sequence encoding the transmembrane domain of the second CAR;
endo 2 is a nucleic acid sequence encoding the endodomain of the second CAR;

which nucleic acid sequence, when expressed in a T cell, encodes a polypeptide which is cleaved at the cleavage site such that the first and second CARs are co-expressed at the T cell surface.

19. A nucleic acid sequence according to paragraph 18, wherein coexpr encodes a sequence comprising a self-cleaving peptide.

20. A nucleic acid sequence according to paragraph 18 or 19, wherein alternative codons are used in regions of sequence encoding the same or similar amino acid sequences, in order to avoid homologous recombination.

21. A kit which comprises
   (i) a first nucleic acid sequence encoding the first chimeric antigen receptor (CAR) as defined in any of paragraphs 1 to 16, which nucleic acid sequence has the following structure:

AgB1-spacer1-TM1-endo1 in which

AgB1 is a nucleic acid sequence encoding the antigen-binding domain of the first CAR;

spacer 1 is a nucleic acid sequence encoding the spacer of the first CAR;

TM1 is a nucleic acid sequence encoding the transmembrane domain of the first CAR;

endo 1 is a nucleic acid sequence encoding the endodomain of the first CAR; and
   (ii) a second nucleic acid sequence encoding the second chimeric antigen receptor (CAR) as defined in any of paragraphs 1 to 16, which nucleic acid sequence has the following structure:

AgB2-spacer2-TM2-endo2

AgB2 is a nucleic acid sequence encoding the antigen-binding domain of the second CAR;

spacer 2 is a nucleic acid sequence encoding the spacer of the second CAR;

TM2 is a nucleic acid sequence encoding the transmembrane domain of the second CAR;

endo 2 is a nucleic acid sequence encoding the endodomain of the second CAR.

22. A kit comprising: a first vector which comprises the first nucleic acid sequence as defined in paragraph 21; and a second vector which comprises the first nucleic acid sequence as defined in paragraph 21.

23. A kit according to paragraph 22, wherein the vectors are integrating viral vectors or transposons.

24. A vector comprising a nucleic acid sequence according to any of paragraphs 17 to 20.

25. A retroviral vector or a lentiviral vector or a transposon according to paragraph 24.

26. A method for making a T cell according to any of paragraphs 1 to 16, which comprises the step of introducing: a nucleic acid sequence according to any of paragraphs 17 to 20; a first nucleic acid sequence and a second nucleic acid sequence as defined in paragraph 21; and/or a first vector and a second vector as defined in paragraph 22 or a vector according to paragraph 24 or 25, into a T cell.

27. A method according to paragraph 24, wherein the T cell is from a sample isolated from a subject.

28. A pharmaceutical composition comprising a plurality of T cells according to any of paragraphs 1 to 16.

29. A method for treating and/or preventing a disease, which comprises the step of administering a pharmaceutical composition according to paragraph 28 to a subject.

30. A method according to paragraph 29, which comprises the following steps:
   (i) isolation of a T cell-containing sample from a subject;
   (ii) transduction or transfection of the T cells with: a nucleic acid sequence according to any of paragraphs 17 to 20; a first nucleic acid sequence and a second nucleic acid sequence as defined in paragraph 21; a first vector and a second vector as defined in paragraph 22 or 23 or a vector according to paragraph 24 or 25; and
   (iii) administering the T cells from (ii) to a the subject.

31. A method according to paragraph 29 or 30, wherein the disease is a cancer.

32. A pharmaceutical composition according to paragraph 28 for use in treating and/or preventing a disease.

33. The use of a T cell according to any of paragraphs 1 to 16 in the manufacture of a medicament for treating and/or preventing a disease.

DETAILED DESCRIPTION

Chimeric Antigen Receptors (CARs)

Figure 1:
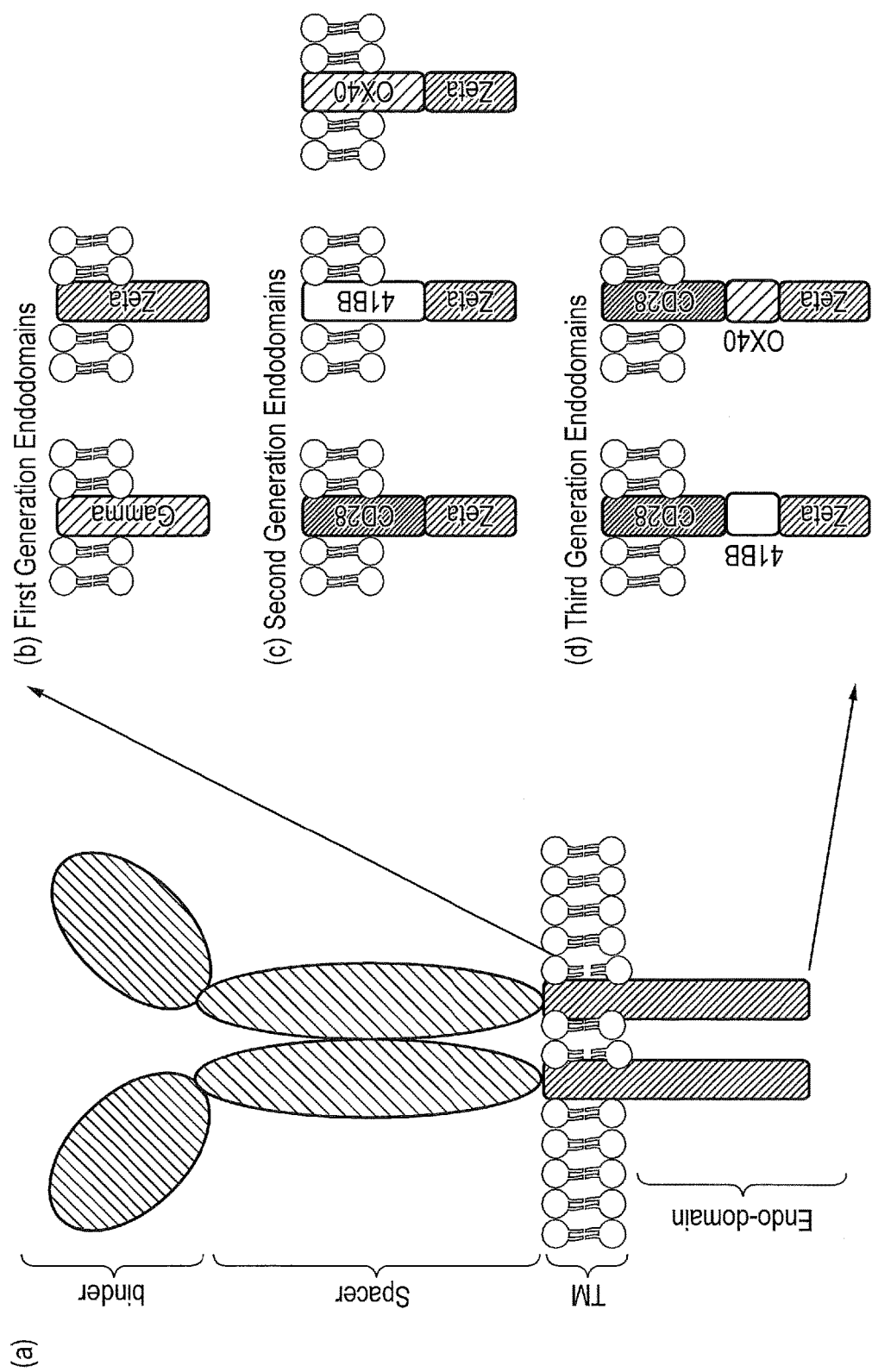
FIG. 1: (a) Generalized architecture of a CAR: A binding domain recognizes antigen; the spacer elevates the binding domain from the cell surface; the trans-membrane domain anchors the protein to the membrane and the endodomain transmits signals. (b) to (d): Different generations and permutations of CAR endodomains: (b) initial designs transmitted ITAM signals alone through FcεR1-γ or CD3ζ endodomain, while later designs transmitted additional (c) one or (d) two co-stimulatory signals in cis.
Figure 2:
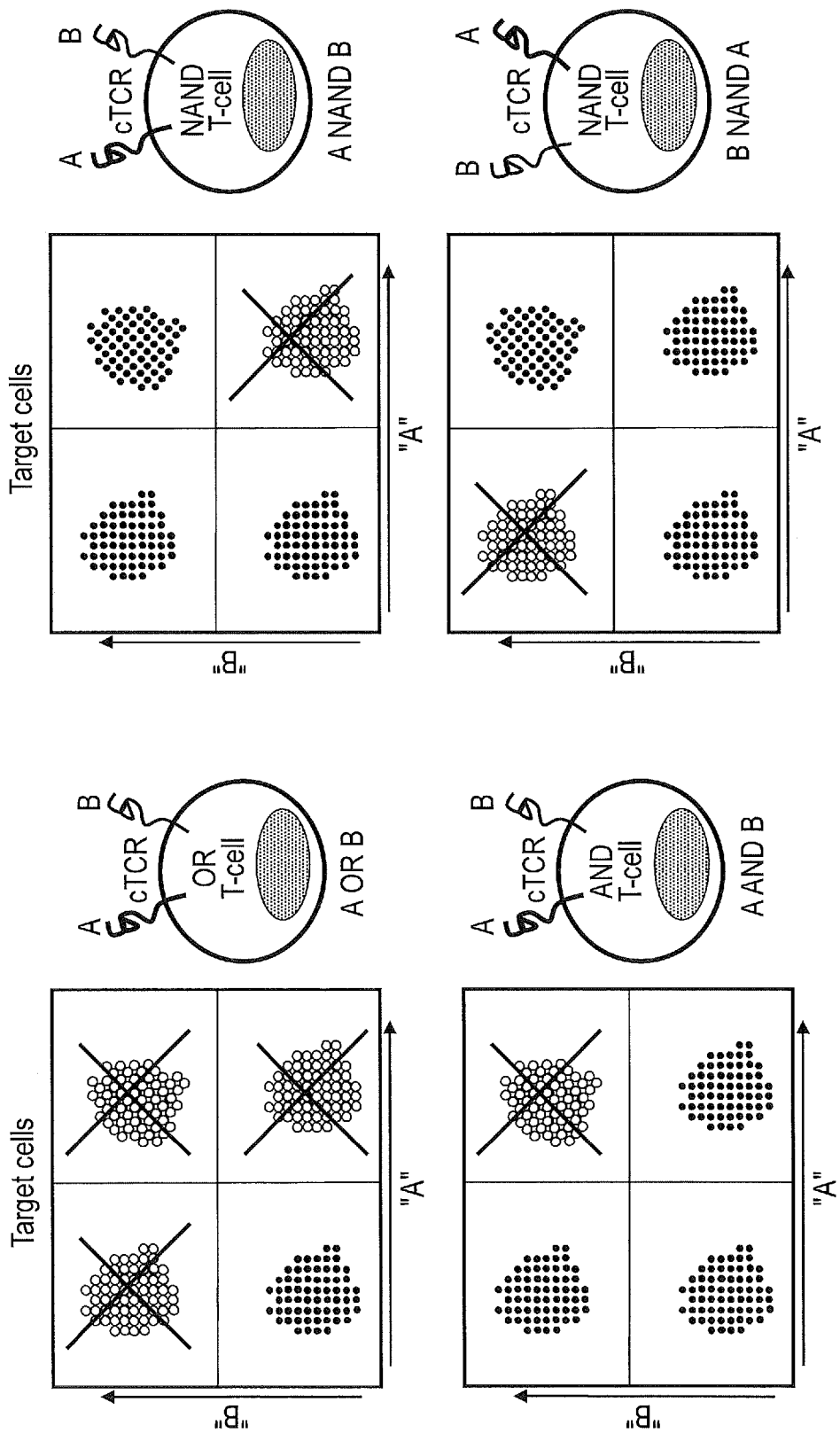
FIG. 2: Schematic diagram illustrating the invention

CARs, which are shown schematically in FIG. 1, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1. More compact spacers can suffice e.g. the stalk from CD8α and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to T cells using, for example, retroviral vectors. Lentiviral vectors may be employed. In this way, a large number of cancer-specific T cells can be generated for adoptive cell transfer. When the CAR binds the target-antigen, this results in the transmission of an activating signal to the T-cell it is expressed on. Thus the CAR directs the specificity and cytotoxicity of the T cell towards tumour cells expressing the targeted antigen.

The first aspect of the invention relates to a T-cell which co-expresses a first CAR and a second CAR such that a T-cell can recognize a desired pattern of expression on target cells in the manner of a logic gate as detailed in the truth tables: table 1, 2 and 3.

Both the first and second (and optionally subsequent) CARs comprise:

(i) an antigen-binding domain;
(ii) a spacer;
(iii) a transmembrane domain; and
(iii) an intracellular domain.

TABLE 1

Truth Table for CAR OR GATE

| Antigen A | Antigen B | Response |
|---|---|---|
| Absent | Absent | No activation |
| Absent | Present | Activation |
| Present | Absent | Activation |
| Present | Present | Activation |

TABLE 2

Truth Table for CAR AND GATE

| Antigen A | Antigen B | Response |
|---|---|---|
| Absent | Absent | No activation |
| Absent | Present | No Activation |
| Present | Absent | No Activation |
| Present | Present | Activation |

TABLE 3

Truth Table for CAR AND NOT GATE

| Antigen A | Antigen B | Response |
|---|---|---|
| Absent | Absent | No activation |
| Absent | Present | No Activation |
| Present | Absent | Activation |
| Present | Present | No Activation |

The first and second CAR of the T cell of the present invention may be produced as a polypeptide comprising both CARs, together with a cleavage site.

SEQ ID No. 1 to 5 give examples of such polypeptides, which each comprise two CARs. The CAR may therefore comprise one or other part of the following amino acid sequences, which corresponds to a single CAR.

SEQ ID No 1 is a CAR OR gate which recognizes CD19 OR CD33

SEQ ID No 2 Is a CAR AND gate which recognizes CD19 AND CD33 using a CD148 phosphatase SEQ ID No 3 Is an alternative implementation of the CAR AND GATE which recognizes CD19 AND CD33 which uses a CD45 phosphatase SEQ ID No 4 Is a CAR AND NOT GATE which recognizes CD19 AND NOT CD33 based on PTPN6 phosphatase SEQ ID No 5 Is an alternative implementation of the CAR AND NOT gate which recognizes CD19 AND NOT CD33 and is based on an ITIM containing endodomain from LAIR1

SEQ ID No 6. Is a further alternative implementation of the CAR AND NOT gate which recognizes CD19 AND NOT CD33 and recruits a PTPN6-CD148 fusion protein to an ITIM containing endodomain.

```
                                                        SEQ ID No. 1
MSLPVTALLLPLALLLHAARPDIQMTQTTSSLSASLGDRVTISCRASQDI
SKYLNWYQQKPDGTVKLLIYHTSRLHSGVPSRFSGSGSGTDYSLTISNLE
QEDIATYFCQQGNTLPYTFGGGTKLEITKAGGGGSGGGGSGGGGSGGGGS
EVKLQESGPGLVAPSQSLSVTCTVSGVSLPDYGVSWIRQPPRKGLEWLGV
IWGSETTYYNSALKSRLTIIKDNSKSQVFLKMNSLQTDDTAIYYCAKHYY
YGGSYAMDYWGQGTSVTVSSDPTTTPAPRPPTPAPTIASQPLSLRPEACR
PAAGGAVHTRGLDFACDIFWVLVVVGGVLACYSLLVTVAFIIFWVRRVKF
SRSADAPAYQQGQNQLYNELNLGRREEYDVLDKRRGRDPEMGGKPRRKNP
QEGLYNELQKDKMAEAYSEIGMKGERRRGKGHDGLYQGLSTATKDTYDAL
HMQALPPRRAEGRGSLLTCGDVEENPGPMAVPTQVLGLLLLWLTDARCDI
QMTQSPSSLSASVGDRVTITCRASEDIYFNLVWYQQKPGKAPKLLIYDTN
RLADGVPSRFSGSGSGTQYTLTISSLQPEDFATYYCQHYKNYPLTFGQGT
KLEIKRSGGGGSGGGGSGGGGSGGGGSRSEVQLVESGGGLVQPGGSLRLS
CAASGFTLSNYGMHWIRQAPGKGLEWVSSISLNGGSTYYRDSVKGRFTIS
RDNAKSTLYLQMNSLRAEDTAVYYCAAQDAYTGGYFDYWGQGTLVTVSSM
DPAEPKSPDKTHTCPPCPAPPVAGPSVFLFPPKPKDTLMIARTPEVTCVV
VDVSHEDPEVKFNWYVDGVEVHNAKTKPREEQYNSTYRWSVLTVLHQDWL
NGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDK
SRWQQGNVFSCSVMHEALHNHYTQKSLSLSPGKKDPKFWVLVVVGGVLAC
YSLLVTVAFIIFWVRSRVKFSRSADAPAYQQGQNQLYNELNLGRREEYDV
LDKRRGRDPEMGGKPRRKNPQEGLYNELQKDKMAEAYSEIGMKGERRRGK
GHDGLYQGLSTATKDTYDALHMQALPPR

SEQ ID No. 2
MSLPVTALLLPLALLLHAARPDIQMTQTTSSLSASLGDRVTISCRASQDI
SKYLNWYQQKPDGTVKLLIYHTSRLHSGVPSRFSGSGSGTDYSLTISNLE
QEDIATYFCQQGNTLPYTFGGGTKLEITKAGGGGSGGGGSGGGGSGGGGS
EVKLQESGPGLVAPSQSLSVTCTVSGVSLPDYGVSWIRQPPRKGLEWLGV
IWGSETTYYNSALKSRLTIIKDNSKSQVFLKMNSLQTDDTAIYYCAKHYY
YGGSYAMDYWGQGTSVTVSSDPTTTPAPRPPTPAPTIASQPLSLRPEACR
PAAGGAVHTRGLDFACDIFWVLVVVGGVLACYSLLVTVAFIIFWVRRVKF
SRSADAPAYQQGQNQLYNELNLGRREEYDVLDKRRGRDPEMGGKPRRKNP
QEGLYNELQKDKMAEAYSEIGMKGERRRGKGHDGLYQGLSTATKDTYDAL
HMQALPPRRAEGRGSLLTCGDVEENPGPMAVPTQVLGLLLLWLTDARCDI
QMTQSPSSLSASVGDRVTITCRASEDIYFNLVWYQQKPGKAPKLLIYDTN
RLADGVPSRFSGSGSGTQYTLTISSLQPEDFATYYCQHYKNYPLTFGQGT
KLEIKRSGGGGSGGGGSGGGGSGGGGSRSEVQLVESGGGLVQPGGSLRLS
CAASGFTLSNYGMHWIRQAPGKGLEWVSSISLNGGSTYYRDSVKGRFTIS
RDNAKSTLYLQMNSLRAEDTAVYYCAAQDAYTGGYFDYWGQGTLVTVSSM
DPAEPKSPDKTHTCPPCPAPPVAGPSVFLFPPKPKDTLMIARTPEVTCVV
VDVSHEDPEVKFNWYVDGVEVHNAKTKPREEQYNSTYRVVSVLTVLHQDW
```

LNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVD
KSRWQQGNVFSCSVMHEALHNHYTQKSLSLSPGKKDPKAVFGCIFGALVI
VTVGGFIFWRKRKDAKNNEVSFSQIKPKKSKLIRVENFEAYFKKQQADS
NCGFAEEYEDLKLVGISQPKYAAELAENRGKNRYNNVLPYDISRVKLSVQ
THSTDDYINANYMPGYHSKKDFIATQGPLPNTLKDFWRMVWEKNVYAIIM
LTKCVEQGRTKCEEYWPSKQAQDYGDITVAMTSEIVLPEWTIRDFTVKNI
QTSESHPLRQFHFTSWPDHGVPDTTDLLINFRYLVRDYMKQSPPESPILV
HCSAGVGRTGTFIAIDRLIYQIENENTVDVYGIVYDLRMHRPLMVQTEDQ
YVFLNQCVLDIVRSQKDSKVDLIYQNTTAMTIYENLAPVTTFGKTNGYIA

SEQ ID No. 3
MSLPVTALLLPLALLLHAARPDIQMTQTTSSLSASLGDRVTISCRASQDI
SKYLNWYQQKPDGTVKLLIYHTSRLHSGVPSRFSGSGSGTDYSLTISNLE
QEDIATYFCQQGNTLPYTFGGGTKLEITKAGGGGSGGGGSGGGGSGGGGS
EVKLQESGPGLVAPSQSLSVTCTVSGVSLPDYGVSWIRQPPRKGLEWLGV
IWGSETTYYNSALKSRLTIIKDNSKSQVFLKMNSLQTDDTAIYYCAKHYY
YGGSYAMDYWGQGTSVTVSSDPTTTPAPRPPTPAPTIASQPLSLRPEACR
PAAGGAVHTRGLDFACDIFWVLVVVGGVLACYSLLVTVAFIIFWVRRVKF
SRSADAPAYQQGQNQLYNELNLGRREEYDVLDKRRGRDPEMGGKPRRKNP
QEGLYNELQKDKMAEAYSEIGMKGERRRGKHDGLYQGLSTATKDTYDAL
HMQALPPRRAEGRGSLLTCGDVEENPGPMAVPTQVLGLLLLWLTDARCDI
QMTQSPSSLSASVGDRVTITCRASEDIYFNLVWYQQKPGKAPKLLIYDTN
RLADGVPSRFSGSGSGTQYTLTISSLQPEDFATYYCQHYKNYPLTFGQGT
KLEIKRSGGGGSGGGGSGGGGSGGGGSRSEVQLVESGGGLVQPGGSLRLS
CAASGFTLSNYGMHWIRQAPGKGLEWVSSISLNGGSTYYRDSVKGRFTIS
RDNAKSTLYLQMNSLRAEDTAVYYCAAQDAYTGGYFDYWGQGTLVTVSSM
DPAEPKSPDKTHTCPPCPAPPVAGPSVFLFPPKPKDTLMIARTPEVTCVV
VDVSHEDPEVKFNWYVDGVEVHNAKTKPREEQYNSTYRWSVLTVLHQDWL
NGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDK
SRWQQGNVFSCSVMHEALHNHYTQKSLSLSPGKKDPKALIAFLAFLIIVT
SIALLWLYKIYDLHKKRSCNLDEQQELVERDDEKQLMNVEPIHADILLET
YKRKIADEGRLFLAEFQSIPRVFSKFPIKEARKPFNQNKNRYVDILPYDY
NRVELSEINGDAGSNYINASYIDGFKEPRKYIAAQGPRDETVDDFWRMIW
EQKATVIVMVTRCEEGNRNKCAEYWPSMEEGTRAFGDVVVKINQHKRCPD
YIIQKLNIVNKKEKATGREVTHIQFTSWPDHGVPEDPHLLLKLRRRVNAF
SNFFSGPIVVHCSAGVGRTGTYIGIDAMLEGLEAENKVDVYGYWKLRRQR
CLMVQVEAQYILIHQALVEYNQFGETEVNLSELHPYLHNMKKRDPPSEPS
PLEAEFQRLPSYRSWRTQHIGNQEENKSKNRNSNVIPYDYNRVPLKHELE
MSKESEHDSDESSDDDSDSEEPSKYINASFIMSYWKPEVMIAAQGPLKET
IGDFWQMIFQRKVKVIVMLTELKHGDQEICAQYWGEGKQTYGDIEVDLKD

TDKSSTYTLRVFELRHSKRKDSRTVYQYQYTNWSVEQLPAEPKELISMIQ
VVKQKLPQKNSSEGNKHHKSTPLLIHCRDGSQQTGIFCALLNLLESAETE
EVVDIFQVVKALRKARPGMVSTFEQYQFLYDVIASTYPAQNGQVKKNNHQ
EDKIEFDNEVDKVKQDANCVNPLGAPEKLPEAKEQAEGSEPTSGTEGPEH
SVNGPASPALNQGS

SEQ ID No. 4
MSLPVTALLLPLALLLHAARPDIQMTQTTSSLSASLGDRVTISCRASQDI
SKYLNWYQQKPDGTVKLLIYHTSRLHSGVPSRFSGSGSGTDYSLTISNLE
QEDIATYFCQQGNTLPYTFGGGTKLEITKAGGGGSGGGGSGGGGSGGGGS
EVKLQESGPGLVAPSQSLSVTCTVSGVSLPDYGVSWIRQPPRKGLEWLGV
IWGSETTYYNSALKSRLTIIKDNSKSQVFLKMNSLQTDDTAIYYCAKHYY
YGGSYAMDYWGQGTSVTVSSDPTTTPAPRPPTPAPTIASQPLSLRPEACR
PAAGGAVHTRGLDFACDIFWVLVVVGGVLACYSLLVTVAFIIFWVRRVKF
SRSADAPAYQQGQNQLYNELNLGRREEYDVLDKRRGRDPEMGGKPRRKNP
QEGLYNELQKDKMAEAYSEIGMKGERRRGKHDGLYQGLSTATKDTYDAL
HMQALPPRRAEGRGSLLTCGDVEENPGPMAVPTQVLGLLLLWLTDARCDI
QMTQSPSSLSASVGDRVTITCRASEDIYFNLVWYQQKPGKAPKLLIYDTN
RLADGVPSRFSGSGSGTQYTLTISSLQPEDFATYYCQHYKNYPLTFGQGT
KLEIKRSGGGGSGGGGSGGGGSGGGGSRSEVQLVESGGGLVQPGGSLRLS
CAASGFTLSNYGMHWIRQAPGKGLEWVSSISLNGGSTYYRDSVKGRFTIS
RDNAKSTLYLQMNSLRAEDTAVYYCAAQDAYTGGYFDYWGQGTLVTVSSM
DPATTTKPVLRTPSPVHPTGTSQPQRPEDCRPRGSVKGTGLDFACDIYWA
PLAGICVALLLSLIITLICYHRSRKRVCKSGGGSFWEEFESLQKQEVKNL
HQRLEGQRPENKGKNRYKNILPFDHSRVILQGRDSNIPGSDYINANYIKN
QLLGPDENAKTYIASQGCLEATVNDFWQMAWQENSRVIVMTTREVEKGRN
KCVPYWPEVGMQRAYGPYSVTNCGEHDTTEYKLRTLQVSPLDNGDLIREI
WHYQYLSWPDHGVPSEPGGVLSFLDQINQRQESLPHAGPIIVHCSAGIGR
TGTIIVIDMLMENISTKGLDCDIDIQKTIQMVRAQRSGMVQTEAQYKFIY
VAIAQFIETTKKKL

SEQ ID No. 5
MSLPVTALLLPLALLLHAARPDIQMTQTTSSLSASLGDRVTISCRASQDI
SKYLNWYQQKPDGTVKLLIYHTSRLHSGVPSRFSGSGSGTDYSLTISNLE
QEDIATYFCQQGNTLPYTFGGGTKLEITKAGGGGSGGGGSGGGGSGGGGS
EVKLQESGPGLVAPSQSLSVTCTVSGVSLPDYGVSWIRQPPRKGLEWLGV
IWGSETTYYNSALKSRLTIIKDNSKSQVFLKMNSLQTDDTAIYYCAKHYY
YGGSYAMDYWGQGTSVTVSSDPTTTPAPRPPTPAPTIASQPLSLRPEACR
PAAGGAVHTRGLDFACDIFWVLVVVGGVLACYSLLVTVAFIIFWVRRVKF
SRSADAPAYQQGQNQLYNELNLGRREEYDVLDKRRGRDPEMGGKPRRKNP
QEGLYNELQKDKMAEAYSEIGMKGERRRGKHDGLYQGLSTATKDTYDAL
HMQALPPRRAEGRGSLLTCGDVEENPGPMAVPTQVLGLLLLWLTDARCDI
QMTQSPSSLSASVGDRVTITCRASEDIYFNLVWYQQKPGKAPKLLIYDTN

```
                                   -continued
RLADGVPSRFSGSGSGTQYTLTISSLQPEDFATYYCQHYKNYPLTFGQGT

KLEIKRSGGGGSGGGGSGGGGSGGGGSRSEVQLVESGGGLVQPGGSLRLS

CAASGFTLSNYGMHWIRQAPGKGLEWVSSISLNGGSTYYRDSVKGRFTIS

RDNAKSTLYLQMNSLRAEDTAVYYCAAQDAYTGGYFDYWGQGTLVTVSSM

DPATTTKPVLRTPSPVHPTGTSQPQRPEDCRPRGSVKGTGLDFACDILIG

VSWFLFCLLLLVLFCLHRQNQIKQGPPRSKDEEQKPQQRPDLAVDVLERT

ADKATVNGLPEKDRETDTSALAAGSSQEVTYAQLDHWALTQRTARAVSPQ

STKPMAESITYAAVARH

SEQ ID No. 6
MSLPVTALLLPLALLLHAARPDIQMTQTTSSLSASLGDRVTISCRASQDI

SKYLNWYQQKPDGTVKLLIYHTSRLHSGVPSRFSGSGSGTDYSLTISNLE

QEDIATYFCQQGNTLPYTFGGGTKLEITKAGGGGSGGGGSGGGGSGGGGS

EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSSDPTTTPAPRPPTPAPTIASQPLSLRPEACR

PAAGGAVHTRGLDFACDIFWVLVVVGGVLACYSLLVTVAFIIFWVRRVKF

SRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDAL

HMQALPPRRAEGRGSLLTCGDVEENPGPMAVPTQVLGLLLLWLTDARCDI

QMTQSPSSLSASVGDRVTITCRASEDIYFNLVWYQQKPGKAPKLLIYDTN

RLADGVPSRFSGSGSGTQYTLTISSLQPEDFATYYCQHYKNYPLTFGQGT

KLEIKRSGGGGSGGGGSGGGGSGGGGSRSEVQLVESGGGLVQPGGSLRLS

CAASGFTLSNYGMHWIRQAPGKGLEWVSSISLNGGSTYYRDSVKGRFTIS

RDNAKSTLYLQMNSLRAEDTAVYYCAAQDAYTGGYFDYWGQGTLVTVSSM

DPATTTKPVLRTPSPVHPTGTSQPQRPEDCRPRGSVKGTGLDFACDILIG

VSVVFLFCLLLLVLFCLHRQNQIKQGPPRSKDEEQKPQQRPDLAVDVLER

TADKATVNGLPEKDRETDTSALAAGSSQEVTYAQLDHWALTQRTARAVSP

QSTKPMAESITYAAVARHRAEGRGSLLTCGDVEENPGPWYHGHMSGGQAE

TLLQAKGEPWTFLVRESLSQPGDFVLSVLSDQPKAGPGSPLRVTHIKVMC

EGGRYTVGGLETFDSLTDLVEHFKKTGIEEASGAFVYLRQPYSGGGGSFE

AYFKKQQADSNCGFAEEYEDLKLVGISQPKYAAELAENRGKNRYNNVLPY

DISRVKLSVQTHSTDDYINANYMPGYHSKKDFIATQGPLPNTLKDFWRMV

WEKNVYAIIMLTKCVEQGRTKCEEYWPSKQAQDYGDITVAMTSEIVLPEW

TIRDFTVKNIQTSESHPLRQFHFTSWPDHGVPDTTDLLINFRYLVRDYMK

QSPPESPILVHCSAGVGRTGTFIAIDRLIYQIENENTVDVYGIVYDLRMH

RPLMVQTEDQYVFLNQCVLDIVRSQKDSKVDLIYQNTTAMTIYENLAPVT

TFGKTNGYIASGS
```

The CAR may comprise a variant of the CAR-encoding part of the sequence shown as SEQ ID No. 1, 2, 3, 4, 5 or 6 having at least 80, 85, 90, 95, 98 or 99% sequence identity, provided that the variant sequence is a CAR having the required properties.

Methods of sequence alignment are well known in the art and are accomplished using suitable alignment programs. The % sequence identity refers to the percentage of amino acid or nucleotide residues that are identical in the two sequences when they are optimally aligned. Nucleotide and protein sequence homology or identity may be determined using standard algorithms such as a BLAST program (Basic Local Alignment Search Tool at the National Center for Biotechnology Information) using default parameters, which is publicly available at http://blast.ncbi.nlm.nih.gov. Other algorithms for determining sequence identity or homology include: LALIGN (http://wvww.ebi.ac.uk/Tools/psa/lalign/ and http://www.ebi.ac.uk/Tools/psa/laliqn/nucleotide.html), AMAS (Analysis of Multiply Aligned Sequences, at http://www.compbio.dundee.ac.uk/Software/Amas/amas.html), FASTA (http://www.ebi.ac.uk/Tools/sss/fasta/), Clustal Omega (http://www.ebi.ac.uk/Tools/msa/clustalo/), SIM (http://web.expasy.org/sim/), and EMBOSS Needle (http://www.ebi.ac.ukfTools/psa/emboss_needle/nucleotide.html).

CAR Logical OR Gate

In this embodiment, the antigen binding domains of the first and second CARs of the present invention bind to different antigens and both CARs comprise an activating endodomain. Both CARs have different spacer domains to prevent cross-pairing of the two different receptors. A T cell can hence be engineered to activate upon recognition of either or both antigens. This is useful in the field of oncology as indicated by the Goldie-Coldman hypothesis: sole targeting of a single antigen may result in tumour escape by modulation of said antigen due to the high mutation rate inherent in most cancers. By simultaneously targeting two antigens, the probably of such escape is exponentially reduced.

Various tumour associated antigens are known as shown in the following Table 4. For a given disease, the first CAR and second CAR may bind to two different TAAs associated with that disease. In this way, tumour escape by modulating a single antigen is prevented, since a second antigen is also targeted. For example, when targeting a B-cell malignancy, both CD19 and CD20 can be simultaneously targeted. In this embodiment, it is important that the two CARs do not heterodimerize.

TABLE 4

| Cancer type | TAA |
| --- | --- |
| Diffuse Large B-cell Lymphoma | CD19, CD20 |
| Breast cancer | ErbB2, MUC1 |
| AML | CD13, CD33 |
| Neuroblastoma | GD2, NCAM |
| B-CLL | CD19, CD52 |
| Colorectal cancer | Folate binding protein, CA-125 |

Kinetic Segregation Model

Subsequent pairing of CARs to generate the AND gate and the AND NOT gate are based on the kinetic segregation model (KS) of T-cell activation. This is a functional model, backed by experimental data, which explains how antigen recognition by a T-cell receptor is converted into downstream activation signals. Briefly: at the ground state, the signalling components on the T-cell membrane are in dynamic homeostasis whereby dephosphorylated ITAMs are favoured over phosphorylated ITAMs. This is due to greater activity of the transmembrane CD45/CD148 phosphatases over membrane-tethered kinases such as lck. When a T-cell engages a target cell through a T-cell receptor (or CAR) recognition of cognate antigen, tight immunological synapses form. This close juxtapositioning of the T-cell and target membranes excludes CD45/CD148 due to their large ectodomains which cannot fit into the synapse. Segregation of a high concentration of T-cell receptor associated ITAMs and kinases in the synapse, in the absence of phosphatases, leads to a state whereby phosphorylated ITAMs are favoured. ZAP70 recognizes a threshold of phosphorylated ITAMs and propagates a T-cell activation signal. This advanced understanding of T-cell activation is exploited by the present invention. In particular, the invention is based on this understanding of how ectodomains of different length and/or bulk and/or charge and/or configuration and/or glycosylation result in differential segregation upon synapse formation.

The CAR Logical AND Gate

In this embodiment, one CAR comprises an activating endodomain and one CAR comprises an inhibitory endodomain whereby the inhibitory CAR constitutively inhibits the first activating CAR, but upon recognition of its cognate antigen releases its inhibition of the activating CAR. In this manner, a T-cell can be engineered to trigger only if a target cell expresses both cognate antigens. This behaviour is achieved by the activating CAR comprising an activating endodomain containing ITAM domains for example the endodomain of CD3 Zeta, and the inhibitory CAR comprising the endodomain from a phosphatase able to dephosphorylate an ITAM (e.g. CD45 or CD148). Crucially, the spacer domains of both CARs are significantly different in size and/or shape and/or charge etc. When only the activating CAR is ligated, the inhibitory CAR is in solution on the T-cell surface and can diffuse in and out of the synapse inhibiting the activating CAR. When both CARs are ligated, due to differences in spacer properties, the activating and inhibitory CAR are differentially segregated allowing the activating CAR to trigger T-cell activation unhindered by the inhibiting CAR.

This is of considerable utility in the field of cancer therapy. Currently, immunotherapies typically target a single antigen. Most cancers cannot be differentiated from normal tissues on the basis of a single antigen. Hence, considerable "on-target off-tumour" toxicity occurs whereby normal tissues are damaged by the therapy. For instance, whilst targeting CD20 to treat B-cell lymphomas with Rituximab, the entire normal B-cell compartment is depleted. For instance, whilst targeting CD52 to treat chronic lymphocytic leukaemia, the entire lymphoid compartment is depleted. For instance, whilst targeting CD33 to treat acute myeloid leukaemia, the entire myeloid compartment is damaged etc. By restricting activity to a pair of antigens, much more refined targeting, and hence less toxic therapy can be developed. A practical example is targeting of CLL which expresses both CD5 and CD19. Only a small proportion of normal B-cells express both antigens, so the off-target toxicity of targeting both antigens with a logical AND gate is substantially less than targeting each antigen individually.

The design of the present invention is a considerable improvement on previous implementation as described by Wilkie et al. ((2012). *J. Clin. Immunol.* 32, 1059-1070) and then tested in vivo (Kloss et al (2013) *Nat. Biotechnol.* 31, 71-75). In this implementation, the first CAR comprises of an activating endodomain, and the second a co-stimulatory domain. This way, a T-cell only receives an activating and co-stimulatory signal when both antigens are present. However, the T-cell still will activate in the sole presence of the first antigen resulting in the potential for off-target toxicity. Further, the implementation of the present invention allows for multiple compound linked gates whereby a cell can interpret a complex pattern of antigens.

TABLE 5

| Cancer Type | Antigens |
| --- | --- |
| Chronic Lymphocytic Leukaemia | CD5, CD19 |
| Neuroblastoma | ALK, GD2 |
| Glioma | EGFR, Vimentin |
| Multiple myeloma | BCMA, CD138 |
| Renal Cell Carcinoma | Carbonic anhydrase IX, G250 |
| T-ALL | CD2, N-Cadherin |
| Prostate Cancer | PSMA, hepsin (or others) |

The CAR Logical AND NOT Gate

In this embodiment, one CAR comprises an activating endodomain and one CAR comprises an inhibitory endodomain such that this inhibitory CAR is only active when it recognizes its cognate antigen. Hence a T-cell engineered in this manner is activated in response to the sole presence of the first antigen but is not activated when both antigens are present. This invention is implemented by inhibitory CARs with a spacer that co-localise with the first CAR but either the phosphatase activity of the inhibitory CAR should not be so potent that it inhibits in solution, or the inhibitory endodomain in fact recruits a phosphatase solely when the inhibitory CAR recognizes its cognate target. Such endodomains are termed "ligation-on" or semi-inhibitory herein.

This invention is of use in refining targeting when a tumour can be distinguished from normal tissue by the presence of tumour associated antigen and the loss of an antigen expressed on normal tissue. The AND NOT gate is of considerable utility in the field of oncology as it allows targeting of an antigen which is expressed by a normal cell, which normal cell also expresses the antigen recognised by the CAR comprising the activating endodomain. An example of such an antigen is CD33 which is expressed by normal stem cells and acute myeloid leukaemia (AML) cells. CD34 is expressed on stem cells but not typically expressed on AML cells. A T-cell recognizing CD33 AND NOT CD34 would result in destruction of leukaemia cells but sparing of normal stem cells.

Potential antigen pairs for use with AND NOT gates are shown in Table 6.

TABLE 6

| Disease | TAA | Normal cell which expresses TAA | Antigen expressed by normal cell but not cancer cell |
| --- | --- | --- | --- |
| AML | CD33 | stem cells | CD34 |
| Myeloma | BCMA | Dendritic cells | CD1c |
| B-CLL | CD160 | Natural Killer cells | CD56 |
| Prostate cancer | PSMA | Neural Tissue | NCAM |
| Bowel cancer | A33 | Normal bowel epithelium | HLA class I |

Compound Gates

The kinetic segregation model with the above components allows compound gates to be made e.g. a T-cell which triggers in response to patterns of more than two target antigens. For example, it is possible to make a T cell which only triggers when three antigens are present (A AND B AND C). Here, a cell expresses three CARs, each recognizing antigens A, B and C. One CAR is excitatory and two are inhibitory, which each CAR having spacer domains which result in differential segregation. Only when all three are ligated, will the T-cell activate. A further example: (A OR B) AND C: here, CARs recognizing antigens A and B are activating and have spacers which co-localise, while CAR recognizing antigen C is inhibitory and has a spacer which results in different co-segregation. A further example (A AND NOT B) AND C: Here CAR against antigen A has an activating endodomain and co-localises with CAR against antigen B which has a conditionally inhibiting endodomain. CAR against antigen C has a spacer who segregates differently from A or B and is inhibitory. In fact, ever more complex boolean logic can be programmed with these simple components of the invention with any number of CARs and spacers.

Signal Peptide

The CARs of the T cell of the present invention may comprise a signal peptide so that when the CAR is expressed inside a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The signal peptide may comprise the SEQ ID No. 7, 8 or 9 or a variant thereof having 5, 4, 3, 2 or 1 amino acid mutations (insertions, substitutions or additions) provided that the signal peptide still functions to cause cell surface expression of the CAR.

SEQ ID No. 7: MGTSLLCWMALCLLGADHADG

The signal peptide of SEQ ID No. 7 is compact and highly efficient. It is predicted to give about 95% cleavage after the terminal glycine, giving efficient removal by signal peptidase.

SEQ ID No. 8: MSLPVTALLLPLALLLHAARP

The signal peptide of SEQ ID No. 8 is derived from IgG1.

SEQ ID No. 9: MAVPTQVLGLLLLWLTDARC

The signal peptide of SEQ ID No. 9 is derived from CD8.

The signal peptide for the first CAR may have a different sequence from the signal peptide of the second CAR (and from the 3$^{rd}$ CAR and 4$^{th}$ CAR etc).

Antigen Binding Domain

The antigen binding domain is the portion of the CAR which recognizes antigen. Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain antibody; an artificial single binder such as a Darpin (designed ankyrin repeat protein); or a single-chain derived from a T-cell receptor.

The antigen binding domain may comprise a domain which is not based on the antigen binding site of an antibody. For example the antigen binding domain may comprise a domain based on a protein/peptide which is a soluble ligand for a tumour cell surface receptor (e.g. a soluble peptide such as a cytokine or a chemokine); or an extracellular domain of a membrane anchored ligand or a receptor for which the binding pair counterpart is expressed on the tumour cell.

Examples 11 to 13 relate to a CAR which binds BCMA, in which the antigen binding domain comprises APRIL, a ligand for BCMA.

The antigen binding domain may be based on a natural ligand of the antigen.

The antigen binding domain may comprise an affinity peptide from a combinatorial library or a de novo designed affinity protein/peptide.

Spacer Domain

CARs comprise a spacer sequence to connect the antigen-binding domain with the transmembrane domain and spatially separate the antigen-binding domain from the endodomain. A flexible spacer allows the antigen-binding domain to orient in different directions to facilitate binding.

In the T cell of the present invention, the first and second CARs comprise different spacer molecules. For example, the spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs.

Examples of amino acid sequences for these spacers are given below:

```
SEQ ID No. 10 (hinge-CH2CH3 of human IgG1)
AEPKSPDKTHTCPPCPAPPVAGPSVFLFPPKPKDTLMIARTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGKKD

SEQ ID No. 11 (human CD8 stalk):
TTTPAPRPPTPAPTIASQPLSLRPEACRPAAGGAVHTRGLDFACDI

SEQ ID No. 12 (human IgG1 hinge):
AEPKSPDKTHTCPPCPKDPK

SEQ ID No. 13 (CD2 ectodomain)
KEITNALETWGALGQDINLDIPSFQMSDDIDDIKWEKTSDKKKIAQFRKE

KETFKEKDTYKLFKNGTLKIKHLKTDDQDIYKVSIYDTKGKNVLEKIFDL

KIQERVSKPKISWTCINTTLTCEVMNGTDPELNLYQDGKHLKLSQRVITH

KWTTSLSAKFKCTAGNKVSKESSVEPVSCPEKGLD

SEQ ID no. 14 (CD34 ectodomain)
SLDNNGTATPELPTQGTFSNVSTNVSYQETTTPSTLGSTSLHPVSQHGNE

ATTNITETTVKFTSTSVITSVYGNTNSSVQSQTSVISTVFTTPANVSTPE

TTLKPSLSPGNVSDLSTTSTSLATSPTKPYTSSSPILSDIKAEIKCSGIR

EVKLTQGICLEQNKTSSCAEFKKDRGEGLARVLCGEEQADADAGAQVCSL

LLAQSEVRPQCLLLVLANRTEISSKLQLMKKHQSDLKKLGILDFTEQDVA

SHQSYSQKT
```

Since CARs are typically homodimers (see FIG. 1a), cross-pairing may result in a heterodimeric chimeric antigen receptor. This is undesirable for various reasons, for example: (1) the epitope may not be at the same "level" on the target cell so that a cross-paired CAR may only be able to bind to one antigen; (2) the VH and VL from the two different scFv could swap over and either fail to recognize target or worse recognize an unexpected and unpredicted antigen. For the "OR" gate and the "AND NOT" gate, the spacer of the first CAR is sufficiently different from the spacer of the second CAR in order to avoid cross-pairing. The amino acid sequence of the first spacer may share less that 50%, 40%, 30% or 20% identity at the amino acid level with the second spacer.

In other aspects of the invention (for example the AND gate) it is important that the spacer of the first CAR has a different length, and/or charge and/or shape and/or configuration and/or glycosylation, such that when both first and second CARs bind their target antigen, the difference in spacer charge or dimensions results in spatial separation of the two types of CAR to different parts of the membrane to result in activation as predicted by the kinetic separation model. In these aspects, the different length, shape and/or configuration of the spacers is carefully chosen bearing in mind the size and binding epitope on the target antigen to allow differential segregation upon cognate target recognition. For example the IgG1 Hinge, CD8 stalk, IgG1 Fc, ectodomain of CD34, ectodomain of CD45 are expected to differentially segregate.

Examples of spacer pairs which differentially segregate and are therefore suitable for use with the AND gate are shown in the following Table:

| Stimulatory CAR spacer | Inhibitory CAR spacer |
| --- | --- |
| Human-CD8STK | Human-IgG-Hinge-CH2CH3 |
| Human-CD3z ectodomain | Human-IgG-Hinge-CH2CH3 |
| Human-IgG-Hinge | Human-IgG-Hinge-CH2CH3 |
| Human-CD28STK | Human-IgG-Hinge-CH2CH3 |
| Human-CD8STK | Human-IgM-Hinge-CH2CH3CD4 |
| Human-CD3z ectodomain | Human-IgM-Hinge-CH2CH3CD4 |
| Human-IgG-Hinge | Human-IgM-Hinge-CH2CH3CD4 |
| Human-CD28STK | Human-IgM-Hinge-CH2CH3CD4 |

In other aspects of the invention (for example the AND NOT gate), it is important that the spacer be sufficiently different as to prevent cross-pairing, but to be sufficiently similar to co-localise. Pairs of orthologous spacer sequences may be employed. Examples are murine and human CD8 stalks, or alternatively spacer domains which are monomeric—for instance the ectodomain of CD2.

Examples of spacer pairs which co-localise and are therefore suitable for use with the AND NOT gate are shown in the following Table:

| Stimulatory CAR spacer | Inhibitory CAR spacer |
| --- | --- |
| Human-CD8aSTK | Mouse CD8aSTK |
| Human-CD28STK | Mouse CD8aSTK |
| Human-IgG-Hinge | Human-CD3z ectodomain |
| Human-CD8aSTK | Mouse CD28STK |
| Human-CD28STK | Mouse CD28STK |
| Human-IgG-Hinge-CH2CH3 | Human-IgM-Hinge-CH2CH3CD4 |

All the spacer domains mentioned above form homodimers. However the mechanism is not limited to using homodimeric receptors and should work with monomeric receptors as long as the spacer is sufficiently rigid. An example of such a spacer is CD2 or truncated CD22.

Transmembrane Domain

The transmembrane domain is the sequence of the CAR that spans the membrane.

A transmembrane domain may be any protein structure which is thermodynamically stable in a membrane. This is typically an alpha helix comprising of several hydrophobic residues.

The transmembrane domain of any transmembrane protein can be used to supply the transmembrane portion of the invention. The presence and span of a transmembrane domain of a protein can be determined by those skilled in the art using the TMHMM algorithm (http://www.cbs.dtu.dk/services/TMHMM-2.0/). Further, given that the transmembrane domain of a protein is a relatively simple structure, i.e a polypeptide sequence predicted to form a hydrophobic alpha helix of sufficient length to span the membrane, an artificially designed TM domain may also be used (U.S. Pat. No. 7,052,906 B1 describes synthetic transmembrane components).

The transmembrane domain may be derived from CD28, which gives good receptor stability.

Activating Endodomain

The endodomain is the signal-transmission portion of the CAR. After antigen recognition, receptors cluster, native CD45 and CD148 are excluded from the synapse and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, chimeric CD28 and OX40 can be used with CD3-Zeta to transmit a proliferative/survival signal, or all three can be used together.

Where the T cell of the present invention comprises a CAR with an activating endodomain, it may comprise the CD3-Zeta endodomain alone, the CD3-Zeta endodomain with that of either CD28 or OX40 or the CD28 endodomain and OX40 and CD3-Zeta endodomain.

Any endodomain which contains an ITAM motif can act as an activation endodomain in this invention. Several proteins are known to contain endodomains with one or more ITAM motifs. Examples of such proteins include the CD3 epsilon chain, the CD3 gamma chain and the CD3 delta chain to name a few. The ITAM motif can be easily recognized as a tyrosine separated from a leucine or isoleucine by any two other amino acids, giving the signature YxxL/I. Typically, but not always, two of these motifs are separated by between 6 and 8 amino acids in the tail of the molecule (YxxL/Ix(6-8)YxxL/1). Hence, one skilled in the art can readily find existing proteins which contain one or more ITAM to transmit an activation signal. Further, given the motif is simple and a complex secondary structure is not required, one skilled in the art can design polypeptides containing artificial ITAMs to transmit an activation signal (see WO 2000063372, which relates to synthetic signalling molecules).

The transmembrane and intracellular T-cell signalling domain (endodomain) of a CAR with an activating endodomain may comprise the sequence shown as SEQ ID No. 15, 16 or 17 or a variant thereof having at least 80% sequence identity.

SEQ ID No. 15 Comprising CD28 Transmembrane Domain and CD3 Z Endodomain

FWVLVVVGGVLACYSLLVTVAFIIFWVRRVKFSRSADAPAYQQGQNQLYN

ELNLGRREEYDVLDKRRGRDPEMGGKPRRKNPQEGLYNELQKDKMAEAYS

EIGMKGERRRGKGHDGLYQGLSTATKDTYDALHMQALPPR

SEQ ID No. 16 Comprising CD28 Transmembrane Domain and CD28 and CD3 Zeta Endodomains

FWVLVWGGVLACYSLLVTVAFIIFWVRSKRSRLLHSDYMNMTPRRPGPTR

KHYQPYAPPRDFAAYRSRVKFSRSADAPAYQQGQNQLYNELNLGRREEYD

VLDKRRGRDPEMGGKPRRKNPQEGLYNELQKDKMAEAYSEIGMKGERRRG

KGHDGLYQGLSTATKDTYDALHMQALPPR

SEQ ID No. 17 Comprising CD28 Transmembrane Domain and CD28, OX40 and CD3 Zeta Endodomains.

FWVLVVVGGVLACYSLLVTVAFIIFWVRSKRSRLLHSDYMNMTPRRPGPT

RKHYQPYAPPRDFAAYRSRDQRLPPDAHKPPGGGSFRTPIQEEQADAHST

LAKIRVKFSRSADAPAYQQGQNQLYNELNLGRREEYDVLDKRRGRDPEMG

GKPRRKNPQEGLYNELQKDKMAEAYSEIGMKGERRRGKGHDGLYQGLSTA

TKDTYDALHMQALPPR

A variant sequence may have at least 80%, 85%, 90%, 95%, 98% or 99% sequence identity to SEQ ID No. 15, 16 or 17, provided that the sequence provides an effective trans-membrane domain and an effective intracellular T cell signaling domain.

"Ligation-Off" Inhibitory Endodomain

In the embodiment referred above as the AND gate, one of the CARs comprises an inhibitory endodomain such that the inhibitory CAR inhibits T-cell activation by the activating CAR in the absence of inhibitory CAR ligation, but does not significantly inhibit T-cell activation by the activating CAR when the inhibitory CAR is ligated. This is termed a "ligation-off" inhibitory endodomain.

In this case, the spacer of the inhibitory CAR is of a different length, charge, shape and/or configuration and/or glycosylation from the spacer of the activating CAR, such that when both receptors are ligated, the difference in spacer dimensions results in isolation of the activating CARs and the inhibitory CARs in different membrane compartments of the immunological synapse, so that the activating endodomain is released from inhibition by the inhibitory endodomain.

The inhibitory endodomains for use in a ligation-off inhibitory CAR may therefore comprise any sequence which inhibits T-cell signaling by the activating CAR when it is in the same membrane compartment (i.e. in the absence of the antigen for the inhibitory CAR) but which does not significantly inhibit T cell signaling when it is isolated in a separate part of the membrane from the inhibitory CAR.

The ligation-off inhibitory endodomain may be or comprise a tyrosine phosphatase, such as a receptor-like tyrosine phosphatase. An inhibitory endodomain may be or comprise any tyrosine phosphatase that is capable of inhibiting the TCR signalling when only the stimulatory receptor is ligated. An inhibitory endodomain may be or comprise any tyrosine phosphatase with a sufficiently fast catalytic rate for phosphorylated ITAMs that is capable of inhibiting the TCR signalling when only the stimulatory receptor is ligated.

For example, the inhibitory endodomain of an AND gate may comprise the endodomain of CD148 or CD45. CD148 and CD45 have been shown to act naturally on the phosphorylated tyrosines up-stream of TCR signalling.

CD148 is a receptor-like protein tyrosine phosphatase which negatively regulates TCR signaling by interfering with the phosphorylation and function of PLCγ1 and LAT.

CD45 present on all hematopoetic cells, is a protein tyrosine phosphatase which is capable of regulating signal transduction and functional responses, again by phosphorylating PLC γ1.

An inhibitory endodomain may comprise all of part of a receptor-like tyrosine phosphatase. The phosphatase may interfere with the phosphorylation and/or function of elements involved in T-cell signalling, such as PLCγ1 and/or LAT.

The transmembrane and endodomain of CD45 and CD148 is shown as SEQ ID No. 18 and No. 19 respectively.
SEQ ID 18—CD45 Trans-Membrane and Endodomain Sequence

ALIAFLAFLIIVTSIALLVVLYKIYDLHKKRSCNLDEQQELVERDDEKQL

MNVEPIHADILLETYKRKIADEGRLFLAEFQSIPRVFSKFPIKEARKPFN

QNKNRYVDILPYDYNRVELSEINGDAGSNYINASYIDGFKEPRKYIAAQG

PRDETVDDFWRMIWEQKATVIVMVTRCEEGNRNKCAEYWPSMEEGTRAFG

DVWKINQHKRCPDYIIQKLNIVNKKEKATGREVTHIQFTSWPDHGVPEDP

HLLLKLRRRVNAFSNFFSGPIVVHCSAGVGRTGTYIGIDAMLEGLEAENK

VDVYGYVVKLRRQRCLMVQVEAQYILIHQALVEYNQFGETEVNLSELHPY

LHNMKKRDPPSEPSPLEAEFQRLPSYRSWRTQHIGNQEENKSKNRNSNVI

PYDYNRVPLKHELEMSKESEHDSDESSDDDSDSEEPSKYINASFIMSYWK

PEVMIAAQGPLKETIGDFWQMIFQRKVKVIVMLTELKHGDQEICAQYWGE

GKQTYGDIEVDLKDTDKSSTYTLRVFELRHSKRKDSRTVYQYQYTNWSVE

QLPAEPKELISMIQVVKQKLPQKNSSEGNKHHKSTPLLIHCRDGSQQTGI

FCALLNLLESAETEEVVDIFQVVKALRKARPGMVSTFEQYQFLYDVIAST

YPAQNGQVKKNNHQEDKIEFDNEVDKVKQDANCVNPLGAPEKLPEAKEQA

EGSEPTSGTEGPEHSVNGPASPALNQGS

SEQ ID 19—CD148 Trans-Membrane and Endodomain Sequence

AVFGCIFGALVIVTVGGFIFWRKKRKDAKNNEVSFSQIKPKKSKLIRVEN

FEAYFKKQQADSNCGFAEEYEDLKLVGISQPKYAAELAENRGKNRYNNVL

PYDISRVKLSVQTHSTDDYINANYMPGYHSKKDFIATQGPLPNTLKDFWR

MVWEKNVYAIIMLTKCVEQGRTKCEEYWPSKQAQDYGDITVAMTSEIVLP

EWTIRDFTVKNIQTSESHPLRQFHFTSWPDHGVPDTTDLLINFRYLVRDY

MKQSPPESPILVHCSAGVGRTGTFIAIDRLIYQIENENTVDVYGIVYDLR

MHRPLMVQTEDQYVFLNQCVLDIVRSQKDSKVDLIYQNTTAMTIYENLAP

VTTFGKTNGYIA

An inhibitory CAR may comprise all or part of SEQ ID No 18 or 19 (for example, it may comprise the phosphatase function of the endodomain). It may comprise a variant of the sequence or part thereof having at least 80% sequence identity, as long as the variant retains the capacity to basally inhibit T cell signalling by the activating CAR.

Other spacers and endodomains may be tested for example using the model system exemplified herein. Target cell populations can be created by transducing a suitable cell line such as a SupT1 cell line either singly or doubly to establish cells negative for both antigens (the wild-type), positive for either and positive for both (e.g. CD19−CD33−, CD19+CD33−, CD19−CD33+ and CD19+CD33+). T cells such as the mouse T cell line BW5147 which releases IL-2 upon activation may be transduced with pairs of CARs and their ability to function in a logic gate measured through measurement of IL-2 release (for example by ELISA). For example, it is shown in Example 4 that both CD148 and CD45 endodomains can function as inhibitory CARs in combination with an activating CAR containing a CD3 Zeta endodomain. These CARs rely upon a short/non-bulky CD8 stalk spacer on one CAR and a bulky Fc spacer on the other CAR to achieve AND gating. When both receptors are ligated, the difference in spacer dimensions results in isolation of the different receptors in different membrane compartments, releasing the CD3 Zeta receptor from inhibition by the CD148 or CD45 endodomains. In this way, activation only occurs once both receptors are activated. It can be readily seen that this modular system can be used to test alternative spacer pairs and inhibitory endodomains. If the spacers do not achieve isolation following ligation of both receptors, the inhibition would not be released and so no activation would occur. If the inhibitory endodomain under test is ineffective, activation would be expected in the presence of ligation of the activating CAR irrespective of the ligation status of the inhibitory CAR.

"Ligation-on" Endodomain

In the embodiment referred above as the AND NOT gate, one of the CARs comprises a "ligation-on" inhibitory endodomain such that the inhibitory CAR does not significantly inhibit T-cell activation by the activating CAR in the absence of inhibitory CAR ligation, but inhibits T-cell activation by the activating CAR when the inhibitory CAR is ligated.

The "ligation-on" inhibitory endodomain may be or comprise a tyrosine phosphatase that is incapable of inhibiting the TCR signalling when only the stimulatory receptor is ligated.

The "ligation-on" inhibitory endodomain may be or comprise a tyrosine phosphatase with a sufficiently slow catalytic rate for phosphorylated ITAMs that is incapable of inhibiting the TCR signalling when only the stimulatory receptor is ligated but it is capable of inhibiting the TCR signalling response when concentrated at the synapse. Concentration at the synapse is achieved through inhibitory receptor ligation.

If a tyrosine phosphatase has a catalytic rate which is too fast for a "ligation-on" inhibitory endodomain, then it is possible to tune-down the catalytic rates of phosphatase through modification such as point mutations and short linkers (which cause steric hindrance) to make it suitable for a "ligation-on" inhibitory endodomain.

In this first embodiment the endodomain may be or comprise a phosphatase which is considerably less active than CD45 or CD148, such that significant dephosphorylation of ITAMS only occurs when activating and inhibitory endodomains are co-localised. Many suitable sequences are known in the art. For example, the inhibitory endodomain of a NOT AND gate may comprise all or part of a protein-tyrosine phosphatase such as PTPN6.

Protein tyrosine phosphatases (PTPs) are signaling molecules that regulate a variety of cellular processes including cell growth, differentiation, mitotic cycle, and oncogenic transformation. The N-terminal part of this PTP contains two tandem Src homolog (SH2) domains, which act as protein phospho-tyrosine binding domains, and mediate the interaction of this PTP with its substrates. This PTP is expressed primarily in hematopoietic cells, and functions as an important regulator of multiple signaling pathways in hematopoietic cells.

The inhibitor domain may comprise all of PTPN6 (SEQ ID No. 20) or just the phosphatase domain (SEQ ID No. 21).

SEQ ID 20—Sequence of PTPN6
MVRWFHRDLSGLDAETLLKGRGVHGSFLARPSRKN-QGDFSLSVRVGDQVTHIRIQNSGDF YDLYGGEK-FATLTELVEYYTQQQGVLQDRDGTIIHLKYPLNC-SDPTSERWYHGHMSGGQA ETLLQAKGEPWTFLVRESLSQPGDFVLSVLSDQPK-AGPGSPLRVTHIKVMCEGGRYTVGG LETFDSLT-DLVEHFKKTGIEEASGAFVYLRQPYYATRVNAADI-ENRVLELNKKQESEDTAKA GFWEEFESLQKQEVKNLHQRLEGQRPENKGKNRYK-NILPFDHSRVILQGRDSNIPGSDYIN ANYIKNQLLGP-DENAKTYIASQGCLEATVNDFWQMAWQEN-SRVIVMTTREVEKGRNKCVP YWPEVGMQRAYGPYSVTNCGEHDTTEYKL-RTLQVSPLDNGDLIREIWHYQYLSWPDHGV PSEPG-GVLSFLDQINQRQESLPHAGPIIVHCSAGIGRTGTI-IVIDMLMENISTKGLDCDIDIQKT IQMVRAQRSGMVQTEAQYKFIYVAIAQFIETTKK-KLEVLQSQKGQESEYGNITYPPAMKNAH AKAS-RTSSKHKEDVYENLHTKNKREEKVKKQRSADKEK-SKGSLKRK SEQ ID 21—Sequence of Phosphatase Domain of PTPN6
FWEEFESLQKQEVKNLHQRLEGQRPENKGKNRYK-NILPFDHSRVILQGRDSNIPGSDYINA NYIKNQLLGP-DENAKTYIASQGCLEATVNDFWQMAWQEN-SRVIVMTTREVEKGRNKCVPY WPEVGMQRAYGPYSVTNCGEHDTTEYKLRTLQVS-PLDNGDLIREIWHYQYLSWPDHGVP SEPGGVLS-FLDQINQRQESLPHAGPIIVHCSAGIGRTGTIIVIDML-MENISTKGLDCDIDIQKTI QMVRAQRSGMVQTEAQYKFIYVAIAQF A second embodiment of a ligation-on inhibitory endodomain is an ITIM (Immunoreceptor Tyrosine-based Inhibition motif) containing endodomain such as that from CD22, LAIR-1, the Killer inhibitory receptor family (KIR), LILRB1, CTLA4, PD-1, BTLA etc. When phosphorylated, ITIMs recruits endogenous PTPN6 through its SH2 domain. If co-localised with an ITAM containing endodomain, dephosphorylation occurs and the activating CAR is inhibited.

An ITIM is a conserved sequence of amino acids (S/IN/LxYxxI/V/L) that is found in the cytoplasmic tails of many inhibitory receptors of the immune system. One skilled in the art can easily find protein domains containing an ITIM. A list of human candidate ITIM-containing proteins has been generated by proteome-wide scans (Staub, et at (2004) Cell. Signal. 16, 435-456). Further, since the consensus sequence is well known and little secondary structure appears to be required, one skilled in the art could generate an artificial ITIM.

ITIM endodomains from PDCD1, BTLA4, LILRB1, LAIR1, CTLA4, KIR2DL1, KIR2DL4, KIR2DL5, KIR3DL1 and KIR3DL3 are shown in SEQ ID 22 to 31 respectively

```
PDCD1 endodomain
                                          SEQ ID 22
CSRAARGTIGARRTGQPLKEDPSAVPVFSVDYGELDFQWREKTPEPPVPC

VPEQTEYATIVFPSGMGTSSPARRGSADGPRSAQPLRPEDGHCSWPL

BTLA4
                                          SEQ ID 23
KLQRRWKRTQSQQGLQENSSGQSFFVRNKKVRRAPLSEGPHSLGCYNPMM

EDGISYTTLRFPEMNIPRTGDAESSEMQRPPPDCDDTVTYSALHKRQVGD

YENVIPDFPEDEGIHYSELIQFGVGERPQAQENVDYVILKH

LILRB1
                                          SEQ ID 24
LRHRRQGKHWTSTQRKADFQHPAGAVGPEPTDRGLQWRSSPAADAQEENL

YAAVKHTQPEDGVEMDTRSPHDEDPQAVTYAEVKHSRPRREMASPPSPLS

GEFLDTKDRQAEEDRQMDTEAAASEAPQDVTYAQLHSLTLRREATEPPPS

QEGPSPAVPSIYATLAIH

LAIR1
                                          SEQ ID 25
HRQNQIKQGPPRSKDEEQKPQQRPDLAVDVLERTADKATVNGLPEKDRET

DTSALAAGSSQEVTYAQLDHWALTQRTARAVSPQSTKPMAESITYAAVAR

H

CTLA4
                                          SEQ ID 26
FLLWILAAVSSGLFFYSFLLTAVSLSKMLKKRSPLTTGVYVKMPPTEPEC

EKQFQPYFIPIN

KIR2DL1
                                          SEQ ID 27
GNSRHLHVLIGTSWIIPFAILLFFLLHRWCANKKNAWMDQEPAGNRTVNR

EDSDEQDPQEVTYTQLNHCVFTQRKITRPSQRPKTPPTDIIVYTELPNAE

SRSKVVSCP

KIR2DL4
                                          SEQ ID 28
GIARHLHAVIRYSVAIILFTILPFFLLHRWCSKKKENAAVMNQEPAGHRT

VNREDSDEQDPQEVTYAQLDHCIFTQRKITGPSQRSKRPSTDTSVCIELP

NAEPRALSPAHEHHSQALMGSSRETTALSQTQLASSNVPAAGI

KIR2DL5
                                          SEQ ID 29
TGIRRHLHILIGTSVAIILFIILFFFLLHCCCSNKKNAAVMDQEPAGDRT

VNREDSDDQDPQEVTYAQLDHCVFTQTKITSPSQRPKTPPTDTTMYMELP

NAKPRSLSPAHKHHSQALRGSSRETTALSQNRVASSHVPAAGI

KIR3DL1
                                          SEQ ID 30
KDPRHLHILIGTSVVIILFILLLFFLLHLWCSNKKNAAVMDQEPAGNRTA

NSEDSDEQDPEEVTYAQLDHCVFTQRKITRPSQRPKTPPTDTILYTELPN

AKPRSKVVSCP

KIR3DL3
                                          SEQ ID 31
KDPGNSRHLHVLIGTSWIIPFAILLFFLLHRWCANKKNAVVMDQEPAGNR

TVNREDSDEQDPQEVTYAQLNHCVFTQRKITRPSQRPKTPPTDTSV
```

A third embodiment of a ligation-on inhibitory endodomain is an ITIM containing endodomain co-expressed with a fusion protein. The fusion protein may comprise at least part of a protein-tyrosine phosphatase and at least part of a receptor-like tyrosine phosphatase. The fusion may comprise one or more SH2 domains from the protein-tyrosine phosphatase. For example, the fusion may be between a PTPN6 SH2 domain and CD45 endodomain or between a PTPN6 SH2 domain and CD148 endodomain. When phosphorylated, the ITIM domains recruit the fusion protein bring the highly potent CD45 or CD148 phosphatase to proximity to the activating endodomain blocking activation. SEQUENCES of Fusion Proteins are Listed 32 and 33

```
PTPN6-CD45 fusion protein
                                          SEQ ID 32
WYHGHMSGGQAETLLQAKGEPWTFLVRESLSQPGDFVLSVLSDQPKAGPG

SPLRVTHIKVMCEGGRYTVGGLETFDSLTDLVEHFKKTGIEEASGAFVYL

RQPYKIYDLHKKRSCNLDEQQELVERDDEKQLMNVEPIHADILLETYKRK

IADEGRLFLAEFQSIPRVFSKFPIKEARKPFNQNKNRYVDILPYDYNRVE

LSEINGDAGSNYINASYIDGFKEPRKYIAAQGPRDETVDDFWRMIWEQKA

TVIVMVTRCEEGNRNKCAEYWPSMEEGTRAFGDVVVKINQHKRCPDYIIQ

KLNIVNKKEKATGREVTHIQFTSWPDHGVPEDPHLLLKLRRRVNAFSNFF

SGPIVVHCSAGVGRTGTYIGIDAMLEGLEAENKVDVYGYVVKLRRQRCLM

VQVEAQYILIHQALVEYNQFGETEVNLSELHPYLHNMKKRDPPSEPSPLE

AEFQRLPSYRSWRTQHIGNQEENKSKNRNSNVIPYDYNRVLKHELEMSKE

SEHDSDESSDDDSDSEEPSKYINASFIMSYWKPEVMIAAQGPLKETIGDF

MIQRKVKVIVMLTELKHGDQEICAQYWGEGKQTYGDIEVDLKDTDKSSTY

TLRVFELRHSKRKDSRTVYQYQYTNWSVEQLPAEPKELISMIQVVKQKLP

QKNSSEGNKHHKSTPLLIHCRDGSQQTGIFCALLNLLESAETEEVVDIFQ

VVKALRKARPGMVSTFEQYQFLYDVIASTYPAQNGQVKKNNHQEDKIEFD

NEVDKVKQDANCVNPLGAPEKLPEAKEQAEGSEPTSGTEGPEHSVNGPAS

PALNQGS

PTPN6-CD148 fusion
                                          SEQ ID 33
ETLLQAKGEPWTFLVRESLSQPGDFVLSVLSDQPKAGPGSPLRVTHIKVM

CEGGRYTVGGLETFDSLTDLVEHFKKTGIEEASGAFVYLRQPYRKKRKDA

KNNEVSFSQIKPKKSKLIRVENFEAYFKKQQADSNCGFAEEYEDLKLVGI

SQPKYAAELAENRGKNRYNNVLPYDISRVKLSVQTHSTDDYINANYMPGY

HSKKDFIATQGPLPNTLKDFWRMVWEKNVYAIIMLTKCVEQGRTKCEEYW

PSKQAQDYGDITVAMTSEIVLPEWTIRDFTVKNIQTSESHPLRQFHFTSW

PDHGVPDTTDLLINFRYLVRDYMKQSPPESPILVHCSAGVGRTGTFIAID

RLIYQIENENTVDVYGIVYDLRMHRPLMVQTEDQYVFLNQCVLDIVRSQK

DSKVDLIYQNTTAMTIYENLAPVTTFGKTNGYIA
```

A ligation-on inhibitory CAR may comprise all or part of SEQ ID No 20 or 21. It may comprise all or part of SEQ ID 22 to 31. It may comprise all or part of SEQ ID 22 to 31 co-expressed with either SEQ ID 32 or 33. It may comprise a variant of the sequence or part thereof having at least 80% sequence identity, as long as the variant retains the capacity to inhibit T cell signaling by the activating CAR upon ligation of the inhibitory CAR.

As above, alternative spacers and endodomains may be tested for example using the model system exemplified herein. It is shown in Example 5 that the PTPN6 endodomain can function as a semi-inhibitory CAR in combination with an activating CAR containing a CD3 Zeta endodomain. These CARs rely upon a human CD8 stalk spacer on one CAR and a mouse CD8 stalk spacer on the other CAR. The orthologous sequences prevent cross pairing. However, when both receptors are ligated, the similarity between the spacers results in co-segregation of the different receptors in the same membrane compartments. This results in inhibition of the CD3 Zeta receptor by the PTPN6 endodomain. If only the activating CAR is ligated the PTPN6 endodomain is not sufficiently active to prevent T cell activation. In this way, activation only occurs if the activating CAR is ligated and the inhibitory CAR is not ligated (AND NOT gating). It can be readily seen that this modular system can be used to test alternative spacer pairs and inhibitory domains. If the spacers do not achieve co-segregation following ligation of both receptors, the inhibition would not be effective and so activation would occur. If the semi-inhibitory endodomain under test is ineffective, activation would be expected in the presence of ligation of the activating CAR irrespective of the ligation status of the semi-inhibitory CAR.

Co-Expression Site

The second aspect of the invention relates to a nucleic acid which encodes the first and second CARs.

The nucleic acid may produce a polypeptide which comprises the two CAR molecules joined by a cleavage site. The cleavage site may be self-cleaving, such that when the polypeptide is produced, it is immediately cleaved into the first and second CARs without the need for any external cleavage activity.

Various self-cleaving sites are known, including the Foot-and-Mouth disease virus (FMDV) 2a self-cleaving peptide, which has the sequence shown as SEQ ID No. 34:

```
                                            SEQ ID No. 34
RAEGRGSLLTCGDVEENPGP.
```

The co-expressing sequence may be an internal ribosome entry sequence (IRES). The co-expressing sequence may be an internal promoter.

Cell

The first aspect of the invention relates to a cell which co-expresses a first CAR and a second CAR at the cell surface.

The cell may be any eukaryotic cell capable of expressing a CAR at the cell surface, such as an immunological cell.

In particular the cell may be an immune effector cell such as a T cell or a natural killer (NK) cell T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytotoxic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The T cell of the invention may be any of the T cell types mentioned above, in particular a CTL.

Natural killer (NK) cells are a type of cytolytic cell which forms part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CAR cells of the invention may be any of the cell types mentioned above.

CAR-expressing cells, such as CAR-expressing T or NK cells, may either be created ex vivo either from a patient's own peripheral blood (1$^{st}$ party), or in the setting of a haematopoietic stem cell transplant from donor peripheral blood (2$^{nd}$ party), or peripheral blood from an unconnected donor (3$^{rd}$ party).

The present invention also provide a cell composition comprising CAR expressing T cells and/or CAR expressing NK cells according to the present invention. The cell composition may be made by transducing or transfecting a blood-sample ex vivo with a nucleic acid according to the present invention.

Alternatively, CAR-expressing cells may be derived from ex vivo differentiation of inducible progenitor cells or embryonic progenitor cells to the relevant cell type, such as T cells. Alternatively, an immortalized cell line such as a T-cell line which retains its lytic function and could act as a therapeutic may be used.

In all these embodiments, CAR cells are generated by introducing DNA or RNA coding for the CARs by one of many means including transduction with a viral vector, transfection with DNA or RNA.

A CAR T cell of the invention may be an ex vivo T cell from a subject. The T cell may be from a peripheral blood mononuclear cell (PBMC) sample. T cells may be activated and/or expanded prior to being transduced with CAR-encoding nucleic acid, for example by treatment with an anti-CD3 monoclonal antibody.

A CAR T cell of the invention may be made by:
(i) isolation of a T cell-containing sample from a subject or other sources listed above; and
(ii) transduction or transfection of the T cells with one or more nucleic acid sequence(s) encoding the first and second CAR.

The T cells may then by purified, for example, selected on the basis of co-expression of the first and second CAR.

Nucleic Acid Sequences

The second aspect of the invention relates to one or more nucleic acid sequence(s) which codes for a first CAR and a second CAR as defined in the first aspect of the invention.

The nucleic acid sequence may comprise one of the following sequences, or a variant thereof
SEQ ID 35 OR gate
SEQ ID 36 AND gate using CD45
SEQ ID 37 AND gate using CD148
SEQ ID 38 AND NOT gate using PTPN6 as endodomain
SEQ ID 39 AND NOT gate using LAIR1 endodomain
SEQ ID 40 AND NOT gate using LAIR1 and PTPN6 SH2 fusion with CD148 phosphatase

```
SEQ ID No. 35:
>MP13974.SFG.aCD19fmc63-CD8STK-CD28tmZ-2A-
aCD33glx-HCH2CH3pvaa-CD28tmZw
ATGAGCCTGCCCGTGACCGCCCTGCTGCTGCCCCTGGCCCTGCTGCTGCA

CGCCGCCAGACCAGACATCCAGATGACCCAGACCACCAGCAGCCTGAGCG

CCAGCCTGGGCGACCGGGTGACCATCAGCTGCAGAGCCAGCCAGGACATC

AGCAAGTACCTGAACTGGTACCAGCAGAAGCCCGACGGCACCGTGAAGCT

GCTGATCTACCACACCAGCCGGCTGCACAGCGGCGTGCCCAGCCGGTTCA

GCGGCAGCGGCAGCGGCACCGACTACAGCCTGACCATCAGCAACCTGGAG

CAGGAGGACATCGCCACCTACTTCTGCCAGCAGGGCAACACCCTGCCCTA

CACCTTCGGAGGCGGCACCAAGCTGGAGATCACCAAGGCCGGAGGCGGAG

GCTCTGGCGGAGGCGGCTCTGGCGGAGGCGGCTCTGGCGGAGGCGGCAGC

GAGGTGAAGCTGCAGGAGTCTGGCCCAGGCCTGGTGGCCCCAAGCCAGAG

CCTGAGCGTGACCTGCACCGTGAGCGGCGTGAGCCTGCCCGACTACGGCG

TGAGCTGGATCAGGCAGCCCCCACGGAAGGGCCTGGAGTGGCTGGGCGTG

ATCTGGGGCAGCGAGACCACCTACTACAACAGCGCCCTGAAGAGCCGGCT

GACCATCATCAAGGACAACAGCAAGAGCCAGGTGTTCCTGAAGATGAACA
```

```
GCCTGCAGACCGACGACACCGCCATCTACTACTGCGCCAAGCACTACTAC

TATGGCGGCAGCTACGCTATGGACTACTGGGGCCAGGGCACCAGCGTGAC

CGTGAGCTCAGATCCCACCACGACGCCAGCGCCGCGACCACCAACACCGG

CGCCCACCATCGCGTCGCAGCCCCTGTCCCTGCGCCCAGAGGCGTGCCGG

CCAGCGGCGGGGGCGCAGTGCACACGAGGGGGCTGGACTTCGCCTGTGA

TATCTTTTGGGTGCTGGTGGTGGTTGGTGGAGTCCTGGCTTGCTATAGCT

TGCTAGTAACAGTGGCCTTTATTATTTTCTGGGTGAGGAGAGTGAAGTTC

AGCAGGAGCGCAGACGCCCCCGCGTACCAGCAGGGCCAGAACCAGCTCTA

TAACGAGCTCAATCTAGGACGAAGAGAGGAGTACGATGTTTTGGACAAGA

GACGTGGCCGGGACCCTGAGATGGGGGGAAAGCCGAGAAGGAAGAACCCT

CAGGAAGGCCTGTACAATGAACTGCAGAAAGATAAGATGGCGGAGGCCTA

CAGTGAGATTGGGATGAAAGGCGAGCGCCGGAGGGGCAAGGGGCACGATG

GCCTTTACCAGGGTCTCAGTACAGCCACCAAGGACACCTACGACGCCCTT

CACATGCAGGCCCTGCCTCCTCGCAGAGCCGAGGGCAGGGGAAGTCTTCT

AACATGCGGGACGTGGAGGAAAATCCCGGGCCCATGGCCGTGCCCACTC

AGGTCCTGGGGTTGTTGCTACTGTGGCTTACAGATGCCAGATGTGACATC

CAGATGACACAGTCTCCATCTTCCCTGTCTGCATCTGTCGGAGATCGCGT

CACCATCACCTGTCGAGCAAGTGAGGACATTTATTTTAATTTAGTGTGGT

ATCAGCAGAAACCAGGAAAGGCCCCTAAGCTCCTGATCTATGATACAAAT

CGCTTGGCAGATGGGGTCCCATCACGGTTCAGTGGCTCTGGATCTGGCAC

ACAGTATACTCTAACCATAAGTAGCCTGCAACCCGAAGATTTCGCAACCT

ATTATTGTCAACACTATAAGAATTATCCGCTCACGTTCGGTCAGGGGACC

AAGCTGGAAATCAAAAGATCTGGTGGCGGAGGGTCAGGAGGCGGAGGCAG

CGGAGGCGGTGGCTCGGGAGGCGGAGGCTCGAGATCTGAGGTGCAGTTGG

TGGAGTCTGGGGGCGGCTTGGTGCAGCCTGGAGGGTCCCTGAGGCTCTCC

TGTGCAGCCTCAGGATTCACTCTCAGTAATTATGGCATGCACTGGATCAG

GCAGGCTCCAGGGAAGGGTCTGGAGTGGGTCTCGTCTATTAGTCTTAATG

GTGGTAGCACTTACTATCGAGACTCCGTGAAGGGCCGATTCACTATCTCC

AGGGACAATGCAAAAAGCACCCTCTACCTTCAAATGAATAGTCTGAGGGC

CGAGGACACGGCCGTCTATTACTGTGCAGCACAGGACGCTTATACGGGAG

GTTACTTTGATTACTGGGGCCAAGGAACGCTGGTCACAGTCTCGTCTATG

GATCCCGCCGAGCCCAAATCTCCTGACAAAACTCACACATGCCCACCGTG

CCCAGCACCTCCCGTGGCCGGCCCGTCAGTCTTCCTCTTCCCCCCAAAAC

CCAAGGACACCCTCATGATCGCCCGGACCCCTGAGGTCACATGCGTGGTG

GTGGACGTGAGCCACGAAGACCCTGAGGTCAAGTTCAACTGGTACGTGGA

CGGCGTGGAGGTGCATAATGCCAAGACAAAGCCGCGGGAGGAGCAGTACA

ACAGCACGTACCGTGTGGTCAGCGTCCTCACCGTCCTGCACCAGGACTGG

CTGAATGGCAAGGAGTACAAGTGCAAGGTCTCCAACAAAGCCCTCCCAGC

CCCCATCGAGAAAACCATCTCCAAAGCCAAAGGGCAGCCCCGAGAACCAC

AGGTGTACACCCTGCCCCCATCCCGGGATGAGCTGACCAAGAACCAGGTC
```

-continued
AGCCTGACCTGCCTGGTCAAAGGCTTCTATCCCAGCGACATCGCCGTGGA

GTGGGAGAGCAATGGGCAACCGGAGAACAACTACAAGACCACGCCTCCCG

TGCTGGACTCCGACGGCTCCTTCTTCCTCTACAGCAAGCTCACCGTGGAC

AAGAGCAGGTGGCAGCAGGGGAACGTCTTCTCATGCTCCGTGATGCATGA

GGCCCTGCACAATCACTATACCCAGAAATCTCTGAGTCTGAGCCCAGGCA

AGAAGGACCCCAAGTTCTGGGTCCTGGTGGTGGTGGGAGGCGTGCTGGCC

TGTTACTCTCCTGGTGACCGTGGCCTTCATCATCTTTTGGGTGCGCTC

CCGGGTGAAGTTTTCTCGCTCTGCCGATGCCCCAGCCTATCAGCAGGGCC

AGAATCAGCTGTACAATGAACTGAACCTGGGCAGGCGGGAGGAGTACGAC

GTGCTGGATAAGCGGAGAGGCAGAGACCCCGAGATGGGCGGCAAACCACG

GCGCAAAAATCCCCAGGAGGGACTCTATAACGAGCTGCAGAAGGACAAAA

TGGCCGAGGCCTATTCCGAGATCGGCATGAAGGGAGAGAGAAGACGCGGA

AAGGGCCACGACGGCCTGTATCAGGGATTGTCCACCGCTACAAAAGATAC

ATATGATGCCCTGCACATGCAGGCCCTGCCACCCAGATGA

SEQ ID No. 36
>MP14802.SFG.aCD19fmc63_clean-CD8STK-
CD28tmZ-2A-aCD33glx-HCH2CH3pvaa-dCD45
ATGAGCCTGCCCGTGACCGCCCTGCTGCTGCCCCTGGCCCTGCTGCTGCA

CGCCGCCAGACCAGACATCCAGATGACCCAGACCACCAGCAGCCTGAGCG

CCAGCCTGGGCGACCGGGTGACCATCAGCTGCAGAGCCAGCCAGGACATC

AGCAAGTACCTGAACTGGTACCAGCAGAAGCCCGACGGCACCGTGAAGCT

GCTGATCTACCACACCAGCCGGCTGCACAGCGGCGTGCCCAGCCGGTTCA

GCGGCAGCGGCAGCGGCACCGACTACAGCCTGACCATCAGCAACCTGGAG

CAGGAGGACATCGCCACCTACTTCTGCCAGCAGGGCAACACCCTGCCCTA

CACCTTCGGAGGCGGCACCAAGCTGGAGATCACCAAGGCCGGAGGCGGAG

GCTCTGGCGGAGGCGGCTCTGGCGGAGGCGGCTCTGGCGGAGGCGGCAGC

GAGGTGAAGCTGCAGGAGTCTGGCCCAGGCCTGGTGGCCCCAAGCCAGAG

CCTGAGCGTGACCTGCACCGTGAGCGGCGTGAGCCTGCCCGACTACGGCG

TGAGCTGGATCAGGCAGCCCCCACGGAAGGGCCTGGAGTGGCTGGGCGTG

ATCTGGGGCAGCGAGACCACCTACTACAACAGCGCCCTGAAGAGCCGGCT

GACCATCATCAAGGACAACAGCAAGAGCCAGGTGTTCCTGAAGATGAACA

GCCTGCAGACCGACGACACCGCCATCTACTACTGCGCCAAGCACTACTAC

TATGGCGGCAGCTACGCTATGGACTACTGGGGCCAGGGCACCAGCGTGAC

CGTGAGCTCAGATCCCACCACGACGCCAGCGCCGCGACCACCAACACCGG

CGCCCACCATCGCGTCGCAGCCCCTGTCCCTGCGCCCAGAGGCGTGCCGG

CCAGCGGCGGGGGCGCAGTGCACACGAGGGGGCTGGACTTCGCCTGTGA

TATCTTTTGGGTGCTGGTGGTGGTTGGTGGAGTCCTGGCTTGCTATAGCT

TGCTAGTAACAGTGGCCTTTATTATTTTCTGGGTGAGGAGTGAAGTTC

AGCAGGAGCGCAGACGCCCCGCGTACCAGCAGGGCCAGAACCAGCTCTA

TAACGAGCTCAATCTAGGACGAAGAGAGGAGTACGATGTTTTGGACAAGA

GACGTGGCCGGGACCCTGAGATGGGGGAAAGCCGAGAAGGAAGAACCCT

CAGGAAGGCCTGTACAATGAACTGCAGAAAGATAAGATGGCGGAGGCCTA

-continued
CAGTGAGATTGGGATGAAAGGCGAGCGCCGGAGGGGCAAGGGGCACGATG

GCCTTTACCAGGGTCTCAGTACAGCCACCAAGGACACCTACGACGCCCTT

CACATGCAGGCCCTGCCTCCTCGCAGAGCCGAGGGCAGGGGAAGTCTTCT

AACATGCGGGACGTGGAGGAAAATCCCGGGCCCATGGCCGTGCCCACTC

AGGTCCTGGGGTTGTTGCTACTGTGGCTTACAGATGCCAGATGTGACATC

CAGATGACACAGTCTCCATCTTCCCTGTCTGCATCTGTCGGAGATCGCGT

CACCATCACCTGTCGAGCAAGTGAGGACATTTATTTTAATTTAGTGTGGT

ATCAGCAGAAACCAGGAAAGGCCCCTAAGCTCCTGATCTATGATACAAAT

CGCTTGGCAGATGGGGTCCCATCACGGTTCAGTGGCTCTGGATCTGGCAC

ACAGTATACTCTAACCATAAGTAGCCTGCAACCCGAAGATTTCGCAACCT

ATTATTGTCAACACTATAAGAATTATCCGCTCACGTTCGGTCAGGGGACC

AAGCTGGAAATCAAAAGATCTGGTGGCGGAGGGTCAGGAGGCGGAGGCAG

CGGAGGCGGTGGCTCGGGAGGCGGAGGCTCGAGATCTGAGGTGCAGTTGG

TGGAGTCTGGGGGCGGCTTGGTGCAGCCTGGAGGGTCCCTGAGGCTCTCC

TGTGCAGCCTCAGGATTCACTCTCAGTAATTATGGCATGCACTGGATCAG

GCAGGCTCCAGGGAAGGGTCTGGAGTGGGTCTCGTCTATTAGTCTTAATG

GTGGTAGCACTTACTATCGAGACTCCGTGAAGGGCCGATTCACTATCTCC

AGGGACAATGCAAAAAGCACCCTCTACCTTCAAATGAATAGTCTGAGGGC

CGAGGACACGGCCGTCTATTACTGTGCAGCACAGGACGCTTATACGGGAG

GTTACTTTGATTACTGGGGCCAAGGAACGCTGGTCACAGTCTCGTCTATG

GATCCCGCCGAGCCCAAATCTCCTGACAAAACTCACACATGCCCACCGTG

CCCAGCACCTCCCGTGGCCGGCCCCGTCAGTCTTCCTCTTCCCCCCAAAAC

CCAAGGACACCCTCATGATCGCCCGGACCCCTGAGGTCACATGCGTGGTG

GTGGACGTGAGCCACGAAGACCCTGAGGTCAAGTTCAACTGGTACGTGGA

CGGCGTGGAGGTGCATAATGCCAAGACAAAGCCGCGGGAGGAGCAGTACA

ACAGCACGTACCGTGTGGTCAGCGTCCTCACCGTCCTGCACCAGGACTGG

CTGAATGGCAAGGAGTACAAGTGCAAGGTCTCCAACAAAGCCCTCCCAGC

CCCCATCGAGAAAACCATCTCCAAAGCCAAAGGGCAGCCCCGAGAACCAC

AGGTGTACACCCTGCCCCCATCCCGGGATGAGCTGACCAAGAACCAGGTC

AGCCTGACCTGCCTGGTCAAAGGCTTCTATCCCAGCGACATCGCCGTGGA

GTGGGAGAGCAATGGGCAACCGGAGAACAACTACAAGACCACGCCTCCCG

TGCTGGACTCCGACGGCTCCTTCTTCCTCTACAGCAAGCTCACCGTGGAC

AAGAGCAGGTGGCAGCAGGGGAACGTCTTCTCATGCTCCGTGATGCATGA

GGCCCTGCACAATCACTATACCCAGAAATCTCTGAGTCTGAGCCCAGGCA

AGAAGGACCCCAAGGCACTGATAGCATTTCTGGCATTTCTGATTATTGTG

ACATCAATAGCCCTGCTTGTTGTTCTCTACAAAATCTATGATCTACATAA

GAAAAGATCCTGCAATTTAGATGAACAGCAGGAGCTTGTTGAAAGGGATG

ATGAAAACAACTGATGAATGTGGAGCCAATCCATGCAGATATTTTGTTG

GAAACTTATAAGAGGAAGATTGCTGATGAAGGAAGACTTTTTCTGGCTGA

ATTTCAGAGCATCCCGCGGGTGTTCAGCAAGTTTCCTATAAAGGAAGCTC

GAAAGCCCTTTAACCAGAATAAAAACCGTTATGTTGACATTCTTCCTTAT

GATTATAACCGTGTTGAACTCTCTGAGATAAACGGAGATGCAGGGTCAAA

CTACATAAATGCCAGCTATATTGATGGTTTCAAAGAACCCAGGAAATACA

TTGCTGCACAAGGTCCCAGGGATGAAACTGTTGATGATTTCTGGAGGATG

ATTTGGGAACAGAAAGCCACAGTTATTGTCATGGTCACTCGATGTGAAGA

AGGAAACAGGAACAAGTGTGCAGAATACTGGCCGTCAATGGAAGAGGGCA

CTCGGGCTTTTGGAGATGTTGTTGTAAAGATCAACCAGCACAAAAGATGT

CCAGATTACATCATTCAGAAATTGAACATTGTAAATAAAAAAGAAAAAGC

AACTGGAAGAGAGGTGACTCACATTCAGTTCACCAGCTGGCCAGACCACG

GGGTGCCTGAGGATCCTCACTTGCTCCTCAAACTGAGAAGGAGAGTGAAT

GCCTTCAGCAATTTCTTCAGTGGTCCCATTGTGGTGCACTGCAGTGCTGG

TGTTGGGCGCACAGGAACCTATATCGGAATTGATGCCATGCTAGAAGGCC

TGGAAGCCGAGAACAAAGTGGATGTTTATGGTTATGTTGTCAAGCTAAGG

CGACAGAGATGCCTGATGGTTCAAGTAGAGGCCCAGTACATCTTGATCCA

TCAGGCTTTGGTGGAATACAATCAGTTTGGAGAAACAGAAGTGAATTTGT

CTGAATTACATCCATATCTACATAACATGAAGAAAAGGGATCCACCCAGT

GAGCCGTCTCCACTAGAGGCTGAATTCCAGAGACTTCCTTCATATAGGAG

CTGGAGGACACAGCACATTGGAAATCAAGAAGAAAATAAAAGTAAAAACA

GGAATTCTAATGTCATCCCATATGACTATAACAGAGTGCCACTTAAACAT

GAGCTGGAAATGAGTAAAGAGAGTGAGCATGATTCAGATGAATCCTCTGA

TGATGACAGTGATTCAGAGGAACCAAGCAAATACATCAATGCATCTTTTA

TAATGAGCTACTGGAAACCTGAAGTGATGATTGCTGCTCAGGGACCACTG

AAGGAGACCATTGGTGACTTTTGGCAGATGATCTTCCAAAGAAAAGTCAA

AGTTATTGTTATGCTGACAGAACTGAAACATGGAGACCAGGAAATCTGTG

CTCAGTACTGGGGAGAAGGAAAGCAAACATATGGAGATATTGAAGTTGAC

CTGAAAGACACAGACAAATCTTCAACTTATACCCTTCGTGTCTTTGAACT

GAGACATTCCAAGAGGAAAGACTCTCGAACTGTGTACCAGTACCAATATA

CAAACTGGAGTGTGGAGCAGCTTCCTGCAGAACCCAAGGAATTAATCTCT

ATGATTCAGGTCGTCAAACAAAAACTTCCCCAGAAGAATTCCTCTGAAGG

GAACAAGCATCACAAGAGTACACCTCTACTCATTCACTGCAGGGATGGAT

CTCAGCAAACGGGAATATTTTGTGCTTTGTTAAATCTCTTAGAAAGTGCG

GAAACAGAAGAGGTAGTGGATATTTTTCAAGTGGTAAAAGCTCTACGCAA

AGCTAGGCCAGGCATGGTTTCCACATTCGAGCAATATCAATTCCTATATG

ACGTCATTGCCAGCACCTACCCTGCTCAGAATGGACAAGTAAAGAAAAAC

AACCATCAAGAAGATAAAATTGAATTTGATAATGAAGTGGACAAAGTAAA

GCAGGATGCTAATTGTGTTAATCCACTTGGTGCCCCAGAAAAGCTCCCTG

AAGCAAAGGAACAGGCTGAAGGTTCTGAACCCACGAGTGGCACTGAGGGG

CCAGAACATTCTGTCAATGGTCCTGCAAGTCCAGCTTTAAATCAAGGTTC

ATAG

SEQ ID No. 37:
>MP14801.SFG.aCD19fmc63_clean-CD8STK-
CD28tmZ-2A-aCD33glx-HCH2CH3pvaa-dCD148
ATGAGCCTGCCCGTGACCGCCCTGCTGCTGCCCCTGGCCCTGCTGCTGCA

CGCCGCCAGACCAGACATCCAGATGACCCAGACCACCAGCAGCCTGAGCG

CCAGCCTGGGCGACCGGGTGACCATCAGCTGCAGAGCCAGCCAGGACATC

AGCAAGTACCTGAACTGGTACCAGCAGAAGCCCGACGGCACCGTGAAGCT

GCTGATCTACCACACCAGCCGGCTGCACAGCGGCGTGCCCAGCCGGTTCA

GCGGCAGCGGCAGCGGCACCGACTACAGCCTGACCATCAGCAACCTGGAG

CAGGAGGACATCGCCACCTACTTCTGCCAGCAGGGCAACACCCTGCCCTA

CACCTTCGGAGGCGGCACCAAGCTGGAGATCACCAAGGCCGGAGGCGGAG

GCTCTGGCGGAGGCGGCTCTGGCGGAGGCGGCTCTGGCGGAGGCGGCAGC

GAGGTGAAGCTGCAGGAGTCTGGCCCAGGCCTGGTGGCCCCAAGCCAGAG

CCTGAGCGTGACCTGCACCGTGAGCGGCGTGAGCCTGCCCGACTACGGCG

TGAGCTGGATCAGGCAGCCCCCACGGAAGGGCCTGGAGTGGCTGGGCGTG

ATCTGGGGCAGCGAGACCACCTACTACAACAGCGCCCTGAAGAGCCGGCT

GACCATCATCAAGGACAACAGCAAGAGCCAGGTGTTCCTGAAGATGAACA

GCCTGCAGACCGACGACACCGCCATCTACTACTGCGCCAAGCACTACTAC

TATGGCGGCAGCTACGCTATGGACTACTGGGGCCAGGGCACCAGCGTGAC

CGTGAGCTCAGATCCCACCACGACGCCAGCGCCGCGACCACCAACACCGG

CGCCCACCATCGCGTCGCAGCCCCTGTCCCTGCGCCCAGAGGCGTGCCGG

CCAGCGGCGGGGGGCGCAGTGCACACGAGGGGGCTGGACTTCGCCTGTGA

TATCTTTTGGGTGCTGGTGGTGGTTGGTGGAGTCCTGGCTTGCTATAGCT

TGCTAGTAACAGTGGCCTTTATTATTTTCTGGGTGAGGAGTAAGAGGAGC

AGGCTCCTGCACAGTGACTACATGAACATGACTCCCCGCCGCCCCGGGCC

CACCCGCAAGCATTACCAGCCCTATGCCCCACCACGCGACTTCGCAGCCT

ATCGCTCCAGAGTGAAGTTCAGCAGGAGCGCAGACGCCCCCGCGTACCAG

CAGGGCCAGAACCAGCTCTATAACGAGCTCAATCTAGGACGAAGAGAGGA

GTACGATGTTTTGGACAAGAGACGTGGCCGGGACCCTGAGATGGGGGGAA

AGCCGAGAAGGAAGAACCCTCAGGAAGGCCTGTACAATGAACTGCAGAAA

GATAAGATGGCGGAGGCCTACAGTGAGATTGGGATGAAAGGCGAGCGCCG

GAGGGGCAAGGGGCACGATGGCCTTTACCAGGGTCTCAGTACAGCCACCA

AGGACACCTACGACGCCCTTCACATGCAGGCCCTGCCTCCTCGCAGAGCC

GAGGCAGGGGAAGTCTTCTAACATGCGGGACGTGGAGGAAAATCCCGGGC

CCATGGCCGTGCCCACTCAGGTCCTGGGGTTGTTGCTACTGTGGCTTACA

GATGCCAGATGTGACATCCAGATGACACAGTCTCCATCTTCCCTGTCTGC

ATCTGTCGGAGATCGCGTCACCATCACCTGTCGAGCAAGTGAGGACATTT

ATTTTAATTTAGTGTGGTATCAGCAGAAACCAGGAAAGGCCCCTAAGCTC

CTGATCTATGATACAAATCGCTTGGCAGATGGGGTCCCATCACGGTTCAG

TGGCTCTGGATCTGGCACACAGTATACTCTAACCATAAGTAGCCTGCAAC

CCGAAGATTTCGCAACCTATTATTGTCAACACTATAAGAATTATCCGCTC

ACGTTCGGTCAGGGGACCAAGCTGGAAATCAAAGATCTGGTGGCGGAGGG

TCAGGAGGCGGAGGCAGCGGAGGCGGTGGCTCGGGAGGCGGAGGCTCGAG

ATCTGAGGTGCAGTTGGTGGAGTCTGGGGGCGGCTTGGTGCAGCCTGGAG

GGTCCCTGAGGCTCTCC

-continued

```
TGTGCAGCCTCAGGATTCACTCTCAGTAATTATGGCATGCACTGGATCAG
GCAGGCTCCAGGGAAGGGTCTGGAGTGGGTCTCGTCTATTAGTCTTAATG
GTGGTAGCACTTACTATCGAGACTCCGTGAAGGGCCGATTCACTATCTCC
AGGGACAATGCAAAAAGCACCCTCTACCTTCAAATGAATAGTCTGAGGGC
CGAGGACACGGCCGTCTATTACTGTGCAGCACAGGACGCTTATACGGGAG
GTTACTTTGATTACTGGGGCCAAGGAACGCTGGTCACAGTCTCGTCTATG
GATCCCGCCGAGCCCAAATCTCCTGACAAAACTCACACATGCCCACCGTG
CCCAGCACCTCCCGTGGCCGGCCCGTCAGTCTTCCTCTTCCCCCCAAAAC
CCAAGGACACCCTCATGATCGCCCGGACCCCTGAGGTCACATGCGTGGTG
GTGGACGTGAGCCACGAAGACCCTGAGGTCAAGTTCAACTGGTACGTGGA
CGGCGTGGAGGTGCATAATGCCAAGACAAAGCCGCGGGAGGAGCAGTACA
ACAGCACGTACCGTGTGGTCAGCGTCCTCACCGTCCTGCACCAGGACTGG
CTGAATGGCAAGGAGTACAAGTGCAAGGTCTCCAACAAAGCCCTCCCAGC
CCCCATCGAGAAAACCATCTCCAAAGCCAAAGGGCAGCCCCGAGAACCAC
AGGTGTACACCCTGCCCCCATCCCGGGATGAGCTGACCAAGAACCAGGTC
AGCCTGACCTGCCTGGTCAAAGGCTTCTATCCCAGCGACATCGCCGTGGA
GTGGGAGAGCAATGGGCAACCGGAGAACAACTACAAGACCACGCCTCCCG
TGCTGGACTCCGACGGCTCCTTCTTCCTCTACAGCAAGCTCACCGTGGAC
AAGAGCAGGTGGCAGCAGGGGAACGTCTTCTCATGCTCCGTGATGCATGA
GGCCCTGCACAATCACTATACCCAGAAATCTCTGAGTCTGAGCCCAGGCA
AGAAGGACCCCAAGGCGGTTTTTGGCTGTATCTTTGGTGCCCTGGTTATT
GTGACTGTGGGAGGCTTCATCTTCTGGAGAAGAAGAGGAAAGATGCAAA
GAATAATGAAGTGTCCTTTTCTCAAATTAAACCTAAAAAATCTAAGTTAA
TCAGAGTGGAGAATTTTGAGGCCTACTTCAAGAAGCAGCAAGCTGACTCC
AACTGTGGGTTCGCAGAGGAATACGAAGATCTGAAGCTTGTTGGAATTAG
TCAACCTAAATATGCAGCAGAACTGGCTGAGAATAGAGGAAAGAATCGCT
ATAATAATGTTCTGCCCTATGATATTTCCCGTGTCAAACTTTCGGTCCAG
ACCCATTCAACGGATGACTACATCAATGCCAACTACATGCCTGGCTACCA
CTCCAAGAAAGATTTTATTGCCACACAAGGACCTTTACCGAACACTTTGA
AAGATTTTTGGCGTATGGTTTGGGAGAAAAATGTATATGCCATCATTATG
TTGACTAAATGTGTTGAACAGGGAAGAACCAAATGTGAGGAGTATTGGCC
CTCCAAGCAGGCTCAGGACTATGGAGACATAACTGTGGCAATGACATCAG
AAATTGTTCTTCCGGAATGGACCATCAGAGATTTCACAGTGAAAAATATC
CAGACAAGTGAGAGTCACCCTCTGAGACAGTTCCATTTCACCTCCTGGCC
AGACCACGGTGTTCCCGACACCACTGACCTGCTCATCAACTTCCGGTACC
TCGTTCGTGACTACATGAAGCAGAGTCCTCCCGAATCGCCGATTCTGGTG
CATTGCAGTGCTGGGGTCGGAAGGACGGGCACTTTCATTGCCATTGATCG
TCTCATCTACCAGATAGAGAATGAGAACACCGTGGATGTGTATGGGATTG
TGTATGACCTTCGAATGCATAGGCCTTTAATGGTGCAGACAGAGGACCAG
TATGTTTTCCTCAATCAGTGTGTTTTGGATATTGTCAGATCCCAGAAAGA
```

-continued

```
CTCAAAAGTAGATCTTATCTACCAGAACACAACTGCAATGACAATCTATG
AAAACCTTGCGCCCGTGACCACATTTGGAAAGACCAATGGTTACATCGCC
TAA
```

SEQ ID No. 38
>16076.SFG.aCD19fmc63-CD8STK-CD28tmZ-2A-
aCD33glx-muCD8STK-tm-dPTPN6
```
ATGAGCCTGCCCGTGACCGCCCTGCTGCTGCCCCTGGCCCTGCTGCTGCA
CGCCGCCAGACCAGACATCCAGATGACCCAGACCACCAGCAGCCTGAGCG
CCAGCCTGGGCGACCGGGTGACCATCAGCTGCAGAGCCAGCCAGGACATC
AGCAAGTACCTGAACTGGTACCAGCAGAAGCCCGACGGCACCGTGAAGCT
GCTGATCTACCACACCAGCCGGCTGCACAGCGGCGTGCCCAGCCGGTTCA
GCGGCAGCGGCAGCGGCACCGACTACAGCCTGACCATCAGCAACCTGGAG
CAGGAGGACATCGCCACCTACTTCTGCCAGCAGGGCAACACCCTGCCCTA
CACCTTCGGAGGCGGCACCAAGCTGGAGATCACCAAGGCCGGAGGCGGAG
GCTCTGGCGGAGGCGGCTCTGGCGGAGGCGGCTCTGGCGGAGGCGGCAGC
GAGGTGAAGCTGCAGGAGTCTGGCCCAGGCCTGGTGGCCCCAAGCCAGAG
CCTGAGCGTGACCTGCACCGTGAGCGGCGTGAGCCTGCCCGACTACGGCG
TGAGCTGGATCAGGCAGCCCCACGGAAGGGCCTGGAGTGGCTGGGCGTG
ATCTGGGGCAGCGAGACCACCTACTACAACAGCGCCCTGAAGAGCCGGCT
GACCATCATCAAGGACAACAGCAAGAGCCAGGTGTTCCTGAAGATGAACA
GCCTGCAGACCGACGACACCGCCATCTACTACTGCGCCAAGCACTACTAC
TATGGCGGCAGCTACGCTATGGACTACTGGGGCCAGGGCACCAGCGTGAC
CGTGAGCTCAGATCCCACCACGACGCCAGCGCCGCGACCACCAACACCGG
CGCCCACCATCGCGTCGCAGCCCCTGTCCCTGCGCCCAGAGGCGTGCCGG
CCAGCGGCGGGGGCGCAGTGCACACGAGGGGGCTGGACTTCGCCTGTGA
TATCTTTTGGGTGCTGGTGGTGGTTGGTGGAGTCCTGGCTTGCTATAGCT
TGCTAGTAACAGTGGCCTTTATTATTTTCTGGGTGAGGAGAGTGAAGTTC
AGCAGGAGCGCAGACGCCCCCGCGTACCAGCAGGGCCAGAACCAGCTCTA
TAACGAGCTCAATCTAGGACGAAGAGAGGAGTACGATGTTTTGGACAAGA
GACGTGGCCGGGACCCTGAGATGGGGGGAAAGCCGAGAAGGAAGAACCCT
CAGGAAGGCCTGTACAATGAACTGCAGAAAGATAAGATGGCGGAGGCCTA
CAGTGAGATTGGGATGAAAGGCGAGCGCCGGAGGGGCAAGGGGCACGATG
GCCTTTACCAGGGTCTCAGTACAGCCACCAAGGACACCTACGACGCCCTT
CACATGCAGGCCCTGCCTCCTCGCAGAGCCGAGGGCAGGGGAAGTCTTCT
AACATGCGGGACGTGGAGGAAATCCCGGGCCCATGGCCGTGCCCACTC
AGGTCCTGGGGTTGTTGCTACTGTGGCTTACAGATGCCAGATGTGACATC
CAGATGACACAGTCTCCATCTTCCCTGTCTGCATCTGTCGGAGATCGCGT
CACCATCACCTGTCGAGCAAGTGAGGACATTTATTTTAATTTAGTGTGGT
ATCAGCAGAAACCAGGAAAGGCCCCTAAGCTCCTGATCTATGATACAAAT
CGCTTGGCAGATGGGGTCCCATCACGGTTCAGTGGCTCTGGATCTGGCAC
ACAGTATACTCTAACCATAAGTAGCCTGCAACCCGAAGATTTCGCAACCT
ATTATTGTCAACACTATAAGAATTATCCGCTCACGTTCGGTCAGGGGACC
```

-continued

AAGCTGGAAATCAAAAGATCTGGTGGCGGAGGGTCAGGAGGCGGAGGCAG
CGGAGGCGGTGGCTCGGGAGGCGGAGGCTCGAGATCTGAGGTGCAGTTGG
TGGAGTCTGGGGGCGGCTTGGTGCAGCCTGGAGGGTCCCTGAGGCTCTCC
TGTGCAGCCTCAGGATTCACTCTCAGTAATTATGGCATGCACTGGATCAG
GCAGGCTCCAGGGAAGGGTCTGGAGTGGGTCTCGTCTATTAGTCTTAATG
GTGGTAGCACTTACTATCGAGACTCCGTGAAGGGCCGATTCACTATCTCC
AGGGACAATGCAAAAGCACCCTCTACCTTCAAATGAATAGTCTGAGGGC
CGAGGACACGGCCGTCTATTACTGTGCAGCACAGGACGCTTATACGGGAG
GTTACTTTGATTACTGGGGCCAAGGAACGCTGGTCACAGTCTCGTCTATG
GATCCCGCCACCACAACCAAGCCCGTGCTGCGGACCCCAAGCCCTGTGCA
CCCTACCGGCACCAGCCAGCCTCAGAGACCCGAGGACTGCCGGCCTCGGG
GCAGCGTGAAGGGCACCGGCCTGGACTTCGCCTGCGACATCTACTGGGCA
CCTCTGGCCGGAATATGCGTGGCACTGCTGCTGAGCCTCATCATCACCCT
GATCTGTTATCACCGAAGCCGCAAGCGGGTGTGTAAAAGTGGAGGCGGAA
GCTTCTGGGAGGAGTTTGAGAGTTTGCAGAAGCAGGAGGTGAAGAACTTG
CACCAGCGTCTGGAAGGGCAGCGGCCAGAGAACAAGGGCAAGAACCGCTA
CAAGAACATTCTCCCCTTTGACCACAGCCGAGTGATCCTGCAGGGACGGG
ACAGTAACATCCCCGGGTCCGACTACATCAATGCCAACTACATCAAGAAC
CAGCTGCTAGGCCCTGATGAGAACGCTAAGACCTACATCGCCAGCCAGGG
CTGTCTGGAGGCCACGGTCAATGACTTCTGGCAGATGGCGTGGCAGGAGA
ACAGCCGTGTCATCGTCATGACCACCCGAGAGGTGGAGAAAGGCCGGAAC
AAATGCGTCCCATACTGGCCCGAGGTGGGCATGCAGCGTGCTTATGGGCC
CTACTCTGTGACCAACTGCGGGGAGCATGACACAACCGAATACAAACTCC
GTACCTTACAGGTCTCCCCGCTGGACAATGGAGACCTGATTCGGGAGATC
TGGCATTACCAGTACCTGAGCTGGCCCGACCACGGGGTCCCCAGTGAGCC
TGGGGGTGTCCTCAGCTTCCTGGACCAGATCAACCAGCGGCAGGAAAGTC
TGCCTCACGCAGGGCCCATCATCGTGCACTGCAGCGCCGGCATCGGCCGC
ACAGGCACCATCATTGTCATCGACATGCTCATGGAGAACATCTCCACCAA
GGGCCTGGACTGTGACATTGACATCCAGAAGACCATCCAGATGGTGCGGG
CGCAGCGCTCGGGCATGGTGCAGACGGAGGCGCAGTACAAGTTCATCTAC
GTGGCCATCGCCCAGTTCATTGAAACCACTAAGAAGAAGCTGTGA

SEQ ID No. 39
>MP16091.SFG.aCD19fmc63-CD8STK-CD28tmZ-2A-
aCD33glx-muCD8STK-LAIR1tm-endo
ATGAGCCTGCCCGTGACCGCCCTGCTGCTGCCCCTGGCCCTGCTGCTGCA
CGCCGCCAGACCAGACATCCAGATGACCCAGACCACCAGCAGCCTGAGCG
CCAGCCTGGGCGACCGGGTGACCATCAGCTGCAGAGCCAGCCAGGACATC
AGCAAGTACCTGAACTGGTACCAGCAGAAGCCCGACGGCACCGTGAAGCT
GCTGATCTACCACACCAGCCGGCTGCACAGCGGCGTGCCCAGCCGGTTCA
GCGGCAGCGGCAGCGGCACCGACTACAGCCTGACCATCAGCAACCTGGAG
CAGGAGGACATCGCCACCTACTTCTGCCAGCAGGGCAACACCCTGCCCTA
CACCTTCGGAGGCGGCACCAAGCTGGAGATCACCAAGGCCGGAGGCGGAG -continued GCTCTGGCGGAGGCGGCTCTGGCGGAGGCGGCTCTGGCGGAGGCGGCAGC
GAGGTGAAGCTGCAGGAGTCTGGCCCAGGCCTGGTGGCCCCAAGCCAGAG
CCTGAGCGTGACCTGCACCGTGAGCGGCGTGAGCCTGCCCGACTACGGCG
TGAGCTGGATCAGGCAGCCCCCACGGAAGGGCCTGGAGTGGCTGGGCGTG
ATCTGGGGCAGCGAGACCACCTACTACAACAGCGCCCTGAAGAGCCGGCT
GACCATCATCAAGGACAACAGCAAGAGCCAGGTGTTCCTGAAGATGAACA
GCCTGCAGACCGACGACACCGCCATCTACTACTGCGCCAAGCACTACTAC
TATGGCGGCAGCTACGCTATGGACTACTGGGGCCAGGGCACCAGCGTGAC
CGTGAGCTCAGATCCCACCACGACGCCAGCGCCGCGACCACCAACACCGG
CGCCCACCATCGCGTCGCAGCCCCTGTCCCTGCGCCCAGAGGCGTGCCGG
CCAGCGGCGGGGGCGCAGTGCACACGAGGGGGCTGGACTTCGCCTGTGA
TATCTTTTGGGTGCTGGTGGTGGTTGGTGGAGTCCTGGCTTGCTATAGCT
TGCTAGTAACAGTGGCCTTTATTATTTTCTGGGTGAGGAGAGTGAAGTTC
AGCAGGAGCGCAGACGCCCCCGCGTACCAGCAGGGCCAGAACCAGCTCTA
TAACGAGCTCAATCTAGGACGAAGAGAGGAGTACGATGTTTTGGACAAGA
GACGTGGCCGGGACCCTGAGATGGGGGGAAAGCCGAGAAGGAAGAACCCT
CAGGAAGGCCTGTACAATGAACTGCAGAAAGATAAGATGGCGGAGGCCTA
CAGTGAGATTGGGATGAAAGGCGAGCGCCGGAGGGGCAAGGGGCACGATG
GCCTTTACCAGGGTCTCAGTACAGCCACCAAGGACACCTACGACGCCCTT
CACATGCAGGCCCTGCCTCCTCGCAGAGCCGAGGGCAGGGGAAGTCTTCT
AACATGCGGGACGTGGAGGAAAATCCCGGGCCCATGGCCGTGCCCACTC
AGGTCCTGGGGTTGTTGCTACTGTGGCTTACAGATGCCAGATGTGACATC
CAGATGACACAGTCTCCATCTTCCCTGTCTGCATCGTCGGAGATCGCGT
CACCATCACCTGTCGAGCAAGTGAGGACATTTATTTTAATTTAGTGTGGT
ATCAGCAGAAACCAGGAAAGGCCCCTAAGCTCCTGATCTATGATACAAAT
CGCTTGGCAGATGGGGTCCCATCACGGTTCAGTGGCTCTGGATCTGGCAC
ACAGTATACTCTAACCATAAGTAGCCTGCAACCCGAAGATTTCGCAACCT
ATTATTGTCAACACTATAAGAATTATCCGCTCACGTTCGGTCAGGGGACC
AAGCTGGAAATCAAAAGATCTGGTGGCGGAGGGTCAGGAGGCGGAGGCAG
CGGAGGCGGTGGCTCGGGAGGCGGAGGCTCGAGATCTGAGGTGCAGTTGG
TGGAGTCTGGGGGCGGCTTGGTGCAGCCTGGAGGGTCCCTGAGGCTCTCC
TGTGCAGCCTCAGGATTCACTCTCAGTAATTATGGCATGCACTGGATCAG
GCAGGCTCCAGGGAAGGGTCTGGAGTGGGTCTCGTCTATTAGTCTTAATG
GTGGTAGCACTTACTATCGAGACTCCGTGAAGGGCCGATTCACTATCTCC
AGGGACAATGCAAAAGCACCCTCTACCTTCAAATGAATAGTCTGAGGGC
CGAGGACACGGCCGTCTATTACTGTGCAGCACAGGACGCTTATACGGGAG
GTTACTTTGATTACTGGGGCCAAGGAACGCTGGTCACAGTCTCGTCTATG
GATCCCGCCACCACAACCAAGCCCGTGCTGCGGACCCCAAGCCCTGTGCA
CCCTACCGGCACCAGCCAGCCTCAGAGACCCGAGGACTGCCGGCCTCGGG
GCAGCGTGAAGGGCACCGGCCTGGACTTCGCCTGCGACATTCTCATCGGG
GTCTCAGTGGTCTTCCTCTTCTGTCTCCTCCTCCTGGTCCTCTTCTGCCT -continued

CCATCGCCAGAATCAGATAAAGCAGGGGCCCCCCAGAAGCAAGGACGAGG

AGCAGAAGCCACAGCAGAGGCCTGACCTGGCTGTTGATGTTCTAGAGAGG

ACAGCAGACAAGGCCACAGTCAATGGACTTCCTGAGAAGGACCGGGAGAC

CGACACCAGCGCCCTGGCTGCAGGGAGTTCCCAGGAGGTGACGTATGCTC

AGCTGGACCACTGGGCCCTCACACAGAGGACAGCCCGGGCTGTGTCCCCA

CAGTCCACAAAGCCCATGGCCGAGTCCATCACGTATGCAGCCGTTGCCAG

ACACTGA

SEQ ID no. 40
>MP16092.SFG.aCD19fmc63-CD8STK-CD28tmZ-2A-
aCD33glx-muCD8STK-LAIR1tm-endo-2A-
PTPN6_SH2-dCD148
ATGAGCCTGCCCGTGACCGCCCTGCTGCTGCCCCTGGCCCTGCTGCTGCA

CGCCGCCAGACCAGACATCCAGATGACCCAGACCACCAGCAGCCTGAGCG

CCAGCCTGGGCGACCGGGTGACCATCAGCTGCAGAGCCAGCCAGGACATC

AGCAAGTACCTGAACTGGTACCAGCAGAAGCCCGACGGCACCGTGAAGCT

GCTGATCTACCACACCAGCCGGCTGCACAGCGGCGTGCCCAGCCGGTTCA

GCGGCAGCGGCAGCGGCACCGACTACAGCCTGACCATCAGCAACCTGGAG

CAGGAGGACATCGCCACCTACTTCTGCCAGCAGGGCAACACCCTGCCCTA

CACCTTCGGAGGCGGCACCAAGCTGGAGATCACCAAGGCCGGAGGCGGAG

GCTCTGGCGGAGGCGGCTCTGGCGGAGGCGGCTCTGGCGGAGGCGGCAGC

GAGGTGAAGCTGCAGGAGTCTGGCCCAGGCCTGGTGGCCCCAAGCCAGAG

CCTGAGCGTGACCTGCACCGTGAGCGGCGTGAGCCTGCCCGACTACGGCG

TGAGCTGGATCAGGCAGCCCCCACGGAAGGGCCTGGAGTGGCTGGGCGTG

ATCTGGGGCAGCGAGACCACCTACTACAACAGCGCCCTGAAGAGCCGGCT

GACCATCATCAAGGACAACAGCAAGAGCCAGGTGTTCCTGAAGATGAACA

GCCTGCAGACCGACGACACCGCCATCTACTACTGCGCCAAGCACTACTAC

TATGGCGGCAGCTACGCTATGGACTACTGGGGCCAGGGCACCAGCGTGAC

CGTGAGCTCAGATCCCACCACGACGCCAGCGCCGCGACCACCAACACCGG

CGCCCACCATCGCGTCGCAGCCCCTGTCCCTGCGCCCAGAGGCGTGCCGG

CCAGCGGCGGGGGCGCAGTGCACACGAGGGGGCTGGACTTCGCCTGTGA

TATCTTTTGGGTGCTGGTGGTGGTTGGTGGAGTCCTGGCTTGCTATAGCT

TGCTAGTAACAGTGGCCTTTATTATTTTCTGGGTGAGGAGAGTGAAGTTC

AGCAGGAGCGCAGACGCCCCCGCGTACCAGCAGGGCCAGAACCAGCTCTA

TAACGAGCTCAATCTAGGACGAAGAGAGGAGTACGATGTTTTGGACAAGA

GACGTGGCCGGGACCCTGAGATGGGGGGAAAGCCGAGAAGGAAGAACCCT

CAGGAAGGCCTGTACAATGAACTGCAGAAAGATAAGATGGCGGAGGCCTA

CAGTGAGATTGGGATGAAAGGCGAGCGCCGGAGGGGCAAGGGGCACGATG

GCCTTTACCAGGGTCTCAGTACAGCCACCAAGGACACCTACGACGCCCTT

CACATGCAGGCCCTGCCTCCTCGCAGAGCCGAGGGCAGGGGAAGTCTTCT

AACATGCGGGGACGTGGAGGAAAATCCCGGGCCCATGGCCGTGCCCACTC

AGGTCCTGGGGTTGTTGCTACTGTGGCTTACAGATGCCAGATGTGACATC

CAGATGACACAGTCTCCATCTTCCCTGTCTGCATCTGTCGGAGATCGCGT

CACCATCACCTGTCGAGCAAGTGAGGACATTTATTTTTAATTTAGTGTGGT

ATCAGCAGAAACCAGGAAAGGCCCCTAAGCTCCTGATCTATGATACAAAT

CGCTTGGCAGATGGGGTCCCATCACGGTTCAGTGGCTCTGGATCTGGCAC

ACAGTATACTCTAACCATAAGTAGCCTGCAACCCGAAGATTTCGCAACCT

ATTATTGTCAACACTATAAGAATTATCCGCTCACGTTCGGTCAGGGGACC

AAGCTGGAAATCAAAAGATCTGGTGGCGGAGGGTCAGGAGGCGGAGGCAG

CGGAGGCGGTGGCTCGGGAGGCGGAGGCTCGAGATCTGAGGTGCAGTTGG

TGGAGTCTGGGGGCGGCTTGGTGCAGCCTGGAGGGTCCCTGAGGCTCTCC

TGTGCAGCCTCAGGATTCACTCTCAGTAATTATGGCATGCACTGGATCAG

GCAGGCTCCAGGGAAGGGTCTGGAGTGGGTCTCGTCTATTAGTCTTAATG

GTGGTAGCACTTACTATCGAGACTCCGTGAAGGGCCGATTCACTATCTCC

AGGGACAATGCAAAAAGCACCCTCTACCTTCAAATGAATAGTCTGAGGGC

CGAGGACACGGCCGTCTATTACTGTGCAGCACAGGACGCTTATACGGGAG

GTTACTTTGATTACTGGGGCCAAGGAACGCTGGTCACAGTCTCGTCTATG

GATCCCGCCACCACAACCAAGCCCGTGCTGCGGACCCCAAGCCCTGTGCA

CCCTACCGGCACCAGCCAGCCTCAGAGACCCGAGGACTGCCGGCCTCGGG

GCAGCGTGAAGGGCACCGGCCTGGACTTCGCCTGCGACATTCTCATCGGG

GTCTCAGTGGTCTTCCTCTTCTGTCTCCTCCTCCTGGTCCTCTTCTGCCT

CCATCGCCAGAATCAGATAAAGCAGGGGCCCCCCAGAAGCAAGGACGAGG

AGCAGAAGCCACAGCAGAGGCCTGACCTGGCTGTTGATGTTCTAGAGAGG

ACAGCAGACAAGGCCACAGTCAATGGACTTCCTGAGAAGGACCGGGAGAC

CGACACCAGCGCCCTGGCTGCAGGGAGTTCCCAGGAGGTGACGTATGCTC

AGCTGGACCACTGGGCCCTCACACAGAGGACAGCCCGGGCTGTGTCCCCA

CAGTCCACAAAGCCCATGGCCGAGTCCATCACGTATGCAGCCGTTGCCAG

ACACAGGGCAGAAGGAAGAGGTAGCCTGCTGACTTGCGGGGACGTGGAAG

AGAACCCAGGGCCATGGTATCATGGCCACATGTCTGGCGGGCAGGCAGAG

ACGCTGCTGCAGGCCAAGGGCGAGCCCTGGACTTTCTTGTGCGTGAGAG

CCTCAGCCAGCCTGGAGACTTCGTGCTTTCTGTGCTCAGTGACCAGCCCA

AGGCTGGCCCAGGCTCCCCGCTCAGGGTCACCCACATCAAGGTCATGTGC

GAGGGTGGACGCTACACAGTGGGTGGTTTGGAGACCTTCGACAGCCTCAC

GGACCTGGTGGAGCATTTCAAGAAGACGGGGATTGAGGAGGCCTCAGGCG

CCTTTGTCTACCTGCGGCAGCCGTACAGCGGTGGCGGTGGCAGCTTTGAG

GCCTACTTCAAGAAGCAGCAAGCTGACTCCAACTGTGGGTTCGCAGAGGA

ATACGAAGATCTGAAGCTTGTTGGAATTAGTCAACCTAAATATGCAGCAG

AACTGGCTGAGAATAGAGGAAAGAATCGCTATAATAATGTTCTGCCCTAT

GATATTTCCCGTGTCAAACTTTCGGTCCAGACCCATTCAACGGATGACTA

CATCAATGCCAACTACATGCCTGGCTACCACTCCAAGAAAGATTTATTG

CCACACAAGGACCTTTACCGAACACTTTGAAAGATTTTGGCGTATGGTT

TGGGAGAAAAATGTATATGCCATCATTATGTTGACTAAATGTGTTGAACA

GGGAAGAACCAAATGTGAGGAGTATTGGCCCTCCAAGCAGGCTCAGGACT

ATGGAGACATAACTGTGGCAATGACATCAGAAATTGTTCTTCCGGAATGG

```
ACCATCAGAGATTTCACAGTGAAAAATATCCAGACAAGTGAGAGTCACCC
TCTGAGACAGTTCCATTTCACCTCCTGGCCAGACCACGGTGTTCCCGACA
CCACTGACCTGCTCATCAACTTCCGGTACCTCGTTCGTGACTACATGAAG
CAGAGTCCTCCCGAATCGCCGATTCTGGTGCATTGCAGTGCTGGGGTCGG
AAGGACGGGCACTTTCATTGCCATTGATCGTCTCATCTACCAGATAGAGA
ATGAGAACACCGTGGATGTGTATGGGATTGTGTATGACCTTCGAATGCAT
AGGCCTTTAATGGTGCAGACAGAGGACCAGTATGTTTTCCTCAATCAGTG
TGTTTTGGATATTGTCAGATCCCAGAAAGACTCAAAAGTAGATCTTATCT
ACCAGAACACAACTGCAATGACAATCTATGAAAACCTTGCGCCCGTGACC
ACATTTGGAAAGACCAATGGTTACATCGCCAGCGGTAGCTAA
```

The nucleic acid sequence may encode the same amino acid sequence as that encoded by SEQ ID No. 35, 36, 37, 38, 39 or 40, but may have a different nucleic acid sequence, due to the degeneracy of the genetic code. The nucleic acid sequence may have at least 80, 85, 90, 95, 98 or 99% identity to the sequence shown as SEQ ID No. 35, 36, 37, 38, 39 or 40, provided that it encodes a first CAR and a second CAR as defined in the first aspect of the invention.

Vector

The present invention also provides a vector, or kit of vectors which comprises one or more CAR-encoding nucleic acid sequence(s). Such a vector may be used to introduce the nucleic acid sequence(s) into a host cell so that it expresses the first and second CARs.

The vector may, for example, be a plasmid or a viral vector, such as a retroviral vector or a lentiviral vector, or a transposon based vector or synthetic mRNA.

The vector may be capable of transfecting or transducing a T cell.

Pharmaceutical Composition

The present invention also relates to a pharmaceutical composition containing a plurality of CAR-expressing cells, such as T cells or NK cells according to the first aspect of the invention. The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The T cells of the present invention may be capable of killing target cells, such as cancer cells. The target cell may be recognisable by a defined pattern of antigen expression, for example the expression of antigen A AND antigen B; the expression of antigen A OR antigen B; or the expression of antigen A AND NOT antigen B or complex iterations of these gates.

T cells of the present invention may be used for the treatment of an infection, such as a viral infection.

T cells of the invention may also be used for the control of pathogenic immune responses, for example in autoimmune diseases, allergies and graft-vs-host rejection.

T cells of the invention may be used for the treatment of a cancerous disease, such as bladder cancer, breast cancer, colon cancer, endometrial cancer, kidney cancer (renal cell), leukemia, lung cancer, melanoma, non-Hodgkin lymphoma, pancreatic cancer, prostate cancer and thyroid cancer.

It is particularly suited for treatment of solid tumours where the availability of good selective single targets is limited.

T cells of the invention may be used to treat: cancers of the oral cavity and pharynx which includes cancer of the tongue, mouth and pharynx; cancers of the digestive system which includes oesophageal, gastric and colorectal cancers; cancers of the liver and biliary tree which includes hepatocellular carcinomas and cholangiocarcinomas; cancers of the respiratory system which includes bronchogenic cancers and cancers of the larynx; cancers of bone and joints which includes osteosarcoma; cancers of the skin which includes melanoma; breast cancer; cancers of the genital tract which include uterine, ovarian and cervical cancer in women, prostate and testicular cancer in men; cancers of the renal tract which include renal cell carcinoma and transitional cell carcinomas of the utterers or bladder; brain cancers including gliomas, glioblastoma multiforme and medullobastomas; cancers of the endocrine system including thyroid cancer, adrenal carcinoma and cancers associated with multiple endocrine neoplasm syndromes; lymphomas including Hodgkin's lymphoma and non-Hodgkin lymphoma; Multiple Myeloma and plasmacytomas; leukaemias both acute and chronic, myeloid or lymphoid; and cancers of other and unspecified sites including neuroblastoma.

Treatment with the T cells of the invention may help prevent the escape or release of tumour cells which often occurs with standard approaches.

The invention will now be further described by way of Examples, which are meant to serve to assist one of ordinary skill in the art in carrying out the invention and are not intended in any way to limit the scope of the invention.

EXAMPLES

Example 1—Creation of Target Cell Populations

For the purposes of proving the principle of the invention, receptors based on anti-CD19 and anti-CD33 were arbitrarily chosen. Using retroviral vectors, CD19 and CD33 were cloned. These proteins were truncated so that they do not signal and could be stably expressed for prolonged periods. Next, these vectors were used to transduce the SupT1 cell line either singly or doubly to establish cells negative for both antigen (the wild-type), positive for either and positive for both. The expression data are shown in FIG. 3.

Example 2—Design and Function of the OR Gate

To construct the OR gate, a pair of receptors recognizing CD19 and CD33 were co-expressed. Different spacers were used to prevent cross-pairing. Both receptors had a transmembrane domain derived from CD28 to improve surface stability and an endodomain derived from that of CD3 Zeta to provide a simple activating signal. In this way, a pair of independent $1^{st}$ generation CARs were co-expressed. The retroviral vector cassette used to co-express the sequences utilizes a foot-and-mouth 2A self-cleaving peptide to allow co-expression 1:1 of both receptors. The cassette design is shown in FIG. 4, and the protein structures in FIG. 5. The nucleotide sequence of homologous regions was codon-wobbled to prevent recombination during retroviral vector reverse transcription.

Example 3—Testing the OR Gate

Expression of both CARs was tested on the T-cell surface by staining with cognate antigen fused to Fc. By using different species of Fc domains (mouse for CD19 and rabbit for CD33), co-expression of both CARs was determined on the cell surface by staining with different secondary antibodies conjugated with different fluorophores. This is shown in FIG. 6.

Functional testing was then carried out using the mouse T-cell line BW5147. This cell line releases IL2 upon activation allowing a simple quantitative readout. These T-cells were co-cultured with increasing amounts of the artificial target cells described above. T-cells responded to target cells expressing either antigen, as shown by IL2 release measured by ELISA. Both CARs were shown to be expressed on the cell surfaces and the T-cells were shown to respond to either or both antigens. These data are show in FIG. 7.

Example 4—Design and Function of the AND Gate

The AND gate combines a simple activating receptor with a receptor which basally inhibits activity, but whose inhibition is turned off once the receptor is ligated. This was achieved by combining a standard 1$^{st}$ generation CAR with a short/non-bulky CD8 stalk spacer and a CD3 Zeta endodomain with a second receptor with a bulky Fc spacer whose endodomain contained either CD148 or CD45 endodomains. When both receptors are ligated, the difference in spacer dimensions results in isolation of the different receptors in different membrane compartments, releasing the CD3 Zeta receptor from inhibition by the CD148 or CD45 endodomains. In this way, activation only occurs once both receptors are activated. CD148 and CD45 were chosen for this as they function in this manner natively: for instance, the very bulky CD45 ectodomain excludes the entire receptor from the immunological synapse. The expression cassette is depicted in FIG. 8 and the subsequent proteins in FIG. 9.

Surface staining for the different specificity showed that both receptor pairs could be effectively expressed on the cell surface shown in FIG. 10. Function in BW5147 shows that the T-cell is only activated in the presence of both antigens (FIG. 11).

Example 5—Demonstration of Generalizability of the AND Gate

To ensure that the observations were not a manifestation of some specific characteristic of CD19/CD33 and their binders which had been used, the two targeting scFvs were swapped such that now, the activation (ITAM) signal was transmitted upon recognition of CD33, rather than CD19; and the inhibitory (CD148) signal was transmitted upon recognition of CD19, rather than of CD33. Since CD45 and CD148 endodomains are considered to be functionally similar, experimentation was restricted to AND gates with CD148 endodomain. This should still result in a functional AND gate. T-cells expressing the new logic gate where challenged with targets bearing either CD19 or CD33 alone, or both. The T-cells responded to targets expressing both CD19 and CD33, but not to targets expressing only one or none of these antigens. This shows that the AND gate is still functional in this format (FIG. 18B).

On the same lines, it was sought to establish how generalizable our AND gate is: the AND gate should be generalizable across different targets. While there may be lesser or greater fidelity of the gate given relative antigen density, cognate scFv binding kinetics and precise distance of the scFv binding epitope, one would expect to see some AND gate manifestations with a wide set of targets and binders. To test this, three additional AND gates were generated. Once again, experimentation was restricted to the CD148 version of the AND gate. The second scFv from the original CD148 AND gate was replaced with the anti-GD2 scFv huK666 (SEQ ID 41 and SEQ ID 42), or with the anti-CD5 scFv (SEQ ID 43 and SEQ ID 44), or the anti-EGFRvIII scFv MR1.1 (SEQ ID 45 AND SEQ ID 46) to generate the following CAR AND gates: CD19 AND GD2; CD19 AND CD5; CD19 AND EGFRvIII. The following artificial antigen expressing cell lines were also generated: by transducing SupT1, and our SupT1.CD19 with GM3 and GD2 synthases SupT1.GD2 and SupT1.CD19.GD2 were generated. By transducing SupT1 and SupT1.CD19 with a retroviral vector coding for EGFRvIII SupT1.EGFRvIII and SupT1.CD19.EGFRvIII were generated. Since CD5 is expressed on SupT1 cells, a different cell line was used to generate the target cells: 293T cells were generated which express CD19 alone, CD5 alone and both CD5 and CD19 together. Expression was confirmed by flow-cytometry (FIG. 19). T-cells expressing the three new CAR AND gates were challenged with SupT1.CD19 and respective cognate double positive and single positive target cells. All three AND gates demonstrated reduced activation by the double positive cell lines in comparison with the single positive targets (FIG. 20). This demonstrates generalizability of the AND gate design to arbitrary targets and cognate binders.

Example 6—Experimental Proof of Kinetic Segregation Model of CAR AND Gate

The aim was to prove the model that differential segregation caused by different spacers is the central mechanism behind the ability to generate these logic CAR gates. The model is that if only the activating CAR is ligated, the potent inhibiting 'ligation off' type CAR is in solution in the membrane and can inhibit the activating CAR. Once both CARs are ligated, if both CAR spacers are sufficiently different, they will segregate within the synapse and not co-localize. Hence, a key requirement is that the spacers are sufficiently different. If the model is correct, if both spacers are sufficiently similar so they co-localize when both receptors are ligated, the gate will fail to function. To test this, the "bulky" Fc spacer in the original CAR we replaced with a murine CD8 spacer. It was predicted that this has the similar length, bulk and charge as human CD8 but so should not cross-pair with it. Hence, the new gate had a first CAR which recognizes CD19, a human CD8 stalk spacer and an activatory endodomain; while the second CAR recognizes CD33, has a mouse CD8 stalk spacer and a CD148 endodomain (FIG. 18C). T-cells were transduced to express this new CAR gate. These T-cells were then challenged with SupT1 cells expressing CD19 alone, CD33 alone or CD19 and CD33 together. T-cells did not respond to SupT1 cells expressing either antigen alone as per the original AND gate. However, CAR T-cells failed to respond to SupT1 cells expressing both antigens, thereby confirming the model (FIG. 18C). A functional AND gate requires both CARs to have spacers sufficiently different so that they do not co-localize within an immunological synapse (FIGS. 23A and B).

Example 7—Design and Function of an AND NOT Gate

Phosphatases such as CD45 and CD148 are so potent that even a small amount entering an immunological synapse can inhibit ITAM activation. This is the basis of inhibition of the logical AND gate. Other classes of phosphatases are not as potent e.g. PTPN6 and related phosphatases. It was predicted that a small amount of PTPN6 entering a synapse by diffusion would not inhibit activation. In addition, it was predicted that if an inhibitory CAR had a sufficiently similar spacer to an activating CAR, it could co-localize within a synapse if both CARs were ligated. In this case, large amounts of the inhibitory endodomain would be sufficient to stop the ITAMS from activating when both antigens were present. In this way, an AND NOT gate could be created.

For the NOT AND gate, the second signal needs to "veto" activation. This is done by bringing an inhibitory signal into the immunological synapse, for example by bringing in the phosphatase of an enzyme such as PTPN6. We hence generated an initial AND NOT gate as follows: two CARs co-expressed whereby the first recognizes CD19, has a human CD8 stalk spacer and an activating endodomain; co-expressed with an anti-CD33 CAR with a mouse CD8 stalk spacer and an endodomain comprising of the catalytic domain of PTPN6 (SEQ ID 38, FIG. 13 A with B). A suitable cassette is shown in FIG. 12 and preliminary functional data are shown in FIG. 14.

In addition, an alternative strategy was developed for generating an AND NOT gate. Immune Tyrosinase Inhibitory Motifs (ITIMs) are activated in a similar manner to ITAMS, in that they become phosphorylated by Ick upon clustering and exclusion of phosphatases. Instead of triggering activation by binding ZAP70, phosphorylated ITIMs recruit phosphatases like PTPN6 through their cognate SH2 domains. An ITIM can function as an inhibitory endodomain, as long as the spacers on the activating and inhibiting CARs can co-localize. To generate this construct, an AND NOT gate was generated as follows: two CARs co-expressed—the first recognizes CD19, has a human CD8 stalk spacer and an activating endodomain; co-expressed with an anti-CD33 CAR with a mouse CD8 stalk spacer and an ITIM containing endodomain derived from that of LAIR1 (SEQ ID 39, FIG. 13 A with C).

A further, more complex AND NOT gate was also developed, whereby an ITIM is enhanced by the presence of an additional chimeric protein: an intracellular fusion of the SH2 domain is of PTPN6 and the endodomain of CD148. In this design three proteins are expressed—the first recognizes CD19, has a human CD8 stalk spacer and an activating endodomain; co-expressed with an anti-CD33 CAR with a mouse CD8 stalk spacer and an ITIM containing endodomain derived from that of LAIR1. A further 2A peptide, allows co-expression of the PTPN6-CD148 fusion (SEQ ID 40, FIGS. 13 A and D). It was predicted that these AND NOT gates would have a different range of inhibition: PTPN6-CD148>PTPN6>>ITIM.

T-cells were transduced with these gates and challenged with targets expressing either CD19 or CD33 alone, or both CD19 and CD33 together. All three gates responded to targets expressing only CD19, but not targets expressing both CD19 and CD33 together (FIG. 21), confirming that all three of the AND NOT gates were functional.

Example 8—Experimental Proof of Kinetic Segregation Model of PTPN6 Based AND NOT Gate The model of the AND NOT gate centres around the fact that the nature of the spacers used in both CARs is pivotal for the correct function of the gate. In the functional AND NOT gate with PTPN6, both CAR spacers are sufficiently similar that when both CARs are ligated, both co-localize within the synapse so the high concentration even the weak PTPN6 is sufficient to inhibit activation. If the spacers were different, segregation in the synapse will isolate the PTPN6 from the ITAM allowing activation disrupting the AND NOT gate. To test this, a control was generated replacing the murine CD8 stalk spacer with that of Fc. In this case, the test gate consisted of two CARs, the first recognizes CD19, has a human CD8 stalk spacer and an ITAM endodomain; while the second CAR recognizes CD33, has an Fc spacer and an endodomain comprising of the phosphatase from PTPN6. This gate activates in response to CD19, but also activates in response to CD19 and CD33 together (FIG. 22B, where function of this gate is compared with that of the original AND NOT, and the control AND gate variant described in Example 6). This experimental data proves the model that for a functional AND NOT gate with PTPN6, co-localizing spacers are needed.

Example 9—Experimental Proof of Kinetic Segregation Model of ITIM Based AND NOT Gate Similar to the PTPN6 based AND NOT gate, the ITIM based gate also requires co-localization in an immunological synapse to function as an AND NOT gate. To prove this hypothesis, a control ITIM based gate was generated as follows: two CARs co-expressed—the first recognizes CD19, has a human CD8 stalk spacer and an activating endodomain; co-expressed with an anti-CD33 CAR with an Fc spacer and an ITIM containing endodomain derived from that of LAIR1. The activity of this gate was compared with that of the original ITIM based AND NOT gate. In this case, the modified gate activated in response to targets expressing CD19, but also activated in response to cells expressing both CD19 and CD33. These data indicate that ITIM based AND NOT gates follow the kinetic segregation based model and a correct spacer must be selected to create a functional gate (FIG. 23B).

Example 10—Summary of Model of CAR Logic Gates Generated by Kinetic Segregation

Based on current understanding of the kinetic-segregation model and the experimental data described herein, a summary of the model for a two-CAR gate is presented in FIG. 24. The Figure shows a cell expressing two CARs, each recognizing a different antigen. When either or both CARs recognize a target antigen on a cell, a synapse forms and native CD45 and CD148 are excluded from the synapse due to the bulk of their ectodomain. This sets the stage for T-cell activation. In the case that the target cell bears only one cognate antigen, the cognate CAR is ligated and the cognate CAR segregates into the synapse. The unligated CAR remains in solution on the T-cell membrane and can diffuse in and out of the synapse so that an area of high local concentration of ligated CAR with low concentration of unligated CAR forms. In this case, if the ligated CAR has an ITAM and the non-ligated CAR has 'ligation off' type inhibitory endodomain such as that of CD148, the amount of non-ligated CAR is sufficient to inhibit activation and the gate is off. In contrast, in this case, if the ligated CAR has an ITAM and the non-ligated CAR has a 'ligation on' type inhibitory endodomain such as PTPN6, the amount of non-ligated CAR is insufficient to inhibit and the gate is on. When challenged by a target cell bearing both cognate antigens, both cognate CARs are ligated and form part of an immunological synapse. Importantly, if the CAR spacers are sufficiently similar, the CARs co-localize in the synapse but if the CAR spacers are sufficiently different the CARs segregate within the synapse. In this latter case, areas of membrane form whereby high concentrations of one CAR are present but the other CAR is absent. In this case since segregation is complete, even if the inhibitory endodomain is a 'ligation off' type, the gate is on. In the former case, areas of membrane form with high concentrations of both CARs mixed together. In this case, since both endodomains are concentrated, even if the inhibitory endodomain is 'ligation on' type, the gate is off. By selecting the correct combination of spacer and endodomain logic can be programmed into a CAR T-cell.

Based on our work above, we have established a series of design rules to allow generation of logic-gated CARs (illustrated in FIG. 31). To generate an "antigen A OR antigen B" gated CAR T-cell, anti-A and anti-B CARs must be generated such that (1) each CAR has a spacer which simply allows antigen access and synapse formation such that the CAR functions, and (2) Each CAR has an activating endodomain; To generate an "antigen A AND NOT B" gated CAR T-cell, anti-A and anti-B CARs must be generated such that (1) both CARs have spacers which do not cross-pair, but which will allow the CARs to co-segregate upon recognition of both cognate antigens on the target cell, (2) and one CAR has an activating endodomain, while the other CAR has an endodomain which comprises or recruits a weak phosphatase (e.g. PTPN6); (3) To generate an "antigen A AND antigen B" gated CAR T-cell, anti-A and anti-B CARs must be generated such that (1) one CAR has a spacer sufficiently different from the other CAR such that both CARs will not co-segregate upon recognition of both cognate antigens on the target cell, (2) one CAR has an activating endodomain, while the other car has an endodomain which comprises of a potent phosphatase (e.g. that of CD45 or CD148). The correct spacers to achieve the desired effect can be selected from a set of spacers with known size/shape etc as well as taking into consideration size/shape etc of the target antigen (for instance see FIG. 30) and the location of the cognate epitope on the target antigen.

SEQ ID No 41:
SFG.aCD19-CD8STK-CD28tmZ-2A-aGD2-HCH2CH3pvaa-dCD148
MSLPVTALLLPLALLLHAARPDIQMTQTTSSLSASLGDRVTISCRASQDI

SKYLNWYQQKPDGTVKLLIYHTSRLHSGVPSRFSGSGSGTDYSLTISNLE

QEDIATYFCQQGNTLPYTFGGGTKLEITKAGGGGSGGGGSGGGGSGGGGS

EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSSDPTTTPAPRPPTPAPTIASQPLSLRPEACR

PAAGGAVHTRGLDFACDIFWVLVVVGGVLACYSLLVTVAFIIFWVRRVKF

SRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDAL

HMQALPPRRAEGRGSLLTCGDVEENPGPMETDTLLLWVLLLWVPGSTGQV

QLQESGPGLVKPSQTLSITCTVSGFSLASYNIHWVRQPPGKGLEWLGVIW

AGGSTNYNSALMSRLTISKDNSKNQVFLKMSSLTAADTAVYYCAKRSDDY

SWFAYWGQGTLVTVSSGGGGSGGGGSGGGGSENQMTQSPSSLSASVGDRV

TMTCRASSSVSSSYLHWYQQKSGKAPKVWIYSTSNLASGVPSRFSGSGSG

TDYTLTISSLQPEDFATYYCQQYSGYPITFGQGTKVEIKRSDPAEPKSPD

KTHTCPPCPAPPVAGPSVFLFPPKPKDTLMIARTPEVTCVVVDVSHEDPE

VKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNV

FSCSVMHEALHNHYTQKSLSLSPGKKDPKAVFGCIFGALVIVTVGGFIFW

RKKRKDAKNNEVSFSQIKPKKSKLIRVENFEAYFKKQQADSNCGFAEEYE

DLKLVGISQPKYAAELAENRGKNRYNNVLPYDISRVKLSVQTHSTDDYIN

ANYMPGYHSKKDFIATQGPLPNTLKDFWRMVWEKNVYAIIMLTKCVEQGR

TKCEEYWPSKQAQDYGDITVAMTSEIVLPEWTIRDFTVKNIQTSESHPLR

QFHFTSWPDHGVPDTTDLLINFRYLVRDYMKQSPPESPILVHCSAGVGRT

GTFIAIDRLIYQIENENTVDVYGIVYDLRMHRPLMVQTEDQYVFLNQCVL

DIVRSQKDSKVDLIYQNTTAMTIYENLAPVTTFGKTNGYIA

SEQ ID No. 42:
SFG.aCD19-CD8STK-CD28tmZ-2A-aGD2-HCH2CH3pvaa-dCD148
ATGAGCCTGCCCGTGACCGCCCTGCTGCTGCCCCTGGCCCTGCTGCTGCA

CGCCGCCAGACCAGACATCCAGATGACCCAGACCACCAGCAGCCTGAGCG

CCAGCCTGGGCGACCGGGTGACCATCAGCTGCAGAGCCAGCCAGGACATC

AGCAAGTACCTGAACTGGTACCAGCAGAAGCCCGACGGCACCGTGAAGCT

GCTGATCTACCACACCAGCCGGCTGCACAGCGGCGTGCCCAGCCGGTTCA

GCGGCAGCGGCAGCGGCACCGACTACAGCCTGACCATCAGCAACCTGGAG

CAGGAGGACATCGCCACCTACTTCTGCCAGCAGGGCAACACCCTGCCCTA

CACCTTCGGAGGCGGCACCAAGCTGGAGATCACCAAGGCCGGAGGCGGAG

GCTCTGGCGGAGGCGGCTCTGGCGGAGGCGGCTCTGGCGGAGGCGGCAGC

GAGGTGAAGCTGCAGGAGTCTGGCCCAGGCCTGGTGGCCCCAAGCCAGAG

CCTGAGCGTGACCTGCACCGTGAGCGGCGTGAGCCTGCCCGACTACGGCG

TGAGCTGGATCAGGCAGCCCCCACGGAAGGGCCTGGAGTGGCTGGGCGTG

ATCTGGGGCAGCGAGACCACCTACTACAACAGCGCCCTGAAGAGCCGGCT

GACCATCATCAAGGACAACAGCAAGAGCCAGGTGTTCCTGAAGATGAACA

GCCTGCAGACCGACGACACCGCCATCTACTACTGCGCCAAGCACTACTAC

TATGGCGGCAGCTACGCTATGGACTACTGGGGCCAGGGCACCAGCGTGAC

CGTGAGCTCAGATCCCACCACGACGCCAGCGCCGCGACCACCAACACCGG

CGCCCACCATCGCGTCGCAGCCCCTGTCCCTGCGCCCAGAGGCGTGCCGG

CCAGCGGCGGGGGCGCAGTGCACACGAGGGGGCTGGACTTCGCCTGTGA

TATCTTTTGGGTGCTGGTGGTGGTTGGTGGAGTCCTGGCTTGCTATAGCT

TGCTAGTAACAGTGGCCTTTATTATTTTCTGGGTGAGGAGAGTGAAGTTC

AGCAGGAGCGCAGACGCCCCCGCGTACCAGCAGGGCCAGAACCAGCTCTA

TAACGAGCTCAATCTAGGACGAAGAGAGGAGTACGATGTTTTGGACAAGA

GACGTGGCCGGGACCCTGAGATGGGGGGAAAGCCGAGAAGGAAGAACCCT

CAGGAAGGCCTGTACAATGAACTGCAGAAAGATAAGATGGCGGAGGCCTA

CAGTGAGATTGGGATGAAAGGCGAGCGCCGGAGGGGCAAGGGGCACGATG

GCCTTTACCAGGGTCTCAGTACAGCCACCAAGGACACCTACGACGCCCTT

```
CACATGCAGGCCCTGCCTCCTCGCAGAGCCGAGGGCAGGGGAAGTCTTCT
AACATGCGGGGACGTGGAGGAAAATCCCGGGCCCATGGAGACCGACACCC
TGCTGCTGTGGGTGCTGCTGCTGTGGGTGCCAGGCAGCACCGGCCAGGTC
CAGCTGCAGGAGTCTGGCCCAGGCCTGGTGAAGCCCAGCCAGACCCTGAG
CATCACCTGCACCGTGAGCGGCTTCAGCCTGGCCAGCTACAACATCCACT
GGGTGCGGCAGCCCCCAGGCAAGGGCCTGGAGTGGCTGGGCGTGATCTGG
GCTGGCGGCAGCACCAACTACAACAGCGCCCTGATGAGCCGGCTGACCAT
CAGCAAGGACAACAGCAAGAACCAGGTGTTCCTGAAGATGAGCAGCCTGA
CAGCCGCCGACACCGCCGTGTACTACTGCGCCAAGCGGAGCGACGACTAC
AGCTGGTTCGCCTACTGGGGCCAGGGCACCCTGGTGACCGTGAGCTCTGG
CGGAGGCGGCTCTGGCGGAGGCGGCTCTGGCGGAGGCGGCAGCGAGAACC
AGATGACCCAGAGCCCCAGCAGCTTGAGCGCCAGCGTGGGCGACCGGGTG
ACCATGACCTGCAGAGCCAGCAGCAGCGTGAGCAGCAGCTACCTGCACTG
GTACCAGCAGAAGAGCGGCAAGGCCCCAAAGGTGTGGATCTACAGCACCA
GCAACCTGGCCAGCGGCGTGCCCAGCCGGTTCAGCGGCAGCGGCAGCGGC
ACCGACTACACCCTGACCATCAGCAGCCTGCAGCCCGAGGACTTCGCCAC
CTACTACTGCCAGCAGTACAGCGGCTACCCCATCACCTTCGGCCAGGGCA
CCAAGGTGGAGATCAAGCGGTCGGATCCCGCCGAGCCCAAATCTCCTGAC
AAAACTCACACATGCCCACCGTGCCCAGCACCTCCCGTGCCGGCCCGTC
AGTCTTCCTCTTCCCCCCAAAACCCAAGGACACCCTCATGATCGCCCGGA
CCCCTGAGGTCACATGCGTGGTGGTGGACGTGAGCCACGAAGACCCTGAG
GTCAAGTTCAACTGGTACGTGGACGGCGTGGAGGTGCATAATGCCAAGAC
AAAGCCGCGGGAGGAGCAGTACAACAGCACGTACCGTGTGGTCAGCGTCC
TCACCGTCCTGCACCAGGACTGGCTGAATGGCAAGGAGTACAAGTGCAAG
GTCTCCAACAAAGCCCTCCCAGCCCCCATCGAGAAAACCATCTCCAAAGC
CAAAGGGCAGCCCCGAGAACCACAGGTGTACACCCTGCCCCCATCCCGGG
ATGAGCTGACCAAGAACCAGGTCAGCCTGACCTGCCTGGTCAAAGGCTTC
TATCCCAGCGACATCGCCGTGGAGTGGGAGAGCAATGGGCAACCGGAGAA
CAACTACAAGACCACGCCTCCCGTGCTGGACTCCGACGGCTCCTTCTTCC
TCTACAGCAAGCTCACCGTGGACAAGAGCAGGTGGCAGCAGGGGAACGTC
TTCTCATGCTCCGTGATGCATGAGGCCCTGCACAATCACTATACCCAGAA
ATCTCTGAGTCTGAGCCCAGGCAAGAAGGACCCCAAGGCGGTTTTTGGCT
GTATCTTTGGTGCCCTGGTTATTGTGACTGTGGGAGGCTTCATCTTCTGG
AGAAAGAAGAGGAAAGATGCAAAGAATAATGAAGTGTCCTTTTCTCAAAT
TAAACCTAAAAAATCTAAGTTAATCAGAGTGGAGAATTTTGAGGCCTACT
TCAAGAAGCAGCAAGCTGACTCCAACTGTGGGTTCGCAGAGGAATACGAA
GATCTGAAGCTTGTTGGAATTAGTCAACCTAAATATGCAGCAGAACTGGC
TGAGAATAGAGGAAAGAATCGCTATAATAATGTTCTGCCCTATGATATTT
CCCGTGTCAAACTTCGGTCCAGACCCATTCAACGGATGACTACATCAAT
GCCAACTACATGCCTGGCTACCACTCCAAGAAAGATTTTATTGCCACACA
AGGACCTTTACCGAACACTTTGAAAGATTTTTGGCGTATGGTTTGGGAGA
AAAATGTATATGCCATCATTATGTTGACTAAATGTGTTGAACAGGGAAGA
ACCAAATGTGAGGAGTATTGGCCCTCCAAGCAGGCTCAGGACTATGAGA
CATAACTGTGGCAATGACATCAGAAATTGTTCTTCCGGAATGGACCATCA
GAGATTTCACAGTGAAAAATATCCAGACAAGTGAGAGTCACCCTCTGAGA
CAGTTCCATTTCACCTCCTGGCCAGACCACGGTGTTCCCGACACCACTGA
CCTGCTCATCAACTTCCGGTACCTCGTTCGTGACTACATGAAGCAGAGTC
CTCCCGAATCGCCGATTCTGGTGCATTGCAGTGCTGGGGTCGGAAGGACG
GGCACTTTCATTGCCATTGATCGTCTCATCTACCAGATAGAGAATGAGAA
CACCGTGGATGTGTATGGGATTGTGTATGACCTTCGAATGCATAGGCCTT
TAATGGTGCAGACAGAGGACCAGTATGTTTTCCTCAATCAGTGTGTTTTG
GATATTGTCAGATCCCAGAAAGACTCAAAAGTAGATCTTATCTACCAGAA
CACAACTGCAATGACAATCTATGAAAACCTTGCGCCCGTGACCACATTTG
GAAAGACCAATGGTTACATCGCCTAA

SEQ ID No. 43:
SFG.aCD19-CD8STK-CD28tmZ-2A-aCD5-HCH2CH3pvaa-
dCD148
MSLPVTALLLPLALLLHAARPDIQMTQTTSSLSASLGDRVTISCRASQDI
SKYLNWYQQKPDGTVKLLIYHTSRLHSGVPSRFSGSGSGTDYSLTISNLE
QEDIATYFCQQGNTLPYTFGGGTKLEITKAGGGSGGGGSGGGGSGGGGS
EVKLQESGPGLVAPSQSLSVTCTVSGVSLPDYGVSWIRQPPRKGLEWLGV
IWGSETTYYNSALKSRLTIIKDNSKSQVFLKMNSLQTDDTAIYYCAKHYY
YGGSYAMDYWGQGTSVTVSSDPTTTPAPRPPTPAPTIASQPLSLRPEACR
PAAGGAVHTRGLDFACDIFWVLVVVGGVLACYSLLVTVAFIIFWVRRVKF
SRSADAPAYQQGQNQLYNELNLGRREEYDVLDKRRGRDPEMGGKPRRKNP
QEGLYNELQKDKMAEAYSEIGMKGERRRGKGHDGLYQGLSTATKDTYDAL
HMQALPPRRAEGRGSLLTCGDVEENPGPMETDTLLLWVLLLWVPGSTGQV
TLKESGPGILKPSQTLSLTCSFSGFSLSTSGMGVGWIRQPSGKGLEWLAH
IWWDDDVYYNPSLKNQLTISKDASRDQVFLKITNLDTADTATYYCVRRRA
TGTGFDYWGQGTTLTVSSGGGGSGGGGSGGGGSNIVMTQSHKFMSTSVGD
RVSIACKASQDVGTAVAWYQQKPGQSPKLLIYWTSTRHTGVPDRFTGSGS
GTDFTLTITNVQSEDLADYFCHQYNSYNTFGSGTRLELKRSDPAEPKSPD
KTHTCPPCPAPPVAGPSVFLFPPKPKDTLMIARTPEVTCVWDVSHEDPEV
KFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVF
SCSVMHEALHNHYTQKSLSLSPGKKDPKAVFGCIFGALVIVTVGGFIFWR
KKRKDAKNNEVSFSQIKPKKSKLIRVENFEAYFKKQQADSNCGFAEEYED
LKLVGISQPKYAAELAENRGKNRYNNVLPYDISRVKLSVQTHSTDDYINA
NYMPGYHSKKDFIATQGPLPNTLKDFWRMVWEKNVYAIIMLTKCVEQGRT
KCEEYWPSKQAQDYGDITVAMTSEIVLPEWTIRDFTVKNIQTSESHPLRQ
FHFTSWPDHGVPDTTDLLINFRYLVRDYMKQSPPESPILVHCSAGVGRTG
```

TFIAIDRLIYQIENENTVDVYGIVYDLRMHRPLMVQTEDQYVFLNQCVLD
IVRSQKDSKVDLIYQNTTAMTIYENLAPVTTFGKTNGYIA

SEQ ID No. 44:
SFG.aCD19-CD8STK-CD28tmZ-2A-aCD5-HCH2CH3pvaa-
dCD148
ATGAGCCTGCCCGTGACCGCCCTGCTGCTGCCCCTGGCCCTGCTGCTGCA

CGCCGCCAGACCAGACATCCAGATGACCCAGACCACCAGCAGCCTGAGCG

CCAGCCTGGGCGACCGGGTGACCATCAGCTGCAGAGCCAGCCAGGACATC

AGCAAGTACCTGAACTGGTACCAGCAGAAGCCCGACGGCACCGTGAAGCT

GCTGATCTACCACACCAGCCGGCTGCACAGCGGCGTGCCCAGCCGGTTCA

GCGGCAGCGGCAGCGGCACCGACTACAGCCTGACCATCAGCAACCTGGAG

CAGGAGGACATCGCCACCTACTTCTGCCAGCAGGGCAACACCCTGCCCTA

CACCTTCGGAGGCGGCACCAAGCTGGAGATCACCAAGGCCGGAGGCGGAG

GCTCTGGCGGAGGCGGCTCTGGCGGAGGCGGCTCTGGCGGAGGCGGCAGC

GAGGTGAAGCTGCAGGAGTCTGGCCCAGGCCTGGTGGCCCCAAGCCAGAG

CCTGAGCGTGACCTGCACCGTGAGCGGCGTGAGCCTGCCCGACTACGGCG

TGAGCTGGATCAGGCAGCCCCCACGGAAGGGCCTGGAGTGGCTGGGCGTG

ATCTGGGGCAGCGAGACCACCTACTACAACAGCGCCCTGAAGAGCCGGCT

GACCATCATCAAGGACAACAGCAAGAGCCAGGTGTTCCTGAAGATGAACA

GCCTGCAGACCGACGACACCGCCATCTACTACTGCGCCAAGCACTACTAC

TATGGCGGCAGCTACGCTATGGACTACTGGGGCCAGGGCACCAGCGTGAC

CGTGAGCTCAGATCCCACCACGACGCCAGCGCCGCGACCACCAACACCGG

CGCCCACCATCGCGTCGCAGCCCCTGTCCCTGCGCCCAGAGGCGTGCCGG

CCAGCGGCGGGGGCGCAGTGCACACGAGGGGGCTGGACTTCGCCTGTGA

TATCTTTTGGGTGCTGGTGGTGGTTGGTGGAGTCCTGGCTTGCTATAGCT

TGCTAGTAACAGTGGCCTTTATTATTTTCTGGGTGAGGAGAGTGAAGTTC

AGCAGGAGCGCAGACGCCCCCGCGTACCAGCAGGGCCAGAACCAGCTCTA

TAACGAGCTCAATCTAGGACGAAGAGAGGAGTACGATGTTTTGGACAAGA

GACGTGGCCGGGACCCTGAGATGGGGGGAAAGCCGAGAAGGAAGAACCCT

CAGGAAGGCCTGTACAATGAACTGCAGAAAGATAAGATGGCGGAGGCCTA

CAGTGAGATTGGGATGAAAGGCGAGCGCCGGAGGGGCAAGGGGCACGATG

GCCTTTACCAGGGTCTCAGTACAGCCACCAAGGACACCTACGACGCCCTT

CACATGCAGGCCCTGCCTCCTCGCAGAGCCGAGGGCAGGGGAAGTCTTCT

AACATGCGGGACGTGGAGGAAAATCCCGGGCCCATGGAGACCGACACCC

TGCTGCTGTGGGTGCTGCTGCTGTGGGTGCCCGGCAGCACCGGCCAGGTG

ACCCTGAAGGAGAGCGGTCCCGGCATCCTGAAGCCCAGCCAGACCCTGAG

CCTGACCTGCAGCTTCAGCGGCTTCAGCCTGAGCACCAGCGGCATGGGCG

TGGGCTGGATTCGGCAGCCCAGCGGCAAGGGCCTGGAGTGGCTGGCCCAC

ATCTGGTGGGACGACGACGTGTACTACAACCCCAGCCTGAAGAACCAGCT

GACCATCAGCAAGGACGCCAGCGGGACCAGGTGTTCCTGAAGATCACCA

ACCTGGACACCGCCGACACCGCCACCTACTACTGCGTGCGGCGCGGGCC

ACCGGCACCGGCTTCGACTACTGGGGCCAGGGCACCACCCTGACCGTGAG

CAGCGGTGGCGGTGGCAGCGGCGGCGGCGGAAGCGGAGGTGGTGGCAGCA

ACATCGTGATGACCCAGAGCCACAAGTTCATGAGCACCAGCGTGGGCGAC

CGGGTGAGCATCGCCTGCAAGGCCAGCCAGGACGTGGGCACCGCCGTGGC

CTGGTACCAGCAGAAGCCTGGCCAGAGCCCCAAGCTGCTGATCTACTGGA

CCAGCACCCGGCACACCGGCGTGCCCGACCGGTTCACCGGCAGCGGCAGC

GGCACCGACTTCACCCTGACCATCACCAACGTGCAGAGCGAGGACCTGGC

CGACTACTTCTGCCACCAGTACAACAGCTACAACACCTTCGGCAGCGGCA

CCCGGCTGGAGCTGAAGCGGTCGGATCCCGCCGAGCCCAAATCTCCTGAC

AAAACTCACACATGCCCACCGTGCCCAGCACCTCCCGTGGCCGGCCCGTC

AGTCTTCCTCTTCCCCCCAAAACCCAAGGACACCCTCATGATCGCCCGGA

CCCCTGAGGTCACATGCGTGGTGGTGGACGTGAGCCACGAAGACCCTGAG

GTCAAGTTCAACTGGTACGTGGACGGCGTGGAGGTGCATAATGCCAAGAC

AAAGCCGCGGGAGGAGCAGTACAACAGCACGTACCGTGTGGTCAGCGTCC

TCACCGTCCTGCACCAGGACTGGCTGAATGGCAAGGAGTACAAGTGCAAG

GTCTCCAACAAAGCCCTCCCAGCCCCCATCGAGAAAACCATCTCCAAAGC

CAAAGGGCAGCCCCGAGAACCACAGGTGTACACCCTGCCCCCATCCCGGG

ATGAGCTGACCAAGAACCAGGTCAGCCTGACCTGCCTGGTCAAAGGCTTC

TATCCCAGCGACATCGCCGTGGAGTGGGAGAGCAATGGGCAACCGGAGAA

CAACTACAAGACCACGCCTCCCGTGCTGGACTCCGACGGCTCCTTCTTCC

TCTACAGCAAGCTCACCGTGGACAAGAGCAGGTGGCAGCAGGGGAACGTC

TTCTCATGCTCCGTGATGCATGAGGCCCTGCACAATCACTATACCCAGAA

ATCTCTGAGTCTGAGCCCAGGCAAGAAGGACCCCAAGGCGGTTTTTGGCT

GTATCTTTGTGCCCTGGTTATTGTGACTGTGGGAGGCTTCATCTTCTGG

AGAAAGAAGAGGAAAGATGCAAAGAATAATGAAGTGTCCTTTTCTCAAAT

TAAACCTAAAAAATCTAAGTTAATCAGAGTGGAGAATTTTGAGGCCTACT

TCAAGAAGCAGCAAGCTGACTCCAACTGTGGGTTCGCAGAGGAATACGAA

GATCTGAAGCTTGTTGGAATTAGTCAACCTAAATATGCAGCAGAACTGGC

TGAGAATAGAGGAAAGAATCGCTATAATAATGTTCTGCCCTATGATATTT

CCCGTGTCAAACTTTCGGTCCAGACCCATTCAACGGATGACTACATCAAT

GCCAACTACATGCCTGGCTACCACTCCAAGAAAGATTTATTGCCACACA

AGGACCTTTACCGAACACTTTGAAAGATTTTGGCGTATGGTTTGGGAGA

AAAATGTATATGCCATCATTATGTTGACTAAATGTGTTGAACAGGGAAGA

ACCAAATGTGAGGAGTATTGGCCCTCCAAGCAGGCTCAGGACTATGGAGA

CATAACTGTGGCAATGACATCAGAAATTGTTCTTCCGGAATGGACCATCA

GAGATTTCACAGTGAAAAATATCCAGACAAGTGAGAGTCACCCTCTGAGA

CAGTTCCATTTCACCTCCTGGCCAGACCACGGTGTTCCCGACACCACTGA

CCTGCTCATCAACTTCCGGTACCTCGTTCGTGACTACATGAAGCAGAGTC

CTCCCGAATCGCCGATTCTGGTGCATTGCAGTGCTGGGGTCGGAAGGACG

GGCACTTTCATTGCCATTGATCGTCTCATCTACCAGATAGAGAATGAGAA

CACCGTGGATGTGTATGGGATTGTGTATGACCTTCGAATGCATAGGCCTT

TAATGGTGCAGACAGAGGACCAGTATGTTTTCCTCAATCAGTGTGTTTTG

-continued

GATATTGTCAGATCCCAGAAAGACTCAAAAGTAGATCTTATCTACCAGAA

CACAACTGCAATGACAATCTATGAAAACCTTGCGCCCGTGACCACATTTG

GAAAGACCAATGGTTACATCGCCTAA

SEQ ID No. 45:
SFG.aCD19-CD8STK-CD28tmZ-2A-aEGFRvIII-HCH2CH3pvaa-
dCD148
MSLPVTALLLPLALLLHAARPDIQMTQTTSSLSASLGDRVTISCRASQDI

SKYLNWYQQKPDGTVKLLIYHTSRLHSGVPSRFSGSGSGTDYSLTISNLE

QEDIATYFCQQGNTLPYTFGGGTKLEITKAGGGGSGGGGSGGGGSGGGGS

EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSSDPTTTPAPRPPTPAPTIASQPLSLRPEACR

PAAGGAVHTRGLDFACDIFWVLVVVGGVLACYSLLVTVAFIIFWVRRVKF

SRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDAL

HMQALPPRRAEGRGSLLTCGDVEENPGPMETDTLLLWVLLLWVPGSTGQV

KLQQSGGGLVKPGASLKLSCVTSGFTFRKFGMSWVRQTSDKRLEWVASIS

TGGYNTYYSDNVKGRFTISRENAKNTLYLQMSSLKSEDTALYYCTRGYSS

TSYAMDYWGQGTTVTVSSGGGGSGGGGSGGGGSDIELTQSPASLSVATGE

KVTIRCMTSTDIDDDMNWYQQKPGEPPKFLISEGNTLRPGVPSRFSSSGT

GTDFVFTIENTLSEDVGDYYCLQSFNVPLTFGDGTKLEIKRSDPAEPKSP

DKTHTCPPCPAPPVAGPSVFLFPPKPKDTLMIARTPEVTCVVVDVSHEDP

EVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGN

VFSCSVMHEALHNHYTQKSLSLSPGKKDPKAVFGCIFGALVIVTVGGFIF

WRKKRKDAKNNEVSFSQIKPKKSKLIRVENFEAYFKKQQADSNCGFAEEY

EDLKLVGISQPKYAAELAENRGKNRYNNVLPYDISRVKLSVQTHSTDDYI

NANYMPGYHSKKDFIATQGPLPNTLKDFWRMVWEKNVYAIIMLTKCVEQG

RTKCEEYWPSKQAQDYGDITVAMTSEIVLPEWTIRDFTVKNIQTSESHPL

RQFHFTSWPDHGVPDTTDLLINFRYLVRDYMKQSPPESPILVHCSAGVGR

TGTFIAIDRLIYQIENENTVDVYGIVYDLRMHRPLMVQTEDQYVFLNQCV

LDIVRSQKDSKVDLIYQNTTAMTIYENLAPVTTFGKTNGYIA

SEQ ID No. 46:
SFG.aCD19-CD8STK-CD28tmZ-2A-aEGFRvIII-HCH2CH3pvaa-
dCD148
ATGAGCCTGCCCGTGACCGCCCTGCTGCTGCCCCTGGCCCTGCTGCTGCA

CGCCGCCAGACCAGACATCCAGATGACCCAGACCACCAGCAGCCTGAGCG

CCAGCCTGGGCGACCGGGTGACCATCAGCTGCAGAGCCAGCCAGGACATC

AGCAAGTACCTGAACTGGTACCAGCAGAAGCCCGACGGCACCGTGAAGCT

GCTGATCTACCACACCAGCCGGCTGCACAGCGGCGTGCCCAGCCGGTTCA

GCGGCAGCGGCAGCGGCACCGACTACAGCCTGACCATCAGCAACCTGGAG

CAGGAGGACATCGCCACCTACTTCTGCCAGCAGGGCAACACCCTGCCCTA

CACCTTCGGAGGCGGCACCAAGCTGGAGATCACCAAGGCCGGAGGCGGAG

GCTCTGGCGGAGGCGGCTCTGGCGGAGGCGGCTCTGGCGGAGGCGGCAGC

GAGGTGAAGCTGCAGGAGTCTGGCCCAGGCCTGGTGGCCCCAAGCCAGAG

CCTGAGCGTGACCTGCACCGTGAGCGGCGTGAGCCTGCCCGACTACGGCG

TGAGCTGGATCAGGCAGCCCCCACGGAAGGGCCTGGAGTGGCTGGGCGTG

ATCTGGGGCAGCGAGACCACCTACTACAACAGCGCCCTGAAGAGCCGGCT

GACCATCATCAAGGACAACAGCAAGAGCCAGGTGTTCCTGAAGATGAACA

GCCTGCAGACCGACGACACCGCCATCTACTACTGCGCCAAGCACTACTAC

TATGGCGGCAGCTACGCTATGGACTACTGGGGCCAGGGCACCAGCGTGAC

CGTGAGCTCAGATCCCACCACGACGCCAGCGCCGCGACCACCAACACCGG

CGCCCACCATCGCGTCGCAGCCCCTGTCCCTGCGCCCAGAGGCGTGCCGG

CCAGCGGCGGGGGCGCAGTGCACACGAGGGGGCTGGACTTCGCCTGTGA

TATCTTTTGGGTGCTGGTGGTGGTTGGTGGAGTCCTGGCTTGCTATAGCT

TGCTAGTAACAGTGGCCTTTATTATTTTCTGGGTGAGGAGAGTGAAGTTC

AGCAGGAGCGCAGACGCCCCCGCGTACCAGCAGGGCCAGAACCAGCTCTA

TAACGAGCTCAATCTAGGACGAAGAGAGGAGTACGATGTTTTGGACAAGA

GACGTGGCCGGGACCCTGAGATGGGGGGAAAGCCGAGAAGGAAGAACCCT

CAGGAAGGCCTGTACAATGAACTGCAGAAAGATAAGATGGCGGAGGCCTA

CAGTGAGATTGGGATGAAAGGCGAGCGCCGGAGGGGCAAGGGGCACGATG

GCCTTTACCAGGGTCTCAGTACAGCCACCAAGGACACCTACGACGCCCTT

CACATGCAGGCCCTGCCTCCTCGCAGAGCCGAGGGCAGGGGAAGTCTTCT

AACATGCGGGGACGTGGAGGAAAATCCCGGGCCCATGGAGACCGACACCC

TGCTGCTGTGGGTGCTGCTGCTGTGGGTGCCCGGCAGCACCGGCCAGGTG

AAGCTGCAGCAGAGCGGCGGAGGCCTGGTGAAGCCCGGCGCCAGCCTGAA

GCTGAGCTGCGTGACCAGCGGCTTCACCTTCCGGAAGTTCGGCATGAGCT

GGGTGCGGCAGACCAGCGACAAGCGGCTGGAGTGGGTGGCCAGCATCAGC

ACCGGCGGCTACAACACCTACTACAGCGACAACGTGAAGGGCCGGTTCAC

CATCAGCCGGGAGAACGCCAAGAACACCCTGTACCTGCAGATGAGCAGCC

TGAAGAGCGAGGACACCGCCCTGTACTACTGCACCCGGGGCTACAGCAGC

ACCAGCTACGCTATGGACTACTGGGGCCAGGGCACCACCGTGACAGTGAG

CAGCGGCGGAGGAGGCAGTGGTGGGGTGGATCTGGCGGAGGTGGCAGCG

ACATCGAGCTGACCCAGAGCCCCGCCAGCCTGAGCGTGGCCACCGGCGAG

AAGGTGACCATCCGGTGCATGACCAGCACCGACATCGACGACGACATGAA

CTGGTACCAGCAGAAGCCCGGCGAGCCCCCAAAGTTCCTGATCAGCGAGG

GCAACACCCTGCGGCCCGGCGTGCCCAGCCGGTTCAGCAGCAGCGGCACC

GGCACCGACTTCGTGTTCACCATCGAGAACACCCTGAGCGAGGACGTGGG

CGACTACTACTGCCTGCAGAGCTTCAACGTGCCCCTGACCTTCGGCGACG

GCACCAAGCTGGAGATCAAGCGGTCGGATCCCGCCGAGCCCAAATCTCCT

GACAAAACTCACACATGCCCACCGTGCCCAGCACCTCCCGTGGCCGGCCC

GTCAGTCTTCCTCTTCCCCCCAAAACCCAAGGACACCCTCATGATCGCCC

GGACCCCTGAGGTCACATGCGTGGTGGTGGACGTGAGCCACGAAGACCCT

-continued

```
GAGGTCAAGTTCAACTGGTACGTGGACGGCGTGGAGGTGCATAATGCCAA

GACAAAGCCGCGGGAGGAGCAGTACAACAGCACGTACCGTGTGGTCAGCG

TCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAA

AGCCAAAGGGCAGCCCCGAGAACCACAGGTGTACACCCTGCCCCATCCC

GGGATGAGCTGACCAAGAACCAGGTCAGCCTGACCTGCCTGGTCAAAGGC

TTCTATCCCAGCGACATCGCCGTGGAGTGGGAGAGCAATGGGCAACCGGA

GAACAACTACAAGACCACGCCTCCCGTGCTGGACTCCGACGGCTCCTTCT

TCCTCTACAGCAAGCTCACCGTGGACAAGAGCAGGTGGCAGCAGGGGAAC

GTCTTCTCATGCTCCGTGATGCATGAGGCCCTGCACAATCACTATACCCA

GAAATCTCTGAGTCTGAGCCCAGGCAAGAAGGACCCCAAGGCGGTTTTTG

GCTGTATCTTTGGTGCCCTGGTTATTGTGACTGTGGGAGGCTTCATCTTC

TGGAGAAAGAAGAGGAAAGATGCAAAGAATAATGAAGTGTCCTTTTCTCA

AATTAAACCTAAAAAATCTAAGTTAATCAGAGTGGAGAATTTTGAGGCCT

ACTTCAAGAAGCAGCAAGCTGACTCCAACTGTGGGTTCGCAGAGGAATAC

GAAGATCTGAAGCTTGTTGGAATTAGTCAACCTAAATATGCAGCAGAACT

GGCTGAGAATAGAGGAAAGAATCGCTATAATAATGTTCTGCCCTATGATA

TTTCCCGTGTCAAACTTTCGGTCCAGACCCATTCAACGGATGACTACATC

AATGCCAACTACATGCCTGGCTACCACTCCAAGAAAGATTTTATTGCCAC

ACAAGGACCTTTACCGAACACTTTGAAAGATTTTTGGCGTATGGTTTGGG

AGAAAAATGTATATGCCATCATTATGTTGACTAAATGTGTTGAACAGGGA

AGAACCAAATGTGAGGAGTATTGGCCCTCCAAGCAGGCTCAGGACTATGG

AGACATAACTGTGGCAATGACATCAGAAATTGTTCTTCCGGAATGGACCA

TCAGAGATTTCACAGTGAAAAATATCCAGACAAGTGAGAGTCACCCTCTG

AGACAGTTCCATTTCACCTCCTGGCCAGACCACGGTGTTCCCGACACCAC

TGACCTGCTCATCAACTTCCGGTACCTCGTTCGTGACTACATGAAGCAGA

GTCCTCCCGAATCGCCGATTCTGGTGCATTGCAGTGCTGGGGTCGGAAGG

ACGGGCACTTTCATTGCCATTGATCGTCTCATCTACCAGATAGAGAATGA

GAACACCGTGGATGTGTATGGGATTGTGTATGACCTTCGAATGCATAGGC

CTTTAATGGTGCAGACAGAGGACCAGTATGTTTTCCTCAATCAGTGTGTT

TTGGATATTGTCAGATCCCAGAAAGACTCAAAAGTAGATCTTATCTACCA

GAACACAACTGCAATGACAATCTATGAAAACCTTGCGCCCGTGACCACAT

TTGGAAAGACCAATGGTTACATCGCCTAA
```

Example 11—Design and Construction of APRIL Based CARs

APRIL in its natural form is a secreted type II protein. The use of APRIL as a BCMA binding domain for a CAR requires conversion of this type II secreted protein to a type I membrane bound protein and for this protein to be stable and to retain binding to BCMA in this form. To generate candidate molecules, the extreme amino-terminus of APRIL was deleted to remove binding to proteoglycans. Next, a signal peptide was added to direct the nascent protein to the endoplasmic reticulum and hence the cell surface. Also, because the nature of spacer used can alter the function of a CAR, three different spacer domains were tested: an APRIL based CAR was generated comprising (i) a human IgG1 spacer altered to remove Fc binding motifs; (ii) a CD8 stalk; and (iii) the IgG1 hinge alone (cartoon in FIG. 25 and amino acid sequences in FIG. 26). These CARs were expressed in a bicistronic retroviral vector (FIG. 27A) so that a marker protein-truncated CD34 could be co-expressed as a convenient marker gene.

Example 12—Expression and Function of APRIL Based CARs

The aim of this study was to test whether the APRIL based CARs which had been constructed were expressed on the cell surface and whether APRIL had folded to form the native protein. T-cells were transduced with these different CAR constructs and stained using a commercially available anti-APRIL mAb, along with staining for the marker gene and analysed by flow-cytometry. The results of this experiment are shown in FIG. 27B where APRIL binding is plotting against marker gene fluorescence. These data show that in this format, the APRIL based CARs are expressed on the cell surface and APRIL folds sufficiently to be recognized by an anti-APRIL mAb.

Next, it was determined whether APRIL in this format could recognize BCMA and TACI. Recombinant BCMA and TACI were generated as fusions with mouse IgG2a-Fc. These recombinant proteins were incubated with the transduced T-cells. After this, the cells were washed and stained with an anti-mouse fluorophore conjugated antibody and an antibody to detect the marker gene conjugated to a different fluorophore. The cells were analysed by flow cytometry and the results are presented in FIG. 27C. The different CARs were able to bind both BCMA and TACI. Surprisingly, the CARs were better able to bind BCMA than TACI. Also, surprisingly CARs with a CD8 stalk or IgG1 hinge spacer were better able to bind BCMA and TACI than CAR with an Fc spacer.

Example 13—APRIL Based Chimeric Antigen Receptors are Active Against BCMA Expressing Cells T-cells from normal donors were transduced with the different APRIL CARs and tested against SupT1 cells either wild-type, or engineered to express BCMA and TACI. Several different assays were used to determine function. A classical chromium release assay was performed. Here, the target cells (the SupT1 cells) were labelled with 51Cr and mixed with effectors (the transduced T-cells) at different ratio. Lysis of target cells was determined by counting 51Cr in the co-culture supernatant (FIG. 28A shows the cumulative data).

In addition, supernatant from T-cells cultured 1:1 with SupT1 cells was assayed by ELISA for Interferon-gamma (FIG. 28B shows cumulative data). Measurement of T-cell expansion after one week of co-culture with SupT1 cells was also performed (FIG. 28C). T-cells were counted by flow-cytometry calibrated with counting beads. These experimental data show that APRIL based CARs can kill BCMA expressing targets. Further, these data show that CARs based on the CD8 stalk or IgG1 hinge performed better than the Fc-pvaa based CAR.

Example 14—Functional Analysis of the AND Pate in Primary Cells

PBMCs were isolated from blood and stimulated using PHA and IL-2. Two days later the cells were transduced on retronectin coated plates with retro virus containing the CD19:CD33 AND gate construct. On day 5 the expression level of the two CARs translated by the AND gate construct was evaluated via flow cytometry and the cells were depleted of CD56+ cells (predominantly NK cells). On day 6 the PBMCs were placed in a co-culture with target cells at a 1:2 effector to target cell ratio. On day 8 the supernatant was collected and analysed for IFN-gamma secretion via ELISA (FIG. 29).

These data demonstrate that the AND gate functions in primary cells.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cell biology or related fields are intended to be within the scope of the following claims.

---

The invention claimed is:

1. A T cell or natural killer (NK) cell which co-expresses a first chimeric antigen receptor (CAR) and second CAR at the cell surface, each CAR comprising:
   (i) an antigen-binding domain;
   (ii) a spacer
   (iii) a trans-membrane domain; and
   (iv) an endodomain
   wherein the antigen binding domains of the first and second CARs bind to different antigens,
   wherein the spacer of the first CAR is different from the spacer of the second CAR such that when both first and second CARs bind their target antigen, the difference in spacer dimensions results in spatial separation of the activating and inhibitory CARs to different parts of the membrane,
   wherein one of the first or second CARs is an activating CAR comprising an activating endodomain and the other CAR is an inhibitory CAR comprising a ligation-off inhibitory endodomain, and
   wherein the ligation-off inhibitory endodomain comprises a CD148 or CD45 tyrosine phosphatase domain.

2. The T or NK cell according to claim 1, wherein either the first spacer or the second spacer comprises a CD8 stalk and the other spacer comprises the hinge, CH2 and CH3 domain of IgG-I.

3. The T or NK cell according to claim 1, wherein the antigen-binding domain of the first CAR binds CD5 and the antigen-binding domain of the second CAR binds CD19.

4. A nucleic acid sequence encoding both first and second chimeric antigen receptors (CARs) as defined in claim 1.

5. The nucleic acid sequence according to claim 4, which has the following structure:
   AgB1-spacer1-TM1-endo1-coexpr-AbB2-spacer2-TM2-endo2 in which AgB1 is a nucleic acid sequence encoding the antigen-binding domain of the first CAR;
   spacer 1 is a nucleic acid sequence encoding the spacer of the first CAR;
   TM1 is a a nucleic acid sequence encoding the transmembrane domain of the first CAR;
   endo 1 is a nucleic acid sequence encoding the endodomain of the first CAR;
   coexpr is a nucleic acid sequence enabling co-expression of both CARs AgB2 is a nucleic acid sequence encoding the antigen-binding domain of the second CAR;
   spacer 2 is a nucleic acid sequence encoding the spacer of the second CAR;
   TM2 is a a nucleic acid sequence encoding the transmembrane domain of the second CAR;
   endo 2 is a nucleic acid sequence encoding the endodomain of the second CAR;
   which nucleic acid sequence, when expressed in a T cell, encodes a polypeptide which is cleaved at the cleavage site such that the first and second CARs are co-expressed at the T cell surface.

6. The nucleic acid sequence according to claim 5, wherein coexpr encodes a sequence comprising a self-cleaving peptide.

7. The nucleic acid sequence according to claim 5, wherein alternative codons are used in regions of sequence encoding the same or similar amino acid sequences, in order to avoid homologous recombination.

8. A kit which comprises
   (i) a first nucleic acid sequence encoding the first chimeric antigen receptor (CAR) as defined in claim 1, which nucleic acid sequence has the following structure: AgB1-spacer1-TM1-endo1 in which
      AgB1 is a nucleic acid sequence encoding the antigen-binding domain of the first CAR;
      spacer 1 is a nucleic acid sequence encoding the spacer of the first CAR;
      TM1 is a nucleic acid sequence encoding the transmembrane domain of the first CAR;
      endo 1 is a nucleic acid sequence encoding the endodomain of the first CAR; and
   (ii) a second nucleic acid sequence encoding the second chimeric antigen receptor (CAR) as defined in claim 1, which nucleic acid sequence has the following structure:
   AgB2-spacer2-TM2-endo2
      AgB2 is a nucleic acid sequence encoding the antigen-binding domain of the second CAR;
      spacer 2 is a nucleic acid sequence encoding the spacer of the second CAR;
      TM2 is a a nucleic acid sequence encoding the transmembrane domain of the second CAR;
      endo 2 is a nucleic acid sequence encoding the endodomain of the second CAR.

9. The kit comprising: a first vector which comprises the first nucleic acid sequence as defined in claim 8; and a second vector which comprises the first nucleic acid sequence as defined in claim 8.

10. A vector comprising a nucleic acid sequence according to claim 4.

11. The vector according to claim 10 which is a retroviral vector or a lentiviral vector or a transposon.

12. A method for making a T or NK cell according to claim 1, which comprises the step of introducing: a nucleic acid sequence according to claim 4; a first nucleic acid sequence and a second nucleic acid sequence as defined in claim 8; and/or a first vector and a second vector as defined in claim 9, or a vector according to claim 10, into a T or NK cell.

13. The method according to claim 12, wherein the T or NK cell is from a sample isolated from a subject.

14. A pharmaceutical composition comprising a plurality of T or NK cells according to claim 1.

15. A method for treating a cancer, which comprises the step of administering a pharmaceutical composition according to claim 14 to a subject.

16. The method according to claim 15, which comprises the following steps:
   (i) isolation of a T cell-containing sample from a subject;
   (ii) transduction or transfection of the T cells with: a nucleic acid sequence according to claim 4; a first nucleic acid sequence and a second nucleic acid sequence as defined in claim 8; a first vector and a second vector as defined in claim 9 or a vector according to claim 10; and
   (iii) administering the T cells from (ii) to the subject.

* * * * *

UNITED STATES PATENT AND TRADEMARK OFFICE
CERTIFICATE OF CORRECTION

PATENT NO.        : 10,172,886 B2                                Page 1 of 1
APPLICATION NO.   : 15/037414
DATED             : January 8, 2019
INVENTOR(S)       : Martin Pulé et al.

It is certified that error appears in the above-identified patent and that said Letters Patent is hereby corrected as shown below:

On the Title Page

At item (57), Line 4, "spacer (iii)" should be -- spacer; (iii) --.

In the Claims

At Column 217, Line 28, "spacer" should be -- spacer; --.

At Column 217, Line 30, "endodomain" should be -- endodomain; --.

At Column 217, Line 49, "IgG-I." should be -- IgG1. --.

At Column 217, Line 62, "is a a" should be -- is a --.

At Column 217, Line 67, "CARs" should be -- CARs; --.

At Column 218, Line 27, "is a a" should be -- is a --.

At Column 218, Line 42, "comprises" should be -- comprises: --.

At Column 218, Line 64, "is a a" should be -- is a --.

At Column 219, Line 13, "claim 8; and/or a" should be -- claim 8; a --.

At Column 219, Line 14, "claim 9," should be -- claim 9; --.

Signed and Sealed this
Nineteenth Day of November, 2019

Andrei Iancu
*Director of the United States Patent and Trademark Office*

SEQUENCE LISTING

<160> NUMBER OF SEQ ID NOS: 53

<210> SEQ ID NO 1
<211> LENGTH: 1129
<212> TYPE: PRT
<213> ORGANISM: Artificial Sequence
<220> FEATURE:
<223> OTHER INFORMATION: Chimeric antigen receptor (CAR)

<400> SEQUENCE: 1

```
Met Ser Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Lys Ala Gly Gly Gly Gly Ser Gly Gly Gly Gly Ser Gly Gly Gly Gly
    130                 135                 140

Ser Gly Gly Gly Gly Ser Glu Val Lys Leu Gln Glu Ser Gly Pro Gly
145                 150                 155                 160

Leu Val Ala Pro Ser Gln Ser Leu Ser Val Thr Cys Thr Val Ser Gly
                165                 170                 175

Val Ser Leu Pro Asp Tyr Gly Val Ser Trp Ile Arg Gln Pro Pro Arg
            180                 185                 190

Lys Gly Leu Glu Trp Leu Gly Val Ile Trp Gly Ser Glu Thr Thr Tyr
        195                 200                 205

Tyr Asn Ser Ala Leu Lys Ser Arg Leu Thr Ile Ile Lys Asp Asn Ser
    210                 215                 220

Lys Ser Gln Val Phe Leu Lys Met Asn Ser Leu Gln Thr Asp Asp Thr
225                 230                 235                 240

Ala Ile Tyr Tyr Cys Ala Lys His Tyr Tyr Tyr Gly Gly Ser Tyr Ala
                245                 250                 255

Met Asp Tyr Trp Gly Gln Gly Thr Ser Val Thr Val Ser Ser Asp Pro
            260                 265                 270
```

```
Thr Thr Thr Pro Ala Pro Arg Pro Thr Pro Ala Pro Thr Ile Ala
        275                 280                 285
Ser Gln Pro Leu Ser Leu Arg Pro Glu Ala Cys Arg Pro Ala Ala Gly
290                 295                 300
Gly Ala Val His Thr Arg Gly Leu Asp Phe Ala Cys Asp Ile Phe Trp
305                 310                 315                 320
Val Leu Val Val Val Gly Gly Val Leu Ala Cys Tyr Ser Leu Leu Val
                325                 330                 335
Thr Val Ala Phe Ile Ile Phe Trp Val Arg Arg Val Lys Phe Ser Arg
            340                 345                 350
Ser Ala Asp Ala Pro Ala Tyr Gln Gln Gly Gln Asn Gln Leu Tyr Asn
        355                 360                 365
Glu Leu Asn Leu Gly Arg Arg Glu Glu Tyr Asp Val Leu Asp Lys Arg
370                 375                 380
Arg Gly Arg Asp Pro Glu Met Gly Gly Lys Pro Arg Arg Lys Asn Pro
385                 390                 395                 400
Gln Glu Gly Leu Tyr Asn Glu Leu Gln Lys Asp Lys Met Ala Glu Ala
                405                 410                 415
Tyr Ser Glu Ile Gly Met Lys Gly Glu Arg Arg Arg Gly Lys Gly His
            420                 425                 430
Asp Gly Leu Tyr Gln Gly Leu Ser Thr Ala Thr Lys Asp Thr Tyr Asp
        435                 440                 445
Ala Leu His Met Gln Ala Leu Pro Pro Arg Arg Ala Glu Gly Arg Gly
450                 455                 460
Ser Leu Leu Thr Cys Gly Asp Val Glu Glu Asn Pro Gly Pro Met Ala
465                 470                 475                 480
Val Pro Thr Gln Val Leu Gly Leu Leu Leu Leu Trp Leu Thr Asp Ala
                485                 490                 495
Arg Cys Asp Ile Gln Met Thr Gln Ser Pro Ser Ser Leu Ser Ala Ser
            500                 505                 510
Val Gly Asp Arg Val Thr Ile Thr Cys Arg Ala Ser Glu Asp Ile Tyr
        515                 520                 525
Phe Asn Leu Val Trp Tyr Gln Gln Lys Pro Gly Lys Ala Pro Lys Leu
530                 535                 540
Leu Ile Tyr Asp Thr Asn Arg Leu Ala Asp Gly Val Pro Ser Arg Phe
545                 550                 555                 560
Ser Gly Ser Gly Ser Gly Thr Gln Tyr Thr Leu Thr Ile Ser Ser Leu
                565                 570                 575
Gln Pro Glu Asp Phe Ala Thr Tyr Tyr Cys Gln His Tyr Lys Asn Tyr
            580                 585                 590
Pro Leu Thr Phe Gly Gln Gly Thr Lys Leu Glu Ile Lys Arg Ser Gly
        595                 600                 605
Gly Gly Gly Ser Gly Gly Gly Gly Ser Gly Gly Gly Gly Ser Gly Gly
610                 615                 620
Gly Gly Ser Arg Ser Glu Val Gln Leu Val Glu Ser Gly Gly Gly Leu
625                 630                 635                 640
Val Gln Pro Gly Gly Ser Leu Arg Leu Ser Cys Ala Ala Ser Gly Phe
                645                 650                 655
Thr Leu Ser Asn Tyr Gly Met His Trp Ile Arg Gln Ala Pro Gly Lys
            660                 665                 670
Gly Leu Glu Trp Val Ser Ser Ile Ser Leu Asn Gly Gly Ser Thr Tyr
        675                 680                 685
```

```
Tyr Arg Asp Ser Val Lys Gly Arg Phe Thr Ile Ser Arg Asp Asn Ala
690                 695                 700

Lys Ser Thr Leu Tyr Leu Gln Met Asn Ser Leu Arg Ala Glu Asp Thr
705                 710                 715                 720

Ala Val Tyr Tyr Cys Ala Ala Gln Asp Ala Tyr Thr Gly Gly Tyr Phe
            725                 730                 735

Asp Tyr Trp Gly Gln Gly Thr Leu Val Thr Val Ser Ser Met Asp Pro
            740                 745                 750

Ala Glu Pro Lys Ser Pro Asp Lys Thr His Thr Cys Pro Pro Cys Pro
            755                 760                 765

Ala Pro Pro Val Ala Gly Pro Ser Val Phe Leu Phe Pro Pro Lys Pro
770                 775                 780

Lys Asp Thr Leu Met Ile Ala Arg Thr Pro Glu Val Thr Cys Val Val
785                 790                 795                 800

Val Asp Val Ser His Glu Asp Pro Glu Val Lys Phe Asn Trp Tyr Val
                805                 810                 815

Asp Gly Val Glu Val His Asn Ala Lys Thr Lys Pro Arg Glu Glu Gln
            820                 825                 830

Tyr Asn Ser Thr Tyr Arg Val Val Ser Val Leu Thr Val Leu His Gln
            835                 840                 845

Asp Trp Leu Asn Gly Lys Glu Tyr Lys Cys Lys Val Ser Asn Lys Ala
850                 855                 860

Leu Pro Ala Pro Ile Glu Lys Thr Ile Ser Lys Ala Lys Gly Gln Pro
865                 870                 875                 880

Arg Glu Pro Gln Val Tyr Thr Leu Pro Pro Ser Arg Asp Glu Leu Thr
                885                 890                 895

Lys Asn Gln Val Ser Leu Thr Cys Leu Val Lys Gly Phe Tyr Pro Ser
            900                 905                 910

Asp Ile Ala Val Glu Trp Glu Ser Asn Gly Gln Pro Glu Asn Asn Tyr
            915                 920                 925

Lys Thr Thr Pro Pro Val Leu Asp Ser Asp Gly Ser Phe Phe Leu Tyr
930                 935                 940

Ser Lys Leu Thr Val Asp Lys Ser Arg Trp Gln Gln Gly Asn Val Phe
945                 950                 955                 960

Ser Cys Ser Val Met His Glu Ala Leu His Asn His Tyr Thr Gln Lys
                965                 970                 975

Ser Leu Ser Leu Ser Pro Gly Lys Lys Asp Pro Lys Phe Trp Val Leu
            980                 985                 990

Val Val Val Gly Gly Val Leu Ala Cys Tyr Ser Leu Leu Val Thr Val
            995                 1000                1005

Ala Phe Ile Ile Phe Trp Val Arg Ser Arg Val Lys Phe Ser Arg
1010                1015                1020

Ser Ala Asp Ala Pro Ala Tyr Gln Gln Gly Gln Asn Gln Leu Tyr
1025                1030                1035

Asn Glu Leu Asn Leu Gly Arg Arg Glu Glu Tyr Asp Val Leu Asp
1040                1045                1050

Lys Arg Arg Gly Arg Asp Pro Glu Met Gly Gly Lys Pro Arg Arg
1055                1060                1065

Lys Asn Pro Gln Glu Gly Leu Tyr Asn Glu Leu Gln Lys Asp Lys
1070                1075                1080

Met Ala Glu Ala Tyr Ser Glu Ile Gly Met Lys Gly Glu Arg Arg
1085                1090                1095

Arg Gly Lys Gly His Asp Gly Leu Tyr Gln Gly Leu Ser Thr Ala
```

```
                    1100                1105                1110
Thr Lys Asp Thr Tyr Asp Ala Leu His Met Gln Ala Leu Pro Pro
        1115                1120                1125
Arg
```

```
<210> SEQ ID NO 2
<211> LENGTH: 1350
<212> TYPE: PRT
<213> ORGANISM: Artificial Sequence
<220> FEATURE:
<223> OTHER INFORMATION: Chimeric antigen receptor (CAR)

<400> SEQUENCE: 2

Met Ser Leu Pro Val Thr Ala Leu Leu Leu Pro Leu Ala Leu Leu Leu
1               5                   10                  15
His Ala Ala Arg Pro Asp Ile Gln Met Thr Gln Thr Thr Ser Ser Leu
            20                  25                  30
Ser Ala Ser Leu Gly Asp Arg Val Thr Ile Ser Cys Arg Ala Ser Gln
        35                  40                  45
Asp Ile Ser Lys Tyr Leu Asn Trp Tyr Gln Gln Lys Pro Asp Gly Thr
    50                  55                  60
Val Lys Leu Leu Ile Tyr His Thr Ser Arg Leu His Ser Gly Val Pro
65                  70                  75                  80
Ser Arg Phe Ser Gly Ser Gly Ser Gly Thr Asp Tyr Ser Leu Thr Ile
                85                  90                  95
Ser Asn Leu Glu Gln Glu Asp Ile Ala Thr Tyr Phe Cys Gln Gln Gly
            100                 105                 110
Asn Thr Leu Pro Tyr Thr Phe Gly Gly Gly Thr Lys Leu Glu Ile Thr
        115                 120                 125
Lys Ala Gly Gly Gly Gly Ser Gly Gly Gly Gly Ser Gly Gly Gly Gly
    130                 135                 140
Ser Gly Gly Gly Gly Ser Glu Val Lys Leu Gln Glu Ser Gly Pro Gly
145                 150                 155                 160
Leu Val Ala Pro Ser Gln Ser Leu Ser Val Thr Cys Thr Val Ser Gly
                165                 170                 175
Val Ser Leu Pro Asp Tyr Gly Val Ser Trp Ile Arg Gln Pro Pro Arg
            180                 185                 190
Lys Gly Leu Glu Trp Leu Gly Val Ile Trp Gly Ser Glu Thr Thr Tyr
        195                 200                 205
Tyr Asn Ser Ala Leu Lys Ser Arg Leu Thr Ile Ile Lys Asp Asn Ser
    210                 215                 220
Lys Ser Gln Val Phe Leu Lys Met Asn Ser Leu Gln Thr Asp Asp Thr
225                 230                 235                 240
Ala Ile Tyr Tyr Cys Ala Lys His Tyr Tyr Gly Gly Ser Tyr Ala
                245                 250                 255
Met Asp Tyr Trp Gly Gln Gly Thr Ser Val Thr Val Ser Ser Asp Pro
            260                 265                 270
Thr Thr Thr Pro Ala Pro Arg Pro Pro Thr Pro Ala Pro Thr Ile Ala
        275                 280                 285
Ser Gln Pro Leu Ser Leu Arg Pro Glu Ala Cys Arg Pro Ala Ala Gly
    290                 295                 300
Gly Ala Val His Thr Arg Gly Leu Asp Phe Ala Cys Asp Ile Phe Trp
305                 310                 315                 320
Val Leu Val Val Val Gly Gly Val Leu Ala Cys Tyr Ser Leu Leu Val
                325                 330                 335
```

```
Thr Val Ala Phe Ile Ile Phe Trp Val Arg Val Lys Phe Ser Arg
            340                 345                 350

Ser Ala Asp Ala Pro Ala Tyr Gln Gln Gly Gln Asn Gln Leu Tyr Asn
            355                 360                 365

Glu Leu Asn Leu Gly Arg Arg Glu Glu Tyr Asp Val Leu Asp Lys Arg
        370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
            405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
        435                 440                 445

Ala Leu His Met Gln Ala Leu Pro Pro Arg Arg Ala Glu Gly Arg Gly
        450                 455                 460

Ser Leu Leu Thr Cys Gly Asp Val Glu Glu Asn Pro Gly Pro Met Ala
465                 470                 475                 480

Val Pro Thr Gln Val Leu Gly Leu Leu Leu Leu Trp Leu Thr Asp Ala
            485                 490                 495

Arg Cys Asp Ile Gln Met Thr Gln Ser Pro Ser Ser Leu Ser Ala Ser
            500                 505                 510

Val Gly Asp Arg Val Thr Ile Thr Cys Arg Ala Ser Glu Asp Ile Tyr
            515                 520                 525

Phe Asn Leu Val Trp Tyr Gln Gln Lys Pro Gly Lys Ala Pro Lys Leu
            530                 535                 540

Leu Ile Tyr Asp Thr Asn Arg Leu Ala Asp Gly Val Pro Ser Arg Phe
545                 550                 555                 560

Ser Gly Ser Gly Ser Gly Thr Gln Tyr Thr Leu Thr Ile Ser Ser Leu
            565                 570                 575

Gln Pro Glu Asp Phe Ala Thr Tyr Tyr Cys Gln His Tyr Lys Asn Tyr
            580                 585                 590

Pro Leu Thr Phe Gly Gln Gly Thr Lys Leu Glu Ile Lys Arg Ser Gly
            595                 600                 605

Gly Gly Gly Ser Gly Gly Gly Gly Ser Gly Gly Gly Gly Ser Gly Gly
            610                 615                 620

Gly Gly Ser Arg Ser Glu Val Gln Leu Val Glu Ser Gly Gly Gly Leu
625                 630                 635                 640

Val Gln Pro Gly Gly Ser Leu Arg Leu Ser Cys Ala Ala Ser Gly Phe
            645                 650                 655

Thr Leu Ser Asn Tyr Gly Met His Trp Ile Arg Gln Ala Pro Gly Lys
            660                 665                 670

Gly Leu Glu Trp Val Ser Ser Ile Ser Leu Asn Gly Gly Ser Thr Tyr
            675                 680                 685

Tyr Arg Asp Ser Val Lys Gly Arg Phe Thr Ile Ser Arg Asp Asn Ala
        690                 695                 700

Lys Ser Thr Leu Tyr Leu Gln Met Asn Ser Leu Arg Ala Glu Asp Thr
705                 710                 715                 720

Ala Val Tyr Tyr Cys Ala Ala Gln Asp Ala Tyr Thr Gly Gly Tyr Phe
            725                 730                 735

Asp Tyr Trp Gly Gln Gly Thr Leu Val Thr Val Ser Ser Met Asp Pro
            740                 745                 750
```

```
Ala Glu Pro Lys Ser Pro Asp Lys Thr His Thr Cys Pro Cys Pro
            755                 760                 765
Ala Pro Pro Val Ala Gly Pro Ser Val Phe Leu Phe Pro Pro Lys Pro
770                 775                 780
Lys Asp Thr Leu Met Ile Ala Arg Thr Pro Glu Val Thr Cys Val Val
785                 790                 795                 800
Val Asp Val Ser His Glu Asp Pro Glu Val Lys Phe Asn Trp Tyr Val
                805                 810                 815
Asp Gly Val Glu Val His Asn Ala Lys Thr Lys Pro Arg Glu Glu Gln
            820                 825                 830
Tyr Asn Ser Thr Tyr Arg Val Val Ser Val Leu Thr Val Leu His Gln
                835                 840                 845
Asp Trp Leu Asn Gly Lys Glu Tyr Lys Cys Lys Val Ser Asn Lys Ala
850                 855                 860
Leu Pro Ala Pro Ile Glu Lys Thr Ile Ser Lys Ala Lys Gly Gln Pro
865                 870                 875                 880
Arg Glu Pro Gln Val Tyr Thr Leu Pro Pro Ser Arg Asp Glu Leu Thr
                885                 890                 895
Lys Asn Gln Val Ser Leu Thr Cys Leu Val Lys Gly Phe Tyr Pro Ser
            900                 905                 910
Asp Ile Ala Val Glu Trp Glu Ser Asn Gly Gln Pro Glu Asn Asn Tyr
            915                 920                 925
Lys Thr Thr Pro Pro Val Leu Asp Ser Asp Gly Ser Phe Phe Leu Tyr
930                 935                 940
Ser Lys Leu Thr Val Asp Lys Ser Arg Trp Gln Gln Gly Asn Val Phe
945                 950                 955                 960
Ser Cys Ser Val Met His Glu Ala Leu His Asn His Tyr Thr Gln Lys
                965                 970                 975
Ser Leu Ser Leu Ser Pro Gly Lys Lys Asp Pro Lys Ala Val Phe Gly
            980                 985                 990
Cys Ile Phe Gly Ala Leu Val Ile Val Thr Val Gly Gly Phe Ile Phe
            995                 1000                1005
Trp Arg Lys Lys Arg Lys Asp Ala Lys Asn Asn Glu Val Ser Phe
      1010                1015                1020
Ser Gln Ile Lys Pro Lys Lys Ser Lys Leu Ile Arg Val Glu Asn
      1025                1030                1035
Phe Glu Ala Tyr Phe Lys Lys Gln Gln Ala Asp Ser Asn Cys Gly
      1040                1045                1050
Phe Ala Glu Glu Tyr Glu Asp Leu Lys Leu Val Gly Ile Ser Gln
      1055                1060                1065
Pro Lys Tyr Ala Ala Glu Leu Ala Glu Asn Arg Gly Lys Asn Arg
      1070                1075                1080
Tyr Asn Asn Val Leu Pro Tyr Asp Ile Ser Arg Val Lys Leu Ser
      1085                1090                1095
Val Gln Thr His Ser Thr Asp Asp Tyr Ile Asn Ala Asn Tyr Met
      1100                1105                1110
Pro Gly Tyr His Ser Lys Lys Asp Phe Ile Ala Thr Gln Gly Pro
      1115                1120                1125
Leu Pro Asn Thr Leu Lys Asp Phe Trp Arg Met Val Trp Glu Lys
      1130                1135                1140
Asn Val Tyr Ala Ile Ile Met Leu Thr Lys Cys Val Glu Gln Gly
      1145                1150                1155
Arg Thr Lys Cys Glu Glu Tyr Trp Pro Ser Lys Gln Ala Gln Asp
```

```
                1160                1165                1170
Tyr Gly Asp Ile Thr Val Ala Met Thr Ser Glu Ile Val Leu Pro
    1175                1180                1185

Glu Trp Thr Ile Arg Asp Phe Thr Val Lys Asn Ile Gln Thr Ser
    1190                1195                1200

Glu Ser His Pro Leu Arg Gln Phe His Phe Thr Ser Trp Pro Asp
    1205                1210                1215

His Gly Val Pro Asp Thr Thr Asp Leu Leu Ile Asn Phe Arg Tyr
    1220                1225                1230

Leu Val Arg Asp Tyr Met Lys Gln Ser Pro Pro Glu Ser Pro Ile
    1235                1240                1245

Leu Val His Cys Ser Ala Gly Val Gly Arg Thr Gly Thr Phe Ile
    1250                1255                1260

Ala Ile Asp Arg Leu Ile Tyr Gln Ile Glu Asn Glu Asn Thr Val
    1265                1270                1275

Asp Val Tyr Gly Ile Val Tyr Asp Leu Arg Met His Arg Pro Leu
    1280                1285                1290

Met Val Gln Thr Glu Asp Gln Tyr Val Phe Leu Asn Gln Cys Val
    1295                1300                1305

Leu Asp Ile Val Arg Ser Gln Lys Asp Ser Lys Val Asp Leu Ile
    1310                1315                1320

Tyr Gln Asn Thr Thr Ala Met Thr Ile Tyr Glu Asn Leu Ala Pro
    1325                1330                1335

Val Thr Thr Phe Gly Lys Thr Asn Gly Tyr Ile Ala
    1340                1345                1350

<210> SEQ ID NO 3
<211> LENGTH: 1717
<212> TYPE: PRT
<213> ORGANISM: Artificial Sequence
<220> FEATURE:
<223> OTHER INFORMATION: Chimeric antigen receptor (CAR)

<400> SEQUENCE: 3

Met Ser Leu Pro Val Thr Ala Leu Leu Leu Pro Leu Ala Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
                35                  40                  45

Asp Ile Ser Lys Tyr Leu Asn Trp Tyr Gln Gln Lys Pro Asp Gly Thr
50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
                100                 105                 110

Asn Thr Leu Pro Tyr Thr Phe Gly Gly Gly Thr Lys Leu Glu Ile Thr
                115                 120                 125

Lys Ala Gly Gly Gly Gly Ser Gly Gly Gly Gly Ser Gly Gly Gly Gly
                130                 135                 140

Ser Gly Gly Gly Gly Ser Glu Val Lys Leu Gln Glu Ser Gly Pro Gly
145                 150                 155                 160

Leu Val Ala Pro Ser Gln Ser Leu Ser Val Thr Cys Thr Val Ser Gly
```

```
                    165                 170                 175
Val Ser Leu Pro Asp Tyr Gly Val Ser Trp Ile Arg Gln Pro Pro Arg
                180                 185                 190
Lys Gly Leu Glu Trp Leu Gly Val Ile Trp Gly Ser Glu Thr Thr Tyr
            195                 200                 205
Tyr Asn Ser Ala Leu Lys Ser Arg Leu Thr Ile Ile Lys Asp Asn Ser
        210                 215                 220
Lys Ser Gln Val Phe Leu Lys Met Asn Ser Leu Gln Thr Asp Asp Thr
225                 230                 235                 240
Ala Ile Tyr Tyr Cys Ala Lys His Tyr Tyr Gly Gly Ser Tyr Ala
                245                 250                 255
Met Asp Tyr Trp Gly Gln Gly Thr Ser Val Thr Val Ser Ser Asp Pro
                260                 265                 270
Thr Thr Thr Pro Ala Pro Arg Pro Pro Thr Pro Ala Pro Thr Ile Ala
                275                 280                 285
Ser Gln Pro Leu Ser Leu Arg Pro Glu Ala Cys Arg Pro Ala Ala Gly
            290                 295                 300
Gly Ala Val His Thr Arg Gly Leu Asp Phe Ala Cys Asp Ile Phe Trp
305                 310                 315                 320
Val Leu Val Val Val Gly Gly Val Leu Ala Cys Tyr Ser Leu Leu Val
                325                 330                 335
Thr Val Ala Phe Ile Ile Phe Trp Val Arg Arg Val Lys Phe Ser Arg
                340                 345                 350
Ser Ala Asp Ala Pro Ala Tyr Gln Gln Gly Gln Asn Gln Leu Tyr Asn
            355                 360                 365
Glu Leu Asn Leu Gly Arg Arg Glu Glu Tyr Asp Val Leu Asp Lys Arg
        370                 375                 380
Arg Gly Arg Asp Pro Glu Met Gly Gly Lys Pro Arg Arg Lys Asn Pro
385                 390                 395                 400
Gln Glu Gly Leu Tyr Asn Glu Leu Gln Lys Asp Lys Met Ala Glu Ala
                405                 410                 415
Tyr Ser Glu Ile Gly Met Lys Gly Glu Arg Arg Arg Gly Lys Gly His
                420                 425                 430
Asp Gly Leu Tyr Gln Gly Leu Ser Thr Ala Thr Lys Asp Thr Tyr Asp
            435                 440                 445
Ala Leu His Met Gln Ala Leu Pro Pro Arg Arg Ala Glu Gly Arg Gly
        450                 455                 460
Ser Leu Leu Thr Cys Gly Asp Val Glu Glu Asn Pro Gly Pro Met Ala
465                 470                 475                 480
Val Pro Thr Gln Val Leu Gly Leu Leu Leu Leu Trp Leu Thr Asp Ala
                485                 490                 495
Arg Cys Asp Ile Gln Met Thr Gln Ser Pro Ser Ser Leu Ser Ala Ser
                500                 505                 510
Val Gly Asp Arg Val Thr Ile Thr Cys Arg Ala Ser Glu Asp Ile Tyr
            515                 520                 525
Phe Asn Leu Val Trp Tyr Gln Gln Lys Pro Gly Lys Ala Pro Lys Leu
        530                 535                 540
Leu Ile Tyr Asp Thr Asn Arg Leu Ala Asp Gly Val Pro Ser Arg Phe
545                 550                 555                 560
Ser Gly Ser Gly Ser Gly Thr Gln Tyr Thr Leu Thr Ile Ser Ser Leu
                565                 570                 575
Gln Pro Glu Asp Phe Ala Thr Tyr Tyr Cys Gln His Tyr Lys Asn Tyr
                580                 585                 590
```

-continued

Pro Leu Thr Phe Gly Gln Gly Thr Lys Leu Glu Ile Lys Arg Ser Gly
            595                 600                 605

Gly Gly Gly Ser Gly Gly Gly Ser Gly Gly Gly Ser Gly Gly
610                 615                 620

Gly Gly Ser Arg Ser Glu Val Gln Leu Val Glu Ser Gly Gly Gly Leu
625                 630                 635                 640

Val Gln Pro Gly Gly Ser Leu Arg Leu Ser Cys Ala Ala Ser Gly Phe
                645                 650                 655

Thr Leu Ser Asn Tyr Gly Met His Trp Ile Arg Gln Ala Pro Gly Lys
            660                 665                 670

Gly Leu Glu Trp Val Ser Ile Ser Leu Asn Gly Gly Ser Thr Tyr
        675                 680                 685

Tyr Arg Asp Ser Val Lys Gly Arg Phe Thr Ile Ser Arg Asp Asn Ala
        690                 695                 700

Lys Ser Thr Leu Tyr Leu Gln Met Asn Ser Leu Arg Ala Glu Asp Thr
705                 710                 715                 720

Ala Val Tyr Tyr Cys Ala Ala Gln Asp Ala Tyr Thr Gly Gly Tyr Phe
                725                 730                 735

Asp Tyr Trp Gly Gln Gly Thr Leu Val Thr Val Ser Ser Met Asp Pro
            740                 745                 750

Ala Glu Pro Lys Ser Pro Asp Lys Thr His Thr Cys Pro Pro Cys Pro
        755                 760                 765

Ala Pro Pro Val Ala Gly Pro Ser Val Phe Leu Phe Pro Pro Lys Pro
    770                 775                 780

Lys Asp Thr Leu Met Ile Ala Arg Thr Pro Glu Val Thr Cys Val Val
785                 790                 795                 800

Val Asp Val Ser His Glu Asp Pro Glu Val Lys Phe Asn Trp Tyr Val
                805                 810                 815

Asp Gly Val Glu Val His Asn Ala Lys Thr Lys Pro Arg Glu Glu Gln
            820                 825                 830

Tyr Asn Ser Thr Tyr Arg Val Val Ser Val Leu Thr Val Leu His Gln
        835                 840                 845

Asp Trp Leu Asn Gly Lys Glu Tyr Lys Cys Lys Val Ser Asn Lys Ala
    850                 855                 860

Leu Pro Ala Pro Ile Glu Lys Thr Ile Ser Lys Ala Lys Gly Gln Pro
865                 870                 875                 880

Arg Glu Pro Gln Val Tyr Thr Leu Pro Pro Ser Arg Asp Glu Leu Thr
                885                 890                 895

Lys Asn Gln Val Ser Leu Thr Cys Leu Val Lys Gly Phe Tyr Pro Ser
            900                 905                 910

Asp Ile Ala Val Glu Trp Glu Ser Asn Gly Gln Pro Glu Asn Asn Tyr
        915                 920                 925

Lys Thr Thr Pro Pro Val Leu Asp Ser Asp Gly Ser Phe Phe Leu Tyr
    930                 935                 940

Ser Lys Leu Thr Val Asp Lys Ser Arg Trp Gln Gln Gly Asn Val Phe
945                 950                 955                 960

Ser Cys Ser Val Met His Glu Ala Leu His Asn His Tyr Thr Gln Lys
                965                 970                 975

Ser Leu Ser Leu Ser Pro Gly Lys Lys Asp Pro Lys Ala Leu Ile Ala
            980                 985                 990

Phe Leu Ala Phe Leu Ile Ile Val  Thr Ser Ile Ala Leu  Leu Val Val
        995                 1000                1005

```
Leu Tyr Lys Ile Tyr Asp Leu His Lys Lys Arg Ser Cys Asn Leu
    1010            1015            1020

Asp Glu Gln Gln Glu Leu Val Glu Arg Asp Glu Lys Gln Leu
    1025            1030            1035

Met Asn Val Glu Pro Ile His Ala Asp Ile Leu Leu Glu Thr Tyr
    1040            1045            1050

Lys Arg Lys Ile Ala Asp Glu Gly Arg Leu Phe Leu Ala Glu Phe
    1055            1060            1065

Gln Ser Ile Pro Arg Val Phe Ser Lys Phe Pro Ile Lys Glu Ala
    1070            1075            1080

Arg Lys Pro Phe Asn Gln Asn Lys Asn Arg Tyr Val Asp Ile Leu
    1085            1090            1095

Pro Tyr Asp Tyr Asn Arg Val Glu Leu Ser Glu Ile Asn Gly Asp
    1100            1105            1110

Ala Gly Ser Asn Tyr Ile Asn Ala Ser Tyr Ile Asp Gly Phe Lys
    1115            1120            1125

Glu Pro Arg Lys Tyr Ile Ala Ala Gln Gly Pro Arg Asp Glu Thr
    1130            1135            1140

Val Asp Asp Phe Trp Arg Met Ile Trp Glu Gln Lys Ala Thr Val
    1145            1150            1155

Ile Val Met Val Thr Arg Cys Glu Glu Gly Asn Arg Asn Lys Cys
    1160            1165            1170

Ala Glu Tyr Trp Pro Ser Met Glu Glu Gly Thr Arg Ala Phe Gly
    1175            1180            1185

Asp Val Val Lys Ile Asn Gln His Lys Arg Cys Pro Asp Tyr
    1190            1195            1200

Ile Ile Gln Lys Leu Asn Ile Val Asn Lys Lys Glu Lys Ala Thr
    1205            1210            1215

Gly Arg Glu Val Thr His Ile Gln Phe Thr Ser Trp Pro Asp His
    1220            1225            1230

Gly Val Pro Glu Asp Pro His Leu Leu Leu Lys Leu Arg Arg Arg
    1235            1240            1245

Val Asn Ala Phe Ser Asn Phe Phe Ser Gly Pro Ile Val Val His
    1250            1255            1260

Cys Ser Ala Gly Val Gly Arg Thr Gly Thr Tyr Ile Gly Ile Asp
    1265            1270            1275

Ala Met Leu Glu Gly Leu Glu Ala Glu Asn Lys Val Asp Val Tyr
    1280            1285            1290

Gly Tyr Val Val Lys Leu Arg Arg Gln Arg Cys Leu Met Val Gln
    1295            1300            1305

Val Glu Ala Gln Tyr Ile Leu Ile His Gln Ala Leu Val Glu Tyr
    1310            1315            1320

Asn Gln Phe Gly Glu Thr Glu Val Asn Leu Ser Glu Leu His Pro
    1325            1330            1335

Tyr Leu His Asn Met Lys Lys Arg Asp Pro Pro Ser Glu Pro Ser
    1340            1345            1350

Pro Leu Glu Ala Glu Phe Gln Arg Leu Pro Ser Tyr Arg Ser Trp
    1355            1360            1365

Arg Thr Gln His Ile Gly Asn Gln Glu Glu Asn Lys Ser Lys Asn
    1370            1375            1380

Arg Asn Ser Asn Val Ile Pro Tyr Asp Tyr Asn Arg Val Pro Leu
    1385            1390            1395

Lys His Glu Leu Glu Met Ser Lys Glu Ser Glu His Asp Ser Asp
```

```
                  1400               1405               1410

Glu Ser Ser Asp Asp Ser Asp Ser Glu Pro Ser Lys Tyr
    1415               1420               1425

Ile Asn Ala Ser Phe Ile Met Ser Tyr Trp Lys Pro Glu Val Met
    1430               1435               1440

Ile Ala Ala Gln Gly Pro Leu Lys Glu Thr Ile Gly Asp Phe Trp
    1445               1450               1455

Gln Met Ile Phe Gln Arg Lys Val Lys Val Ile Val Met Leu Thr
    1460               1465               1470

Glu Leu Lys His Gly Asp Gln Glu Ile Cys Ala Gln Tyr Trp Gly
    1475               1480               1485

Glu Gly Lys Gln Thr Tyr Gly Asp Ile Glu Val Asp Leu Lys Asp
    1490               1495               1500

Thr Asp Lys Ser Ser Thr Tyr Thr Leu Arg Val Phe Glu Leu Arg
    1505               1510               1515

His Ser Lys Arg Lys Asp Ser Arg Thr Val Tyr Gln Tyr Gln Tyr
    1520               1525               1530

Thr Asn Trp Ser Val Glu Gln Leu Pro Ala Glu Pro Lys Glu Leu
    1535               1540               1545

Ile Ser Met Ile Gln Val Val Lys Gln Lys Leu Pro Gln Lys Asn
    1550               1555               1560

Ser Ser Glu Gly Asn Lys His His Lys Ser Thr Pro Leu Leu Ile
    1565               1570               1575

His Cys Arg Asp Gly Ser Gln Gln Thr Gly Ile Phe Cys Ala Leu
    1580               1585               1590

Leu Asn Leu Leu Glu Ser Ala Glu Thr Glu Glu Val Val Asp Ile
    1595               1600               1605

Phe Gln Val Val Lys Ala Leu Arg Lys Ala Arg Pro Gly Met Val
    1610               1615               1620

Ser Thr Phe Glu Gln Tyr Gln Phe Leu Tyr Asp Val Ile Ala Ser
    1625               1630               1635

Thr Tyr Pro Ala Gln Asn Gly Gln Val Lys Lys Asn Asn His Gln
    1640               1645               1650

Glu Asp Lys Ile Glu Phe Asp Asn Glu Val Asp Lys Val Lys Gln
    1655               1660               1665

Asp Ala Asn Cys Val Asn Pro Leu Gly Ala Pro Glu Lys Leu Pro
    1670               1675               1680

Glu Ala Lys Glu Gln Ala Glu Gly Ser Glu Pro Thr Ser Gly Thr
    1685               1690               1695

Glu Gly Pro Glu His Ser Val Asn Gly Pro Ala Ser Pro Ala Leu
    1700               1705               1710

Asn Gln Gly Ser
    1715

<210> SEQ ID NO 4
<211> LENGTH: 1114
<212> TYPE: PRT
<213> ORGANISM: Artificial Sequence
<220> FEATURE:
<223> OTHER INFORMATION: Chimeric antigen receptor (CAR)

<400> SEQUENCE: 4

Met Ser Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
```

-continued

```
            20                  25                  30
Ser Ala Ser Leu Gly Asp Arg Val Thr Ile Ser Cys Arg Ala Ser Gln
        35                  40                  45
Asp Ile Ser Lys Tyr Leu Asn Trp Tyr Gln Gln Lys Pro Asp Gly Thr
    50                  55                  60
Val Lys Leu Leu Ile Tyr His Thr Ser Arg Leu His Ser Gly Val Pro
65                  70                  75                  80
Ser Arg Phe Ser Gly Ser Gly Ser Gly Thr Asp Tyr Ser Leu Thr Ile
                85                  90                  95
Ser Asn Leu Glu Gln Glu Asp Ile Ala Thr Tyr Phe Cys Gln Gln Gly
            100                 105                 110
Asn Thr Leu Pro Tyr Thr Phe Gly Gly Gly Thr Lys Leu Glu Ile Thr
        115                 120                 125
Lys Ala Gly Gly Gly Ser Gly Gly Gly Ser Gly Gly Gly Gly
    130                 135                 140
Ser Gly Gly Gly Ser Glu Val Lys Leu Gln Glu Ser Gly Pro Gly
145                 150                 155                 160
Leu Val Ala Pro Ser Gln Ser Leu Ser Val Thr Cys Thr Val Ser Gly
                165                 170                 175
Val Ser Leu Pro Asp Tyr Gly Val Ser Trp Ile Arg Gln Pro Pro Arg
            180                 185                 190
Lys Gly Leu Glu Trp Leu Gly Val Ile Trp Gly Ser Glu Thr Thr Tyr
        195                 200                 205
Tyr Asn Ser Ala Leu Lys Ser Arg Leu Thr Ile Ile Lys Asp Asn Ser
    210                 215                 220
Lys Ser Gln Val Phe Leu Lys Met Asn Ser Leu Gln Thr Asp Asp Thr
225                 230                 235                 240
Ala Ile Tyr Tyr Cys Ala Lys His Tyr Tyr Gly Gly Ser Tyr Ala
                245                 250                 255
Met Asp Tyr Trp Gly Gln Gly Thr Ser Val Thr Val Ser Ser Asp Pro
            260                 265                 270
Thr Thr Thr Pro Ala Pro Arg Pro Pro Thr Pro Ala Pro Thr Ile Ala
        275                 280                 285
Ser Gln Pro Leu Ser Leu Arg Pro Glu Ala Cys Arg Pro Ala Ala Gly
    290                 295                 300
Gly Ala Val His Thr Arg Gly Leu Asp Phe Ala Cys Asp Ile Phe Trp
305                 310                 315                 320
Val Leu Val Val Val Gly Gly Val Leu Ala Cys Tyr Ser Leu Leu Val
                325                 330                 335
Thr Val Ala Phe Ile Ile Phe Trp Val Arg Arg Val Lys Phe Ser Arg
            340                 345                 350
Ser Ala Asp Ala Pro Ala Tyr Gln Gln Gly Gln Asn Gln Leu Tyr Asn
        355                 360                 365
Glu Leu Asn Leu Gly Arg Arg Glu Glu Tyr Asp Val Leu Asp Lys Arg
    370                 375                 380
Arg Gly Arg Asp Pro Glu Met Gly Gly Lys Pro Arg Arg Lys Asn Pro
385                 390                 395                 400
Gln Glu Gly Leu Tyr Asn Glu Leu Gln Lys Asp Lys Met Ala Glu Ala
                405                 410                 415
Tyr Ser Glu Ile Gly Met Lys Gly Glu Arg Arg Arg Gly Lys Gly His
            420                 425                 430
Asp Gly Leu Tyr Gln Gly Leu Ser Thr Ala Thr Lys Asp Thr Tyr Asp
        435                 440                 445
```

```
Ala Leu His Met Gln Ala Leu Pro Pro Arg Arg Ala Glu Gly Arg Gly
    450                 455                 460

Ser Leu Leu Thr Cys Gly Asp Val Glu Glu Asn Pro Gly Pro Met Ala
465                 470                 475                 480

Val Pro Thr Gln Val Leu Gly Leu Leu Leu Trp Leu Thr Asp Ala
                485                 490                 495

Arg Cys Asp Ile Gln Met Thr Gln Ser Pro Ser Ser Leu Ser Ala Ser
                500                 505                 510

Val Gly Asp Arg Val Thr Ile Thr Cys Arg Ala Ser Glu Asp Ile Tyr
            515                 520                 525

Phe Asn Leu Val Trp Tyr Gln Gln Lys Pro Gly Lys Ala Pro Lys Leu
530                 535                 540

Leu Ile Tyr Asp Thr Asn Arg Leu Ala Asp Gly Val Pro Ser Arg Phe
545                 550                 555                 560

Ser Gly Ser Gly Ser Gly Thr Gln Tyr Thr Leu Thr Ile Ser Ser Leu
                565                 570                 575

Gln Pro Glu Asp Phe Ala Thr Tyr Tyr Cys Gln His Tyr Lys Asn Tyr
                580                 585                 590

Pro Leu Thr Phe Gly Gln Gly Thr Lys Leu Glu Ile Lys Arg Ser Gly
            595                 600                 605

Gly Gly Gly Ser Gly Gly Gly Gly Ser Gly Gly Gly Gly Ser Gly Gly
            610                 615                 620

Gly Gly Ser Arg Ser Glu Val Gln Leu Val Glu Ser Gly Gly Gly Leu
625                 630                 635                 640

Val Gln Pro Gly Gly Ser Leu Arg Leu Ser Cys Ala Ala Ser Gly Phe
                645                 650                 655

Thr Leu Ser Asn Tyr Gly Met His Trp Ile Arg Gln Ala Pro Gly Lys
            660                 665                 670

Gly Leu Glu Trp Val Ser Ser Ile Ser Leu Asn Gly Gly Ser Thr Tyr
            675                 680                 685

Tyr Arg Asp Ser Val Lys Gly Arg Phe Thr Ile Ser Arg Asp Asn Ala
            690                 695                 700

Lys Ser Thr Leu Tyr Leu Gln Met Asn Ser Leu Arg Ala Glu Asp Thr
705                 710                 715                 720

Ala Val Tyr Tyr Cys Ala Ala Gln Asp Ala Tyr Thr Gly Gly Tyr Phe
                725                 730                 735

Asp Tyr Trp Gly Gln Gly Thr Leu Val Thr Val Ser Ser Met Asp Pro
            740                 745                 750

Ala Thr Thr Thr Lys Pro Val Leu Arg Thr Pro Ser Pro Val His Pro
            755                 760                 765

Thr Gly Thr Ser Gln Pro Gln Arg Pro Glu Asp Cys Arg Pro Arg Gly
    770                 775                 780

Ser Val Lys Gly Thr Gly Leu Asp Phe Ala Cys Asp Ile Tyr Trp Ala
785                 790                 795                 800

Pro Leu Ala Gly Ile Cys Val Ala Leu Leu Leu Ser Leu Ile Ile Thr
                805                 810                 815

Leu Ile Cys Tyr His Arg Ser Arg Lys Arg Val Cys Lys Ser Gly Gly
            820                 825                 830

Gly Ser Phe Trp Glu Glu Phe Glu Ser Leu Gln Lys Gln Glu Val Lys
            835                 840                 845

Asn Leu His Gln Arg Leu Glu Gly Gln Arg Pro Glu Asn Lys Gly Lys
850                 855                 860
```

Asn Arg Tyr Lys Asn Ile Leu Pro Phe Asp His Ser Arg Val Ile Leu
865                 870                 875                 880

Gln Gly Arg Asp Ser Asn Ile Pro Gly Ser Asp Tyr Ile Asn Ala Asn
            885                 890                 895

Tyr Ile Lys Asn Gln Leu Leu Gly Pro Asp Glu Asn Ala Lys Thr Tyr
        900                 905                 910

Ile Ala Ser Gln Gly Cys Leu Glu Ala Thr Val Asn Asp Phe Trp Gln
            915                 920                 925

Met Ala Trp Gln Glu Asn Ser Arg Val Ile Val Met Thr Thr Arg Glu
    930                 935                 940

Val Glu Lys Gly Arg Asn Lys Cys Val Pro Tyr Trp Pro Glu Val Gly
945                 950                 955                 960

Met Gln Arg Ala Tyr Gly Pro Tyr Ser Val Thr Asn Cys Gly Glu His
            965                 970                 975

Asp Thr Thr Glu Tyr Lys Leu Arg Thr Leu Gln Val Ser Pro Leu Asp
        980                 985                 990

Asn Gly Asp Leu Ile Arg Glu Ile Trp His Tyr Gln Tyr Leu Ser Trp
    995                 1000                1005

Pro Asp His Gly Val Pro Ser Glu Pro Gly Gly Val Leu Ser Phe
    1010                1015                1020

Leu Asp Gln Ile Asn Gln Arg Gln Glu Ser Leu Pro His Ala Gly
    1025                1030                1035

Pro Ile Ile Val His Cys Ser Ala Gly Ile Gly Arg Thr Gly Thr
    1040                1045                1050

Ile Ile Val Ile Asp Met Leu Met Glu Asn Ile Ser Thr Lys Gly
    1055                1060                1065

Leu Asp Cys Asp Ile Asp Ile Gln Lys Thr Ile Gln Met Val Arg
    1070                1075                1080

Ala Gln Arg Ser Gly Met Val Gln Thr Glu Ala Gln Tyr Lys Phe
    1085                1090                1095

Ile Tyr Val Ala Ile Ala Gln Phe Ile Glu Thr Thr Lys Lys Lys
    1100                1105                1110

Leu

<210> SEQ ID NO 5
<211> LENGTH: 918
<212> TYPE: PRT
<213> ORGANISM: Artificial Sequence
<220> FEATURE:
<223> OTHER INFORMATION: Chimeric antigen receptor (CAR)

<400> SEQUENCE: 5

Met Ser Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
            85                  90                  95

Ser Asn Leu Glu Gln Glu Asp Ile Ala Thr Tyr Phe Cys Gln Gln Gly

-continued

```
                100                 105                 110
Asn Thr Leu Pro Tyr Thr Phe Gly Gly Gly Thr Lys Leu Glu Ile Thr
                115                 120                 125

Lys Ala Gly Gly Gly Ser Gly Gly Gly Ser Gly Gly Gly Gly
    130                 135                 140

Ser Gly Gly Gly Ser Glu Val Lys Leu Gln Glu Ser Gly Pro Gly
145                 150                 155                 160

Leu Val Ala Pro Ser Gln Ser Leu Ser Val Thr Cys Thr Val Ser Gly
                165                 170                 175

Val Ser Leu Pro Asp Tyr Gly Val Ser Trp Ile Arg Gln Pro Pro Arg
                180                 185                 190

Lys Gly Leu Glu Trp Leu Gly Val Ile Trp Gly Ser Glu Thr Thr Tyr
                195                 200                 205

Tyr Asn Ser Ala Leu Lys Ser Arg Leu Thr Ile Ile Lys Asp Asn Ser
                210                 215                 220

Lys Ser Gln Val Phe Leu Lys Met Asn Ser Leu Gln Thr Asp Asp Thr
225                 230                 235                 240

Ala Ile Tyr Tyr Cys Ala Lys His Tyr Tyr Gly Gly Ser Tyr Ala
                245                 250                 255

Met Asp Tyr Trp Gly Gln Gly Thr Ser Val Thr Val Ser Ser Asp Pro
                260                 265                 270

Thr Thr Thr Pro Ala Pro Arg Pro Pro Thr Pro Ala Pro Thr Ile Ala
                275                 280                 285

Ser Gln Pro Leu Ser Leu Arg Pro Glu Ala Cys Arg Pro Ala Ala Gly
                290                 295                 300

Gly Ala Val His Thr Arg Gly Leu Asp Phe Ala Cys Asp Ile Phe Trp
305                 310                 315                 320

Val Leu Val Val Val Gly Gly Val Leu Ala Cys Tyr Ser Leu Leu Val
                325                 330                 335

Thr Val Ala Phe Ile Ile Phe Trp Val Arg Arg Val Lys Phe Ser Arg
                340                 345                 350

Ser Ala Asp Ala Pro Ala Tyr Gln Gln Gly Gln Asn Gln Leu Tyr Asn
                355                 360                 365

Glu Leu Asn Leu Gly Arg Arg Glu Glu Tyr Asp Val Leu Asp Lys Arg
                370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
                420                 425                 430

Asp Gly Leu Tyr Gln Gly Leu Ser Thr Ala Thr Lys Asp Thr Tyr Asp
                435                 440                 445

Ala Leu His Met Gln Ala Leu Pro Pro Arg Arg Ala Glu Gly Arg Gly
                450                 455                 460

Ser Leu Leu Thr Cys Gly Asp Val Glu Glu Asn Pro Gly Pro Met Ala
465                 470                 475                 480

Val Pro Thr Gln Val Leu Gly Leu Leu Leu Leu Trp Leu Thr Asp Ala
                485                 490                 495

Arg Cys Asp Ile Gln Met Thr Gln Ser Pro Ser Ser Leu Ser Ala Ser
                500                 505                 510

Val Gly Asp Arg Val Thr Ile Thr Cys Arg Ala Ser Glu Asp Ile Tyr
                515                 520                 525
```

-continued

```
Phe Asn Leu Val Trp Tyr Gln Gln Lys Pro Gly Lys Ala Pro Lys Leu
    530                 535                 540

Leu Ile Tyr Asp Thr Asn Arg Leu Ala Asp Gly Val Pro Ser Arg Phe
545                 550                 555                 560

Ser Gly Ser Gly Ser Gly Thr Gln Tyr Thr Leu Thr Ile Ser Ser Leu
            565                 570                 575

Gln Pro Glu Asp Phe Ala Thr Tyr Tyr Cys Gln His Tyr Lys Asn Tyr
        580                 585                 590

Pro Leu Thr Phe Gly Gln Gly Thr Lys Leu Glu Ile Lys Arg Ser Gly
    595                 600                 605

Gly Gly Gly Ser Gly Gly Gly Ser Gly Gly Gly Ser Gly Gly
610                 615                 620

Gly Gly Ser Arg Ser Glu Val Gln Leu Val Glu Ser Gly Gly Gly Leu
625                 630                 635                 640

Val Gln Pro Gly Gly Ser Leu Arg Leu Ser Cys Ala Ala Ser Gly Phe
                645                 650                 655

Thr Leu Ser Asn Tyr Gly Met His Trp Ile Arg Gln Ala Pro Gly Lys
            660                 665                 670

Gly Leu Glu Trp Val Ser Ser Ile Ser Leu Asn Gly Gly Ser Thr Tyr
        675                 680                 685

Tyr Arg Asp Ser Val Lys Gly Arg Phe Thr Ile Ser Arg Asp Asn Ala
    690                 695                 700

Lys Ser Thr Leu Tyr Leu Gln Met Asn Ser Leu Arg Ala Glu Asp Thr
705                 710                 715                 720

Ala Val Tyr Tyr Cys Ala Ala Gln Asp Ala Tyr Thr Gly Gly Tyr Phe
                725                 730                 735

Asp Tyr Trp Gly Gln Gly Thr Leu Val Thr Val Ser Ser Met Asp Pro
            740                 745                 750

Ala Thr Thr Thr Lys Pro Val Leu Arg Thr Pro Ser Pro Val His Pro
        755                 760                 765

Thr Gly Thr Ser Gln Pro Gln Arg Pro Glu Asp Cys Arg Pro Arg Gly
    770                 775                 780

Ser Val Lys Gly Thr Gly Leu Asp Phe Ala Cys Asp Ile Leu Ile Gly
785                 790                 795                 800

Val Ser Val Val Phe Leu Phe Cys Leu Leu Leu Val Leu Phe Cys
                805                 810                 815

Leu His Arg Gln Asn Gln Ile Lys Gln Gly Pro Pro Arg Ser Lys Asp
            820                 825                 830

Glu Glu Gln Lys Pro Gln Gln Arg Pro Asp Leu Ala Val Asp Val Leu
        835                 840                 845

Glu Arg Thr Ala Asp Lys Ala Thr Val Asn Gly Leu Pro Glu Lys Asp
    850                 855                 860

Arg Glu Thr Asp Thr Ser Ala Leu Ala Ala Gly Ser Ser Gln Glu Val
865                 870                 875                 880

Thr Tyr Ala Gln Leu Asp His Trp Ala Leu Thr Gln Arg Thr Ala Arg
                885                 890                 895

Ala Val Ser Pro Gln Ser Thr Lys Pro Met Ala Glu Ser Ile Thr Tyr
            900                 905                 910

Ala Ala Val Ala Arg His
            915
```

<210> SEQ ID NO 6
<211> LENGTH: 1363

<212> TYPE: PRT
<213> ORGANISM: Artificial Sequence
<220> FEATURE:
<223> OTHER INFORMATION: Chimeric antigen receptor (CAR)

<400> SEQUENCE: 6

Met Ser Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Lys Ala Gly Gly Gly Gly Ser Gly Gly Gly Gly Ser Gly Gly Gly Gly
    130                 135                 140

Ser Gly Gly Gly Gly Ser Glu Val Lys Leu Gln Glu Ser Gly Pro Gly
145                 150                 155                 160

Leu Val Ala Pro Ser Gln Ser Leu Ser Val Thr Cys Thr Val Ser Gly
                165                 170                 175

Val Ser Leu Pro Asp Tyr Gly Val Ser Trp Ile Arg Gln Pro Pro Arg
            180                 185                 190

Lys Gly Leu Glu Trp Leu Gly Val Ile Trp Gly Ser Glu Thr Thr Tyr
        195                 200                 205

Tyr Asn Ser Ala Leu Lys Ser Arg Leu Thr Ile Ile Lys Asp Asn Ser
    210                 215                 220

Lys Ser Gln Val Phe Leu Lys Met Asn Ser Leu Gln Thr Asp Asp Thr
225                 230                 235                 240

Ala Ile Tyr Tyr Cys Ala Lys His Tyr Tyr Gly Gly Ser Tyr Ala
                245                 250                 255

Met Asp Tyr Trp Gly Gln Gly Thr Ser Val Thr Val Ser Ser Asp Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Phe Trp
305                 310                 315                 320

Val Leu Val Val Val Gly Gly Val Leu Ala Cys Tyr Ser Leu Leu Val
                325                 330                 335

Thr Val Ala Phe Ile Ile Phe Trp Val Arg Arg Val Lys Phe Ser Arg
            340                 345                 350

Ser Ala Asp Ala Pro Ala Tyr Gln Gln Gly Gln Asn Gln Leu Tyr Asn
        355                 360                 365

Glu Leu Asn Leu Gly Arg Arg Glu Glu Tyr Asp Val Leu Asp Lys Arg
    370                 375                 380

-continued

```
Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
            405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
            435                 440                 445

Ala Leu His Met Gln Ala Leu Pro Pro Arg Arg Ala Glu Gly Arg Gly
        450                 455                 460

Ser Leu Leu Thr Cys Gly Asp Val Glu Glu Asn Pro Gly Pro Met Ala
465                 470                 475                 480

Val Pro Thr Gln Val Leu Gly Leu Leu Leu Leu Trp Leu Thr Asp Ala
            485                 490                 495

Arg Cys Asp Ile Gln Met Thr Gln Ser Pro Ser Ser Leu Ser Ala Ser
            500                 505                 510

Val Gly Asp Arg Val Thr Ile Thr Cys Arg Ala Ser Glu Asp Ile Tyr
            515                 520                 525

Phe Asn Leu Val Trp Tyr Gln Gln Lys Pro Gly Lys Ala Pro Lys Leu
530                 535                 540

Leu Ile Tyr Asp Thr Asn Arg Leu Ala Asp Gly Val Pro Ser Arg Phe
545                 550                 555                 560

Ser Gly Ser Gly Ser Gly Thr Gln Tyr Thr Leu Thr Ile Ser Ser Leu
            565                 570                 575

Gln Pro Glu Asp Phe Ala Thr Tyr Tyr Cys Gln His Tyr Lys Asn Tyr
            580                 585                 590

Pro Leu Thr Phe Gly Gln Gly Thr Lys Leu Glu Ile Lys Arg Ser Gly
            595                 600                 605

Gly Gly Gly Ser Gly Gly Gly Ser Gly Gly Gly Ser Gly Gly
            610                 615                 620

Gly Gly Ser Arg Ser Glu Val Gln Leu Val Glu Ser Gly Gly Gly Leu
625                 630                 635                 640

Val Gln Pro Gly Gly Ser Leu Arg Leu Ser Cys Ala Ala Ser Gly Phe
            645                 650                 655

Thr Leu Ser Asn Tyr Gly Met His Trp Ile Arg Gln Ala Pro Gly Lys
            660                 665                 670

Gly Leu Glu Trp Val Ser Ser Ile Ser Leu Asn Gly Gly Ser Thr Tyr
            675                 680                 685

Tyr Arg Asp Ser Val Lys Gly Arg Phe Thr Ile Ser Arg Asp Asn Ala
            690                 695                 700

Lys Ser Thr Leu Tyr Leu Gln Met Asn Ser Leu Arg Ala Glu Asp Thr
705                 710                 715                 720

Ala Val Tyr Tyr Cys Ala Ala Gln Asp Ala Tyr Thr Gly Gly Tyr Phe
            725                 730                 735

Asp Tyr Trp Gly Gln Gly Thr Leu Val Thr Val Ser Ser Met Asp Pro
            740                 745                 750

Ala Thr Thr Thr Lys Pro Val Leu Arg Thr Pro Ser Pro Val His Pro
            755                 760                 765

Thr Gly Thr Ser Gln Pro Gln Arg Pro Glu Asp Cys Arg Pro Arg Gly
            770                 775                 780

Ser Val Lys Gly Thr Gly Leu Asp Phe Ala Cys Asp Ile Leu Ile Gly
785                 790                 795                 800

Val Ser Val Val Phe Leu Phe Cys Leu Leu Leu Leu Val Leu Phe Cys
```

-continued

```
                805                 810                 815
Leu His Arg Gln Asn Gln Ile Lys Gln Gly Pro Pro Arg Ser Lys Asp
            820                 825                 830

Glu Glu Gln Lys Pro Gln Gln Arg Pro Asp Leu Ala Val Asp Val Leu
            835                 840                 845

Glu Arg Thr Ala Asp Lys Ala Thr Val Asn Gly Leu Pro Glu Lys Asp
            850                 855                 860

Arg Glu Thr Asp Thr Ser Ala Leu Ala Ala Gly Ser Ser Gln Glu Val
865                 870                 875                 880

Thr Tyr Ala Gln Leu Asp His Trp Ala Leu Thr Gln Arg Thr Ala Arg
            885                 890                 895

Ala Val Ser Pro Gln Ser Thr Lys Pro Met Ala Glu Ser Ile Thr Tyr
            900                 905                 910

Ala Ala Val Ala Arg His Arg Ala Glu Gly Arg Gly Ser Leu Leu Thr
            915                 920                 925

Cys Gly Asp Val Glu Glu Asn Pro Gly Pro Trp Tyr His Gly His Met
930                 935                 940

Ser Gly Gly Gln Ala Glu Thr Leu Leu Gln Ala Lys Gly Glu Pro Trp
945                 950                 955                 960

Thr Phe Leu Val Arg Glu Ser Leu Ser Gln Pro Gly Asp Phe Val Leu
                965                 970                 975

Ser Val Leu Ser Asp Gln Pro Lys Ala Gly Pro Gly Ser Pro Leu Arg
            980                 985                 990

Val Thr His Ile Lys Val Met Cys Glu Gly Gly Arg Tyr Thr Val Gly
            995                 1000                1005

Gly Leu Glu Thr Phe Asp Ser Leu Thr Asp Leu Val Glu His Phe
    1010                1015                1020

Lys Lys Thr Gly Ile Glu Glu Ala Ser Gly Ala Phe Val Tyr Leu
    1025                1030                1035

Arg Gln Pro Tyr Ser Gly Gly Gly Gly Ser Phe Glu Ala Tyr Phe
    1040                1045                1050

Lys Lys Gln Gln Ala Asp Ser Asn Cys Gly Phe Ala Glu Glu Tyr
    1055                1060                1065

Glu Asp Leu Lys Leu Val Gly Ile Ser Gln Pro Lys Tyr Ala Ala
    1070                1075                1080

Glu Leu Ala Glu Asn Arg Gly Lys Asn Arg Tyr Asn Asn Val Leu
    1085                1090                1095

Pro Tyr Asp Ile Ser Arg Val Lys Leu Ser Val Gln Thr His Ser
    1100                1105                1110

Thr Asp Asp Tyr Ile Asn Ala Asn Tyr Met Pro Gly Tyr His Ser
    1115                1120                1125

Lys Lys Asp Phe Ile Ala Thr Gln Gly Pro Leu Pro Asn Thr Leu
    1130                1135                1140

Lys Asp Phe Trp Arg Met Val Trp Glu Lys Asn Val Tyr Ala Ile
    1145                1150                1155

Ile Met Leu Thr Lys Cys Val Glu Gln Gly Arg Thr Lys Cys Glu
    1160                1165                1170

Glu Tyr Trp Pro Ser Lys Gln Ala Gln Asp Tyr Gly Asp Ile Thr
    1175                1180                1185

Val Ala Met Thr Ser Glu Ile Val Leu Pro Glu Trp Thr Ile Arg
    1190                1195                1200

Asp Phe Thr Val Lys Asn Ile Gln Thr Ser Glu Ser His Pro Leu
    1205                1210                1215
```

```
Arg Gln Phe His Phe Thr Ser Trp Pro Asp His Gly Val Pro Asp
    1220            1225                1230

Thr Thr Asp Leu Leu Ile Asn Phe Arg Tyr Leu Val Arg Asp Tyr
    1235            1240                1245

Met Lys Gln Ser Pro Pro Glu Ser Pro Ile Leu Val His Cys Ser
    1250            1255                1260

Ala Gly Val Gly Arg Thr Gly Thr Phe Ile Ala Ile Asp Arg Leu
    1265            1270                1275

Ile Tyr Gln Ile Glu Asn Glu Asn Thr Val Asp Val Tyr Gly Ile
    1280            1285                1290

Val Tyr Asp Leu Arg Met His Arg Pro Leu Met Val Gln Thr Glu
    1295            1300                1305

Asp Gln Tyr Val Phe Leu Asn Gln Cys Val Leu Asp Ile Val Arg
    1310            1315                1320

Ser Gln Lys Asp Ser Lys Val Asp Leu Ile Tyr Gln Asn Thr Thr
    1325            1330                1335

Ala Met Thr Ile Tyr Glu Asn Leu Ala Pro Val Thr Thr Phe Gly
    1340            1345                1350

Lys Thr Asn Gly Tyr Ile Ala Ser Gly Ser
    1355            1360

<210> SEQ ID NO 7
<211> LENGTH: 21
<212> TYPE: PRT
<213> ORGANISM: Artificial Sequence
<220> FEATURE:
<223> OTHER INFORMATION: Signal peptide

<400> SEQUENCE: 7

Met Gly Thr Ser Leu Leu Cys Trp Met Ala Leu Cys Leu Leu Gly Ala
1               5                   10                  15

Asp His Ala Asp Gly
            20

<210> SEQ ID NO 8
<211> LENGTH: 21
<212> TYPE: PRT
<213> ORGANISM: Artificial Sequence
<220> FEATURE:
<223> OTHER INFORMATION: Signal peptide

<400> SEQUENCE: 8

Met Ser Leu Pro Val Thr Ala Leu Leu Leu Pro Leu Ala Leu Leu Leu
1               5                   10                  15

His Ala Ala Arg Pro
            20

<210> SEQ ID NO 9
<211> LENGTH: 20
<212> TYPE: PRT
<213> ORGANISM: Artificial Sequence
<220> FEATURE:
<223> OTHER INFORMATION: Signal peptide

<400> SEQUENCE: 9

Met Ala Val Pro Thr Gln Val Leu Gly Leu Leu Leu Leu Trp Leu Thr
1               5                   10                  15

Asp Ala Arg Cys
            20
```

<210> SEQ ID NO 10
<211> LENGTH: 234
<212> TYPE: PRT
<213> ORGANISM: Artificial Sequence
<220> FEATURE:
<223> OTHER INFORMATION: Spacer (hinge-CH2CH3 of human IgG1)

<400> SEQUENCE: 10

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp
225                 230

<210> SEQ ID NO 11
<211> LENGTH: 46
<212> TYPE: PRT
<213> ORGANISM: Artificial Sequence
<220> FEATURE:
<223> OTHER INFORMATION: Spacer (human CD8 stalk)

<400> SEQUENCE: 11

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45

<210> SEQ ID NO 12
<211> LENGTH: 20
<212> TYPE: PRT
<213> ORGANISM: Artificial Sequence

```
<220> FEATURE:
<223> OTHER INFORMATION: Spacer (human IgG1 hinge)

<400> SEQUENCE: 12

Ala Glu Pro Lys Ser Pro Asp Lys Thr His Thr Cys Pro Pro Cys Pro
1               5                   10                  15

Lys Asp Pro Lys
            20

<210> SEQ ID NO 13
<211> LENGTH: 185
<212> TYPE: PRT
<213> ORGANISM: Artificial Sequence
<220> FEATURE:
<223> OTHER INFORMATION: Spacer (CD2 ectodomain)

<400> SEQUENCE: 13

Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Asp Ile Asp Asp
            20                  25                  30

Ile Lys Trp Glu Lys Thr Ser Asp Lys Lys Lys Ile Ala Gln Phe Arg
        35                  40                  45

Lys Glu Lys Glu Thr Phe Lys Glu Lys Asp Thr Tyr Lys Leu Phe Lys
    50                  55                  60

Asn Gly Thr Leu Lys Ile Lys His Leu Lys Thr Asp Asp Gln Asp Ile
65                  70                  75                  80

Tyr Lys Val Ser Ile Tyr Asp Thr Lys Gly Lys Asn Val Leu Glu Lys
                85                  90                  95

Ile Phe Asp Leu Lys Ile Gln Glu Arg Val Ser Lys Pro Lys Ile Ser
            100                 105                 110

Trp Thr Cys Ile Asn Thr Thr Leu Thr Cys Glu Val Met Asn Gly Thr
        115                 120                 125

Asp Pro Glu Leu Asn Leu Tyr Gln Asp Gly Lys His Leu Lys Leu Ser
    130                 135                 140

Gln Arg Val Ile Thr His Lys Trp Thr Thr Ser Leu Ser Ala Lys Phe
145                 150                 155                 160

Lys Cys Thr Ala Gly Asn Lys Val Ser Lys Glu Ser Ser Val Glu Pro
                165                 170                 175

Val Ser Cys Pro Glu Lys Gly Leu Asp
            180                 185

<210> SEQ ID NO 14
<211> LENGTH: 259
<212> TYPE: PRT
<213> ORGANISM: Artificial Sequence
<220> FEATURE:
<223> OTHER INFORMATION: Spacer (CD34 ectodomain)

<400> SEQUENCE: 14

Ser Leu Asp Asn Asn Gly Thr Ala Thr Pro Glu Leu Pro Thr Gln Gly
1               5                   10                  15

Thr Phe Ser Asn Val Ser Thr Asn Val Ser Tyr Gln Glu Thr Thr Thr
            20                  25                  30

Pro Ser Thr Leu Gly Ser Thr Ser Leu His Pro Val Ser Gln His Gly
        35                  40                  45

Asn Glu Ala Thr Thr Asn Ile Thr Glu Thr Thr Val Lys Phe Thr Ser
    50                  55                  60
```

Thr Ser Val Ile Thr Ser Val Tyr Gly Asn Thr Asn Ser Ser Val Gln
 65                  70                  75                  80

Ser Gln Thr Ser Val Ile Ser Thr Val Phe Thr Thr Pro Ala Asn Val
                 85                  90                  95

Ser Thr Pro Glu Thr Thr Leu Lys Pro Ser Leu Ser Pro Gly Asn Val
            100                 105                 110

Ser Asp Leu Ser Thr Thr Ser Thr Ser Leu Ala Thr Ser Pro Thr Lys
        115                 120                 125

Pro Tyr Thr Ser Ser Ser Pro Ile Leu Ser Asp Ile Lys Ala Glu Ile
    130                 135                 140

Lys Cys Ser Gly Ile Arg Glu Val Lys Leu Thr Gln Gly Ile Cys Leu
145                 150                 155                 160

Glu Gln Asn Lys Thr Ser Ser Cys Ala Glu Phe Lys Lys Asp Arg Gly
                165                 170                 175

Glu Gly Leu Ala Arg Val Leu Cys Gly Glu Gln Ala Asp Ala Asp
            180                 185                 190

Ala Gly Ala Gln Val Cys Ser Leu Leu Ala Gln Ser Glu Val Arg
        195                 200                 205

Pro Gln Cys Leu Leu Leu Val Leu Ala Asn Arg Thr Glu Ile Ser Ser
    210                 215                 220

Lys Leu Gln Leu Met Lys Lys His Gln Ser Asp Leu Lys Lys Leu Gly
225                 230                 235                 240

Ile Leu Asp Phe Thr Glu Gln Asp Val Ala Ser His Gln Ser Tyr Ser
                245                 250                 255

Gln Lys Thr

<210> SEQ ID NO 15
<211> LENGTH: 140
<212> TYPE: PRT
<213> ORGANISM: Artificial Sequence
<220> FEATURE:
<223> OTHER INFORMATION: CD28 transmembrane domain and CD3 Z endodomains

<400> SEQUENCE: 15

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Arg Val Lys Phe
                20                  25                  30

Ser Arg Ser Ala Asp Ala Pro Ala Tyr Gln Gln Gly Gln Asn Gln Leu
            35                  40                  45

Tyr Asn Glu Leu Asn Leu Gly Arg Arg Glu Glu Tyr Asp Val Leu Asp
    50                  55                  60

Lys Arg Arg Gly Arg Asp Pro Glu Met Gly Gly Lys Pro Arg Arg Lys
65                  70                  75                  80

Asn Pro Gln Glu Gly Leu Tyr Asn Glu Leu Gln Lys Asp Lys Met Ala
                85                  90                  95

Glu Ala Tyr Ser Glu Ile Gly Met Lys Gly Glu Arg Arg Arg Gly Lys
            100                 105                 110

Gly His Asp Gly Leu Tyr Gln Gly Leu Ser Thr Ala Thr Lys Asp Thr
        115                 120                 125

Tyr Asp Ala Leu His Met Gln Ala Leu Pro Pro Arg
    130                 135                 140

<210> SEQ ID NO 16
<211> LENGTH: 180
<212> TYPE: PRT

<213> ORGANISM: Artificial Sequence
<220> FEATURE:
<223> OTHER INFORMATION: CD28 transmembrane domain and CD28 and CD3 Zeta
      endodomains

<400> SEQUENCE: 16

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser Arg Val Lys Phe Ser Arg Ser Ala Asp Ala Pro Ala
65                  70                  75                  80

Tyr Gln Gln Gly Gln Asn Gln Leu Tyr Asn Glu Leu Asn Leu Gly Arg
                85                  90                  95

Arg Glu Glu Tyr Asp Val Leu Asp Lys Arg Arg Gly Arg Asp Pro Glu
            100                 105                 110

Met Gly Gly Lys Pro Arg Arg Lys Asn Pro Gln Glu Gly Leu Tyr Asn
        115                 120                 125

Glu Leu Gln Lys Asp Lys Met Ala Glu Ala Tyr Ser Glu Ile Gly Met
130                 135                 140

Lys Gly Glu Arg Arg Arg Gly Lys Gly His Asp Gly Leu Tyr Gln Gly
145                 150                 155                 160

Leu Ser Thr Ala Thr Lys Asp Thr Tyr Asp Ala Leu His Met Gln Ala
                165                 170                 175

Leu Pro Pro Arg
            180

<210> SEQ ID NO 17
<211> LENGTH: 216
<212> TYPE: PRT
<213> ORGANISM: Artificial Sequence
<220> FEATURE:
<223> OTHER INFORMATION: CD28 transmembrane domain and CD28, OX40 and
      CD3 Zeta endodomains

<400> SEQUENCE: 17

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser Arg Asp Gln Arg Leu Pro Pro Asp Ala His Lys Pro
65                  70                  75                  80

Pro Gly Gly Gly Ser Phe Arg Thr Pro Ile Gln Glu Glu Gln Ala Asp
                85                  90                  95

Ala His Ser Thr Leu Ala Lys Ile Arg Val Lys Phe Ser Arg Ser Ala
            100                 105                 110

Asp Ala Pro Ala Tyr Gln Gln Gly Gln Asn Gln Leu Tyr Asn Glu Leu
        115                 120                 125

Asn Leu Gly Arg Arg Glu Glu Tyr Asp Val Leu Asp Lys Arg Arg Gly

```
                130             135             140
Arg Asp Pro Glu Met Gly Gly Lys Pro Arg Arg Lys Asn Pro Gln Glu
145                 150                 155                 160

Gly Leu Tyr Asn Glu Leu Gln Lys Asp Lys Met Ala Glu Ala Tyr Ser
                165                 170                 175

Glu Ile Gly Met Lys Gly Glu Arg Arg Arg Gly Lys Gly His Asp Gly
                180                 185                 190

Leu Tyr Gln Gly Leu Ser Thr Ala Thr Lys Asp Thr Tyr Asp Ala Leu
                195                 200                 205

His Met Gln Ala Leu Pro Pro Arg
        210                 215

<210> SEQ ID NO 18
<211> LENGTH: 729
<212> TYPE: PRT
<213> ORGANISM: Artificial Sequence
<220> FEATURE:
<223> OTHER INFORMATION: CD45 transmembrane and endodomain

<400> SEQUENCE: 18

Ala Leu Ile Ala Phe Leu Ala Phe Leu Ile Ile Val Thr Ser Ile Ala
1               5                   10                  15

Leu Leu Val Val Leu Tyr Lys Ile Tyr Asp Leu His Lys Lys Arg Ser
                20                  25                  30

Cys Asn Leu Asp Glu Gln Gln Glu Leu Val Glu Arg Asp Asp Glu Lys
            35                  40                  45

Gln Leu Met Asn Val Glu Pro Ile His Ala Asp Ile Leu Leu Glu Thr
        50                  55                  60

Tyr Lys Arg Lys Ile Ala Asp Glu Gly Arg Leu Phe Leu Ala Glu Phe
65                  70                  75                  80

Gln Ser Ile Pro Arg Val Phe Ser Lys Phe Pro Ile Lys Glu Ala Arg
                85                  90                  95

Lys Pro Phe Asn Gln Asn Lys Asn Arg Tyr Val Asp Ile Leu Pro Tyr
            100                 105                 110

Asp Tyr Asn Arg Val Glu Leu Ser Glu Ile Asn Gly Asp Ala Gly Ser
        115                 120                 125

Asn Tyr Ile Asn Ala Ser Tyr Ile Asp Gly Phe Lys Glu Pro Arg Lys
130                 135                 140

Tyr Ile Ala Ala Gln Gly Pro Arg Asp Glu Thr Val Asp Asp Phe Trp
145                 150                 155                 160

Arg Met Ile Trp Glu Gln Lys Ala Thr Val Ile Val Met Val Thr Arg
                165                 170                 175

Cys Glu Glu Gly Asn Arg Asn Lys Cys Ala Glu Tyr Trp Pro Ser Met
            180                 185                 190

Glu Glu Gly Thr Arg Ala Phe Gly Asp Val Val Val Lys Ile Asn Gln
        195                 200                 205

His Lys Arg Cys Pro Asp Tyr Ile Ile Gln Lys Leu Asn Ile Val Asn
        210                 215                 220

Lys Lys Glu Lys Ala Thr Gly Arg Glu Val Thr His Ile Gln Phe Thr
225                 230                 235                 240

Ser Trp Pro Asp His Gly Val Pro Glu Asp Pro His Leu Leu Leu Lys
                245                 250                 255

Leu Arg Arg Arg Val Asn Ala Phe Ser Asn Phe Phe Ser Gly Pro Ile
            260                 265                 270

Val Val His Cys Ser Ala Gly Val Gly Arg Thr Gly Thr Tyr Ile Gly
```

```
                275                 280                 285
Ile Asp Ala Met Leu Glu Gly Leu Glu Ala Glu Asn Lys Val Asp Val
290                 295                 300

Tyr Gly Tyr Val Val Lys Leu Arg Arg Gln Arg Cys Leu Met Val Gln
305                 310                 315                 320

Val Glu Ala Gln Tyr Ile Leu Ile His Gln Ala Leu Val Glu Tyr Asn
                325                 330                 335

Gln Phe Gly Glu Thr Glu Val Asn Leu Ser Glu Leu His Pro Tyr Leu
                340                 345                 350

His Asn Met Lys Lys Arg Asp Pro Pro Ser Glu Pro Ser Pro Leu Glu
                355                 360                 365

Ala Glu Phe Gln Arg Leu Pro Ser Tyr Arg Ser Trp Arg Thr Gln His
370                 375                 380

Ile Gly Asn Gln Glu Asn Lys Ser Lys Asn Arg Asn Ser Asn Val
385                 390                 395                 400

Ile Pro Tyr Asp Tyr Asn Arg Val Pro Leu Lys His Glu Leu Glu Met
                405                 410                 415

Ser Lys Glu Ser Glu His Asp Ser Asp Glu Ser Ser Asp Asp Asp Ser
                420                 425                 430

Asp Ser Glu Glu Pro Ser Lys Tyr Ile Asn Ala Ser Phe Ile Met Ser
                435                 440                 445

Tyr Trp Lys Pro Glu Val Met Ile Ala Ala Gln Gly Pro Leu Lys Glu
450                 455                 460

Thr Ile Gly Asp Phe Trp Gln Met Ile Phe Gln Arg Lys Val Lys Val
465                 470                 475                 480

Ile Val Met Leu Thr Glu Leu Lys His Gly Asp Gln Glu Ile Cys Ala
                485                 490                 495

Gln Tyr Trp Gly Glu Gly Lys Gln Thr Tyr Gly Asp Ile Glu Val Asp
                500                 505                 510

Leu Lys Asp Thr Asp Lys Ser Ser Thr Tyr Thr Leu Arg Val Phe Glu
                515                 520                 525

Leu Arg His Ser Lys Arg Lys Asp Ser Arg Thr Val Tyr Gln Tyr Gln
530                 535                 540

Tyr Thr Asn Trp Ser Val Glu Gln Leu Pro Ala Glu Pro Lys Glu Leu
545                 550                 555                 560

Ile Ser Met Ile Gln Val Val Lys Gln Lys Leu Pro Gln Lys Asn Ser
                565                 570                 575

Ser Glu Gly Asn Lys His His Lys Ser Thr Pro Leu Leu Ile His Cys
                580                 585                 590

Arg Asp Gly Ser Gln Gln Thr Gly Ile Phe Cys Ala Leu Leu Asn Leu
                595                 600                 605

Leu Glu Ser Ala Glu Thr Glu Val Val Asp Ile Phe Gln Val Val
                610                 615                 620

Lys Ala Leu Arg Lys Ala Arg Pro Gly Met Val Ser Thr Phe Glu Gln
625                 630                 635                 640

Tyr Gln Phe Leu Tyr Asp Val Ile Ala Ser Thr Tyr Pro Ala Gln Asn
                645                 650                 655

Gly Gln Val Lys Lys Asn Asn His Gln Glu Asp Lys Ile Glu Phe Asp
                660                 665                 670

Asn Glu Val Asp Lys Val Lys Gln Asp Ala Asn Cys Val Asn Pro Leu
                675                 680                 685

Gly Ala Pro Glu Lys Leu Pro Glu Ala Lys Glu Gln Ala Glu Gly Ser
690                 695                 700
```

```
Glu Pro Thr Ser Gly Thr Gly Pro Glu His Ser Val Asn Gly Pro
705                 710                 715                 720

Ala Ser Pro Ala Leu Asn Gln Gly Ser
                725

<210> SEQ ID NO 19
<211> LENGTH: 362
<212> TYPE: PRT
<213> ORGANISM: Artificial Sequence
<220> FEATURE:
<223> OTHER INFORMATION: CD148 transmembrane and endodomain

<400> SEQUENCE: 19

Ala Val Phe Gly Cys Ile Phe Gly Ala Leu Val Ile Val Thr Val Gly
1               5                   10                  15

Gly Phe Ile Phe Trp Arg Lys Arg Lys Asp Ala Lys Asn Asn Glu
                20                  25                  30

Val Ser Phe Ser Gln Ile Lys Pro Lys Lys Ser Lys Leu Ile Arg Val
            35                  40                  45

Glu Asn Phe Glu Ala Tyr Phe Lys Lys Gln Gln Ala Asp Ser Asn Cys
    50                  55                  60

Gly Phe Ala Glu Glu Tyr Glu Asp Leu Lys Leu Val Gly Ile Ser Gln
65                  70                  75                  80

Pro Lys Tyr Ala Ala Glu Leu Ala Glu Asn Arg Gly Lys Asn Arg Tyr
                85                  90                  95

Asn Asn Val Leu Pro Tyr Asp Ile Ser Arg Val Lys Leu Ser Val Gln
                100                 105                 110

Thr His Ser Thr Asp Asp Tyr Ile Asn Ala Asn Tyr Met Pro Gly Tyr
            115                 120                 125

His Ser Lys Lys Asp Phe Ile Ala Thr Gln Gly Pro Leu Pro Asn Thr
        130                 135                 140

Leu Lys Asp Phe Trp Arg Met Val Trp Glu Lys Asn Val Tyr Ala Ile
145                 150                 155                 160

Ile Met Leu Thr Lys Cys Val Glu Gln Gly Arg Thr Lys Cys Glu Glu
                165                 170                 175

Tyr Trp Pro Ser Lys Gln Ala Gln Asp Tyr Gly Asp Ile Thr Val Ala
                180                 185                 190

Met Thr Ser Glu Ile Val Leu Pro Glu Trp Thr Ile Arg Asp Phe Thr
            195                 200                 205

Val Lys Asn Ile Gln Thr Ser Glu Ser His Pro Leu Arg Gln Phe His
    210                 215                 220

Phe Thr Ser Trp Pro Asp His Gly Val Pro Asp Thr Thr Asp Leu Leu
225                 230                 235                 240

Ile Asn Phe Arg Tyr Leu Val Arg Asp Tyr Met Lys Gln Ser Pro Pro
                245                 250                 255

Glu Ser Pro Ile Leu Val His Cys Ser Ala Gly Val Gly Arg Thr Gly
                260                 265                 270

Thr Phe Ile Ala Ile Asp Arg Leu Ile Tyr Gln Ile Glu Asn Glu Asn
            275                 280                 285

Thr Val Asp Val Tyr Gly Ile Val Tyr Asp Leu Arg Met His Arg Pro
    290                 295                 300

Leu Met Val Gln Thr Glu Asp Gln Tyr Val Phe Leu Asn Gln Cys Val
305                 310                 315                 320

Leu Asp Ile Val Arg Ser Gln Lys Asp Ser Lys Val Asp Leu Ile Tyr
                325                 330                 335
```

Gln Asn Thr Thr Ala Met Thr Ile Tyr Glu Asn Leu Ala Pro Val Thr
                340                 345                 350

Thr Phe Gly Lys Thr Asn Gly Tyr Ile Ala
        355                 360

<210> SEQ ID NO 20
<211> LENGTH: 595
<212> TYPE: PRT
<213> ORGANISM: Artificial Sequence
<220> FEATURE:
<223> OTHER INFORMATION: sequence of PTPN6

<400> SEQUENCE: 20

Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
            20                  25                  30

Arg Lys Asn Gln Gly Asp Phe Ser Leu Ser Val Arg Val Gly Asp Gln
        35                  40                  45

Val Thr His Ile Arg Ile Gln Asn Ser Gly Asp Phe Tyr Asp Leu Tyr
    50                  55                  60

Gly Gly Glu Lys Phe Ala Thr Leu Thr Glu Leu Val Glu Tyr Tyr Thr
65                  70                  75                  80

Gln Gln Gln Gly Val Leu Gln Asp Arg Asp Gly Thr Ile Ile His Leu
                85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Arg Glu Ser Leu Ser Gln Pro Gly Asp
    130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ala Thr Arg Val Asn Ala Ala Asp Ile Glu
    210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
                245                 250                 255

Lys Asn Leu His Gln Arg Leu Glu Gly Gln Arg Pro Glu Asn Lys Gly
            260                 265                 270

Lys Asn Arg Tyr Lys Asn Ile Leu Pro Phe Asp His Ser Arg Val Ile
        275                 280                 285

Leu Gln Gly Arg Asp Ser Asn Ile Pro Gly Ser Asp Tyr Ile Asn Ala
    290                 295                 300

Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
                325                 330                 335

-continued

```
Gln Met Ala Trp Gln Glu Asn Ser Arg Val Ile Val Met Thr Thr Arg
                340                 345                 350
Glu Val Glu Lys Gly Arg Asn Lys Cys Val Pro Tyr Trp Pro Glu Val
                355                 360                 365
Gly Met Gln Arg Ala Tyr Gly Pro Tyr Ser Val Thr Asn Cys Gly Glu
        370                 375                 380
His Asp Thr Thr Glu Tyr Lys Leu Arg Thr Leu Gln Val Ser Pro Leu
385                 390                 395                 400
Asp Asn Gly Asp Leu Ile Arg Glu Ile Trp His Tyr Gln Tyr Leu Ser
                405                 410                 415
Trp Pro Asp His Gly Val Pro Ser Glu Pro Gly Gly Val Leu Ser Phe
                420                 425                 430
Leu Asp Gln Ile Asn Gln Arg Gln Glu Ser Leu Pro His Ala Gly Pro
            435                 440                 445
Ile Ile Val His Cys Ser Ala Gly Ile Gly Arg Thr Gly Thr Ile Ile
        450                 455                 460
Val Ile Asp Met Leu Met Glu Asn Ile Ser Thr Lys Gly Leu Asp Cys
465                 470                 475                 480
Asp Ile Asp Ile Gln Lys Thr Ile Gln Met Val Arg Ala Gln Arg Ser
                485                 490                 495
Gly Met Val Gln Thr Glu Ala Gln Tyr Lys Phe Ile Tyr Val Ala Ile
            500                 505                 510
Ala Gln Phe Ile Glu Thr Thr Lys Lys Lys Leu Glu Val Leu Gln Ser
        515                 520                 525
Gln Lys Gly Gln Glu Ser Glu Tyr Gly Asn Ile Thr Tyr Pro Pro Ala
    530                 535                 540
Met Lys Asn Ala His Ala Lys Ala Ser Arg Thr Ser Ser Lys His Lys
545                 550                 555                 560
Glu Asp Val Tyr Glu Asn Leu His Thr Lys Asn Lys Arg Glu Glu Lys
                565                 570                 575
Val Lys Lys Gln Arg Ser Ala Asp Lys Glu Lys Ser Lys Gly Ser Leu
                580                 585                 590
Lys Arg Lys
        595
```

<210> SEQ ID NO 21
<211> LENGTH: 272
<212> TYPE: PRT
<213> ORGANISM: Artificial Sequence
<220> FEATURE:
<223> OTHER INFORMATION: sequence of phosphatase domain of PTPN6

<400> SEQUENCE: 21

```
Phe Trp Glu Glu Phe Glu Ser Leu Gln Lys Gln Glu Val Lys Asn Leu
1               5                   10                  15
His Gln Arg Leu Glu Gly Gln Arg Pro Glu Asn Lys Gly Lys Asn Arg
            20                  25                  30
Tyr Lys Asn Ile Leu Pro Phe Asp His Ser Arg Val Ile Leu Gln Gly
        35                  40                  45
Arg Asp Ser Asn Ile Pro Gly Ser Asp Tyr Ile Asn Ala Asn Tyr Ile
    50                  55                  60
Lys Asn Gln Leu Leu Gly Pro Asp Glu Asn Ala Lys Thr Tyr Ile Ala
65                  70                  75                  80
Ser Gln Gly Cys Leu Glu Ala Thr Val Asn Asp Phe Trp Gln Met Ala
                85                  90                  95
```

Trp Gln Glu Asn Ser Arg Val Ile Val Met Thr Thr Arg Glu Val Glu
            100                 105                 110

Lys Gly Arg Asn Lys Cys Val Pro Tyr Trp Pro Glu Val Gly Met Gln
        115                 120                 125

Arg Ala Tyr Gly Pro Tyr Ser Val Thr Asn Cys Gly Glu His Asp Thr
    130                 135                 140

Thr Glu Tyr Lys Leu Arg Thr Leu Gln Val Ser Pro Leu Asp Asn Gly
145                 150                 155                 160

Asp Leu Ile Arg Glu Ile Trp His Tyr Gln Tyr Leu Ser Trp Pro Asp
                165                 170                 175

His Gly Val Pro Ser Glu Pro Gly Gly Val Leu Ser Phe Leu Asp Gln
            180                 185                 190

Ile Asn Gln Arg Gln Glu Ser Leu Pro His Ala Gly Pro Ile Ile Val
        195                 200                 205

His Cys Ser Ala Gly Ile Gly Arg Thr Gly Thr Ile Val Ile Asp
    210                 215                 220

Met Leu Met Glu Asn Ile Ser Thr Lys Gly Leu Asp Cys Asp Ile Asp
225                 230                 235                 240

Ile Gln Lys Thr Ile Gln Met Val Arg Ala Gln Arg Ser Gly Met Val
                245                 250                 255

Gln Thr Glu Ala Gln Tyr Lys Phe Ile Tyr Val Ala Ile Ala Gln Phe
            260                 265                 270

<210> SEQ ID NO 22
<211> LENGTH: 97
<212> TYPE: PRT
<213> ORGANISM: Artificial Sequence
<220> FEATURE:
<223> OTHER INFORMATION: PDCD1 endodomain

<400> SEQUENCE: 22

Cys Ser Arg Ala Ala Arg Gly Thr Ile Gly Ala Arg Arg Thr Gly Gln
1               5                   10                  15

Pro Leu Lys Glu Asp Pro Ser Ala Val Pro Val Phe Ser Val Asp Tyr
            20                  25                  30

Gly Glu Leu Asp Phe Gln Trp Arg Glu Lys Thr Pro Glu Pro Pro Val
        35                  40                  45

Pro Cys Val Pro Glu Gln Thr Glu Tyr Ala Thr Ile Val Phe Pro Ser
    50                  55                  60

Gly Met Gly Thr Ser Ser Pro Ala Arg Arg Gly Ser Ala Asp Gly Pro
65                  70                  75                  80

Arg Ser Ala Gln Pro Leu Arg Pro Glu Asp Gly His Cys Ser Trp Pro
                85                  90                  95

Leu

<210> SEQ ID NO 23
<211> LENGTH: 141
<212> TYPE: PRT
<213> ORGANISM: Artificial Sequence
<220> FEATURE:
<223> OTHER INFORMATION: BTLA4 endodomain

<400> SEQUENCE: 23

Lys Leu Gln Arg Arg Trp Lys Arg Thr Gln Ser Gln Gln Gly Leu Gln
1               5                   10                  15

Glu Asn Ser Ser Gly Gln Ser Phe Phe Val Arg Asn Lys Lys Val Arg
            20                  25                  30

```
Arg Ala Pro Leu Ser Glu Gly Pro His Ser Leu Gly Cys Tyr Asn Pro
        35                  40                  45

Met Met Glu Asp Gly Ile Ser Tyr Thr Thr Leu Arg Phe Pro Glu Met
 50                  55                  60

Asn Ile Pro Arg Thr Gly Asp Ala Glu Ser Ser Glu Met Gln Arg Pro
 65                  70                  75                  80

Pro Pro Asp Cys Asp Asp Thr Val Thr Tyr Ser Ala Leu His Lys Arg
                 85                  90                  95

Gln Val Gly Asp Tyr Glu Asn Val Ile Pro Asp Phe Pro Glu Asp Glu
                100                 105                 110

Gly Ile His Tyr Ser Glu Leu Ile Gln Phe Gly Val Gly Glu Arg Pro
            115                 120                 125

Gln Ala Gln Glu Asn Val Asp Tyr Val Ile Leu Lys His
        130                 135                 140

<210> SEQ ID NO 24
<211> LENGTH: 168
<212> TYPE: PRT
<213> ORGANISM: Artificial Sequence
<220> FEATURE:
<223> OTHER INFORMATION: LILRB1 endodomain

<400> SEQUENCE: 24

Leu Arg His Arg Arg Gln Gly Lys His Trp Thr Ser Thr Gln Arg Lys
 1               5                  10                  15

Ala Asp Phe Gln His Pro Ala Gly Ala Val Gly Pro Glu Pro Thr Asp
            20                  25                  30

Arg Gly Leu Gln Trp Arg Ser Ser Pro Ala Ala Asp Ala Gln Glu Glu
        35                  40                  45

Asn Leu Tyr Ala Ala Val Lys His Thr Gln Pro Glu Asp Gly Val Glu
 50                  55                  60

Met Asp Thr Arg Ser Pro His Asp Glu Asp Pro Gln Ala Val Thr Tyr
 65                  70                  75                  80

Ala Glu Val Lys His Ser Arg Pro Arg Arg Glu Met Ala Ser Pro Pro
                 85                  90                  95

Ser Pro Leu Ser Gly Glu Phe Leu Asp Thr Lys Asp Arg Gln Ala Glu
                100                 105                 110

Glu Asp Arg Gln Met Asp Thr Glu Ala Ala Ala Ser Glu Ala Pro Gln
            115                 120                 125

Asp Val Thr Tyr Ala Gln Leu His Ser Leu Thr Leu Arg Arg Glu Ala
        130                 135                 140

Thr Glu Pro Pro Pro Ser Gln Glu Gly Pro Ser Pro Ala Val Pro Ser
145                 150                 155                 160

Ile Tyr Ala Thr Leu Ala Ile His
                165

<210> SEQ ID NO 25
<211> LENGTH: 101
<212> TYPE: PRT
<213> ORGANISM: Artificial Sequence
<220> FEATURE:
<223> OTHER INFORMATION: LAIR1 endodomain

<400> SEQUENCE: 25

His Arg Gln Asn Gln Ile Lys Gln Gly Pro Pro Arg Ser Lys Asp Glu
 1               5                  10                  15

Glu Gln Lys Pro Gln Gln Arg Pro Asp Leu Ala Val Asp Val Leu Glu
```

```
                20                  25                  30

Arg Thr Ala Asp Lys Ala Thr Val Asn Gly Leu Pro Glu Lys Asp Arg
            35                  40                  45

Glu Thr Asp Thr Ser Ala Leu Ala Ala Gly Ser Ser Gln Glu Val Thr
        50                  55                  60

Tyr Ala Gln Leu Asp His Trp Ala Leu Thr Gln Arg Thr Ala Arg Ala
 65                  70                  75                  80

Val Ser Pro Gln Ser Thr Lys Pro Met Ala Glu Ser Ile Thr Tyr Ala
                85                  90                  95

Ala Val Ala Arg His
            100

<210> SEQ ID NO 26
<211> LENGTH: 62
<212> TYPE: PRT
<213> ORGANISM: Artificial Sequence
<220> FEATURE:
<223> OTHER INFORMATION: CTLA4 endodomain

<400> SEQUENCE: 26

Phe Leu Leu Trp Ile Leu Ala Ala Val Ser Ser Gly Leu Phe Phe Tyr
 1               5                  10                  15

Ser Phe Leu Leu Thr Ala Val Ser Leu Ser Lys Met Leu Lys Lys Arg
                20                  25                  30

Ser Pro Leu Thr Thr Gly Val Tyr Val Lys Met Pro Pro Thr Glu Pro
            35                  40                  45

Glu Cys Glu Lys Gln Phe Gln Pro Tyr Phe Ile Pro Ile Asn
        50                  55                  60

<210> SEQ ID NO 27
<211> LENGTH: 111
<212> TYPE: PRT
<213> ORGANISM: Artificial Sequence
<220> FEATURE:
<223> OTHER INFORMATION: KIR2DL1 endodomain

<400> SEQUENCE: 27

Gly Asn Ser Arg His Leu His Val Leu Ile Gly Thr Ser Val Val Ile
 1               5                  10                  15

Ile Pro Phe Ala Ile Leu Leu Phe Phe Leu Leu His Arg Trp Cys Ala
                20                  25                  30

Asn Lys Lys Asn Ala Val Val Met Asp Gln Glu Pro Ala Gly Asn Arg
            35                  40                  45

Thr Val Asn Arg Glu Asp Ser Asp Glu Gln Asp Pro Gln Glu Val Thr
        50                  55                  60

Tyr Thr Gln Leu Asn His Cys Val Phe Thr Gln Arg Lys Ile Thr Arg
 65                  70                  75                  80

Pro Ser Gln Arg Pro Lys Thr Pro Pro Thr Asp Ile Ile Val Tyr Thr
                85                  90                  95

Glu Leu Pro Asn Ala Glu Ser Arg Ser Lys Val Val Ser Cys Pro
            100                 105                 110

<210> SEQ ID NO 28
<211> LENGTH: 143
<212> TYPE: PRT
<213> ORGANISM: Artificial Sequence
<220> FEATURE:
<223> OTHER INFORMATION: KIR2DL4 endodomain

<400> SEQUENCE: 28
```

-continued

Gly Ile Ala Arg His Leu His Ala Val Ile Arg Tyr Ser Val Ala Ile
1               5                   10                  15

Ile Leu Phe Thr Ile Leu Pro Phe Phe Leu Leu His Arg Trp Cys Ser
            20                  25                  30

Lys Lys Lys Glu Asn Ala Ala Val Met Asn Gln Glu Pro Ala Gly His
            35                  40                  45

Arg Thr Val Asn Arg Glu Asp Ser Asp Glu Gln Asp Pro Gln Glu Val
            50                  55                  60

Thr Tyr Ala Gln Leu Asp His Cys Ile Phe Thr Gln Arg Lys Ile Thr
65                  70                  75                  80

Gly Pro Ser Gln Arg Ser Lys Arg Pro Ser Thr Asp Thr Ser Val Cys
            85                  90                  95

Ile Glu Leu Pro Asn Ala Glu Pro Arg Ala Leu Ser Pro Ala His Glu
            100                 105                 110

His His Ser Gln Ala Leu Met Gly Ser Ser Arg Glu Thr Thr Ala Leu
            115                 120                 125

Ser Gln Thr Gln Leu Ala Ser Ser Asn Val Pro Ala Ala Gly Ile
            130                 135                 140

<210> SEQ ID NO 29
<211> LENGTH: 143
<212> TYPE: PRT
<213> ORGANISM: Artificial Sequence
<220> FEATURE:
<223> OTHER INFORMATION: KIR2DL5 endodomain

<400> SEQUENCE: 29

Thr Gly Ile Arg Arg His Leu His Ile Leu Ile Gly Thr Ser Val Ala
1               5                   10                  15

Ile Ile Leu Phe Ile Ile Leu Phe Phe Leu Leu His His Cys Cys Cys
            20                  25                  30

Ser Asn Lys Lys Asn Ala Ala Val Met Asp Gln Glu Pro Ala Gly Asp
            35                  40                  45

Arg Thr Val Asn Arg Glu Asp Ser Asp Gln Asp Pro Gln Glu Val
            50                  55                  60

Thr Tyr Ala Gln Leu Asp His Cys Val Phe Thr Gln Thr Lys Ile Thr
65                  70                  75                  80

Ser Pro Ser Gln Arg Pro Lys Thr Pro Pro Thr Asp Thr Thr Met Tyr
            85                  90                  95

Met Glu Leu Pro Asn Ala Lys Pro Arg Ser Leu Ser Pro Ala His Lys
            100                 105                 110

His His Ser Gln Ala Leu Arg Gly Ser Ser Arg Glu Thr Thr Ala Leu
            115                 120                 125

Ser Gln Asn Arg Val Ala Ser Ser His Val Pro Ala Ala Gly Ile
            130                 135                 140

<210> SEQ ID NO 30
<211> LENGTH: 111
<212> TYPE: PRT
<213> ORGANISM: Artificial Sequence
<220> FEATURE:
<223> OTHER INFORMATION: KIR3DL1 endodomain

<400> SEQUENCE: 30

Lys Asp Pro Arg His Leu His Ile Leu Ile Gly Thr Ser Val Val Ile
1               5                   10                  15

Ile Leu Phe Ile Leu Leu Leu Phe Phe Leu Leu His Leu Trp Cys Ser

```
                    20                  25                  30

Asn Lys Lys Asn Ala Ala Val Met Asp Gln Glu Pro Ala Gly Asn Arg
                35                  40                  45

Thr Ala Asn Ser Glu Asp Ser Asp Glu Gln Asp Pro Glu Glu Val Thr
 50                  55                  60

Tyr Ala Gln Leu Asp His Cys Val Phe Thr Gln Arg Lys Ile Thr Arg
 65                  70                  75                  80

Pro Ser Gln Arg Pro Lys Thr Pro Pro Thr Asp Thr Ile Leu Tyr Thr
                 85                  90                  95

Glu Leu Pro Asn Ala Lys Pro Arg Ser Lys Val Val Ser Cys Pro
                100                 105                 110

<210> SEQ ID NO 31
<211> LENGTH: 97
<212> TYPE: PRT
<213> ORGANISM: Artificial Sequence
<220> FEATURE:
<223> OTHER INFORMATION: KIR3DL3 endodomain

<400> SEQUENCE: 31

Lys Asp Pro Gly Asn Ser Arg His Leu His Val Leu Ile Gly Thr Ser
  1               5                  10                  15

Val Val Ile Ile Pro Phe Ala Ile Leu Leu Phe Phe Leu Leu His Arg
                 20                  25                  30

Trp Cys Ala Asn Lys Lys Asn Ala Val Val Met Asp Gln Glu Pro Ala
                 35                  40                  45

Gly Asn Arg Thr Val Asn Arg Glu Asp Ser Asp Glu Gln Asp Pro Gln
 50                  55                  60

Glu Val Thr Tyr Ala Gln Leu Asn His Cys Val Phe Thr Gln Arg Lys
 65                  70                  75                  80

Ile Thr Arg Pro Ser Gln Arg Pro Lys Thr Pro Pro Thr Asp Thr Ser
                 85                  90                  95

Val

<210> SEQ ID NO 32
<211> LENGTH: 807
<212> TYPE: PRT
<213> ORGANISM: Artificial Sequence
<220> FEATURE:
<223> OTHER INFORMATION: PTPN6-CD45 fusion protein

<400> SEQUENCE: 32

Trp Tyr His Gly His Met Ser Gly Gly Gln Ala Glu Thr Leu Leu Gln
  1               5                  10                  15

Ala Lys Gly Glu Pro Trp Thr Phe Leu Val Arg Glu Ser Leu Ser Gln
                 20                  25                  30

Pro Gly Asp Phe Val Leu Ser Val Leu Ser Asp Gln Pro Lys Ala Gly
                 35                  40                  45

Pro Gly Ser Pro Leu Arg Val Thr His Ile Lys Val Met Cys Glu Gly
 50                  55                  60

Gly Arg Tyr Thr Val Gly Gly Leu Glu Thr Phe Asp Ser Leu Thr Asp
 65                  70                  75                  80

Leu Val Glu His Phe Lys Lys Thr Gly Ile Glu Glu Ala Ser Gly Ala
                 85                  90                  95

Phe Val Tyr Leu Arg Gln Pro Tyr Lys Ile Tyr Asp Leu His Lys Lys
                100                 105                 110

Arg Ser Cys Asn Leu Asp Glu Gln Gln Glu Leu Val Glu Arg Asp Asp
```

```
                 115                 120                 125
Glu Lys Gln Leu Met Asn Val Glu Pro Ile His Ala Asp Ile Leu Leu
130                 135                 140

Glu Thr Tyr Lys Arg Lys Ile Ala Asp Glu Gly Arg Leu Phe Leu Ala
145                 150                 155                 160

Glu Phe Gln Ser Ile Pro Arg Val Phe Ser Lys Phe Pro Ile Lys Glu
                165                 170                 175

Ala Arg Lys Pro Phe Asn Gln Asn Lys Asn Arg Tyr Val Asp Ile Leu
            180                 185                 190

Pro Tyr Asp Tyr Asn Arg Val Glu Leu Ser Glu Ile Asn Gly Asp Ala
        195                 200                 205

Gly Ser Asn Tyr Ile Asn Ala Ser Tyr Ile Asp Gly Phe Lys Glu Pro
    210                 215                 220

Arg Lys Tyr Ile Ala Ala Gln Gly Pro Arg Asp Glu Thr Val Asp Asp
225                 230                 235                 240

Phe Trp Arg Met Ile Trp Glu Gln Lys Ala Thr Val Ile Val Met Val
                245                 250                 255

Thr Arg Cys Glu Glu Gly Asn Arg Asn Lys Cys Ala Glu Tyr Trp Pro
            260                 265                 270

Ser Met Glu Glu Gly Thr Arg Ala Phe Gly Asp Val Val Lys Ile
        275                 280                 285

Asn Gln His Lys Arg Cys Pro Asp Tyr Ile Ile Gln Lys Leu Asn Ile
    290                 295                 300

Val Asn Lys Lys Glu Lys Ala Thr Gly Arg Glu Val Thr His Ile Gln
305                 310                 315                 320

Phe Thr Ser Trp Pro Asp His Gly Val Pro Glu Asp Pro His Leu Leu
                325                 330                 335

Leu Lys Leu Arg Arg Arg Val Asn Ala Phe Ser Asn Phe Phe Ser Gly
            340                 345                 350

Pro Ile Val His Cys Ser Ala Gly Val Gly Arg Thr Gly Thr Tyr
        355                 360                 365

Ile Gly Ile Asp Ala Met Leu Glu Gly Leu Glu Ala Glu Asn Lys Val
    370                 375                 380

Asp Val Tyr Gly Tyr Val Val Lys Leu Arg Arg Gln Arg Cys Leu Met
385                 390                 395                 400

Val Gln Val Glu Ala Gln Tyr Ile Leu Ile His Gln Ala Leu Val Glu
                405                 410                 415

Tyr Asn Gln Phe Gly Glu Thr Glu Val Asn Leu Ser Glu Leu His Pro
            420                 425                 430

Tyr Leu His Asn Met Lys Lys Arg Asp Pro Pro Ser Glu Pro Ser Pro
        435                 440                 445

Leu Glu Ala Glu Phe Gln Arg Leu Pro Ser Tyr Arg Ser Trp Arg Thr
    450                 455                 460

Gln His Ile Gly Asn Gln Glu Glu Asn Lys Ser Lys Asn Arg Asn Ser
465                 470                 475                 480

Asn Val Ile Pro Tyr Asp Tyr Asn Arg Val Leu Lys His Glu Leu Glu
                485                 490                 495

Met Ser Lys Glu Ser Glu His Asp Ser Asp Glu Ser Ser Asp Asp Asp
            500                 505                 510

Ser Asp Ser Glu Glu Pro Ser Lys Tyr Ile Asn Ala Ser Phe Ile Met
        515                 520                 525

Ser Tyr Trp Lys Pro Glu Val Met Ile Ala Ala Gln Gly Pro Leu Lys
    530                 535                 540
```

```
Glu Thr Ile Gly Asp Phe Met Ile Gln Arg Lys Val Lys Val Ile Val
545                 550                 555                 560

Met Leu Thr Glu Leu Lys His Gly Asp Gln Glu Ile Cys Ala Gln Tyr
            565                 570                 575

Trp Gly Glu Gly Lys Gln Thr Tyr Gly Asp Ile Glu Val Asp Leu Lys
        580                 585                 590

Asp Thr Asp Lys Ser Ser Thr Tyr Thr Leu Arg Val Phe Glu Leu Arg
    595                 600                 605

His Ser Lys Arg Lys Asp Ser Arg Thr Val Tyr Gln Tyr Gln Tyr Thr
610                 615                 620

Asn Trp Ser Val Glu Gln Leu Pro Ala Glu Pro Lys Glu Leu Ile Ser
625                 630                 635                 640

Met Ile Gln Val Val Lys Gln Lys Leu Pro Gln Lys Asn Ser Ser Glu
            645                 650                 655

Gly Asn Lys His His Lys Ser Thr Pro Leu Leu Ile His Cys Arg Asp
        660                 665                 670

Gly Ser Gln Gln Thr Gly Ile Phe Cys Ala Leu Leu Asn Leu Leu Glu
    675                 680                 685

Ser Ala Glu Thr Glu Val Val Asp Ile Phe Gln Val Val Lys Ala
690                 695                 700

Leu Arg Lys Ala Arg Pro Gly Met Val Ser Thr Phe Glu Gln Tyr Gln
705                 710                 715                 720

Phe Leu Tyr Asp Val Ile Ala Ser Thr Tyr Pro Ala Gln Asn Gly Gln
            725                 730                 735

Val Lys Lys Asn Asn His Gln Glu Asp Lys Ile Glu Phe Asp Asn Glu
        740                 745                 750

Val Asp Lys Val Lys Gln Asp Ala Asn Cys Val Asn Pro Leu Gly Ala
    755                 760                 765

Pro Glu Lys Leu Pro Glu Ala Lys Glu Gln Ala Glu Gly Ser Glu Pro
770                 775                 780

Thr Ser Gly Thr Glu Gly Pro Glu His Ser Val Asn Gly Pro Ala Ser
785                 790                 795                 800

Pro Ala Leu Asn Gln Gly Ser
                805

<210> SEQ ID NO 33
<211> LENGTH: 434
<212> TYPE: PRT
<213> ORGANISM: Artificial Sequence
<220> FEATURE:
<223> OTHER INFORMATION: PTPN6-CD148 fusion protein

<400> SEQUENCE: 33

Glu Thr Leu Leu Gln Ala Lys Gly Glu Pro Trp Thr Phe Leu Val Arg
1               5                   10                  15

Glu Ser Leu Ser Gln Pro Gly Asp Phe Val Leu Ser Val Leu Ser Asp
            20                  25                  30

Gln Pro Lys Ala Gly Pro Gly Ser Pro Leu Arg Val Thr His Ile Lys
        35                  40                  45

Val Met Cys Glu Gly Gly Arg Tyr Thr Val Gly Gly Leu Glu Thr Phe
    50                  55                  60

Asp Ser Leu Thr Asp Leu Val Glu His Phe Lys Lys Thr Gly Ile Glu
65                  70                  75                  80

Glu Ala Ser Gly Ala Phe Val Tyr Leu Arg Gln Pro Tyr Arg Lys Lys
                85                  90                  95
```

```
Arg Lys Asp Ala Lys Asn Asn Glu Val Ser Phe Ser Gln Ile Lys Pro
            100                 105                 110

Lys Lys Ser Lys Leu Ile Arg Val Glu Asn Phe Glu Ala Tyr Phe Lys
            115                 120                 125

Lys Gln Gln Ala Asp Ser Asn Cys Gly Phe Ala Glu Glu Tyr Glu Asp
            130                 135                 140

Leu Lys Leu Val Gly Ile Ser Gln Pro Lys Tyr Ala Ala Glu Leu Ala
145                 150                 155                 160

Glu Asn Arg Gly Lys Asn Arg Tyr Asn Asn Val Leu Pro Tyr Asp Ile
            165                 170                 175

Ser Arg Val Lys Leu Ser Val Gln Thr His Ser Thr Asp Asp Tyr Ile
            180                 185                 190

Asn Ala Asn Tyr Met Pro Gly Tyr His Ser Lys Lys Asp Phe Ile Ala
            195                 200                 205

Thr Gln Gly Pro Leu Pro Asn Thr Leu Lys Asp Phe Trp Arg Met Val
            210                 215                 220

Trp Glu Lys Asn Val Tyr Ala Ile Ile Met Leu Thr Lys Cys Val Glu
225                 230                 235                 240

Gln Gly Arg Thr Lys Cys Glu Glu Tyr Trp Pro Ser Lys Gln Ala Gln
            245                 250                 255

Asp Tyr Gly Asp Ile Thr Val Ala Met Thr Ser Glu Ile Val Leu Pro
            260                 265                 270

Glu Trp Thr Ile Arg Asp Phe Thr Val Lys Asn Ile Gln Thr Ser Glu
            275                 280                 285

Ser His Pro Leu Arg Gln Phe His Phe Thr Ser Trp Pro Asp His Gly
            290                 295                 300

Val Pro Asp Thr Thr Asp Leu Leu Ile Asn Phe Arg Tyr Leu Val Arg
305                 310                 315                 320

Asp Tyr Met Lys Gln Ser Pro Pro Glu Ser Pro Ile Leu Val His Cys
            325                 330                 335

Ser Ala Gly Val Gly Arg Thr Gly Thr Phe Ile Ala Ile Asp Arg Leu
            340                 345                 350

Ile Tyr Gln Ile Glu Asn Glu Asn Thr Val Asp Val Tyr Gly Ile Val
            355                 360                 365

Tyr Asp Leu Arg Met His Arg Pro Leu Met Val Gln Thr Glu Asp Gln
            370                 375                 380

Tyr Val Phe Leu Asn Gln Cys Val Leu Asp Ile Val Arg Ser Gln Lys
385                 390                 395                 400

Asp Ser Lys Val Asp Leu Ile Tyr Gln Asn Thr Thr Ala Met Thr Ile
            405                 410                 415

Tyr Glu Asn Leu Ala Pro Val Thr Thr Phe Gly Lys Thr Asn Gly Tyr
            420                 425                 430

Ile Ala

<210> SEQ ID NO 34
<211> LENGTH: 20
<212> TYPE: PRT
<213> ORGANISM: Foot-and-mouth disease virus

<400> SEQUENCE: 34

Arg Ala Glu Gly Arg Gly Ser Leu Leu Thr Cys Gly Asp Val Glu Glu
1               5                   10                  15

Asn Pro Gly Pro
            20
```

<210> SEQ ID NO 35
<211> LENGTH: 3390
<212> TYPE: DNA
<213> ORGANISM: Artificial Sequence
<220> FEATURE:
<223> OTHER INFORMATION: Nucleic acid sequences coding for CARs
    (MP13974.SFG.aCD19fmc63-CD8STK-CD28tmZ-2A-aCD33glx-HCH2CH3pvaa-
    CD28tmZw)

<400> SEQUENCE: 35

```
atgagcctgc ccgtgaccgc cctgctgctg cccctggccc tgctgctgca cgccgccaga      60
ccagacatcc agatgaccca gaccaccagc agcctgagcg ccagcctggg cgaccgggtg     120
accatcagct gcagagccag ccaggacatc agcaagtacc tgaactggta ccagcagaag     180
cccgacggca ccgtgaagct gctgatctac cacaccagcc ggctgcacag cggcgtgccc     240
agccggttca gcggcagcgg cagcggcacc gactacagcc tgaccatcag caacctggag     300
caggaggaca tcgccaccta cttctgccag cagggcaaca ccctgcccta caccttcgga     360
ggcggcacca agctggagat caccaaggcc ggaggcggag gctctggcgg aggcggctct     420
ggcggaggcg gctctggcgg aggcggcagc gaggtgaagc tgcaggagtc tggcccaggc     480
ctggtggccc caagccagag cctgagcgtg acctgcaccg tgagcggcgt gagcctgccc     540
gactacggcg tgagctggat caggcagccc cacggaaggg gcctgagtg gctgggcgtg     600
atctggggca gcgagaccac ctactacaac agcgccctga gagccggct gaccatcatc     660
aaggacaaca gcaagagcca ggtgttcctg aagatgaaca gcctgcagac cgacgacacc     720
gccatctact actgcgccaa gcactactac tatggcggca gctacgctat ggactactgg     780
ggccagggca ccagcgtgac cgtgagctca gatcccacca cgacgccagc gccgcgacca     840
ccaacaccgg cgcccaccat cgcgtcgcag cccctgtccc tgcgcccaga ggcgtgccgg     900
ccagcggcgg ggggcgcagt gcacacgagg gggctggact cgcctgtga tatcttttgg     960
gtgctggtgg tggttggtgg agtcctggct tgctatagct tgctagtaac agtggccttt    1020
attattttct gggtgaggag agtgaagttc agcaggagcg cagacgcccc cgcgtaccag    1080
cagggccaga accagctcta taacgagctc aatctaggac gaagagagga gtacgatgtt    1140
ttggacaaga cgtggccg ggaccctgag atgggggaa agccgagaag gaagaaccct    1200
caggaaggcc tgtacaatga actgcagaaa gataagatgg cggaggccta cagtgagatt    1260
gggatgaaag gcgagcgccg gaggggcaag gggcacgatg ccttaccag gtctcagt    1320
acagccacca aggacaccta cgacgccctt cacatgcagg ccctgcctcc tcgcagagcc    1380
gagggcaggg gaagtcttct aacatgcggg gacgtggagg aaaatcccgg gcccatggcc    1440
gtgcccactc aggtcctggg gttgttgcta ctgtggctta cagatgccag atgtgacatc    1500
cagatgacac agtctccatc ttccctgtct gcatctgtcg gagatcgcgt caccatcacc    1560
tgtcagcaa gtaggacat ttattttaat ttagtgtggt atcagcagaa accaggaaag    1620
gccctaagc tcctgatcta tgatacaat cgcttggcag atggggtccc atcacggttc    1680
agtggctctg gatctggcac acagtatact ctaaccataa gtagcctgca acccgaagat    1740
ttcgcaacct attattgtca acactataag aattatccgc tcacgttcgg tcaggggacc    1800
aagctggaaa tcaaaagatc tggtggcgga gggtcaggag gcggaggcag cggaggcgt    1860
ggctcgggag gcgaggctc gagatctgag gtgcagttgg tggagtctgg gggcggcttg    1920
gtgcagcctg gagggtccct gaggctctcc tgtgcagcct caggattcac tctcagtaat    1980
```

| | |
|---|---|
| tatggcatgc actggatcag gcaggctcca gggaagggtc tggagtgggt ctcgtctatt | 2040 |
| agtcttaatg gtggtagcac ttactatcga gactccgtga agggccgatt cactatctcc | 2100 |
| agggacaatg caaaaagcac cctctacctt caaatgaata gtctgagggc cgaggacacg | 2160 |
| gccgtctatt actgtgcagc acaggacgct tatacgggag gttactttga ttactggggc | 2220 |
| caaggaacgc tggtcacagt ctcgtctatg gatcccgccg agcccaaatc tcctgacaaa | 2280 |
| actcacacat gcccaccgtg cccagcacct cccgtggccg gccgtcagt cttcctcttc | 2340 |
| ccccaaaac ccaaggacac cctcatgatc gcccggaccc ctgaggtcac atgcgtggtg | 2400 |
| gtggacgtga gccacgaaga ccctgaggtc aagttcaact ggtacgtgga cggcgtggag | 2460 |
| gtgcataatg ccaagacaaa gccgcgggag gagcagtaca acagcacgta ccgtgtggtc | 2520 |
| agcgtcctca ccgtcctgca ccaggactgg ctgaatggca aggagtacaa gtgcaaggtc | 2580 |
| tccaacaaag ccctcccagc ccccatcgag aaaaccatct ccaaagccaa agggcagccc | 2640 |
| cgagaaccac aggtgtacac cctgccccca tcccgggatg agctgaccaa gaaccaggtc | 2700 |
| agcctgacct gcctggtcaa aggcttctat cccagcgaca tcgccgtgga gtgggagagc | 2760 |
| aatgggcaac cggagaacaa ctacaagacc acgcctcccg tgctggactc cgacggctcc | 2820 |
| ttcttcctct acagcaagct caccgtggac aagagcaggt ggcagcaggg gaacgtcttc | 2880 |
| tcatgctccg tgatgcatga ggccctgcac aatcactata cccagaaatc tctgagtctg | 2940 |
| agcccaggca gaaggaccc caagttctgg gtcctggtgg tggtgggagg cgtgctggcc | 3000 |
| tgttactctc tcctggtgac cgtggccttc atcatctttt gggtgcgctc ccgggtgaag | 3060 |
| tttttctcgct ctgccgatgc cccagcctat cagcagggcc agaatcagct gtacaatgaa | 3120 |
| ctgaacctgg gcaggcggga ggagtacgac gtgctggata gcggagagg cagagacccc | 3180 |
| gagatgggcg gcaaaccacg cgcaaaaat ccccaggagg gactctataa cgagctgcag | 3240 |
| aaggacaaaa tggccgaggc ctattccgag atcggcatga agggagagag aagacgcgga | 3300 |
| aagggccacg acggcctgta tcagggattg tccaccgcta caaagatac atatgatgcc | 3360 |
| ctgcacatgc aggccctgcc acccagatga | 3390 |

<210> SEQ ID NO 36
<211> LENGTH: 5154
<212> TYPE: DNA
<213> ORGANISM: Artificial Sequence
<220> FEATURE:
<223> OTHER INFORMATION: Nucleic acid sequences coding for CARs
(MP14802.SFG.aCD19fmc63_clean-CD8STK-CD28tmZ-2A-aCD33glx-HCH2CH3pvaa-dCD45)

<400> SEQUENCE: 36

| | |
|---|---|
| atgagcctgc ccgtgaccgc cctgctgctg cccctggccc tgctgctgca cgccgccaga | 60 |
| ccagacatcc agatgaccca gaccaccagc agcctgagcg ccagcctggg cgaccgggtg | 120 |
| accatcagct gcagagccag ccaggacatc agcaagtacc tgaactgta ccagcagaag | 180 |
| cccgacggca ccgtgaagct gctgatctac cacaccagcc ggctgcacag cggcgtgccc | 240 |
| agccggttca gcggcagcgg cagcggcacc gactacagcc tgaccatcag caacctggag | 300 |
| caggaggaca tcgccaccta cttctgccag cagggcaaca cctgcccta caccttcgga | 360 |
| ggcggcacca agctggagat caccaaggcc ggaggcggag gctctggcgg aggcggctct | 420 |
| ggcggaggcg gctctggcgg aggcggcagc gaggtgaagc tgcaggagtc tggcccaggc | 480 |
| ctggtggccc aagccagag cctgagcgtg acctgcaccg tgagcggcgt gagcctgccc | 540 |
| gactacggcg tgagctggat caggcagccc ccacggaagg gcctggagtg gctgggcgtg | 600 |

```
atctggggca gcgagaccac ctactacaac agcgccctga agagccggct gaccatcatc    660
aaggacaaca gcaagagcca ggtgttcctg aagatgaaca gcctgcagac cgacgacacc    720
gccatctact actgcgccaa gcactactac tatggcggca gctacgctat ggactactgg    780
ggccagggca ccagcgtgac cgtgagctca gatcccacca cgacgccagc gccgcgacca    840
ccaacaccgg cgcccaccat cgcgtcgcag cccctgtccc tgcgcccaga ggcgtgccgg    900
ccagcggcgg ggggcgcagt gcacacgagg gggctggact cgcctgtga tatcttttgg     960 gtgctggtgg tggttggtgg agtcctggct tgctatagct tgctagtaac agtggccttt   1020
attattttct gggtgaggag agtgaagttc agcaggagcg cagacgcccc cgcgtaccag   1080
cagggccaga accagctcta taacgagctc aatctaggac gaagagagga gtacgatgtt   1140
ttggacaaga cgtggccg ggaccctgag atggggggaa agccgagaag gaagaaccct     1200
caggaaggcc tgtacaatga actgcagaaa gataagatgg cggaggccta cagtgagatt   1260
gggatgaaag gcgagcgccg gaggggcaag gggcacgatg gcctttacca gggtctcagt   1320
acagccacca aggacaccta cgacgccctt cacatgcagg ccctgcctcc tcgcagagcc   1380
gagggcaggg aagtcttct aacatgcggg gacgtggagg aaaatcccgg gcccatggcc    1440
gtgcccactc aggtcctggg gttgttgcta ctgtggctta cagatgccag atgtgacatc   1500
cagatgacac agtctccatc tccctgtct gcatctgtcg gagatcgcgt caccatcacc    1560
tgtcgagcaa gtgaggacat ttattttaat ttagtgtggt atcagcagaa accaggaaag   1620
gcccctaagc tcctgatcta tgatacaaat cgcttggcag atgggtccc atcacggttc     1680 agtggctctg gatctggcac acagtatact ctaaccataa gtagcctgca acccgaagat   1740
ttcgcaacct attattgtca acactataag aattatccgc tcacgttcgg tcaggggacc   1800
aagctggaaa tcaaaagatc tggtggcgga gggtcaggag gcggaggcag cggaggcggt   1860
ggctcgggag gcggaggctc gagatctgag gtgcagttgg tggagtctgg gggcggcttg   1920
gtgcagcctg gagggtccct gaggctctcc tgtgcagcct caggattcac tctcagtaat   1980
tatggcatgc actggatcag gcaggctcca gggaagggtc tggagtgggt ctcgtctatt   2040
agtcttaatg gtggtagcac ttactatcga gactccgtga agggccgatt cactatctcc   2100
agggacaatg caaaaagcac cctctacctt caaatgaata gtctgagggc cgaggacacg   2160
gccgtctatt actgtgcagc acaggacgct tatacggag gttactttga ttactggggc      2220
caaggaacgc tggtcacagt ctcgtctatg gatcccgccg agcccaaatc tcctgacaaa   2280
actcacacat gcccaccgtg cccagcacct cccgtggccg gccgtcagt cttcctcttc    2340 cccccaaaac ccaaggacac cctcatgatc gcccggaccc ctgaggtcac atgcgtggtg   2400
gtggacgtga gccacgaaga ccctgaggtc aagttcaact ggtacgtgga cggcgtggag   2460
gtgcataatg ccaagacaaa gccgcgggag gagcagtaca acagcacgta ccgtgtggtc   2520
agcgtcctca ccgtcctgca ccaggactgg ctgaatggca aggagtacaa gtgcaaggtc   2580
tccaacaaag ccctcccagc ccccatcgag aaaaccatct ccaaagccaa agggcagccc   2640
cgagaaccac aggtgtacac cctgccccca tcccgggatg agctgaccaa gaaccaggtc   2700
agcctgacct gcctggtcaa aggcttctat cccagcgaca tcgccgtgga gtgggagagc   2760
aatgggcaac cggagaacaa ctacaagacc acgcctcccg tgctggactc cgacggctcc   2820
ttcttcctct acagcaagct caccgtggac aagagcaggt ggcagcaggg gaacgtcttc   2880
tcatgctccg tgatgcatga ggccctgcac aatcactata cccagaaatc tctgagtctg   2940
```

```
agcccaggca agaaggaccc caaggcactg atagcatttc tggcatttct gattattgtg   3000
acatcaatag ccctgcttgt tgttctctac aaaatctatg atctacataa gaaaagatcc   3060
tgcaatttag atgaacagca ggagcttgtt gaaagggatg atgaaaaaca actgatgaat   3120
gtggagccaa tccatgcaga tattttgttg gaaacttata agaggaagat tgctgatgaa   3180
ggaagacttt ttctggctga atttcagagc atcccgcggg tgttcagcaa gtttcctata   3240
aaggaagctc gaaagccctt taaccagaat aaaaaccgtt atgttgacat tcttccttat   3300
gattataacc gtgttgaact ctctgagata aacggagatg cagggtcaaa ctacataaat   3360
gccagctata ttgatggttt caaagaaccc aggaaataca ttgctgcaca aggtcccagg   3420
gatgaaactg ttgatgattt ctggaggatg atttgggaac agaaagccac agttattgtc   3480
atggtcactc gatgtgaaga aggaaacagg aacaagtgtg cagaatactg gccgtcaatg   3540
gaagagggca ctcgggcttt tggagatgtt gttgtaaaga tcaaccagca caaagatgt   3600
ccagattaca tcattcagaa attgaacatt gtaaataaaa aagaaaaagc aactggaaga   3660
gaggtgactc acattcagtt caccagctgg ccagaccacg gggtgcctga ggatcctcac   3720
ttgctcctca aactgagaag gagagtgaat gccttcagca atttcttcag tggtcccatt   3780
gtggtgcact gcagtgctgg tgttgggcgc acaggaacct atatcggaat tgatgccatg   3840
ctagaaggcc tggaagccga gaacaaagtg gatgtttatg gttatgttgt caagctaagg   3900
cgacagagat gcctgatggt tcaagtagag gcccagtaca tcttgatcca tcaggctttg   3960
gtggaataca atcagtttgg agaaacagaa gtgaatttgt ctgaattaca tccatatcta   4020
cataacatga gaaaaaggga tccacccagt gagccgtctc cactagaggc tgaattccag   4080
agacttcctt catataggag ctggaggaca cagcacattg gaaatcaaga agaaaataaa   4140
agtaaaaaca ggaattctaa tgtcatccca tatgactata cagagtgcc acttaaacat   4200
gagctggaaa tgagtaaaga gagtgagcat gattcagatg aatcctctga tgatgacagt   4260
gattcagagg aaccaagcaa atacatcaat gcatctttta taatgagcta ctggaaacct   4320
gaagtgatga ttgctgctca gggaccactg aaggagacca ttggtgactt ttggcagatg   4380
atcttccaaa gaaaagtcaa agttattgtt atgctgacag aactgaaaca tggagaccag   4440
gaaatctgtg ctcagtactg gggagaagga aagcaaacat atggagatat tgaagttgac   4500
ctgaaagaca cagacaaatc ttcaacttat acccttcgtg tctttgaact gagacattcc   4560
aagaggaaag actctcgaac tgtgtaccag taccaatata caaactggag tgtggagcag   4620
cttcctgcag aacccaagga attaatctct atgattcagg tcgtcaaaca aaaacttccc   4680
cagaagaatt cctctgaagg gaacaagcat cacaagagta cacctctact cattcactgc   4740
agggatggat ctcagcaaac gggaatattt tgtgctttgt taaatctctt agaaagtgcg   4800
gaaacagaag aggtagtgga tatttttcaa gtggtaaaag ctctacgcaa agctaggcca   4860
ggcatggttt ccacattcga gcaatatcaa ttcctatatg acgtcattgc cagcacctac   4920
cctgctcaga atgacaagt aaagaaaaac aaccatcaag aagataaaat tgaatttgat   4980
aatgaagtgg acaaagtaaa gcaggatgct aattgtgtta atccacttgg tgccccagaa   5040
aagctccctg aagcaaagga acaggctgaa ggttctgaac ccacgagtgg cactgagggg   5100
ccagaacatt ctgtcaatgg tcctgcaagt ccagctttaa atcaaggttc atag         5154
```

<210> SEQ ID NO 37
<211> LENGTH: 4053
<212> TYPE: DNA
<213> ORGANISM: Artificial Sequence
<220> FEATURE:
<223> OTHER INFORMATION: Nucleic acid sequences coding for CARs
(MP14801.SFG.aCD19fmc63_clean-CD8STK-CD28tmZ-2A-aCD33glx-
HCH2CH3pvaa-dCD148)

<400> SEQUENCE: 37

```
atgagcctgc cgtgaccgc cctgctgctg ccctggccc tgctgctgca cgccgccaga      60
ccagacatcc agatgaccca gaccaccagc agcctgagcg ccagcctggg cgaccgggtg    120
accatcagct gcagagccag ccaggacatc agcaagtacc tgaactgta ccagcagaag    180
cccgacggca ccgtgaagct gctgatctac cacaccagcc ggctgcacag cggcgtgccc    240
agccggttca gcggcagcgg cagcggcacc gactacagcc tgaccatcag caacctggag    300
caggaggaca tcgccaccta cttctgccag cagggcaaca ccctgcccta caccttcgga    360
ggcggcacca agctggagat caccaaggcc ggaggcggag gctctggcgg aggcggctct    420
ggcggaggcg gctctggcgg aggcggcagc gaggtgaagc tgcaggagtc tggcccaggc    480
ctggtggccc caagccagag cctgagcgtg acctgcaccg tgagcggcgt gagcctgccc    540
gactacggcg tgagctggat caggcagccc ccacggaagg gcctggagtg gctgggcgtg    600
atctggggca gcgagaccac ctactacaac agcgccctga gagccggct gaccatcatc    660
aaggacaaca gcaagagcca ggtgttcctg aagatgaaca gcctgcagac cgacgacacc    720
gccatctact actgcgccaa gcactactac tatggcggca gctacgctat ggactactgg    780
ggccagggca ccagcgtgac cgtgagctca gatcccacca cgacgccagc cgcgacca    840
ccaacaccgg cgcccaccat cgcgtcgcag cccctgtccc tgcgcccaga ggcgtgccgg    900
ccagcggcgg ggggcgcagt gcacacgagg gggctggact tcgcctgtga tatcttttgg    960
gtgctggtgg tggttggtgg agtcctggct tgctatagct tgctagtaac agtggccttt   1020
attattttct gggtgaggag agtgaagttc agcaggagcg cagacgcccc cgcgtaccag   1080
cagggccaga accagctcta taacgagctc aatctaggac gaagagagga gtacgatgtt   1140
ttggacaaga cgtggccg ggaccctgag atgggggaa agccgagaag gaagaaccct   1200
caggaaggcc tgtacaatga actgcagaaa gataagatgg cggaggccta cagtgagatt   1260
gggatgaaag gcgagcgccg gaggggcaag gggcacgatg gcctttacca gggtctcagt   1320
acagccacca aggacaccta cgacgccctt cacatgcagg ccctgcctcc tcgcagagcc   1380
gagggcaggg gaagtcttct aacatgcggg gacgtggagg aaaatcccgg gcccatggcc   1440
gtgcccactc aggtcctggg gttgttgcta ctgtggctta cagatgccag atgtgacatc   1500
cagatgacac agtctccatc ttccctgtct gcatctgtcg gagatcgcgt caccatcacc   1560
tgtcgagcaa gtgaggacat ttattttaat ttagtgtggt atcagcagaa accaggaaag   1620
gcccctaagc tcctgatcta tgatacaaat cgcttggcag atgggtccc atcacggttc   1680
agtggctctg gatctggcac acagtatact ctaaccataa gtagcctgca acccgaagat   1740
ttcgcaacct attattgtca acactataag aattatccgc tcacgttcgg tcagggggacc   1800
aagctggaaa tcaaaagatc tggtggcgga gggtcaggag gcggaggcag cggaggcggt   1860
ggctcgggag gcgaggctc gagatctgag gtgcagttgg tggagtctgg gggcggcttg   1920
gtgcagcctg gagggtccct gaggctctcc tgtgcagcct caggattcac tctcagtaat   1980
tatggcatgc actggatcag gcaggctcca gggaagggtc tggagtgggt ctcgtctatt   2040
agtcttaatg gtggtagcac ttactatcga gactccgtga agggccgatt cactatctcc   2100
agggacaatg caaaaagcac cctctacctt caaatgaata gtctgagggc cgaggacacg   2160
```

```
gccgtctatt actgtgcagc acaggacgct tatacgggag gttactttga ttactggggc   2220
caaggaacgc tggtcacagt ctcgtctatg gatcccgccg agcccaaatc tcctgacaaa   2280
actcacacat gcccaccgtg cccagcacct cccgtggccg gcccgtcagt cttcctcttc   2340
cccccaaaac ccaaggacac cctcatgatc gcccggaccc ctgaggtcac atgcgtggtg   2400
gtggacgtga gccacgaaga ccctgaggtc aagttcaact ggtacgtgga cggcgtggag   2460
gtgcataatg ccaagacaaa gccgcgggag gagcagtaca acagcacgta ccgtgtggtc   2520
agcgtcctca ccgtcctgca ccaggactgg ctgaatggca aggagtacaa gtgcaaggtc   2580
tccaacaaag ccctcccagc ccccatcgag aaaaccatct ccaaagccaa agggcagccc   2640
cgagaaccac aggtgtacac cctgccccca tcccgggatg agctgaccaa gaaccaggtc   2700
agcctgacct gcctggtcaa aggcttctat cccagcgaca tcgccgtgga gtgggagagc   2760
aatgggcaac cggagaacaa ctacaagacc acgcctcccg tgctggactc cgacggctcc   2820
ttcttcctct acagcaagct caccgtggac aagagcaggt ggcagcaggg gaacgtcttc   2880
tcatgctccg tgatgcatga ggccctgcac aatcactata cccagaaatc tctgagtctg   2940
agcccaggca agaaggaccc caaggcggtt tttggctgta tctttggtgc cctggttatt   3000
gtgactgtgg gaggcttcat cttctggaga agaagagaga agatgcaaaa gaataatgaa   3060
gtgtcctttt ctcaaattaa acctaaaaaa tctaagttaa tcagagtgga gaattttgag   3120
gcctacttca agaagcagca agctgactcc aactgtgggt cgcagaggaa atacgaagat   3180
ctgaagcttg ttggaattag tcaacctaaa tatgcagcag aactggctga aatagagga   3240 aagaatcgct ataataatgt tctgcccctat gatatttccc gtgtcaaact ttcggtccag   3300
acccattcaa cggatgacta catcaatgcc aactacatgc ctggctacca ctccaagaaa   3360 gatttttattg ccacacaagg accttttaccg aacactttga aagattttttg gcgtatggtt   3420 tgggagaaaa atgtatatgc catcattatg ttgactaaat gtgttgaaca gggaagaacc   3480
aaatgtgagg agtattggcc ctccaagcag gctcaggact atggagacat aactgtggca   3540
atgacatcag aaattgttct tccggaatgg accatcagag atttcacagt gaaaaatatc   3600
cagacaagtg agagtcaccc tctgagacag ttccattttca cctcctggcc agaccacggt   3660
gttcccgaca ccactgacct gctcatcaac ttccggtacc tcgttcgtga ctacatgaag   3720
cagagtcctc ccgaatcgcc gattctggtc cattgcagtg ctggggtcgg aaggacgggc   3780
actttcattg ccattgatcg tctcatctac cagatagaga atgagaacac cgtggatgtg   3840
tatgggattg tgtatgacct tcgaatgcat aggcctttaa tggtgcagac agaggaccag   3900 tatgtttttcc tcaatcagtg tgttttggat attgtcagat cccagaaaga ctcaaaagta   3960
gatcttatct accagaacac aactgcaatg caatctatg aaaaccttgc gcccgtgacc   4020
acatttggaa agaccaatgg ttacatcgcc taa                                4053
```

<210> SEQ ID NO 38
<211> LENGTH: 3345
<212> TYPE: DNA
<213> ORGANISM: Artificial Sequence
<220> FEATURE:
<223> OTHER INFORMATION: Nucleic acid sequences coding for CARs
      (16076.SFG.aCD19fmc63-CD8STK-CD28tmZ-2A-aCD33glx-muCD8STK-tm-
      dPTPN6)

<400> SEQUENCE: 38

```
atgagcctgc ccgtgaccgc cctgctgctg cccctggccc tgctgctgca cgccgccaga   60
ccagacatcc agatgaccca gaccaccagc agcctgagcg ccagcctggg cgaccgggtg  120
```

```
accatcagct gcagagccag ccaggacatc agcaagtacc tgaactggta ccagcagaag      180
cccgacggca ccgtgaagct gctgatctac cacaccagcc ggctgcacag cggcgtgccc      240
agccggttca gcggcagcgg cagcggcacc gactacagcc tgaccatcag caacctggag      300
caggaggaca tcgccaccta cttctgccag cagggcaaca ccctgcccta caccttcgga      360
ggcggcacca agctggagat caccaaggcc ggaggcggag gctctggcgg aggcggctct      420
ggcggaggcg gctctggcgg aggcggcagc gaggtgaagc tgcaggagtc tggcccaggc      480
ctggtggccc caagccagag cctgagcgtg acctgcaccg tgagcggcgt gagcctgccc      540
gactacggcg tgagctggat caggcagccc cacggaagg cctggagtg gctgggcgtg       600 atctggggca gcgagaccac ctactacaac agcgccctga gagccggct gaccatcatc      660 aaggacaaca gcaagagcca ggtgttcctg aagatgaaca gcctgcagac cgacgacacc      720
gccatctact actgcgccaa gcactactac tatggcggca gctacgctat ggactactgg      780
ggccagggca ccagcgtgac cgtgagctca gatcccacca cgacgccagc gccgcgacca      840
ccaacaccgg cgcccaccat cgcgtcgcag cccctgtccc tgcgcccaga ggcgtgccgg      900
ccagcggcgg ggggcgcagt gcacacgagg gggctggact tcgcctgtga tatcttttgg      960
gtgctggtgg tggttggtgg agtcctggct tgctatagct tgctagtaac agtggccttt     1020
attattttct gggtgaggag agtgaagttc agcaggagcg cagacgcccc cgcgtaccag     1080
cagggccaga accagctcta taacgagctc aatctaggac gaagagagga gtacgatgtt     1140
ttggacaaga gacgtggccg ggaccctgag atggggggaa agccgagaag gaagaaccct     1200
caggaaggcc tgtacaatga actgcagaaa gataagatgg cggaggccta cagtgagatt     1260
gggatgaaag cgagcgccg gaggggcaag ggcacgatg gcctttacca gggtctcagt      1320
acagccacca aggacaccta cgacgccctt cacatgcagg ccctgcctcc tcgcagagcc     1380
gagggcaggg gaagtcttct aacatgcggg gacgtggagg aaaatcccgg gcccatggcc     1440
gtgcccactc aggtcctggg gttgttgcta ctgtggctta cagatgccag atgtgacatc     1500
cagatgacac agtctccatc ttccctgtct gcatctgtcg gagatcgcgt caccatcacc     1560
tgtcgagcaa gtgaggacat ttattttaat ttagtgtggt atcagcagaa accaggaaag     1620
gcccctaagc tcctgatcta tgatacaaat cgcttggcag atggggtccc atcacggttc     1680
agtggctctg gatctggcac acagtatact ctaaccataa gtagcctgca acccgaagat     1740
ttcgcaacct attattgtca acactataag aattatccgc tcacgttcgg tcagggggacc     1800 aagctggaaa tcaaaagatc tggtggcgga gggtcaggag cggaggcag cggaggcggt      1860 ggctcgggag gcggaggctc gagatctgag gtgcagttgg tggagtctgg gggcggcttg     1920
gtgcagcctg gagggtccct gaggctctcc tgtgcagcct caggattcac tctcagtaat     1980
tatggcatgc actggatcag gcaggctcca gggaagggtc tggagtgggt ctcgtctatt     2040
agtcttaatg gtggtagcac ttactatcga gactccgtga agggccgatt cactatctcc     2100
agggacaatg caaaaagcac cctctacctt caaatgaata gtctgagggc cgaggacacg     2160
gccgtctatt actgtgcagc acaggacgct tatacgggag gttactttga ttactggggc     2220
caaggaacgc tggtcacagt ctcgtctatg gatcccgcca ccacaaccaa gcccgtgctg     2280
cggaccccaa gccctgtgca ccctaccggc accagccagc tcagagaccc gaggactgc      2340 cggcctcggg gcagcgtgaa gggcaccggc ctggacttcg cctgcgacat ctactgggca     2400
cctctggccg gaatatgcgt ggcactgctg ctgagcctca tcatcaccct gatctgttat     2460
```

| | |
|---|---|
| caccgaagcc gcaagcgggt gtgtaaaagt ggaggcggaa gcttctggga ggagtttgag | 2520 |
| agtttgcaga agcaggaggt gaagaacttg caccagcgtc tggaagggca gcggccagag | 2580 |
| aacaagggca agaaccgcta caagaacatt ctccccttg accacagccg agtgatcctg | 2640 |
| cagggacggg acagtaacat ccccgggtcc gactacatca atgccaacta catcaagaac | 2700 |
| cagctgctag gccctgatga aacgctaag acctacatcg ccagccaggg ctgtctggag | 2760 |
| gccacggtca atgacttctg gcagatggcg tggcaggaga acagccgtgt catcgtcatg | 2820 |
| accacccgag aggtggagaa aggccggaac aaatgcgtcc catactggcc cgaggtgggc | 2880 |
| atgcagcgtg cttatgggcc ctactctgtg accaactgcg gggagcatga cacaaccgaa | 2940 |
| tacaaactcc gtaccttaca ggtctccccg ctggacaatg agacctgat tcgggagatc | 3000 |
| tggcattacc agtacctgag ctggcccgac cacggggtcc ccagtgagcc tggggggtgtc | 3060 |
| ctcagcttcc tggaccagat caaccagcgg caggaaagtc tgcctcacgc agggcccatc | 3120 |
| atcgtgcact gcagcgccgg catcggccgc acaggcacca tcattgtcat cgacatgctc | 3180 |
| atggagaaca tctccaccaa gggcctggac tgtgacattg acatccagaa gaccatccag | 3240 |
| atggtgcggg cgcagcgctc gggcatggtg cagacggagg cgcagtacaa gttcatctac | 3300 |
| gtggccatcg cccagttcat tgaaaccact aagaagaagc tgtga | 3345 |

<210> SEQ ID NO 39
<211> LENGTH: 2757
<212> TYPE: DNA
<213> ORGANISM: Artificial Sequence
<220> FEATURE:
<223> OTHER INFORMATION: Nucleic acid sequences coding for CARs
    (MP16091.SFG.aCD19fmc63-CD8STK-CD28tmZ-2A-aCD33glx-muCD8STK-
    LAIR1tm-endo)

<400> SEQUENCE: 39

| | |
|---|---|
| atgagcctgc ccgtgaccgc cctgctgctg ccccctggccc tgctgctgca cgccgccaga | 60 |
| ccagacatcc agatgaccca gaccaccagc agcctgagcg ccagcctggg cgaccgggtg | 120 |
| accatcagct gcagagccag ccaggacatc agcaagtacc tgaactggta ccagcagaag | 180 |
| cccgacggca ccgtgaagct gctgatctac cacaccagcc ggctgcacag cggcgtgccc | 240 |
| agccggttca gcggcagcgg cagcggcacc gactacagcc tgaccatcag caacctggag | 300 |
| caggaggaca tcgccaccta cttctgccag cagggcaaca ccctgcccta caccttcgga | 360 |
| ggcggcacca agctggagat caccaaggcc ggaggcggag gctctggcgg aggcggctct | 420 |
| ggcggaggcg gctctggcgg aggcggcagc gaggtgaagc tgcaggagtc tggcccaggc | 480 |
| ctggtggccc caagccagag cctgagcgtg acctgcaccg tgagcggcgt gagcctgccc | 540 |
| gactacggcg tgagctggat caggcagccc cacggaaagg gcctgagtg gctgggcgtg | 600 |
| atctggggca gcgagaccac ctactacaac agcgccctga agagccggct gaccatcatc | 660 |
| aaggacaaca gcaagagcca ggtgttcctg aagatgaaca gcctgcagac cgacgacacc | 720 |
| gccatctact actgcgccaa gcactactac tatggcggca gctacgctat ggactactgg | 780 |
| ggccagggca ccagcgtgac cgtgagctca gatcccacca cgacgccagc gccgcgacca | 840 |
| ccaacaccgg cgcccaccat cgcgtcgcag ccctgtccc tgcgcccaga ggcgtgccgg | 900 |
| ccagcggcgg ggggcgcagt gcacacgagg gggctggact tcgcctgtga tatcttttgg | 960 |
| gtgctggtgg tggttggtgg agtcctggct tgctatagct tgctagtaac agtggccttt | 1020 |
| attattttct gggtgaggag agtgaagttc agcaggagcg cagacgcccc cgcgtaccag | 1080 |
| cagggccaga accagctcta taacgagctc aatctaggac gaagagagga gtacgatgtt | 1140 |

-continued

```
ttggacaaga gacgtggccg ggaccctgag atggggggaa agccgagaag gaagaaccct    1200
caggaaggcc tgtacaatga actgcagaaa gataagatgg cggaggccta cagtgagatt    1260
gggatgaaag gcgagcgccg gaggggcaag gggcacgatg gcctttacca gggtctcagt    1320
acagccacca aggacaccta cgacgccctt cacatgcagg ccctgcctcc tcgcagagcc    1380
gagggcaggg gaagtcttct aacatgcggg gacgtggagg aaaatcccgg gcccatggcc    1440
gtgcccactc aggtcctggg gttgttgcta ctgtggctta cagatgccag atgtgacatc    1500
cagatgacac agtctccatc ttccctgtct gcatctgtcg gagatcgcgt caccatcacc    1560
tgtcgagcaa gtgaggacat ttattttaat ttagtgtggt atcagcagaa accaggaaag    1620
gcccctaagc tcctgatcta tgatacaaat cgcttggcag atggggtccc atcacggttc    1680
agtggctctg gatctggcac acagtatact ctaaccataa gtagcctgca acccgaagat    1740
ttcgcaacct attattgtca acactataag aattatccgc tcacgttcgg tcaggggacc    1800
aagctggaaa tcaaaagatc tggtggcgga gggtcaggag gcggaggcag cggaggcggt    1860
ggctcgggag gcggaggctc gagatctgag gtgcagttgg tggagtctgg gggcggcttg    1920
gtgcagcctg gagggtccct gaggctctcc tgtgcagcct caggattcac tctcagtaat    1980
tatggcatgc actggatcag gcaggctcca gggaagggtc tggagtgggt ctcgtctatt    2040
agtcttaatg gtggtagcac ttactatcga gactccgtga agggccgatt cactatctcc    2100
agggacaatg caaaaagcac cctctacctt caaatgaata gtctgagggc cgaggacacg    2160
gccgtctatt actgtgcagc acaggacgct tatacgggag gttactttga ttactggggc    2220
caaggaacgc tggtcacagt ctcgtctatg gatcccgcca ccacaaccaa gcccgtgctg    2280
cggaccccaa gccctgtgca ccctaccggc accagccagc ctcagagacc cgaggactgc    2340
cggcctcggg gcagcgtgaa gggcaccggc ctggacttcg cctgcgacat tctcatcggg    2400
gtctcagtgg tcttcctctt ctgtctcctc ctcctggtcc tcttctgcct ccatcgccag    2460
aatcagataa agcaggggcc ccccagaagc aaggacgagg agcagaagcc acagcagagg    2520
cctgacctgg ctgttgatgt tctagagagg acagcagaca aggccacagt caatggactt    2580
cctgagaagg accgggagac cgacaccagc gccctggctg cagggagttc ccaggaggtg    2640
acgtatgctc agctggacca ctgggccctc acacagagga cagcccgggc tgtgtcccca    2700
cagtccacaa agcccatggc cgagtccatc acgtatgcag ccgttgccag acactga       2757
```

<210> SEQ ID NO 40
<211> LENGTH: 4092
<212> TYPE: DNA
<213> ORGANISM: Artificial Sequence
<220> FEATURE:
<223> OTHER INFORMATION: Nucleic acid sequences coding for CARs
       (MP16092.SFG.aCD19fmc63-CD8STK-CD28tmZ-2A-aCD33glx-muCD8STK-
       LAIR1tm-endo-2A-PTPN6_SH2-dCD148)

<400> SEQUENCE: 40

```
atgagcctgc ccgtgaccgc cctgctgctg cccctggccc tgctgctgca cgccgccaga    60
ccagacatcc agatgaccca gaccaccagc agcctgagcg ccagcctggg cgaccgggtg    120
accatcagct gcagagccag ccaggacatc agcaagtacc tgaactggta ccagcagaag    180
cccgacggca ccgtgaagct gctgatctac cacaccagcc ggctgcacag cggcgtgccc    240
agccggttca gcggcagcgg cagcggcacc gactacagcc tgaccatcag caacctggag    300
caggaggaca tcgccaccta cttctgccag cagggcaaca ccctgcccta caccttcgga    360
```

| | |
|---|---|
| ggcggcacca agctggagat caccaaggcc ggaggcggag gctctggcgg aggcggctct | 420 |
| ggcggaggcg gctctggcgg aggcggcagc gaggtgaagc tgcaggagtc tggcccaggc | 480 |
| ctggtggccc caagccagag cctgagcgtg acctgcaccg tgagcggcgt gagcctgccc | 540 |
| gactacggcg tgagctggat caggcagccc ccacggaagg gcctgagtg gctgggcgtg | 600 |
| atctggggca gcgagaccac ctactacaac agcgccctga gagccggct gaccatcatc | 660 |
| aaggacaaca gcaagagcca ggtgttcctg aagatgaaca gcctgcagac cgacgacacc | 720 |
| gccatctact actgcgccaa gcactactac tatggcggca gctacgctat ggactactgg | 780 |
| ggccagggca ccagcgtgac cgtgagctca gatcccacca cgacgccagc gccgcgacca | 840 |
| ccaacaccgg cgcccaccat cgcgtcgcag ccctgtccc tgcgcccaga ggcgtgccgg | 900 |
| ccagcggcgg ggggcgcagt gcacacgagg gggctggact tcgcctgtga tatcttttgg | 960 |
| gtgctggtgg tggttggtgg agtcctggct tgctatagct tgctagtaac agtggccttt | 1020 |
| attattttct gggtgaggag agtgaagttc agcaggagcg cagacgcccc cgcgtaccag | 1080 |
| cagggccaga accagctcta taacgagctc aatctaggac gaagagagga gtacgatgtt | 1140 |
| ttggacaaga cgtggccg ggaccctgag atggggggaa agccgagaag gaagaaccct | 1200 |
| caggaaggcc tgtacaatga actgcagaaa gataagatgg cggaggccta cagtgagatt | 1260 |
| gggatgaaag cgagcgccg gaggggcaag gggcacgatg gcctttacca gggtctcagt | 1320 |
| acagccacca aggacaccta cgacgccctt cacatgcagg ccctgcctcc tcgcagagcc | 1380 |
| gagggcaggg gaagtcttct aacatgcggg gacgtggagg aaaatcccgg gcccatggcc | 1440 |
| gtgcccactc aggtcctggg gttgttgcta ctgtggctta cagatgccag atgtgacatc | 1500 |
| cagatgacac agtctccatc ttccctgtct gcatctgtcg gagatcgcgt caccatcacc | 1560 |
| tgtcgagcaa gtgaggacat ttatttaat ttagtgtggt atcagcagaa accaggaaag | 1620 |
| gcccctaagc tcctgatcta tgatacaaat cgcttggcag atggggtccc atcacggttc | 1680 |
| agtggctctg gatctggcac acagtatact ctaaccataa gtagcctgca acccgaagat | 1740 |
| ttcgcaacct attattgtca acactataag aattatccgc tcacgttcgg tcaggggacc | 1800 |
| aagctggaaa tcaaaagatc tggtggcgga gggtcaggag gcggaggcag cggaggcggt | 1860 |
| ggctcgggag gcggaggctc gagatctgag gtgcagttgg tggagtctgg gggcggcttg | 1920 |
| gtgcagcctg gagggtccct gaggctctcc tgtgcagcct caggattcac tctcagtaat | 1980 |
| tatggcatgc actggatcag gcaggctcca gggaagggtc tggagtgggt ctcgtctatt | 2040 |
| agtcttaatg gtggtagcac ttactatcga gactccgtga agggccgatt cactatctcc | 2100 |
| agggacaatg caaaaagcac cctctacctt caaatgaata gtctgagggc cgaggacacg | 2160 |
| gccgtctatt actgtgcagc acaggacgct tatacgggag gttactttga ttactggggc | 2220 |
| caaggaacgc tggtcacagt ctcgtctatg gatcccgcca ccacaaccaa gcccgtgctg | 2280 |
| cggaccccaa gccctgtgca ccctaccggc accagccagc tcagagacc cgaggactgc | 2340 |
| cggcctcggg gcagcgtgaa gggcaccggc ctggacttcg cctgcgacat tctcatcggg | 2400 |
| gtctcagtgg tcttcctctt ctgtctcctc ctcctggtcc tcttctgcct ccatcgccag | 2460 |
| aatcagataa agcaggggcc ccccagaagc aaggacgagg agcagaagcc acagcagagg | 2520 |
| cctgacctgg ctgttgatgt tctagagagg acagcagaca aggccacagt caatggactt | 2580 |
| cctgagaagg accgggagac cgacaccagc gccctggctg cagggagttc ccaggaggtg | 2640 |
| acgtatgctc agctggacca ctgggccctc acacagagga cagcccgggc tgtgtcccca | 2700 |
| cagtccacaa agcccatggc cgagtccatc acgtatgcag ccgttgccag acacagggca | 2760 |

```
gaaggaagag gtagcctgct gacttgcggg gacgtggaag agaacccagg gccatggtat      2820
catggccaca tgtctggcgg gcaggcagag acgctgctgc aggccaaggg cgagccctgg      2880
acgtttcttg tgcgtgagag cctcagccag cctggagact tcgtgctttc tgtgctcagt      2940
gaccagccca aggctggccc aggctccccg ctcagggtca cccacatcaa ggtcatgtgc      3000
gagggtggac gctacacagt gggtggtttg agaccttcg  acagcctcac ggacctggtg      3060
gagcatttca agaagacggg gattgaggag gcctcaggcg cctttgtcta cctgcggcag      3120
ccgtacagcg gtggcggtgg cagctttgag gcctacttca agaagcagca agctgactcc      3180
aactgtgggt tcgcagagga atacgaagat ctgaagcttg ttggaattag tcaacctaaa      3240
tatgcagcag aactggctga gatagagga  aagaatcgct ataataatgt tctgccctat      3300
gatatttccc gtgtcaaact ttcggtccag acccattcaa cggatgacta catcaatgcc      3360
aactacatgc ctggctacca ctccaagaaa gattttattg ccacacaagg acctttaccg      3420
aacactttga agattttttg gcgtatggtt tgggagaaaa atgtatatgc catcattatg      3480
ttgactaaat gtgttgaaca gggaagaacc aaatgtgagg agtattggcc ctccaagcag      3540
gctcaggact atgagacat  aactgtggca atgacatcag aaattgttct tccggaatgg      3600
accatcagag atttcacagt gaaaaatatc cagacaagtg agagtcaccc tctgagacag      3660
ttccatttca cctcctggcc agaccacggt gttcccgaca ccactgacct gctcatcaac      3720
ttccggtacc tcgttcgtga ctacatgaag cagagtcctc ccgaatcgcc gattctggtg      3780
cattgcagtg ctggggtcgg aaggacgggc actttcattg ccattgatcg tctcatctac      3840
cagatagaga atgagaacac cgtggatgtg tatgggattg tgtatgacct tcgaatgcat      3900
aggcctttaa tggtgcagac agaggaccag tatgttttcc tcaatcagtg tgttttggat      3960
attgtcagat cccagaaaga ctcaaaagta gatcttatct accagaacac aactgcaatg      4020
acaatctatg aaaaccttgc gcccgtgacc acatttggaa agaccaatgg ttacatcgcc      4080
agcggtagct aa                                                         4092
```

<210> SEQ ID NO 41
<211> LENGTH: 1341
<212> TYPE: PRT
<213> ORGANISM: Artificial Sequence
<220> FEATURE:
<223> OTHER INFORMATION: Single-chain variable fragment (scFv)
      SFG.aCD19-CD8STK-CD28tmZ-2A-aGD2-HCH2CH3pvaa-dCD148

<400> SEQUENCE: 41

```
Met Ser Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110
```

-continued

```
Asn Thr Leu Pro Tyr Thr Phe Gly Gly Gly Thr Lys Leu Glu Ile Thr
            115                 120                 125

Lys Ala Gly Gly Gly Gly Ser Gly Gly Gly Gly Ser Gly Gly Gly Gly
130                 135                 140

Ser Gly Gly Gly Gly Ser Glu Val Lys Leu Gln Glu Ser Gly Pro Gly
145                 150                 155                 160

Leu Val Ala Pro Ser Gln Ser Leu Ser Val Thr Cys Thr Val Ser Gly
                165                 170                 175

Val Ser Leu Pro Asp Tyr Gly Val Ser Trp Ile Arg Gln Pro Pro Arg
            180                 185                 190

Lys Gly Leu Glu Trp Leu Gly Val Ile Trp Gly Ser Glu Thr Thr Tyr
        195                 200                 205

Tyr Asn Ser Ala Leu Lys Ser Arg Leu Thr Ile Ile Lys Asp Asn Ser
    210                 215                 220

Lys Ser Gln Val Phe Leu Lys Met Asn Ser Leu Gln Thr Asp Asp Thr
225                 230                 235                 240

Ala Ile Tyr Tyr Cys Ala Lys His Tyr Tyr Gly Gly Ser Tyr Ala
                245                 250                 255

Met Asp Tyr Trp Gly Gln Gly Thr Ser Val Thr Val Ser Ser Asp Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Phe Trp
305                 310                 315                 320

Val Leu Val Val Val Gly Gly Val Leu Ala Cys Tyr Ser Leu Leu Val
                325                 330                 335

Thr Val Ala Phe Ile Ile Phe Trp Val Arg Arg Val Lys Phe Ser Arg
            340                 345                 350

Ser Ala Asp Ala Pro Ala Tyr Gln Gln Gly Gln Asn Gln Leu Tyr Asn
        355                 360                 365

Glu Leu Asn Leu Gly Arg Arg Glu Glu Tyr Asp Val Leu Asp Lys Arg
    370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
        435                 440                 445

Ala Leu His Met Gln Ala Leu Pro Pro Arg Arg Ala Glu Gly Arg Gly
    450                 455                 460

Ser Leu Leu Thr Cys Gly Asp Val Glu Glu Asn Pro Gly Pro Met Glu
465                 470                 475                 480

Thr Asp Thr Leu Leu Leu Trp Val Leu Leu Leu Trp Val Pro Gly Ser
                485                 490                 495

Thr Gly Gln Val Gln Leu Gln Glu Ser Gly Pro Gly Leu Val Lys Pro
            500                 505                 510

Ser Gln Thr Leu Ser Ile Thr Cys Thr Val Ser Gly Phe Ser Leu Ala
        515                 520                 525

Ser Tyr Asn Ile His Trp Val Arg Gln Pro Pro Gly Lys Gly Leu Glu
```

```
                530             535             540
Trp Leu Gly Val Ile Trp Ala Gly Gly Ser Thr Asn Tyr Asn Ser Ala
545                 550             555                 560

Leu Met Ser Arg Leu Thr Ile Ser Lys Asp Asn Ser Lys Asn Gln Val
                565             570             575

Phe Leu Lys Met Ser Ser Leu Thr Ala Ala Asp Thr Ala Val Tyr Tyr
            580             585             590

Cys Ala Lys Arg Ser Asp Asp Tyr Ser Trp Phe Ala Tyr Trp Gly Gln
                595             600             605

Gly Thr Leu Val Thr Val Ser Ser Gly Gly Gly Gly Ser Gly Gly Gly
            610             615             620

Gly Ser Gly Gly Gly Gly Ser Glu Asn Gln Met Thr Gln Ser Pro Ser
625             630             635             640

Ser Leu Ser Ala Ser Val Gly Asp Arg Val Thr Met Thr Cys Arg Ala
                645             650             655

Ser Ser Ser Val Ser Ser Ser Tyr Leu His Trp Tyr Gln Gln Lys Ser
                660             665             670

Gly Lys Ala Pro Lys Val Trp Ile Tyr Ser Thr Ser Asn Leu Ala Ser
            675             680             685

Gly Val Pro Ser Arg Phe Ser Gly Ser Gly Ser Gly Thr Asp Tyr Thr
            690             695             700

Leu Thr Ile Ser Ser Leu Gln Pro Glu Asp Phe Ala Thr Tyr Tyr Cys
705             710             715             720

Gln Gln Tyr Ser Gly Tyr Pro Ile Thr Phe Gly Gln Gly Thr Lys Val
                725             730             735

Glu Ile Lys Arg Ser Asp Pro Ala Glu Pro Lys Ser Pro Asp Lys Thr
            740             745             750

His Thr Cys Pro Pro Cys Pro Ala Pro Val Ala Gly Pro Ser Val
            755             760             765

Phe Leu Phe Pro Pro Lys Pro Lys Asp Thr Leu Met Ile Ala Arg Thr
770             775             780

Pro Glu Val Thr Cys Val Val Asp Val Ser His Glu Asp Pro Glu
785             790             795             800

Val Lys Phe Asn Trp Tyr Val Asp Gly Val Glu Val His Asn Ala Lys
                805             810             815

Thr Lys Pro Arg Glu Glu Gln Tyr Asn Ser Thr Tyr Arg Val Val Ser
            820             825             830

Val Leu Thr Val Leu His Gln Asp Trp Leu Asn Gly Lys Glu Tyr Lys
            835             840             845

Cys Lys Val Ser Asn Lys Ala Leu Pro Ala Pro Ile Glu Lys Thr Ile
850             855             860

Ser Lys Ala Lys Gly Gln Pro Arg Glu Pro Gln Val Tyr Thr Leu Pro
865             870             875             880

Pro Ser Arg Asp Glu Leu Thr Lys Asn Gln Val Ser Leu Thr Cys Leu
                885             890             895

Val Lys Gly Phe Tyr Pro Ser Asp Ile Ala Val Glu Trp Glu Ser Asn
                900             905             910

Gly Gln Pro Glu Asn Asn Tyr Lys Thr Thr Pro Pro Val Leu Asp Ser
            915             920             925

Asp Gly Ser Phe Phe Leu Tyr Ser Lys Leu Thr Val Asp Lys Ser Arg
            930             935             940

Trp Gln Gln Gly Asn Val Phe Ser Cys Ser Val Met His Glu Ala Leu
945             950             955             960
```

```
His Asn His Tyr Thr Gln Lys Ser Leu Ser Leu Ser Pro Gly Lys Lys
            965                 970                 975

Asp Pro Lys Ala Val Phe Gly Cys Ile Phe Gly Ala Leu Val Ile Val
            980                 985                 990

Thr Val Gly Gly Phe Ile Phe Trp Arg Lys Lys Arg Lys Asp Ala Lys
            995                 1000                1005

Asn Asn Glu Val Ser Phe Ser Gln Ile Lys Pro Lys Lys Ser Lys
            1010                1015                1020

Leu Ile Arg Val Glu Asn Phe Glu Ala Tyr Phe Lys Lys Gln Gln
            1025                1030                1035

Ala Asp Ser Asn Cys Gly Phe Ala Glu Glu Tyr Glu Asp Leu Lys
            1040                1045                1050

Leu Val Gly Ile Ser Gln Pro Lys Tyr Ala Ala Glu Leu Ala Glu
            1055                1060                1065

Asn Arg Gly Lys Asn Arg Tyr Asn Asn Val Leu Pro Tyr Asp Ile
            1070                1075                1080

Ser Arg Val Lys Leu Ser Val Gln Thr His Ser Thr Asp Asp Tyr
            1085                1090                1095

Ile Asn Ala Asn Tyr Met Pro Gly Tyr His Ser Lys Lys Asp Phe
            1100                1105                1110

Ile Ala Thr Gln Gly Pro Leu Pro Asn Thr Leu Lys Asp Phe Trp
            1115                1120                1125

Arg Met Val Trp Glu Lys Asn Val Tyr Ala Ile Ile Met Leu Thr
            1130                1135                1140

Lys Cys Val Glu Gln Gly Arg Thr Lys Cys Glu Glu Tyr Trp Pro
            1145                1150                1155

Ser Lys Gln Ala Gln Asp Tyr Gly Asp Ile Thr Val Ala Met Thr
            1160                1165                1170

Ser Glu Ile Val Leu Pro Glu Trp Thr Ile Arg Asp Phe Thr Val
            1175                1180                1185

Lys Asn Ile Gln Thr Ser Glu Ser His Pro Leu Arg Gln Phe His
            1190                1195                1200

Phe Thr Ser Trp Pro Asp His Gly Val Pro Asp Thr Thr Asp Leu
            1205                1210                1215

Leu Ile Asn Phe Arg Tyr Leu Val Arg Asp Tyr Met Lys Gln Ser
            1220                1225                1230

Pro Pro Glu Ser Pro Ile Leu Val His Cys Ser Ala Gly Val Gly
            1235                1240                1245

Arg Thr Gly Thr Phe Ile Ala Ile Asp Arg Leu Ile Tyr Gln Ile
            1250                1255                1260

Glu Asn Glu Asn Thr Val Asp Val Tyr Gly Ile Val Tyr Asp Leu
            1265                1270                1275

Arg Met His Arg Pro Leu Met Val Gln Thr Glu Asp Gln Tyr Val
            1280                1285                1290

Phe Leu Asn Gln Cys Val Leu Asp Ile Val Arg Ser Gln Lys Asp
            1295                1300                1305

Ser Lys Val Asp Leu Ile Tyr Gln Asn Thr Thr Ala Met Thr Ile
            1310                1315                1320

Tyr Glu Asn Leu Ala Pro Val Thr Thr Phe Gly Lys Thr Asn Gly
            1325                1330                1335

Tyr Ile Ala
            1340
```

<210> SEQ ID NO 42
<211> LENGTH: 4026
<212> TYPE: DNA
<213> ORGANISM: Artificial Sequence
<220> FEATURE:
<223> OTHER INFORMATION: Single-chain variable fragment (scFv)
SFG.aCD19-CD8STK-CD28tmZ-2A-aGD2-HCH2CH3pvaa-dCD148

<400> SEQUENCE: 42

| | |
|---|---:|
| atgagcctgc cgtgaccgc cctgctgctg ccctggccc tgctgctgca cgccgccaga | 60 |
| ccagacatcc agatgaccca gaccaccagc agcctgagcg ccagcctggg cgaccgggtg | 120 |
| accatcagct gcagagccag ccaggacatc agcaagtacc tgaactggta ccagcagaag | 180 |
| cccgacggca ccgtgaagct gctgatctac cacaccagcc ggctgcacag cggcgtgccc | 240 |
| agccggttca gcggcagcgg cagcggcacc gactacagcc tgaccatcag caacctggag | 300 |
| caggaggaca tcgccaccta cttctgccag cagggcaaca ccctgcccta caccttcgga | 360 |
| ggcggcacca gctggagat caccaaggcc ggaggcggag ctctggcgg aggcggctct | 420 |
| ggcggaggcg gctctggcgg aggcggcagc gaggtgaagc tgcaggagtc tggcccaggc | 480 |
| ctggtggccc caagccagag cctgagcgtg acctgcaccg tgagcggcgt gagcctgccc | 540 |
| gactacggcg tgagctggat caggcagccc ccacggaagg cctggagtg ctgggcgtg | 600 |
| atctggggca gcgagaccac ctactacaac agcgccctga gagccggct gaccatcatc | 660 |
| aaggacaaca gcaagagcca ggtgttcctg aagatgaaca gcctgcagac cgacgacacc | 720 |
| gccatctact actgcgccaa gcactactac tatggcggca gctacgctat ggactactgg | 780 |
| ggccagggca ccagcgtgac cgtgagctca gatcccacca cgacgccagc cgcgaccca | 840 |
| ccaacaccgg cgcccaccat cgcgtcgcag cccctgtccc tgcgcccaga ggcgtgccgg | 900 |
| ccagcggcgg ggggcgcagt gcacgaggg gggctggact tcgcctgtga tatcttttgg | 960 |
| gtgctggtgg tggttggtgg agtcctggct tgctatagct tgctagtaac agtggccttt | 1020 |
| attatttct gggtgaggag agtgaagttc agcaggagcg cagacgcccc cgcgtaccag | 1080 |
| cagggccaga accagctcta taacgagctc aatctaggac gaagaggag gtacgatgtt | 1140 |
| ttggacaaga cgtggccg ggaccctgag atgggggaa agccgagaag gaagaaccct | 1200 |
| caggaaggcc tgtacaatga actgcagaaa gataagatgg cggaggccta cagtgagatt | 1260 |
| gggatgaaag cgagcgccg gaggggcaag ggcacgatg cctttacca gggtctcagt | 1320 |
| acagccacca aggacaccta cgacgccctt cacatgcagg ccctgcctcc tcgcagagcc | 1380 |
| gagggcaggg gaagtcttct aacatgcggg gacgtggagg aaaatccgg gcccatggag | 1440 |
| accgacaccc tgctgctgtg ggtgctgctg ctgtgggtgc aggcagcac cggccaggtg | 1500 |
| cagctgcagg agtctggccc aggcctggtg aagcccagcc agaccctgag catcacctgc | 1560 |
| accgtgagcg gcttcagcct ggccagctac aacatccact gggtgcggca ccccagggc | 1620 |
| aagggcctgg agtggctggg cgtgatctgg ctggcggca gcaccaacta acagcgcc | 1680 |
| ctgatgagcc ggctgaccat cagcaaggac aacagcaaga accaggtgtt cctgaagatg | 1740 |
| agcagcctga gccgccga caccgccgtg tactactgcg ccaagcggag cgacgactac | 1800 |
| agctggttcg cctactgggg ccagggcacc ctggtgacct gagctctgg cggaggcggc | 1860 |
| tctggcggag cggctctgg cggaggcggc agcgagaacc agatgaccca gagccccagc | 1920 |
| agcttgagcg ccagcgtggg cgaccgggtg accatgacct gcagagccag cagcagcgtg | 1980 |
| agcagcagct acctgcactg gtaccagcag aagagcggca aggcccccaa ggtgtggatc | 2040 |

```
tacagcacca gcaacctggc cagcggcgtg cccagccggt tcagcggcag cggcagcggc   2100
accgactaca ccctgaccat cagcagcctg cagcccgagg acttcgccac ctactactgc   2160
cagcagtaca gcggctaccc catcaccttc ggccagggca ccaaggtgga gatcaagcgg   2220
tcggatcccg ccgagcccaa atctcctgac aaaactcaca catgcccacc gtgcccagca   2280
cctcccgtgg ccggcccgtc agtcttcctc ttccccccaa acccaaggac accctcatg   2340 atcgcccgga cccctgaggt cacatgcgtg gtggtggacg tgagccacga agaccctgag   2400
gtcaagttca actggtacgt ggacggcgtg gaggtgcata atgccaagac aaagccgcgg   2460
gaggagcagt acaacagcac gtaccgtgtg gtcagcgtcc tcaccgtcct gcaccaggac   2520
tggctgaatg gcaaggagta caagtgcaag gtctccaaca aagccctccc agcccccatc   2580
gagaaaacca tctccaaagc caaagggcag ccccgagaac cacaggtgta caccctgccc   2640
ccatcccggg atgagctgac caagaaccag gtcagcctga cctgcctggt caaaggcttc   2700
tatcccagcg acatcgccgt ggagtgggag agcaatgggc aaccggagaa caactacaag   2760
accacgcctc ccgtgctgga ctccgacggc tccttcttcc tctacagcaa gctcaccgtg   2820
gacaagagca ggtggcagca ggggaacgtc ttctcatgct ccgtgatgca tgaggccctg   2880
cacaatcact atacccagaa atctctgagt ctgagcccag gcaagaagga ccccaaggcg   2940 gttttggct gtatctttgg tgccctggtt attgtgactg tgggaggctt catcttctgg   3000
agaaagaaga ggaaagatgc aaagaataat gaagtgtcct tttctcaaat taaacctaaa   3060
aaatctaagt taatcagagt ggagaatttt gaggcctact tcaagaagca gcaagctgac   3120
tccaactgtg ggttcgcaga ggaatacgaa gatctgaagc ttgttggaat tagtcaacct   3180
aaatatgcag cagaactggc tgagaataga ggaaagaatc gctataataa tgttctgccc   3240
tatgatattt cccgtgtcaa actttcggtc cagacccatt caacgatgag ctacatcaat   3300
gccaactaca tgcctggcta ccactccaag aaagatttta ttgccacaca aggacctta   3360 ccgaacactt tgaaagattt ttggcgtatg gtttgggaga aaaatgtata tgccatcatt   3420
atgttgacta atgtgttga acagggaaga accaaatgtg aggagtattg gcctccaag   3480 caggctcagg actatggaga cataactgtg gcaatgacat cagaaattgt tcttccggaa   3540
tggaccatca gagatttcac agtgaaaaat atccagacaa gtgagagtca ccctctgaga   3600
cagttccatt tcacctcctg gccagaccac ggtgttcccg acaccactga cctgctcatc   3660
aacttccggt acctcgttcg tgactacatg aagcagagtc ctccgaatc gccgattctg   3720 gtgcattgca gtgctggggt cggaaggacg ggcacttca ttgccattga tcgtctcatc   3780
taccagatag agaatgagaa caccgtggat gtgtatggga ttgtgtatga ccttcgaatg   3840
cataggcctt taatggtgca gacagaggac cagtatgttt tcctcaatca gtgtgttttg   3900
gatattgtca gatcccagaa agactcaaaa gtagatctta tctaccagaa cacaactgca   3960
atgacaatct atgaaaacct tgcgcccgtg accacatttg aaagaccaa tggttacatc   4020 gcctaa                                                              4026
```

<210> SEQ ID NO 43
<211> LENGTH: 1341
<212> TYPE: PRT
<213> ORGANISM: Artificial Sequence
<220> FEATURE:
<223> OTHER INFORMATION: Single-chain variable fragment (scFv)
      SFG.aCD19-CD8STK-CD28tmZ-2A-aCD5-HCH2CH3pvaa-dCD148

<400> SEQUENCE: 43

```
Met Ser Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
        50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Lys Ala Gly Gly Gly Gly Ser Gly Gly Gly Gly Ser Gly Gly Gly Gly
        130                 135                 140

Ser Gly Gly Gly Gly Ser Glu Val Lys Leu Gln Glu Ser Gly Pro Gly
145                 150                 155                 160

Leu Val Ala Pro Ser Gln Ser Leu Ser Val Thr Cys Thr Val Ser Gly
                165                 170                 175

Val Ser Leu Pro Asp Tyr Gly Val Ser Trp Ile Arg Gln Pro Pro Arg
            180                 185                 190

Lys Gly Leu Glu Trp Leu Gly Val Ile Trp Gly Ser Glu Thr Thr Tyr
        195                 200                 205

Tyr Asn Ser Ala Leu Lys Ser Arg Leu Thr Ile Ile Lys Asp Asn Ser
        210                 215                 220

Lys Ser Gln Val Phe Leu Lys Met Asn Ser Leu Gln Thr Asp Asp Thr
225                 230                 235                 240

Ala Ile Tyr Tyr Cys Ala Lys His Tyr Tyr Gly Gly Ser Tyr Ala
                245                 250                 255

Met Asp Tyr Trp Gly Gln Gly Thr Ser Val Thr Val Ser Ser Asp Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
        290                 295                 300

Gly Ala Val His Thr Arg Gly Leu Asp Phe Ala Cys Asp Ile Phe Trp
305                 310                 315                 320

Val Leu Val Val Val Gly Gly Val Leu Ala Cys Tyr Ser Leu Leu Val
                325                 330                 335

Thr Val Ala Phe Ile Ile Phe Trp Val Arg Arg Val Lys Phe Ser Arg
            340                 345                 350

Ser Ala Asp Ala Pro Ala Tyr Gln Gln Gly Gln Asn Gln Leu Tyr Asn
        355                 360                 365

Glu Leu Asn Leu Gly Arg Arg Glu Tyr Asp Val Leu Asp Lys Arg
        370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
```

-continued

```
                420             425             430
Asp Gly Leu Tyr Gln Gly Leu Ser Thr Ala Thr Lys Asp Thr Tyr Asp
            435                 440                 445
Ala Leu His Met Gln Ala Leu Pro Pro Arg Ala Glu Gly Arg Gly
            450                 455                 460
Ser Leu Leu Thr Cys Gly Asp Val Glu Glu Asn Pro Gly Pro Met Glu
465                 470                 475                 480
Thr Asp Thr Leu Leu Leu Trp Val Leu Leu Leu Trp Val Pro Gly Ser
                485                 490                 495
Thr Gly Gln Val Thr Leu Lys Glu Ser Gly Pro Gly Ile Leu Lys Pro
            500                 505                 510
Ser Gln Thr Leu Ser Leu Thr Cys Ser Phe Ser Gly Phe Ser Leu Ser
            515                 520                 525
Thr Ser Gly Met Gly Val Gly Trp Ile Arg Gln Pro Ser Gly Lys Gly
            530                 535                 540
Leu Glu Trp Leu Ala His Ile Trp Trp Asp Asp Val Tyr Tyr Asn
545                 550                 555                 560
Pro Ser Leu Lys Asn Gln Leu Thr Ile Ser Lys Asp Ala Ser Arg Asp
                565                 570                 575
Gln Val Phe Leu Lys Ile Thr Asn Leu Asp Thr Ala Asp Thr Ala Thr
            580                 585                 590
Tyr Tyr Cys Val Arg Arg Arg Ala Thr Gly Thr Gly Phe Asp Tyr Trp
            595                 600                 605
Gly Gln Gly Thr Thr Leu Thr Val Ser Ser Gly Gly Gly Ser Gly
            610                 615                 620
Gly Gly Gly Ser Gly Gly Gly Ser Asn Ile Val Met Thr Gln Ser
625                 630                 635                 640
His Lys Phe Met Ser Thr Ser Val Gly Asp Arg Val Ser Ile Ala Cys
                645                 650                 655
Lys Ala Ser Gln Asp Val Gly Thr Ala Val Ala Trp Tyr Gln Gln Lys
            660                 665                 670
Pro Gly Gln Ser Pro Lys Leu Leu Ile Tyr Trp Thr Ser Thr Arg His
            675                 680                 685
Thr Gly Val Pro Asp Arg Phe Thr Gly Ser Gly Ser Gly Thr Asp Phe
            690                 695                 700
Thr Leu Thr Ile Thr Asn Val Gln Ser Glu Asp Leu Ala Asp Tyr Phe
705                 710                 715                 720
Cys His Gln Tyr Asn Ser Tyr Asn Thr Phe Gly Ser Gly Thr Arg Leu
                725                 730                 735
Glu Leu Lys Arg Ser Asp Pro Ala Glu Pro Lys Ser Pro Asp Lys Thr
            740                 745                 750
His Thr Cys Pro Pro Cys Pro Ala Pro Pro Val Ala Gly Pro Ser Val
            755                 760                 765
Phe Leu Phe Pro Pro Lys Pro Lys Asp Thr Leu Met Ile Ala Arg Thr
            770                 775                 780
Pro Glu Val Thr Cys Val Val Asp Val Ser His Glu Asp Pro Glu
785                 790                 795                 800
Val Lys Phe Asn Trp Tyr Val Asp Gly Val Glu Val His Asn Ala Lys
                805                 810                 815
Thr Lys Pro Arg Glu Glu Gln Tyr Asn Ser Thr Tyr Arg Val Val Ser
            820                 825                 830
Val Leu Thr Val Leu His Gln Asp Trp Leu Asn Gly Lys Glu Tyr Lys
            835                 840                 845
```

```
Cys Lys Val Ser Asn Lys Ala Leu Pro Ala Pro Ile Glu Lys Thr Ile
    850                 855                 860

Ser Lys Ala Lys Gly Gln Pro Arg Glu Pro Gln Val Tyr Thr Leu Pro
    865                 870                 875                 880

Pro Ser Arg Asp Glu Leu Thr Lys Asn Gln Val Ser Leu Thr Cys Leu
                885                 890                 895

Val Lys Gly Phe Tyr Pro Ser Asp Ile Ala Val Glu Trp Glu Ser Asn
            900                 905                 910

Gly Gln Pro Glu Asn Asn Tyr Lys Thr Thr Pro Pro Val Leu Asp Ser
        915                 920                 925

Asp Gly Ser Phe Phe Leu Tyr Ser Lys Leu Thr Val Asp Lys Ser Arg
    930                 935                 940

Trp Gln Gln Gly Asn Val Phe Ser Cys Ser Val Met His Glu Ala Leu
945                 950                 955                 960

His Asn His Tyr Thr Gln Lys Ser Leu Ser Leu Ser Pro Gly Lys Lys
                965                 970                 975

Asp Pro Lys Ala Val Phe Gly Cys Ile Phe Gly Ala Leu Val Ile Val
            980                 985                 990

Thr Val Gly Gly Phe Ile Phe Trp Arg Lys Lys Arg Lys Asp Ala Lys
            995                 1000                1005

Asn Asn Glu Val Ser Phe Ser Gln Ile Lys Pro Lys Lys Ser Lys
    1010                1015                1020

Leu Ile Arg Val Glu Asn Phe Glu Ala Tyr Phe Lys Lys Gln Gln
    1025                1030                1035

Ala Asp Ser Asn Cys Gly Phe Ala Glu Glu Tyr Glu Asp Leu Lys
    1040                1045                1050

Leu Val Gly Ile Ser Gln Pro Lys Tyr Ala Ala Glu Leu Ala Glu
    1055                1060                1065

Asn Arg Gly Lys Asn Arg Tyr Asn Asn Val Leu Pro Tyr Asp Ile
    1070                1075                1080

Ser Arg Val Lys Leu Ser Val Gln Thr His Ser Thr Asp Asp Tyr
    1085                1090                1095

Ile Asn Ala Asn Tyr Met Pro Gly Tyr His Ser Lys Lys Asp Phe
    1100                1105                1110

Ile Ala Thr Gln Gly Pro Leu Pro Asn Thr Leu Lys Asp Phe Trp
    1115                1120                1125

Arg Met Val Trp Glu Lys Asn Val Tyr Ala Ile Ile Met Leu Thr
    1130                1135                1140

Lys Cys Val Glu Gln Gly Arg Thr Lys Cys Glu Glu Tyr Trp Pro
    1145                1150                1155

Ser Lys Gln Ala Gln Asp Tyr Gly Asp Ile Thr Val Ala Met Thr
    1160                1165                1170

Ser Glu Ile Val Leu Pro Glu Trp Thr Ile Arg Asp Phe Thr Val
    1175                1180                1185

Lys Asn Ile Gln Thr Ser Glu Ser His Pro Leu Arg Gln Phe His
    1190                1195                1200

Phe Thr Ser Trp Pro Asp His Gly Val Pro Asp Thr Thr Asp Leu
    1205                1210                1215

Leu Ile Asn Phe Arg Tyr Leu Val Arg Asp Tyr Met Lys Gln Ser
    1220                1225                1230

Pro Pro Glu Ser Pro Ile Leu Val His Cys Ser Ala Gly Val Gly
    1235                1240                1245
```

```
Arg Thr Gly Thr Phe Ile Ala Ile Asp Arg Leu Ile Tyr Gln Ile
         1250                1255                1260

Glu Asn Glu Asn Thr Val Asp Val Tyr Gly Ile Val Tyr Asp Leu
    1265                1270                1275

Arg Met His Arg Pro Leu Met Val Gln Thr Glu Asp Gln Tyr Val
    1280                1285                1290

Phe Leu Asn Gln Cys Val Leu Asp Ile Val Arg Ser Gln Lys Asp
    1295                1300                1305

Ser Lys Val Asp Leu Ile Tyr Gln Asn Thr Thr Ala Met Thr Ile
    1310                1315                1320

Tyr Glu Asn Leu Ala Pro Val Thr Thr Phe Gly Lys Thr Asn Gly
    1325                1330                1335

Tyr Ile Ala
    1340

<210> SEQ ID NO 44
<211> LENGTH: 4026
<212> TYPE: DNA
<213> ORGANISM: Artificial Sequence
<220> FEATURE:
<223> OTHER INFORMATION: Single-chain variable fragment (scFv)
      SFG.aCD19-CD8STK-CD28tmZ-2A-aCD5-HCH2CH3pvaa-dCD148

<400> SEQUENCE: 44
atgagcctgc cgtgaccgc cctgctgctg ccctggccc tgctgctgca cgccgccaga      60
ccagacatcc agatgaccca gaccaccagc agcctgagcg ccagcctggg cgaccgggtg     120
accatcagct gcagagccag ccaggacatc agcaagtacc tgaactgta ccagcagaag     180 cccgacggca ccgtgaagct gctgatctac cacaccagcc ggctgcacag cggcgtgccc     240
agccggttca gcggcagcgg cagcggcacc gactacagcc tgaccatcag caacctggag     300
caggaggaca tcgccaccta cttctgccag cagggcaaca ccctgcccta ccttcgga      360 ggcggcacca agctggagat caccaaggcc ggaggcggag gctctggcgg aggcggctct     420
ggcggaggcg gctctggcgg aggcggcagc gaggtgaagc tgcaggagtc tggcccaggc     480
ctggtggccc caagccagag cctgagcgtg acctgcaccg tgagcggcgt gagcctgccc     540
gactacggcg tgagctggat caggcagccc ccacggaagg gcctggagtg gctgggcgtg     600
atctggggca gcgagaccac ctactacaac agcgccctga gagccggct gaccatcatc     660 aaggacaaca gcaagagcca ggtgttcctg aagatgaaca gcctgcagac cgacgacacc     720
gccatctact actgcgccaa gcactactac tatggcggca gctacgctat ggactactgg     780
ggccagggca ccagcgtgac cgtgagctca gatcccacca cgacgccagc gccgcgacca     840
ccaacaccgg cgcccaccat cgcgtcgcag cccctgtccc tgcgcccaga ggcgtgccgg     900
ccagcggcgg ggggcgcagt gcacacgagg gggctggact tcgcctgtga tatcttttgg     960
gtgctggtgg tggttggtgg agtcctggct tgctatagct tgctagtaac agtggccttt    1020
attattttct gggtgaggag agtgaagttc agcaggagcg cagacgcccc cgcgtaccag    1080
cagggccaga accagctcta taacgagctc aatctaggac gaagagagga gtacgatgtt    1140
ttggacaaga gacgtggccg ggaccctgag atgggggaa agccgagaag gaagaaccct    1200
caggaaggcc tgtacaatga actgcagaaa gataagatgg cggaggccta cagtgagatt    1260
gggatgaaag gcgagcgccg gaggggcaag gggcacgatg gcctttacca gggtctcagt    1320
acagccacca ggacacccta cgacgccctt cacatgcagg ccctgcctcc tcgcagagcc    1380
gagggcaggg gaagtcttct aacatgcggg gacgtggagg aaaatcccgg gcccatggag    1440
```

```
accgacaccc tgctgctgtg ggtgctgctg ctgtgggtgc ccggcagcac cggccaggtg    1500
accctgaagg agagcggtcc cggcatcctg aagcccagcc agaccctgag cctgacctgc    1560
agcttcagcg gcttcagcct gagcaccagc ggcatgggcg tgggctggat tcggcagccc    1620
agcggcaagg gcctggagtg gctggcccac atctggtggg acgacgacgt gtactacaac    1680
cccagcctga gaaccagct gaccatcagc aaggacgcca gcgggacca ggtgttcctg      1740
aagatcacca acctggacac cgccgacacc gccacctact actgcgtgcg cgccgggcc     1800
accggcaccg gcttcgacta ctggggccag ggcaccaccc tgaccgtgag cagcggtggc    1860
ggtggcagcg gcggcggcgg aagcggaggt ggtggcagca acatcgtgat gacccagagc    1920
cacaagttca tgagcaccag cgtgggcgac cgggtgagca tcgcctgcaa ggccagccag    1980
gacgtgggca ccgccgtggc ctggtaccag cagaagcctg gccagagccc caagctgctg    2040
atctactgga ccagcacccg gcacaccggc gtgcccgacc ggttcaccgg cagcggcagc    2100
ggcaccgact cacccctgac catcaccaac gtgcagagcg aggacctggc cgactacttc    2160
tgccaccagt acaacagcta caacaccttc ggcagcggca cccggctgga gctgaagcgg    2220
tcggatcccg ccgagcccaa atctcctgac aaaactcaca catgcccacc gtgcccagca    2280
cctcccgtgg ccggccgtc agtcttcctc ttccccccaa acccaagga caccctcatg      2340
atcgcccgga cccctgaggt cacatgcgtg gtggtggacg tgagccacga agaccctgag    2400
gtcaagttca actggtacgt ggacggcgtg gaggtgcata atgccaagac aaagccgcgg    2460
gaggagcagt acaacagcac gtaccgtgtg gtcagcgtcc tcaccgtcct gcaccaggac    2520
tggctgaatg gcaaggagta caagtgcaag gtctccaaca agccctccc agcccccatc     2580
gagaaaacca tctccaaagc caaagggcag ccccgagaac cacaggtgta caccctgccc    2640
ccatcccggg atgagctgac caagaaccag gtcagcctga cctgcctggt caaaggcttc    2700
tatcccagcg acatcgccgt ggagtgggag agcaatgggc aaccggagaa caactacaag    2760
accacgcctc ccgtgctgga ctccgacggc tccttcttcc tctacagcaa gctcaccgtg    2820
gacaagagca ggtggcagca ggggaacgtc ttctcatgct ccgtgatgca tgaggccctg    2880
cacaatcact atacccagaa atctctgagt ctgagcccag gcaagaagga ccccaaggcg    2940
gttttttggct gtatctttgg tgccctggtt attgtgactg tgggaggctt catcttctgg    3000
agaaagaaga ggaaagatgc aaagaataat gaagtgtcct tttctcaaat taaacctaaa    3060
aaatctaagt taatcagagt ggagaatttt gaggcctact tcaagaagca gcaagctgac    3120
tccaactgtg ggtcgcaga ggaatacgaa gatctgaagc ttgttggaat tagtcaacct    3180
aaatatgcag cagaactggc tgagaataga ggaaagaatc gctataataa tgttctgccc    3240
tatgatattt cccgtgtcaa actttcggtc cagacccatt caacggatga ctacatcaat    3300
gccaactaca tgcctggcta ccactccaag aaagattta ttgccacaca aggaccttta    3360
ccgaacactt tgaaagattt ttggcgtatg gtttgggaga aaaatgtata tgccatcatt    3420
atgttgacta aatgtgttga acagggaaga accaaatgtg aggagtattg ccctccaag    3480
caggctcagg actatggaga cataactgtg gcaatgacat cagaaattgt tcttccggaa    3540
tggaccatca gagatttcac agtgaaaaat atccagacaa gtgagagtca ccctctgaga    3600
cagttccatt tcacctcctg gccagaccac ggtgttcccg acaccactga cctgctcatc    3660
aacttccggt acctcgttcg tgactacatg aagcagagtc ctccgaatc gccgattctg    3720
gtgcattgca gtgctggggt cggaaggacg ggcacttcca ttgccattga tcgtctcatc    3780
```

| | | |
|---|---|---|
| taccagatag agaatgagaa caccgtggat gtgtatggga ttgtgtatga ccttcgaatg | 3840 |
| cataggcctt taatggtgca gacagaggac cagtatgttt tcctcaatca gtgtgttttg | 3900 |
| gatattgtca gatcccagaa agactcaaaa gtagatctta tctaccagaa cacaactgca | 3960 |
| atgacaatct atgaaaacct tgcgcccgtg accacatttg gaaagaccaa tggttacatc | 4020 |
| gcctaa | 4026 |

<210> SEQ ID NO 45
<211> LENGTH: 1342
<212> TYPE: PRT
<213> ORGANISM: Artificial Sequence
<220> FEATURE:
<223> OTHER INFORMATION: Single-chain variable fragment (scFv)
    SFG.aCD19-CD8STK-CD28tmZ-2A-aEGFRvIII-HCH2CH3pvaa-dCD148

<400> SEQUENCE: 45

Met Ser Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Lys Ala Gly Gly Gly Gly Ser Gly Gly Gly Gly Ser Gly Gly Gly Gly
    130                 135                 140

Ser Gly Gly Gly Gly Ser Glu Val Lys Leu Gln Glu Ser Gly Pro Gly
145                 150                 155                 160

Leu Val Ala Pro Ser Gln Ser Leu Ser Val Thr Cys Thr Val Ser Gly
                165                 170                 175

Val Ser Leu Pro Asp Tyr Gly Val Ser Trp Ile Arg Gln Pro Pro Arg
            180                 185                 190

Lys Gly Leu Glu Trp Leu Gly Val Ile Trp Gly Ser Glu Thr Thr Tyr
        195                 200                 205

Tyr Asn Ser Ala Leu Lys Ser Arg Leu Thr Ile Ile Lys Asp Asn Ser
    210                 215                 220

Lys Ser Gln Val Phe Leu Lys Met Asn Ser Leu Gln Thr Asp Asp Thr
225                 230                 235                 240

Ala Ile Tyr Tyr Cys Ala Lys His Tyr Tyr Tyr Gly Gly Ser Tyr Ala
                245                 250                 255

Met Asp Tyr Trp Gly Gln Gly Thr Ser Val Thr Val Ser Ser Asp Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Phe Trp

```
            305                 310                 315                 320
        Val Leu Val Val Gly Gly Val Leu Ala Cys Tyr Ser Leu Leu Val
                        325                 330                 335

Thr Val Ala Phe Ile Ile Phe Trp Val Arg Arg Val Lys Phe Ser Arg
                        340                 345                 350

Ser Ala Asp Ala Pro Ala Tyr Gln Gln Gly Gln Asn Gln Leu Tyr Asn
                        355                 360                 365

Glu Leu Asn Leu Gly Arg Arg Glu Glu Tyr Asp Val Leu Asp Lys Arg
                370                 375                 380

Arg Gly Arg Asp Pro Glu Met Gly Gly Lys Pro Arg Arg Lys Asn Pro
        385                 390                 395                 400

Gln Glu Gly Leu Tyr Asn Glu Leu Gln Lys Asp Lys Met Ala Glu Ala
                        405                 410                 415

Tyr Ser Glu Ile Gly Met Lys Gly Glu Arg Arg Arg Gly Lys Gly His
                        420                 425                 430

Asp Gly Leu Tyr Gln Gly Leu Ser Thr Ala Thr Lys Asp Thr Tyr Asp
                        435                 440                 445

Ala Leu His Met Gln Ala Leu Pro Pro Arg Arg Ala Glu Gly Arg Gly
                450                 455                 460

Ser Leu Leu Thr Cys Gly Asp Val Glu Glu Asn Pro Gly Pro Met Glu
        465                 470                 475                 480

Thr Asp Thr Leu Leu Leu Trp Val Leu Leu Leu Trp Val Pro Gly Ser
                        485                 490                 495

Thr Gly Gln Val Lys Leu Gln Gln Ser Gly Gly Gly Leu Val Lys Pro
                        500                 505                 510

Gly Ala Ser Leu Lys Leu Ser Cys Val Thr Ser Gly Phe Thr Phe Arg
                        515                 520                 525

Lys Phe Gly Met Ser Trp Val Arg Gln Thr Ser Asp Lys Arg Leu Glu
                        530                 535                 540

Trp Val Ala Ser Ile Ser Thr Gly Gly Tyr Asn Thr Tyr Tyr Ser Asp
        545                 550                 555                 560

Asn Val Lys Gly Arg Phe Thr Ile Ser Arg Glu Asn Ala Lys Asn Thr
                        565                 570                 575

Leu Tyr Leu Gln Met Ser Ser Leu Lys Ser Glu Asp Thr Ala Leu Tyr
                        580                 585                 590

Tyr Cys Thr Arg Gly Tyr Ser Ser Thr Ser Tyr Ala Met Asp Tyr Trp
                        595                 600                 605

Gly Gln Gly Thr Thr Val Thr Val Ser Ser Gly Gly Gly Gly Ser Gly
                610                 615                 620

Gly Gly Gly Ser Gly Gly Gly Gly Ser Asp Ile Glu Leu Thr Gln Ser
        625                 630                 635                 640

Pro Ala Ser Leu Ser Val Ala Thr Gly Glu Lys Val Thr Ile Arg Cys
                        645                 650                 655

Met Thr Ser Thr Asp Ile Asp Asp Asp Met Asn Trp Tyr Gln Gln Lys
                        660                 665                 670

Pro Gly Glu Pro Pro Lys Phe Leu Ile Ser Glu Gly Asn Thr Leu Arg
                        675                 680                 685

Pro Gly Val Pro Ser Arg Phe Ser Ser Ser Gly Thr Gly Thr Asp Phe
                        690                 695                 700

Val Phe Thr Ile Glu Asn Thr Leu Ser Glu Asp Val Gly Asp Tyr Tyr
        705                 710                 715                 720

Cys Leu Gln Ser Phe Asn Val Pro Leu Thr Phe Gly Asp Gly Thr Lys
                        725                 730                 735
```

-continued

Leu Glu Ile Lys Arg Ser Asp Pro Ala Glu Pro Lys Ser Pro Asp Lys
                 740                 745                 750

Thr His Thr Cys Pro Pro Cys Pro Ala Pro Val Ala Gly Pro Ser
        755                 760                 765

Val Phe Leu Phe Pro Pro Lys Pro Lys Asp Thr Leu Met Ile Ala Arg
        770                 775                 780

Thr Pro Glu Val Thr Cys Val Val Asp Val Ser His Glu Asp Pro
785                 790                 795                 800

Glu Val Lys Phe Asn Trp Tyr Val Asp Gly Val Glu Val His Asn Ala
                805                 810                 815

Lys Thr Lys Pro Arg Glu Glu Gln Tyr Asn Ser Thr Tyr Arg Val Val
        820                 825                 830

Ser Val Leu Thr Val Leu His Gln Asp Trp Leu Asn Gly Lys Glu Tyr
        835                 840                 845

Lys Cys Lys Val Ser Asn Lys Ala Leu Pro Ala Pro Ile Glu Lys Thr
        850                 855                 860

Ile Ser Lys Ala Lys Gly Gln Pro Arg Glu Pro Gln Val Tyr Thr Leu
865                 870                 875                 880

Pro Pro Ser Arg Asp Glu Leu Thr Lys Asn Gln Val Ser Leu Thr Cys
                885                 890                 895

Leu Val Lys Gly Phe Tyr Pro Ser Asp Ile Ala Val Glu Trp Glu Ser
                900                 905                 910

Asn Gly Gln Pro Glu Asn Asn Tyr Lys Thr Thr Pro Pro Val Leu Asp
                915                 920                 925

Ser Asp Gly Ser Phe Phe Leu Tyr Ser Lys Leu Thr Val Asp Lys Ser
        930                 935                 940

Arg Trp Gln Gln Gly Asn Val Phe Ser Cys Ser Val Met His Glu Ala
945                 950                 955                 960

Leu His Asn His Tyr Thr Gln Lys Ser Leu Ser Leu Ser Pro Gly Lys
                965                 970                 975

Lys Asp Pro Lys Ala Val Phe Gly Cys Ile Phe Gly Ala Leu Val Ile
                980                 985                 990

Val Thr Val Gly Gly Phe Ile Phe  Trp Arg Lys Lys Arg  Lys Asp Ala
        995                 1000                 1005

Lys Asn  Asn Glu Val Ser Phe  Ser Gln Ile Lys Pro  Lys Lys Ser
        1010                 1015                 1020

Lys Leu  Ile Arg Val Glu Asn  Phe Glu Ala Tyr Phe  Lys Lys Gln
        1025                 1030                 1035

Gln Ala  Asp Ser Asn Cys Gly  Phe Ala Glu Glu Tyr  Glu Asp Leu
        1040                 1045                 1050

Lys Leu  Val Gly Ile Ser Gln  Pro Lys Tyr Ala Ala  Glu Leu Ala
        1055                 1060                 1065

Glu Asn  Arg Gly Lys Asn Arg  Tyr Asn Asn Val Leu  Pro Tyr Asp
        1070                 1075                 1080

Ile Ser  Arg Val Lys Leu Ser  Val Gln Thr His Ser  Thr Asp Asp
        1085                 1090                 1095

Tyr Ile  Asn Ala Asn Tyr Met  Pro Gly Tyr His Ser  Lys Lys Asp
        1100                 1105                 1110

Phe Ile  Ala Thr Gln Gly Pro  Leu Pro Asn Thr Leu  Lys Asp Phe
        1115                 1120                 1125

Trp Arg  Met Val Trp Glu Lys  Asn Val Tyr Ala Ile  Ile Met Leu
        1130                 1135                 1140

| Thr | Lys | Cys | Val | Glu | Gln | Gly | Arg | Thr | Lys | Cys | Glu | Glu | Tyr | Trp |
| | 1145 | | | | | 1150 | | | | | 1155 | | | |
| Pro | Ser | Lys | Gln | Ala | Gln | Asp | Tyr | Gly | Asp | Ile | Thr | Val | Ala | Met |
| 1160 | | | | | 1165 | | | | | 1170 | | | | |
| Thr | Ser | Glu | Ile | Val | Leu | Pro | Glu | Trp | Thr | Ile | Arg | Asp | Phe | Thr |
| 1175 | | | | | 1180 | | | | | 1185 | | | | |
| Val | Lys | Asn | Ile | Gln | Thr | Ser | Glu | Ser | His | Pro | Leu | Arg | Gln | Phe |
| 1190 | | | | | 1195 | | | | | 1200 | | | | |
| His | Phe | Thr | Ser | Trp | Pro | Asp | His | Gly | Val | Pro | Asp | Thr | Thr | Asp |
| 1205 | | | | | 1210 | | | | | 1215 | | | | |
| Leu | Leu | Ile | Asn | Phe | Arg | Tyr | Leu | Val | Arg | Asp | Tyr | Met | Lys | Gln |
| 1220 | | | | | 1225 | | | | | 1230 | | | | |
| Ser | Pro | Pro | Glu | Ser | Pro | Ile | Leu | Val | His | Cys | Ser | Ala | Gly | Val |
| 1235 | | | | | 1240 | | | | | 1245 | | | | |
| Gly | Arg | Thr | Gly | Thr | Phe | Ile | Ala | Ile | Asp | Arg | Leu | Ile | Tyr | Gln |
| 1250 | | | | | 1255 | | | | | 1260 | | | | |
| Ile | Glu | Asn | Glu | Asn | Thr | Val | Asp | Val | Tyr | Gly | Ile | Val | Tyr | Asp |
| 1265 | | | | | 1270 | | | | | 1275 | | | | |
| Leu | Arg | Met | His | Arg | Pro | Leu | Met | Val | Gln | Thr | Glu | Asp | Gln | Tyr |
| 1280 | | | | | 1285 | | | | | 1290 | | | | |
| Val | Phe | Leu | Asn | Gln | Cys | Val | Leu | Asp | Ile | Val | Arg | Ser | Gln | Lys |
| 1295 | | | | | 1300 | | | | | 1305 | | | | |
| Asp | Ser | Lys | Val | Asp | Leu | Ile | Tyr | Gln | Asn | Thr | Thr | Ala | Met | Thr |
| 1310 | | | | | 1315 | | | | | 1320 | | | | |
| Ile | Tyr | Glu | Asn | Leu | Ala | Pro | Val | Thr | Thr | Phe | Gly | Lys | Thr | Asn |
| 1325 | | | | | 1330 | | | | | 1335 | | | | |
| Gly | Tyr | Ile | Ala | | | | | | | | | | | |
| 1340 | | | | | | | | | | | | | | |

<210> SEQ ID NO 46
<211> LENGTH: 4029
<212> TYPE: DNA
<213> ORGANISM: Artificial Sequence
<220> FEATURE:
<223> OTHER INFORMATION: Single-chain variable fragment (scFv)
    SFG.aCD19-CD8STK-CD28tmZ-2A-aEGFRvIII-HCH2CH3pvaa-dCD148

<400> SEQUENCE: 46

```
atgagcctgc cgtgaccgc cctgctgctg cccctggccc tgctgctgca cgccgccaga     60
ccagacatcc agatgaccca gaccaccagc agcctgagcg ccagcctggg cgaccgggtg    120
accatcagct gcagagccag ccaggacatc agcaagtacc tgaactggta ccagcagaag    180
cccgacggca ccgtgaagct gctgatctac cacaccagcc ggctgcacag cggcgtgccc    240
agccggttca gcggcagcgg cagcggcacc gactacagcc tgaccatcag caacctggag    300
caggaggaca tcgccaccta cttctgccag cagggcaaca ccctgcccta caccttcgga    360
ggcggcacca agctggagat caccaaggcc ggaggcggag gctctggcgg aggcggctct    420
ggcggaggcg gctctggcgg aggcggcagc gaggtgaagc tgcaggagtc tggcccaggc    480
ctggtggccc caagccagag cctgagcgtg acctgcaccg tgagcggcgt gagcctgccc    540
gactacggcg tgagctggat caggcagccc cacggaaggg cctggagtg gctgggcgtg    600
atctggggca gcgagaccac ctactacaac agcgccctga gagccggct gaccatcatc    660
aaggacaaca gcaagagcca ggtgttcctg aagatgaaca gcctgcagac cgacgacacc    720
gccatctact actgcgccaa gcactactac atgggcggca gctacgctat ggactactgg    780
```

```
ggccagggca ccagcgtgac cgtgagctca gatcccacca cgacgccagc gccgcgacca    840
ccaacaccgg cgcccaccat cgcgtcgcag cccctgtccc tgcgcccaga ggcgtgccgg    900
ccagcggcgg ggggcgcagt gcacacgagg gggctggact tcgcctgtga tatcttttgg    960
gtgctggtgg tggttggtgg agtcctggct tgctatagct tgctagtaac agtggccttt   1020
attattttct gggtgaggag agtgaagttc agcaggagcg cagacgcccc cgcgtaccag   1080
cagggccaga accagctcta taacgagctc aatctaggac gaagagagga gtacgatgtt   1140
ttggacaaga gacgtggccg ggaccctgag atggggggaa agccgagaag gaagaaccct   1200
caggaaggcc tgtacaatga actgcagaaa gataagatgg cggaggccta cagtgagatt   1260
gggatgaaag gcgagcgccg gagggggcaag gggcacgatg gcctttacca gggtctcagt   1320
acagccacca aggacaccta cgacgccctt cacatgcagg ccctgcctcc tcgcagagcc   1380
gagggcaggg gaagtcttct aacatgcggg gacgtggagg aaaatcccgg gcccatggag   1440
accgacaccc tgctgctgtg ggtgctgctg ctgtgggtgc ccggcagcac cggccaggtg   1500
aagctgcagc agagcggcgg aggcctggtg aagcccggcg ccagcctgaa gctgagctgc   1560
gtgaccagcg gcttcacctt ccggaagttc ggcatgagct gggtgcggca gaccagcgac   1620
aagcggctgg agtgggtggc cagcatcagc accggcggct acaacaccta ctacagcgac   1680
aacgtgaagg gccggttcac catcagccgg gagaacgcca agaacaccct gtacctgcag   1740
atgagcagcc tgaagagcga ggacaccgcc ctgtactact gcacccgggg ctacagcagc   1800
accagctacg ctatggacta ctggggccag ggcaccaccg tgacagtgag cagcggcgga   1860
ggaggcagtg gtggggggtgg atctggcgga ggtggcagcg acatcgagct gacccagagc   1920
cccgccagcc tgagcgtggc caccggcgag aaggtgacca tccggtgcat gaccagcacc   1980
gacatcgacg acgacatgaa ctggtaccag cagaagcccg gcgagccccc aaagttcctg   2040
atcagcgagg gcaacaccct gcggcccggc gtgcccagcc ggttcagcag cagcggcacc   2100
ggcaccgact tcgtgttcac catcgagaac accctgagcg aggacgtggg cgactactac   2160
tgcctgcaga gcttcaacgt gcccctgacc ttcggcgacg gcaccaagct ggagatcaag   2220
cggtcggatc ccgccgagcc caaatctcct gacaaaactc acacatgccc accgtgccca   2280
gcacctcccg tggccggccc gtcagtcttc ctcttccccc caaaacccaa ggacaccctc   2340
atgatcgccc ggacccctga ggtcacatgc gtggtggtgg acgtgagcca cgaagaccct   2400
gaggtcaagt tcaactggta cgtggacggc gtggaggtgc ataatgccaa gacaaagccg   2460
cgggaggagc agtacaacag cacgtaccgt gtggtcagcg tcctcaccgt cctgcaccag   2520
gactggctga atggcaagga gtacaagtgc aaggtctcca acaaagccct cccagccccc   2580
atcgagaaaa ccatctccaa agccaaaggg cagccccgag aaccacaggt gtacaccctg   2640
cccccatccc gggatgagct gaccaagaac caggtcagcc tgacctgcct ggtcaaaggc   2700
ttctatccca gcgacatcgc cgtggagtgg gagagcaatg ggcaaccgga gaacaactac   2760
aagaccacgc ctcccgtgct ggactccgac ggctccttct tcctctacag caagctcacc   2820
gtggacaaga gcaggtggca gcaggggaac gtcttctcat gctccgtgat gcatgaggcc   2880
ctgcacaatc actatacccca gaaatctctg agtctgagcc caggcaagaa gaccccaag   2940 gcggttttg ctgtatctt tggtgccctg gttattgtga ctgtgggagg cttcatcttc   3000
tggagaaaga agaggaaaga tgcaaagaat aatgaagtgt cctttttctca aattaaacct   3060 aaaaaatcta agttaatcag agtggagaat tttgaggcct acttcaagaa gcagcaagct   3120
gactccaact gtgggttcgc agaggaatac gaagatctga agcttgttgg aattagtcaa   3180
```

```
cctaaatatg cagcagaact ggctgagaat agaggaaaga atcgctataa taatgttctg    3240
ccctatgata tttcccgtgt caaactttcg gtccagaccc attcaacgga tgactacatc    3300
aatgccaact acatgcctgg ctaccactcc aagaaagatt ttattgccac acaaggacct    3360
ttaccgaaca ctttgaaaga ttttttggcgt atggtttggg agaaaaatgt atatgccatc    3420
attatgttga ctaaatgtgt tgaacaggga agaaccaaat gtgaggagta ttggccctcc    3480
aagcaggctc aggactatgg agacataact gtggcaatga catcagaaat tgttcttccg    3540
gaatggacca tcagagattt cacagtgaaa aatatccaga caagtgagag tcaccctctg    3600
agacagttcc atttcacctc ctggccagac cacggtgttc ccgacaccac tgacctgctc    3660
atcaacttcc ggtacctcgt tcgtgactac atgaagcaga gtcctcccga atcgccgatt    3720
ctggtgcatt gcagtgctgg ggtcggaagg acgggcactt tcattgccat tgatcgtctc    3780
atctaccaga tagagaatga gaacaccgtg gatgtgtatg ggattgtgta tgaccttcga    3840
atgcataggc ctttaatggt gcagacagag gaccagtatg tttccctcaa tcagtgtgtt    3900
ttggatattg tcagatccca gaaagactca aaagtagatc ttatctacca gaacacaact    3960
gcaatgacaa tctatgaaaa ccttgcgccc gtgaccacat ttggaaagac caatggttac    4020
atcgcctaa                                                           4029
```

<210> SEQ ID NO 47
<211> LENGTH: 6
<212> TYPE: PRT
<213> ORGANISM: Artificial Sequence
<220> FEATURE:
<223> OTHER INFORMATION: Immunoreceptor tyrosine-based inhibition motif
      (ITIM)
<220> FEATURE:
<221> NAME/KEY: MISC_FEATURE
<222> LOCATION: (1)..(1)
<223> OTHER INFORMATION: Xaa may be Ser, Ile, Val or Leu
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa may be Ile, Val or Leu

<400> SEQUENCE: 47

Xaa Xaa Tyr Xaa Xaa Xaa
1               5

<210> SEQ ID NO 48
<211> LENGTH: 1114
<212> TYPE: PRT
<213> ORGANISM: Artificial Sequence
<220> FEATURE:
<223> OTHER INFORMATION: Amino acid sequence of a AND NOT gate
      (16076.SFG.aCD19fmc63-CD8STK-CD28tmZ-2A-aCD33glx-muCD8STK-tm-
      dPTPN6)

<400> SEQUENCE: 48

Met Ser Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

-continued

```
Ser Ala Ser Leu Gly Asp Arg Val Thr Ile Ser Cys Arg Ala Ser Gln
         35                  40                  45
Asp Ile Ser Lys Tyr Leu Asn Trp Tyr Gln Gln Lys Pro Asp Gly Thr
     50                  55                  60
Val Lys Leu Leu Ile Tyr His Thr Ser Arg Leu His Ser Gly Val Pro
 65                  70                  75                  80
Ser Arg Phe Ser Gly Ser Gly Ser Gly Thr Asp Tyr Ser Leu Thr Ile
                 85                  90                  95
Ser Asn Leu Glu Gln Glu Asp Ile Ala Thr Tyr Phe Cys Gln Gln Gly
            100                 105                 110
Asn Thr Leu Pro Tyr Thr Phe Gly Gly Gly Thr Lys Leu Glu Ile Thr
        115                 120                 125
Lys Ala Gly Gly Gly Gly Ser Gly Gly Gly Gly Ser Gly Gly Gly Gly
130                 135                 140
Ser Gly Gly Gly Gly Ser Glu Val Lys Leu Gln Glu Ser Gly Pro Gly
145                 150                 155                 160
Leu Val Ala Pro Ser Gln Ser Leu Ser Val Thr Cys Thr Val Ser Gly
                165                 170                 175
Val Ser Leu Pro Asp Tyr Gly Val Ser Trp Ile Arg Gln Pro Pro Arg
            180                 185                 190
Lys Gly Leu Glu Trp Leu Gly Val Ile Trp Gly Ser Glu Thr Thr Tyr
        195                 200                 205
Tyr Asn Ser Ala Leu Lys Ser Arg Leu Thr Ile Ile Lys Asp Asn Ser
    210                 215                 220
Lys Ser Gln Val Phe Leu Lys Met Asn Ser Leu Gln Thr Asp Asp Thr
225                 230                 235                 240
Ala Ile Tyr Tyr Cys Ala Lys His Tyr Tyr Gly Gly Ser Tyr Ala
                245                 250                 255
Met Asp Tyr Trp Gly Gln Gly Thr Ser Val Thr Val Ser Ser Asp Pro
            260                 265                 270
Thr Thr Thr Pro Ala Pro Arg Pro Pro Thr Pro Ala Pro Thr Ile Ala
        275                 280                 285
Ser Gln Pro Leu Ser Leu Arg Pro Glu Ala Cys Arg Pro Ala Ala Gly
    290                 295                 300
Gly Ala Val His Thr Arg Gly Leu Asp Phe Ala Cys Asp Ile Phe Trp
305                 310                 315                 320
Val Leu Val Val Val Gly Gly Val Leu Ala Cys Tyr Ser Leu Leu Val
                325                 330                 335
Thr Val Ala Phe Ile Ile Phe Trp Val Arg Arg Val Lys Phe Ser Arg
            340                 345                 350
Ser Ala Asp Ala Pro Ala Tyr Gln Gln Gly Gln Asn Gln Leu Tyr Asn
        355                 360                 365
Glu Leu Asn Leu Gly Arg Arg Glu Glu Tyr Asp Val Leu Asp Lys Arg
    370                 375                 380
Arg Gly Arg Asp Pro Glu Met Gly Gly Lys Pro Arg Arg Lys Asn Pro
385                 390                 395                 400
Gln Glu Gly Leu Tyr Asn Glu Leu Gln Lys Asp Lys Met Ala Glu Ala
                405                 410                 415
Tyr Ser Glu Ile Gly Met Lys Gly Glu Arg Arg Arg Gly Lys Gly His
            420                 425                 430
Asp Gly Leu Tyr Gln Gly Leu Ser Thr Ala Thr Lys Asp Thr Tyr Asp
        435                 440                 445
Ala Leu His Met Gln Ala Leu Pro Pro Arg Arg Ala Glu Gly Arg Gly
```

```
                450             455             460
Ser Leu Leu Thr Cys Gly Asp Val Glu Glu Asn Pro Gly Pro Met Ala
465                 470                 475                 480

Val Pro Thr Gln Val Leu Gly Leu Leu Leu Trp Leu Thr Asp Ala
                485                 490                 495

Arg Cys Asp Ile Gln Met Thr Gln Ser Pro Ser Ser Leu Ser Ala Ser
                500                 505                 510

Val Gly Asp Arg Val Thr Ile Thr Cys Arg Ala Ser Glu Asp Ile Tyr
            515                 520                 525

Phe Asn Leu Val Trp Tyr Gln Gln Lys Pro Gly Lys Ala Pro Lys Leu
        530                 535                 540

Leu Ile Tyr Asp Thr Asn Arg Leu Ala Asp Gly Val Pro Ser Arg Phe
545                 550                 555                 560

Ser Gly Ser Gly Ser Gly Thr Gln Tyr Thr Leu Thr Ile Ser Ser Leu
                565                 570                 575

Gln Pro Glu Asp Phe Ala Thr Tyr Tyr Cys Gln His Tyr Lys Asn Tyr
                580                 585                 590

Pro Leu Thr Phe Gly Gln Gly Thr Lys Leu Glu Ile Lys Arg Ser Gly
            595                 600                 605

Gly Gly Gly Ser Gly Gly Gly Ser Gly Gly Gly Ser Gly Gly
        610                 615                 620

Gly Gly Ser Arg Ser Glu Val Gln Leu Val Glu Ser Gly Gly Gly Leu
625                 630                 635                 640

Val Gln Pro Gly Gly Ser Leu Arg Leu Ser Cys Ala Ala Ser Gly Phe
                645                 650                 655

Thr Leu Ser Asn Tyr Gly Met His Trp Ile Arg Gln Ala Pro Gly Lys
                660                 665                 670

Gly Leu Glu Trp Val Ser Ser Ile Ser Leu Asn Gly Gly Ser Thr Tyr
            675                 680                 685

Tyr Arg Asp Ser Val Lys Gly Arg Phe Thr Ile Ser Arg Asp Asn Ala
        690                 695                 700

Lys Ser Thr Leu Tyr Leu Gln Met Asn Ser Leu Arg Ala Glu Asp Thr
705                 710                 715                 720

Ala Val Tyr Tyr Cys Ala Ala Gln Asp Ala Tyr Thr Gly Gly Tyr Phe
                725                 730                 735

Asp Tyr Trp Gly Gln Gly Thr Leu Val Thr Val Ser Ser Met Asp Pro
            740                 745                 750

Ala Thr Thr Thr Lys Pro Val Leu Arg Thr Pro Ser Pro Val His Pro
                755                 760                 765

Thr Gly Thr Ser Gln Pro Gln Arg Pro Glu Asp Cys Arg Pro Arg Gly
        770                 775                 780

Ser Val Lys Gly Thr Gly Leu Asp Phe Ala Cys Asp Ile Tyr Trp Ala
785                 790                 795                 800

Pro Leu Ala Gly Ile Cys Val Ala Leu Leu Leu Ser Leu Ile Ile Thr
                805                 810                 815

Leu Ile Cys Tyr His Arg Ser Arg Lys Arg Val Cys Lys Ser Gly Gly
                820                 825                 830

Gly Ser Phe Trp Glu Glu Phe Glu Ser Leu Gln Lys Gln Glu Val Lys
            835                 840                 845

Asn Leu His Gln Arg Leu Glu Gly Gln Arg Pro Glu Asn Lys Gly Lys
        850                 855                 860

Asn Arg Tyr Lys Asn Ile Leu Pro Phe Asp His Ser Arg Val Ile Leu
865                 870                 875                 880
```

```
Gln Gly Arg Asp Ser Asn Ile Pro Gly Ser Asp Tyr Ile Asn Ala Asn
            885                 890                 895

Tyr Ile Lys Asn Gln Leu Leu Gly Pro Asp Glu Asn Ala Lys Thr Tyr
        900                 905                 910

Ile Ala Ser Gln Gly Cys Leu Glu Ala Thr Val Asn Asp Phe Trp Gln
        915                 920                 925

Met Ala Trp Gln Glu Asn Ser Arg Val Ile Val Met Thr Thr Arg Glu
    930                 935                 940

Val Glu Lys Gly Arg Asn Lys Cys Val Pro Tyr Trp Pro Glu Val Gly
945                 950                 955                 960

Met Gln Arg Ala Tyr Gly Pro Tyr Ser Val Thr Asn Cys Gly Glu His
                965                 970                 975

Asp Thr Thr Glu Tyr Lys Leu Arg Thr Leu Gln Val Ser Pro Leu Asp
            980                 985                 990

Asn Gly Asp Leu Ile Arg Glu Ile Trp His Tyr Gln Tyr Leu Ser Trp
        995                 1000                1005

Pro Asp His Gly Val Pro Ser Glu Pro Gly Gly Val Leu Ser Phe
    1010                1015                1020

Leu Asp Gln Ile Asn Gln Arg Gln Glu Ser Leu Pro His Ala Gly
    1025                1030                1035

Pro Ile Ile Val His Cys Ser Ala Gly Ile Gly Arg Thr Gly Thr
    1040                1045                1050

Ile Ile Val Ile Asp Met Leu Met Glu Asn Ile Ser Thr Lys Gly
    1055                1060                1065

Leu Asp Cys Asp Ile Asp Ile Gln Lys Thr Ile Gln Met Val Arg
    1070                1075                1080

Ala Gln Arg Ser Gly Met Val Gln Thr Glu Ala Gln Tyr Lys Phe
    1085                1090                1095

Ile Tyr Val Ala Ile Ala Gln Phe Ile Glu Thr Thr Lys Lys Lys
    1100                1105                1110

Leu

<210> SEQ ID NO 49
<211> LENGTH: 918
<212> TYPE: PRT
<213> ORGANISM: Artificial Sequence
<220> FEATURE:
<223> OTHER INFORMATION: Amino acid sequence of a AND NOT gate
      (MP16091.SFG.aCD19fmc63-CD8STK-CD28tmZ-2A-aCD33glx-muCD8STK-
      LAIR1tm-endo)

<400> SEQUENCE: 49

Met Ser Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
```

```
                  100                 105                 110
Asn Thr Leu Pro Tyr Thr Phe Gly Gly Gly Thr Lys Leu Glu Ile Thr
                115                 120                 125
Lys Ala Gly Gly Gly Ser Gly Gly Gly Ser Gly Gly Gly Gly
130                 135                 140
Ser Gly Gly Gly Ser Glu Val Lys Leu Gln Glu Ser Gly Pro Gly
145                 150                 155                 160
Leu Val Ala Pro Ser Gln Ser Leu Ser Val Thr Cys Thr Val Ser Gly
                165                 170                 175
Val Ser Leu Pro Asp Tyr Gly Val Ser Trp Ile Arg Gln Pro Pro Arg
                180                 185                 190
Lys Gly Leu Glu Trp Leu Gly Val Ile Trp Gly Ser Glu Thr Thr Tyr
                195                 200                 205
Tyr Asn Ser Ala Leu Lys Ser Arg Leu Thr Ile Ile Lys Asp Asn Ser
                210                 215                 220
Lys Ser Gln Val Phe Leu Lys Met Asn Ser Leu Gln Thr Asp Asp Thr
225                 230                 235                 240
Ala Ile Tyr Tyr Cys Ala Lys His Tyr Tyr Tyr Gly Gly Ser Tyr Ala
                245                 250                 255
Met Asp Tyr Trp Gly Gln Gly Thr Ser Val Thr Val Ser Ser Asp Pro
                260                 265                 270
Thr Thr Thr Pro Ala Pro Arg Pro Pro Thr Pro Ala Pro Thr Ile Ala
                275                 280                 285
Ser Gln Pro Leu Ser Leu Arg Pro Glu Ala Cys Arg Pro Ala Ala Gly
                290                 295                 300
Gly Ala Val His Thr Arg Gly Leu Asp Phe Ala Cys Asp Ile Phe Trp
305                 310                 315                 320
Val Leu Val Val Val Gly Gly Val Leu Ala Cys Tyr Ser Leu Leu Val
                325                 330                 335
Thr Val Ala Phe Ile Ile Phe Trp Val Arg Arg Val Lys Phe Ser Arg
                340                 345                 350
Ser Ala Asp Ala Pro Ala Tyr Gln Gln Gly Gln Asn Gln Leu Tyr Asn
                355                 360                 365
Glu Leu Asn Leu Gly Arg Arg Glu Glu Tyr Asp Val Leu Asp Lys Arg
                370                 375                 380
Arg Gly Arg Asp Pro Glu Met Gly Gly Lys Pro Arg Arg Lys Asn Pro
385                 390                 395                 400
Gln Glu Gly Leu Tyr Asn Glu Leu Gln Lys Asp Lys Met Ala Glu Ala
                405                 410                 415
Tyr Ser Glu Ile Gly Met Lys Gly Glu Arg Arg Arg Gly Lys Gly His
                420                 425                 430
Asp Gly Leu Tyr Gln Gly Leu Ser Thr Ala Thr Lys Asp Thr Tyr Asp
                435                 440                 445
Ala Leu His Met Gln Ala Leu Pro Pro Arg Arg Ala Glu Gly Arg Gly
                450                 455                 460
Ser Leu Leu Thr Cys Gly Asp Val Glu Glu Asn Pro Gly Pro Met Ala
465                 470                 475                 480
Val Pro Thr Gln Val Leu Gly Leu Leu Leu Leu Trp Leu Thr Asp Ala
                485                 490                 495
Arg Cys Asp Ile Gln Met Thr Gln Ser Pro Ser Ser Leu Ser Ala Ser
                500                 505                 510
Val Gly Asp Arg Val Thr Ile Thr Cys Arg Ala Ser Glu Asp Ile Tyr
                515                 520                 525
```

```
Phe Asn Leu Val Trp Tyr Gln Gln Lys Pro Gly Lys Ala Pro Lys Leu
        530                 535                 540

Leu Ile Tyr Asp Thr Asn Arg Leu Ala Asp Gly Val Pro Ser Arg Phe
545                 550                 555                 560

Ser Gly Ser Gly Ser Gly Thr Gln Tyr Thr Leu Thr Ile Ser Ser Leu
                565                 570                 575

Gln Pro Glu Asp Phe Ala Thr Tyr Tyr Cys Gln His Tyr Lys Asn Tyr
            580                 585                 590

Pro Leu Thr Phe Gly Gln Gly Thr Lys Leu Glu Ile Lys Arg Ser Gly
        595                 600                 605

Gly Gly Gly Ser Gly Gly Gly Ser Gly Gly Gly Ser Gly Gly Ser Gly
610                 615                 620

Gly Gly Ser Arg Ser Glu Val Gln Leu Val Glu Ser Gly Gly Gly Leu
625                 630                 635                 640

Val Gln Pro Gly Gly Ser Leu Arg Leu Ser Cys Ala Ala Ser Gly Phe
                645                 650                 655

Thr Leu Ser Asn Tyr Gly Met His Trp Ile Arg Gln Ala Pro Gly Lys
            660                 665                 670

Gly Leu Glu Trp Val Ser Ser Ile Ser Leu Asn Gly Gly Ser Thr Tyr
        675                 680                 685

Tyr Arg Asp Ser Val Lys Gly Arg Phe Thr Ile Ser Arg Asp Asn Ala
690                 695                 700

Lys Ser Thr Leu Tyr Leu Gln Met Asn Ser Leu Arg Ala Glu Asp Thr
705                 710                 715                 720

Ala Val Tyr Tyr Cys Ala Ala Gln Asp Ala Tyr Thr Gly Gly Tyr Phe
                725                 730                 735

Asp Tyr Trp Gly Gln Gly Thr Leu Val Thr Val Ser Ser Met Asp Pro
            740                 745                 750

Ala Thr Thr Thr Lys Pro Val Leu Arg Thr Pro Ser Pro Val His Pro
        755                 760                 765

Thr Gly Thr Ser Gln Pro Gln Arg Pro Glu Asp Cys Arg Pro Arg Gly
770                 775                 780

Ser Val Lys Gly Thr Gly Leu Asp Phe Ala Cys Asp Ile Leu Ile Gly
785                 790                 795                 800

Val Ser Val Val Phe Leu Phe Cys Leu Leu Leu Val Leu Phe Cys
                805                 810                 815

Leu His Arg Gln Asn Gln Ile Lys Gln Gly Pro Pro Arg Ser Lys Asp
            820                 825                 830

Glu Glu Gln Lys Pro Gln Gln Arg Pro Asp Leu Ala Val Asp Val Leu
        835                 840                 845

Glu Arg Thr Ala Asp Lys Ala Thr Val Asn Gly Leu Pro Glu Lys Asp
850                 855                 860

Arg Glu Thr Asp Thr Ser Ala Leu Ala Ala Gly Ser Ser Gln Glu Val
865                 870                 875                 880

Thr Tyr Ala Gln Leu Asp His Trp Ala Leu Thr Gln Arg Thr Ala Arg
                885                 890                 895

Ala Val Ser Pro Gln Ser Thr Lys Pro Met Ala Glu Ser Ile Thr Tyr
            900                 905                 910

Ala Ala Val Ala Arg His
            915

<210> SEQ ID NO 50
<211> LENGTH: 1362
```

<212> TYPE: PRT
<213> ORGANISM: Artificial Sequence
<220> FEATURE:
<223> OTHER INFORMATION: Amino acid sequence of a AND NOT gate
      (MP16092.SFG.aCD19fmc63-CD8STK-CD28tmZ-2A-aCD33glx-muCD8STK-
      LAIR1tm-endo-2A-PTPN6_SH2-dCD148)

<400> SEQUENCE: 50

Met Ser Leu Pro Val Thr Ala Leu Leu Leu Pro Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Lys Ala Gly Gly Gly Gly Ser Gly Gly Gly Gly Ser Gly Gly Gly Gly
    130                 135                 140

Ser Gly Gly Gly Gly Ser Glu Val Lys Leu Gln Glu Ser Gly Pro Gly
145                 150                 155                 160

Leu Val Ala Pro Ser Gln Ser Leu Ser Val Thr Cys Thr Val Ser Gly
                165                 170                 175

Val Ser Leu Pro Asp Tyr Gly Val Ser Trp Ile Arg Gln Pro Pro Arg
            180                 185                 190

Lys Gly Leu Glu Trp Leu Gly Val Ile Trp Gly Ser Glu Thr Thr Tyr
        195                 200                 205

Tyr Asn Ser Ala Leu Lys Ser Arg Leu Thr Ile Ile Lys Asp Asn Ser
    210                 215                 220

Lys Ser Gln Val Phe Leu Lys Met Asn Ser Leu Gln Thr Asp Asp Thr
225                 230                 235                 240

Ala Ile Tyr Tyr Cys Ala Lys His Tyr Tyr Gly Gly Ser Tyr Ala
                245                 250                 255

Met Asp Tyr Trp Gly Gln Gly Thr Ser Val Thr Val Ser Ser Asp Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Phe Trp
305                 310                 315                 320

Val Leu Val Val Val Gly Gly Val Leu Ala Cys Tyr Ser Leu Leu Val
                325                 330                 335

Thr Val Ala Phe Ile Ile Phe Trp Val Arg Arg Val Lys Phe Ser Arg
            340                 345                 350

Ser Ala Asp Ala Pro Ala Tyr Gln Gln Gly Gln Asn Gln Leu Tyr Asn
        355                 360                 365

Glu Leu Asn Leu Gly Arg Arg Glu Glu Tyr Asp Val Leu Asp Lys Arg

```
            370                 375                 380
Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
                420                 425                 430

Asp Gly Leu Tyr Gln Gly Leu Ser Thr Ala Thr Lys Asp Thr Tyr Asp
                435                 440                 445

Ala Leu His Met Gln Ala Leu Pro Pro Arg Arg Ala Glu Gly Arg Gly
                450                 455                 460

Ser Leu Leu Thr Cys Gly Asp Val Glu Glu Asn Pro Gly Pro Met Ala
465                 470                 475                 480

Val Pro Thr Gln Val Leu Gly Leu Leu Leu Leu Trp Leu Thr Asp Ala
                485                 490                 495

Arg Cys Asp Ile Gln Met Thr Gln Ser Pro Ser Ser Leu Ser Ala Ser
                500                 505                 510

Val Gly Asp Arg Val Thr Ile Thr Cys Arg Ala Ser Glu Asp Ile Tyr
                515                 520                 525

Phe Asn Leu Val Trp Tyr Gln Gln Lys Pro Gly Lys Ala Pro Lys Leu
                530                 535                 540

Leu Ile Tyr Asp Thr Asn Arg Leu Ala Asp Gly Val Pro Ser Arg Phe
545                 550                 555                 560

Ser Gly Ser Gly Ser Gly Thr Gln Tyr Thr Leu Thr Ile Ser Ser Leu
                565                 570                 575

Gln Pro Glu Asp Phe Ala Thr Tyr Tyr Cys Gln His Tyr Lys Asn Tyr
                580                 585                 590

Pro Leu Thr Phe Gly Gln Gly Thr Lys Leu Glu Ile Lys Arg Ser Gly
                595                 600                 605

Gly Gly Gly Ser Gly Gly Gly Ser Gly Gly Gly Ser Gly Gly Gly Gly
                610                 615                 620

Gly Gly Ser Arg Ser Glu Val Gln Leu Val Glu Ser Gly Gly Gly Leu
625                 630                 635                 640

Val Gln Pro Gly Gly Ser Leu Arg Leu Ser Cys Ala Ala Ser Gly Phe
                645                 650                 655

Thr Leu Ser Asn Tyr Gly Met His Trp Ile Arg Gln Ala Pro Gly Lys
                660                 665                 670

Gly Leu Glu Trp Val Ser Ser Ile Ser Leu Asn Gly Gly Ser Thr Tyr
                675                 680                 685

Tyr Arg Asp Ser Val Lys Gly Arg Phe Thr Ile Ser Arg Asp Asn Ala
                690                 695                 700

Lys Ser Thr Leu Tyr Leu Gln Met Asn Ser Leu Arg Ala Glu Asp Thr
705                 710                 715                 720

Ala Val Tyr Tyr Cys Ala Ala Gln Asp Ala Tyr Thr Gly Gly Tyr Phe
                725                 730                 735

Asp Tyr Trp Gly Gln Gly Thr Leu Val Thr Val Ser Ser Met Asp Pro
                740                 745                 750

Thr Thr Thr Lys Pro Val Leu Arg Thr Pro Ser Pro Val His Pro Thr
                755                 760                 765

Gly Thr Ser Gln Pro Gln Arg Pro Glu Asp Cys Arg Pro Arg Gly Ser
                770                 775                 780

Val Lys Gly Thr Gly Leu Asp Phe Ala Cys Asp Ile Leu Ile Gly Val
785                 790                 795                 800
```

Ser Val Val Phe Leu Phe Cys Leu Leu Leu Val Leu Phe Cys Leu
                805                 810                 815

His Arg Gln Asn Gln Ile Lys Gln Gly Pro Pro Arg Ser Lys Asp Glu
                820                 825                 830

Glu Gln Lys Pro Gln Gln Arg Pro Asp Leu Ala Val Asp Val Leu Glu
                835                 840                 845

Arg Thr Ala Asp Lys Ala Thr Val Asn Gly Leu Pro Glu Lys Asp Arg
            850                 855                 860

Glu Thr Asp Thr Ser Ala Leu Ala Ala Gly Ser Ser Gln Glu Val Thr
865                 870                 875                 880

Tyr Ala Gln Leu Asp His Trp Ala Leu Thr Gln Arg Thr Ala Arg Ala
                885                 890                 895

Val Ser Pro Gln Ser Thr Lys Pro Met Ala Glu Ser Ile Thr Tyr Ala
                900                 905                 910

Ala Val Ala Arg His Arg Ala Glu Gly Arg Gly Ser Leu Leu Thr Cys
                915                 920                 925

Gly Asp Val Glu Glu Asn Pro Gly Pro Trp Tyr His Gly His Met Ser
            930                 935                 940

Gly Gly Gln Ala Glu Thr Leu Leu Gln Ala Lys Gly Glu Pro Trp Thr
945                 950                 955                 960

Phe Leu Val Arg Glu Ser Leu Ser Gln Pro Gly Asp Phe Val Leu Ser
                965                 970                 975

Val Leu Ser Asp Gln Pro Lys Ala Gly Pro Gly Ser Pro Leu Arg Val
                980                 985                 990

Thr His Ile Lys Val Met Cys Glu Gly Gly Arg Tyr Thr Val Gly Gly
                995                 1000                1005

Leu Glu Thr Phe Asp Ser Leu Thr Asp Leu Val Glu His Phe Lys
        1010                1015                1020

Lys Thr Gly Ile Glu Glu Ala Ser Gly Ala Phe Val Tyr Leu Arg
        1025                1030                1035

Gln Pro Tyr Ser Gly Gly Gly Gly Ser Phe Glu Ala Tyr Phe Lys
        1040                1045                1050

Lys Gln Gln Ala Asp Ser Asn Cys Gly Phe Ala Glu Glu Tyr Glu
        1055                1060                1065

Asp Leu Lys Leu Val Gly Ile Ser Gln Pro Lys Tyr Ala Ala Glu
        1070                1075                1080

Leu Ala Glu Asn Arg Gly Lys Asn Arg Tyr Asn Asn Val Leu Pro
        1085                1090                1095

Tyr Asp Ile Ser Arg Val Lys Leu Ser Val Gln Thr His Ser Thr
        1100                1105                1110

Asp Asp Tyr Ile Asn Ala Asn Tyr Met Pro Gly Tyr His Ser Lys
        1115                1120                1125

Lys Asp Phe Ile Ala Thr Gln Gly Pro Leu Pro Asn Thr Leu Lys
        1130                1135                1140

Asp Phe Trp Arg Met Val Trp Glu Lys Asn Val Tyr Ala Ile Ile
        1145                1150                1155

Met Leu Thr Lys Cys Val Glu Gln Gly Arg Thr Lys Cys Glu Glu
        1160                1165                1170

Tyr Trp Pro Ser Lys Gln Ala Gln Asp Tyr Gly Asp Ile Thr Val
        1175                1180                1185

Ala Met Thr Ser Glu Ile Val Leu Pro Glu Trp Thr Ile Arg Asp
        1190                1195                1200

```
Phe Thr Val Lys Asn Ile Gln Thr Ser Glu Ser His Pro Leu Arg
    1205                1210                1215

Gln Phe His Phe Thr Ser Trp Pro Asp His Gly Val Pro Asp Thr
    1220                1225                1230

Thr Asp Leu Leu Ile Asn Phe Arg Tyr Leu Val Arg Asp Tyr Met
    1235                1240                1245

Lys Gln Ser Pro Pro Glu Ser Pro Ile Leu Val His Cys Ser Ala
    1250                1255                1260

Gly Val Gly Arg Thr Gly Thr Phe Ile Ala Ile Asp Arg Leu Ile
    1265                1270                1275

Tyr Gln Ile Glu Asn Glu Asn Thr Val Asp Val Tyr Gly Ile Val
    1280                1285                1290

Tyr Asp Leu Arg Met His Arg Pro Leu Met Val Gln Thr Glu Asp
    1295                1300                1305

Gln Tyr Val Phe Leu Asn Gln Cys Val Leu Asp Ile Val Arg Ser
    1310                1315                1320

Gln Lys Asp Ser Lys Val Asp Leu Ile Tyr Gln Asn Thr Thr Ala
    1325                1330                1335

Met Thr Ile Tyr Glu Asn Leu Ala Pro Val Thr Thr Phe Gly Lys
    1340                1345                1350

Thr Asn Gly Tyr Ile Ala Ser Gly Ser
    1355                1360

<210> SEQ ID NO 51
<211> LENGTH: 424
<212> TYPE: PRT
<213> ORGANISM: Artificial Sequence
<220> FEATURE:
<223> OTHER INFORMATION: APRIL-based (A proliferation-inducing ligand-
      based) CAR, CD8 stalk APRIL CAR

<400> SEQUENCE: 51

Met Glu Thr Asp Thr Leu Leu Leu Trp Val Leu Leu Leu Trp Val Pro
1               5                   10                  15

Gly Ser Thr Gly Ser Val Leu His Leu Val Pro Ile Asn Ala Thr Ser
                20                  25                  30

Lys Asp Asp Ser Asp Val Thr Glu Val Met Trp Gln Pro Ala Leu Arg
            35                  40                  45

Arg Gly Arg Gly Leu Gln Ala Gln Gly Tyr Gly Val Arg Ile Gln Asp
        50                  55                  60

Ala Gly Val Tyr Leu Leu Tyr Ser Gln Val Leu Phe Gln Asp Val Thr
65                  70                  75                  80

Phe Thr Met Gly Gln Val Val Ser Arg Glu Gly Gln Gly Arg Gln Glu
                85                  90                  95

Thr Leu Phe Arg Cys Ile Arg Ser Met Pro Ser His Pro Asp Arg Ala
            100                 105                 110

Tyr Asn Ser Cys Tyr Ser Ala Gly Val Phe His Leu His Gln Gly Asp
        115                 120                 125

Ile Leu Ser Val Ile Ile Pro Arg Ala Arg Ala Lys Leu Asn Leu Ser
    130                 135                 140

Pro His Gly Thr Phe Leu Gly Phe Val Lys Leu Ser Gly Gly Gly Ser
145                 150                 155                 160

Asp Pro Thr Thr Thr Pro Ala Pro Arg Pro Pro Thr Pro Ala Pro Thr
                165                 170                 175

Ile Ala Ser Gln Pro Leu Ser Leu Arg Pro Glu Ala Cys Arg Pro Ala
            180                 185                 190
```

```
Ala Gly Gly Ala Val His Thr Arg Gly Leu Asp Phe Ala Cys Asp Ile
            195                 200                 205

Phe Trp Val Leu Val Val Gly Gly Val Leu Ala Cys Tyr Ser Leu
        210                 215                 220

Leu Val Thr Val Ala Phe Ile Ile Phe Trp Val Arg Ser Lys Arg Ser
225                 230                 235                 240

Arg Leu Leu His Ser Asp Tyr Met Asn Met Thr Pro Arg Arg Pro Gly
            245                 250                 255

Pro Thr Arg Lys His Tyr Gln Pro Tyr Ala Pro Pro Arg Asp Phe Ala
            260                 265                 270

Ala Tyr Arg Ser Arg Asp Gln Arg Leu Pro Pro Asp Ala His Lys Pro
            275                 280                 285

Pro Gly Gly Gly Ser Phe Arg Thr Pro Ile Gln Glu Glu Gln Ala Asp
            290                 295                 300

Ala His Ser Thr Leu Ala Lys Ile Arg Val Lys Phe Ser Arg Ser Ala
305                 310                 315                 320

Asp Ala Pro Ala Tyr Gln Gln Gly Gln Asn Gln Leu Tyr Asn Glu Leu
            325                 330                 335

Asn Leu Gly Arg Arg Glu Glu Tyr Asp Val Leu Asp Lys Arg Arg Gly
            340                 345                 350

Arg Asp Pro Glu Met Gly Gly Lys Pro Arg Arg Lys Asn Pro Gln Glu
            355                 360                 365

Gly Leu Tyr Asn Glu Leu Gln Lys Asp Lys Met Ala Glu Ala Tyr Ser
            370                 375                 380

Glu Ile Gly Met Lys Gly Glu Arg Arg Arg Gly Lys Gly His Asp Gly
385                 390                 395                 400

Leu Tyr Gln Gly Leu Ser Thr Ala Thr Lys Asp Thr Tyr Asp Ala Leu
            405                 410                 415

His Met Gln Ala Leu Pro Pro Arg
            420

<210> SEQ ID NO 52
<211> LENGTH: 398
<212> TYPE: PRT
<213> ORGANISM: Artificial Sequence
<220> FEATURE:
<223> OTHER INFORMATION: APRIL-based (A proliferation-inducing ligand-
      based) CAR, APRIL IgG1 hinge based CAR

<400> SEQUENCE: 52

Met Glu Thr Asp Thr Leu Leu Leu Trp Val Leu Leu Leu Trp Val Pro
1               5                   10                  15

Gly Ser Thr Gly Ser Val Leu His Leu Val Pro Ile Asn Ala Thr Ser
            20                  25                  30

Lys Asp Asp Ser Asp Val Thr Glu Val Met Trp Gln Pro Ala Leu Arg
        35                  40                  45

Arg Gly Arg Gly Leu Gln Ala Gln Gly Tyr Gly Val Arg Ile Gln Asp
    50                  55                  60

Ala Gly Val Tyr Leu Leu Tyr Ser Gln Val Leu Phe Gln Asp Val Thr
65                  70                  75                  80

Phe Thr Met Gly Gln Val Val Ser Arg Glu Gly Gln Gly Arg Gln Glu
            85                  90                  95

Thr Leu Phe Arg Cys Ile Arg Ser Met Pro Ser His Pro Asp Arg Ala
            100                 105                 110

Tyr Asn Ser Cys Tyr Ser Ala Gly Val Phe His Leu His Gln Gly Asp
```

```
            115                 120                 125
Ile Leu Ser Val Ile Ile Pro Arg Ala Arg Ala Lys Leu Asn Leu Ser
    130                 135                 140

Pro His Gly Thr Phe Leu Gly Phe Val Lys Leu Ser Gly Gly Gly Ser
145                 150                 155                 160

Asp Pro Ala Glu Pro Lys Ser Pro Asp Lys Thr His Thr Cys Pro Pro
                165                 170                 175

Cys Pro Lys Asp Pro Lys Phe Trp Val Leu Val Val Val Gly Gly Val
            180                 185                 190

Leu Ala Cys Tyr Ser Leu Leu Val Thr Val Ala Phe Ile Ile Phe Trp
        195                 200                 205

Val Arg Ser Lys Arg Ser Arg Leu Leu His Ser Asp Tyr Met Asn Met
    210                 215                 220

Thr Pro Arg Arg Pro Gly Pro Thr Arg Lys His Tyr Gln Pro Tyr Ala
225                 230                 235                 240

Pro Pro Arg Asp Phe Ala Ala Tyr Arg Ser Arg Asp Gln Arg Leu Pro
                245                 250                 255

Pro Asp Ala His Lys Pro Pro Gly Gly Gly Ser Phe Arg Thr Pro Ile
            260                 265                 270

Gln Glu Glu Gln Ala Asp Ala His Ser Thr Leu Ala Lys Ile Arg Val
        275                 280                 285

Lys Phe Ser Arg Ser Ala Asp Ala Pro Ala Tyr Gln Gln Gly Gln Asn
    290                 295                 300

Gln Leu Tyr Asn Glu Leu Asn Leu Gly Arg Arg Glu Glu Tyr Asp Val
305                 310                 315                 320

Leu Asp Lys Arg Arg Gly Arg Asp Pro Glu Met Gly Gly Lys Pro Arg
                325                 330                 335

Arg Lys Asn Pro Gln Glu Gly Leu Tyr Asn Glu Leu Gln Lys Asp Lys
            340                 345                 350

Met Ala Glu Ala Tyr Ser Glu Ile Gly Met Lys Gly Glu Arg Arg Arg
        355                 360                 365

Gly Lys Gly His Asp Gly Leu Tyr Gln Gly Leu Ser Thr Ala Thr Lys
    370                 375                 380

Asp Thr Tyr Asp Ala Leu His Met Gln Ala Leu Pro Pro Arg
385                 390                 395
```

<210> SEQ ID NO 53
<211> LENGTH: 614
<212> TYPE: PRT
<213> ORGANISM: Artificial Sequence
<220> FEATURE:
<223> OTHER INFORMATION: APRIL-based (A proliferation-inducing ligand-
      based) CAR, APRIL Fc-pvaa based CAR

<400> SEQUENCE: 53

```
Met Glu Thr Asp Thr Leu Leu Leu Trp Val Leu Leu Leu Trp Val Pro
1               5                   10                  15

Gly Ser Thr Gly Ser Val Leu His Leu Val Pro Ile Asn Ala Thr Ser
                20                  25                  30

Lys Asp Asp Ser Asp Val Thr Glu Val Met Trp Gln Pro Ala Leu Arg
            35                  40                  45

Arg Gly Arg Gly Leu Gln Ala Gln Gly Tyr Gly Val Arg Ile Gln Asp
        50                  55                  60

Ala Gly Val Tyr Leu Leu Tyr Ser Gln Val Leu Phe Gln Asp Val Thr
65                  70                  75                  80
```

```
Phe Thr Met Gly Gln Val Val Ser Arg Glu Gly Gln Gly Arg Gln Glu
             85                  90                  95

Thr Leu Phe Arg Cys Ile Arg Ser Met Pro Ser His Pro Asp Arg Ala
        100                 105                 110

Tyr Asn Ser Cys Tyr Ser Ala Gly Val Phe His Leu His Gln Gly Asp
            115                 120                 125

Ile Leu Ser Val Ile Ile Pro Arg Ala Arg Ala Lys Leu Asn Leu Ser
        130                 135                 140

Pro His Gly Thr Phe Leu Gly Phe Val Lys Leu Ser Gly Gly Gly Ser
145                 150                 155                 160

Asp Pro Ala Glu Pro Lys Ser Pro Asp Lys Thr His Thr Cys Pro Pro
                165                 170                 175

Cys Pro Ala Pro Pro Val Ala Gly Pro Ser Val Phe Leu Phe Pro Pro
            180                 185                 190

Lys Pro Lys Asp Thr Leu Met Ile Ala Arg Thr Pro Glu Val Thr Cys
        195                 200                 205

Val Val Val Asp Val Ser His Glu Asp Pro Glu Val Lys Phe Asn Trp
    210                 215                 220

Tyr Val Asp Gly Val Glu Val His Asn Ala Lys Thr Lys Pro Arg Glu
225                 230                 235                 240

Glu Gln Tyr Asn Ser Thr Tyr Arg Val Val Ser Val Leu Thr Val Leu
                245                 250                 255

His Gln Asp Trp Leu Asn Gly Lys Glu Tyr Lys Cys Lys Val Ser Asn
            260                 265                 270

Lys Ala Leu Pro Ala Pro Ile Glu Lys Thr Ile Ser Lys Ala Lys Gly
        275                 280                 285

Gln Pro Arg Glu Pro Gln Val Tyr Thr Leu Pro Pro Ser Arg Asp Glu
290                 295                 300

Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
            340                 345                 350

Leu Tyr Ser Lys Leu Thr Val Asp Lys Ser Arg Trp Gln Gln Gly Asn
        355                 360                 365

Val Phe Ser Cys Ser Val Met His Glu Ala Leu His Asn His Tyr Thr
    370                 375                 380

Gln Lys Ser Leu Ser Leu Ser Pro Gly Lys Lys Asp Pro Lys Phe Trp
385                 390                 395                 400

Val Leu Val Val Val Gly Gly Val Leu Ala Cys Tyr Ser Leu Leu Val
                405                 410                 415

Thr Val Ala Phe Ile Ile Phe Trp Val Arg Ser Lys Arg Ser Arg Leu
            420                 425                 430

Leu His Ser Asp Tyr Met Asn Met Thr Pro Arg Arg Pro Gly Pro Thr
        435                 440                 445

Arg Lys His Tyr Gln Pro Tyr Ala Pro Pro Arg Asp Phe Ala Ala Tyr
    450                 455                 460

Arg Ser Arg Asp Gln Arg Leu Pro Pro Asp Ala His Lys Pro Pro Gly
465                 470                 475                 480

Gly Gly Ser Phe Arg Thr Pro Ile Gln Glu Glu Gln Ala Asp Ala His
                485                 490                 495

Ser Thr Leu Ala Lys Ile Arg Val Lys Phe Ser Arg Ser Ala Asp Ala
```

-continued

```
               500                 505                 510
Pro Ala Tyr Gln Gln Gly Gln Asn Gln Leu Tyr Asn Glu Leu Asn Leu
            515                 520                 525

Gly Arg Arg Glu Glu Tyr Asp Val Leu Asp Lys Arg Arg Gly Arg Asp
        530                 535                 540

Pro Glu Met Gly Gly Lys Pro Arg Arg Lys Asn Pro Gln Glu Gly Leu
545                 550                 555                 560

Tyr Asn Glu Leu Gln Lys Asp Lys Met Ala Glu Ala Tyr Ser Glu Ile
                565                 570                 575

Gly Met Lys Gly Glu Arg Arg Arg Gly Lys Gly His Asp Gly Leu Tyr
            580                 585                 590

Gln Gly Leu Ser Thr Ala Thr Lys Asp Thr Tyr Asp Ala Leu His Met
        595                 600                 605

Gln Ala Leu Pro Pro Arg
    610
```